(12) United States Patent
Qiu et al.

(10) Patent No.: US 12,011,425 B2
(45) Date of Patent: *Jun. 18, 2024

(54) HEPATITIS B ANTIVIRAL AGENTS

(71) Applicant: ENANTA PHARMACEUTICALS, INC., Watertown, MA (US)

(72) Inventors: Yao-Ling Qiu, Andover, MA (US); Xuri Gao, Newtonville, MA (US); Jorden Kass, Arlington, MA (US); Hui Cao, Belmont, MA (US); Wei Li, Lexington, MA (US); Xiaowen Peng, Sudbury, MA (US); Byung-Chul Suh, Lexington, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/101,258

(22) Filed: Jan. 25, 2023

(65) Prior Publication Data

US 2023/0241012 A1   Aug. 3, 2023

Related U.S. Application Data

(60) Continuation of application No. 17/166,046, filed on Feb. 3, 2021, now Pat. No. 11,596,611, which is a
(Continued)

(51) Int. Cl.
| | |
|---|---|
| A61K 31/167 | (2006.01) |
| A61K 31/337 | (2006.01) |
| A61K 31/34 | (2006.01) |
| A61K 31/351 | (2006.01) |
| A61K 31/357 | (2006.01) |
| A61K 31/397 | (2006.01) |
| A61K 31/401 | (2006.01) |
| A61K 31/4015 | (2006.01) |
| A61K 31/415 | (2006.01) |
| A61K 31/4164 | (2006.01) |
| A61K 31/4192 | (2006.01) |
| A61K 31/421 | (2006.01) |
| A61K 31/426 | (2006.01) |
| A61K 31/4409 | (2006.01) |
| A61K 31/4439 | (2006.01) |
| A61K 31/47 | (2006.01) |
| A61K 31/513 | (2006.01) |
| A61K 31/7028 | (2006.01) |

(Continued)

(52) U.S. Cl.
CPC .......... *A61K 31/167* (2013.01); *A61K 31/337* (2013.01); *A61K 31/34* (2013.01); *A61K 31/351* (2013.01); *A61K 31/357* (2013.01); *A61K 31/397* (2013.01); *A61K 31/401* (2013.01); *A61K 31/4015* (2013.01); *A61K 31/415* (2013.01); *A61K 31/4164* (2013.01); *A61K 31/4192* (2013.01); *A61K 31/421* (2013.01); *A61K 31/426* (2013.01); *A61K 31/4409* (2013.01); *A61K 31/4439* (2013.01); *A61K 31/47* (2013.01); *A61K 31/513* (2013.01); *A61K 31/7028* (2013.01); *A61P 31/20* (2018.01); *C07C 303/00* (2013.01); *C07C 317/44* (2013.01); *A61K 45/06* (2013.01); *C07B 2200/05* (2013.01); *C07C 2601/02* (2017.05); *C07C 2601/04* (2017.05); *C07C 2601/08* (2017.05); *C07C 2601/10* (2017.05); *C07C 2601/14* (2017.05); *C07C 2601/16* (2017.05); *C07C 2602/44* (2017.05); *C07C 2602/50* (2017.05)

(58) Field of Classification Search
CPC ..... A61K 31/167; A61K 31/351; A61P 31/20; C07C 317/44
See application file for complete search history.

(56) References Cited

U.S. PATENT DOCUMENTS

| | | | |
|---|---|---|---|
| 3,385,756 A | 5/1968 | Early et al. | |
| 3,975,532 A | 8/1976 | Miller et al. | |

(Continued)

FOREIGN PATENT DOCUMENTS

| | | |
|---|---|---|
| CN | 102093320 A | 6/2011 |
| CN | 106928215 A | 7/2017 |

(Continued)

OTHER PUBLICATIONS

Clark (Journal of Medicinal Chemistry; 1986, 29, 25-29).*
(Continued)

*Primary Examiner* — Pancham Bakshi
(74) *Attorney, Agent, or Firm* — Edgar W. Harlan; Carolyn S. Elmore; Elmore Patent Law Group, P.C.

(57) ABSTRACT

The present invention discloses compounds of Formula (I), or pharmaceutically acceptable salts, esters, or prodrugs thereof:

$$X\text{-}A\text{-}Y\text{-}L\text{-}R \qquad \text{(I)}$$

which inhibit the protein(s) encoded by hepatitis B virus (HBV) or interfere with the function of the HBV life cycle of the hepatitis B virus and are also useful as antiviral agents. The present invention further relates to pharmaceutical compositions comprising the aforementioned compounds for administration to a subject suffering from HBV infection. The invention also relates to methods of treating an HBV infection in a subject by administering a pharmaceutical composition comprising the compounds of the present invention.

17 Claims, No Drawings

Related U.S. Application Data division of application No. 16/114,842, filed on Aug. 28, 2018, now Pat. No. 10,952,978.

(60) Provisional application No. 62/550,992, filed on Aug. 28, 2017.

(51) Int. Cl.
*A61P 31/20* (2006.01)
*C07C 303/00* (2006.01)
*C07C 317/44* (2006.01)
*A61K 45/06* (2006.01)

(56) References Cited

U.S. PATENT DOCUMENTS

| | | | |
|---|---|---|---|
| 4,285,946 | A | 8/1981 | Kampe et al. |
| 4,507,481 | A | 3/1985 | Davidson et al. |
| 5,510,387 | A | 4/1996 | Leonidov et al. |
| 5,656,644 | A | 8/1997 | Adams et al. |
| 6,420,338 | B1 | 7/2002 | Schneider et al. |
| 6,498,165 | B1 | 12/2002 | Armstrong et al. |
| 6,503,913 | B1 | 1/2003 | Goldmann et al. |
| 6,525,069 | B1 | 2/2003 | Ko et al. |
| 6,667,342 | B1 | 12/2003 | Clarke et al. |
| 7,232,825 | B2 | 6/2007 | Chen et al. |
| 7,312,214 | B2 | 12/2007 | Qiao et al. |
| 7,411,003 | B1 | 8/2008 | Liu et al. |
| 7,615,569 | B2 | 11/2009 | Fulp et al. |
| 7,741,494 | B2 | 6/2010 | Bressi et al. |
| 8,101,643 | B2 | 1/2012 | Qiu et al. |
| 8,202,876 | B2 | 6/2012 | Albaugh et al. |
| 8,420,823 | B2 | 4/2013 | Sato et al. |
| 9,447,086 | B2 | 9/2016 | Liu et al. |
| 9,498,479 | B2 | 11/2016 | Zhang et al. |
| 9,573,941 | B2 | 2/2017 | Liu et al. |
| 9,617,252 | B2 | 4/2017 | Liu |
| 9,845,325 | B2 | 12/2017 | Fu et al. |
| 9,938,301 | B2 | 4/2018 | He et al. |
| 10,179,131 | B2 | 1/2019 | Qiu et al. |
| 10,179,792 | B2 * | 1/2019 | Qiu ................ A61K 31/401 |
| 10,189,846 | B2 | 1/2019 | Qiu et al. |
| 10,253,030 | B2 | 4/2019 | He et al. |
| 10,428,070 | B2 | 10/2019 | Qiu et al. |
| 10,538,532 | B2 | 1/2020 | Qiu et al. |
| 10,640,511 | B2 | 5/2020 | Qiu et al. |
| 10,723,733 | B2 | 7/2020 | Qiu et al. |
| 10,729,688 | B2 | 8/2020 | Qiu et al. |
| 10,865,211 | B2 | 12/2020 | Panarese et al. |
| 10,934,306 | B2 | 3/2021 | Qiu et al. |
| 10,952,978 | B2 * | 3/2021 | Qiu ................ C07D 413/04 |
| 11,058,678 | B2 | 7/2021 | Panarese et al. |
| 11,596,611 | B2 * | 3/2023 | Qiu ................ C07D 491/107 |
| 2002/0068838 | A1 | 6/2002 | Demassey et al. |
| 2003/0232842 | A1 | 12/2003 | Goldmann et al. |
| 2004/0082619 | A1 | 4/2004 | Tada et al. |
| 2004/0209930 | A1 | 10/2004 | Carboni et al. |
| 2005/0113450 | A1 | 5/2005 | Thorarensen et al. |
| 2005/0203119 | A1 | 9/2005 | Ono et al. |
| 2006/0100233 | A1 | 5/2006 | Villa et al. |
| 2007/0219239 | A1 | 9/2007 | Mjalli et al. |
| 2007/0225373 | A1 | 9/2007 | Chen et al. |
| 2009/0023740 | A1 | 1/2009 | Fulp et al. |
| 2009/0036420 | A1 | 2/2009 | Galley et al. |
| 2009/0118268 | A1 | 5/2009 | Riedl et al. |
| 2011/0009622 | A1 | 1/2011 | Jitsuoka et al. |
| 2011/0165118 | A1 | 7/2011 | Chan et al. |
| 2011/0281950 | A1 | 11/2011 | Baiocchi et al. |
| 2012/0009142 | A1 | 1/2012 | Karp et al. |
| 2013/0251673 | A1 | 9/2013 | Hartman et al. |
| 2013/0267517 | A1 | 10/2013 | Guo et al. |
| 2013/0309196 | A1 | 11/2013 | Link et al. |
| 2014/0206666 | A1 | 7/2014 | Guo et al. |
| 2014/0343032 | A1 | 11/2014 | Guo et al. |
| 2014/0357858 | A1 | 12/2014 | Ushioda et al. |
| 2015/0005295 | A1 | 1/2015 | Haché et al. |
| 2015/0038515 | A1 | 2/2015 | Cuconati et al. |
| 2015/0119362 | A1 | 4/2015 | Gurney et al. |
| 2015/0133428 | A1 | 5/2015 | Velaparthi et al. |
| 2015/0152073 | A1 | 6/2015 | Hartman et al. |
| 2015/0152096 | A1 | 6/2015 | Zhang et al. |
| 2015/0197493 | A1 | 7/2015 | Hartman et al. |
| 2015/0210682 | A1 | 7/2015 | Han et al. |
| 2015/0252057 | A1 | 9/2015 | Zhu et al. |
| 2015/0266890 | A1 | 9/2015 | Vandyck et al. |
| 2015/0274653 | A1 | 10/2015 | Vandyck et al. |
| 2016/0115149 | A1 | 4/2016 | Vandyck et al. |
| 2016/0185777 | A1 | 6/2016 | Hartman et al. |
| 2016/0206616 | A1 | 7/2016 | Zhang et al. |
| 2016/0237078 | A9 | 8/2016 | Guo et al. |
| 2016/0264562 | A1 | 9/2016 | Liu et al. |
| 2016/0264563 | A1 | 9/2016 | Ren et al. |
| 2016/0289212 | A1 | 10/2016 | Gao et al. |
| 2016/0296515 | A1 | 10/2016 | Han et al. |
| 2016/0332996 | A1 | 11/2016 | Gao et al. |
| 2016/0347746 | A1 | 12/2016 | Zhang |
| 2017/0014408 | A1 | 1/2017 | Gao et al. |
| 2017/0022150 | A1 | 1/2017 | Gao et al. |
| 2017/0037037 | A1 | 2/2017 | Biswas et al. |
| 2017/0197986 | A1 | 7/2017 | He et al. |
| 2017/0217974 | A1 | 8/2017 | Gao et al. |
| 2017/0240548 | A1 | 8/2017 | Fu et al. |
| 2017/0253609 | A1 | 9/2017 | Gao et al. |
| 2017/0354641 | A1 | 12/2017 | Bastian et al. |
| 2017/0355701 | A1 | 12/2017 | Qiu et al. |
| 2017/0355712 | A1 | 12/2017 | Campbell et al. |
| 2018/0134723 | A1 | 5/2018 | Tets et al. |
| 2018/0312507 | A1 | 11/2018 | Fu et al. |
| 2018/0312512 | A1 | 11/2018 | He et al. |
| 2019/0060258 | A1 | 2/2019 | Qiu et al. |
| 2019/0084994 | A1 | 3/2019 | Qiu et al. |
| 2019/0119288 | A1 | 4/2019 | Qiu et al. |
| 2019/0144448 | A1 | 5/2019 | Kotschy et al. |
| 2019/0144449 | A1 | 5/2019 | Kotschy et al. |
| 2019/0177316 | A1 | 6/2019 | Qiu et al. |
| 2019/0177320 | A1 | 6/2019 | Qiu et al. |
| 2019/0224188 | A1 | 7/2019 | Panarese et al. |
| 2019/0298865 | A1 | 10/2019 | Cuthbertson et al. |
| 2019/0321360 | A1 | 10/2019 | Qiu et al. |
| 2019/0337903 | A1 | 11/2019 | Khan |
| 2020/0095258 | A1 | 3/2020 | Panarese et al. |
| 2020/0165249 | A1 | 5/2020 | Panarese et al. |
| 2021/0079014 | A1 | 3/2021 | Panarese et al. |
| 2021/0115060 | A1 | 4/2021 | Panarese et al. |
| 2023/0241012 | A1 | 8/2023 | Qiu et al. |

FOREIGN PATENT DOCUMENTS

| | | |
|---|---|---|
| CN | 106928245 A | 7/2017 |
| CN | 108530449 A | 9/2018 |
| CN | 108727378 A | 11/2018 |
| CN | 111116577 A | 5/2020 |
| DE | 10109856 A1 | 9/2002 |
| EP | 2280001 A1 | 2/2011 |
| JP | 2010526151 A | 7/2010 |
| JP | 2012526820 A | 11/2012 |
| JP | 2013507350 A | 3/2013 |
| WO | 8702367 A2 | 4/1987 |
| WO | 9504046 A1 | 2/1995 |
| WO | 0168641 A1 | 9/2001 |
| WO | 0168647 A1 | 9/2001 |
| WO | 2004052852 A1 | 6/2004 |
| WO | 2006033995 A2 | 3/2006 |
| WO | 2006067446 A1 | 6/2006 |
| WO | 2008093614 A1 | 8/2008 |
| WO | 2008120759 A1 | 10/2008 |
| WO | 2009131065 A1 | 10/2009 |
| WO | 2009158473 A1 | 12/2009 |
| WO | 2010012442 A2 | 2/2010 |
| WO | 2010123139 A1 | 10/2010 |
| WO | 2011008597 A1 | 1/2011 |
| WO | 2011088561 A1 | 7/2011 |
| WO | 2011151651 A1 | 12/2011 |
| WO | 2013006394 A1 | 1/2013 |

(56) References Cited

FOREIGN PATENT DOCUMENTS

| | | |
|---|---|---|
| WO | 2013096744 A1 | 6/2013 |
| WO | 2013130703 A2 | 9/2013 |
| WO | 2013144129 A1 | 10/2013 |
| WO | 2013163404 A1 | 10/2013 |
| WO | 2013181584 A2 | 12/2013 |
| WO | 2014033170 A1 | 3/2014 |
| WO | 2014106019 A2 | 7/2014 |
| WO | 2014184350 A1 | 11/2014 |
| WO | 2014184365 A1 | 11/2014 |
| WO | 2015005295 A1 | 1/2015 |
| WO | 2015074546 A1 | 5/2015 |
| WO | 2015109130 A1 | 7/2015 |
| WO | 2015113990 A1 | 8/2015 |
| WO | 2015173164 A1 | 11/2015 |
| WO | 2016016370 A1 | 2/2016 |
| WO | 2016023877 A1 | 2/2016 |
| WO | 2016025933 A2 | 2/2016 |
| WO | 2016071215 A1 | 5/2016 |
| WO | 2016089990 A1 | 6/2016 |
| WO | 2016107832 A1 | 7/2016 |
| WO | 2016128335 A1 | 8/2016 |
| WO | 2016177655 A1 | 11/2016 |
| WO | 2017013046 A1 | 1/2017 |
| WO | 2017017042 A1 | 2/2017 |
| WO | 2017017043 A1 | 2/2017 |
| WO | 2017061466 A1 | 4/2017 |
| WO | 2017136403 A1 | 8/2017 |
| WO | 2017140821 A1 | 8/2017 |
| WO | 2017153919 A1 | 9/2017 |
| WO | 2017155844 A1 | 9/2017 |
| WO | 2017205115 A1 | 11/2017 |
| WO | 2017216391 A1 | 12/2017 |
| WO | 2017216685 A1 | 12/2017 |
| WO | 2017216686 A1 | 12/2017 |
| WO | 2018001944 A1 | 1/2018 |
| WO | 2018001952 A1 | 1/2018 |
| WO | 2018019297 A1 | 2/2018 |
| WO | 2018022282 A1 | 2/2018 |
| WO | 2018047109 A1 | 3/2018 |
| WO | 2018073753 A1 | 4/2018 |
| WO | 2018083081 A1 | 5/2018 |
| WO | 2018083106 A1 | 5/2018 |
| WO | 2018083136 A1 | 5/2018 |
| WO | 2018085619 A1 | 5/2018 |
| WO | 2018087345 A1 | 5/2018 |
| WO | 2018130152 A1 | 7/2018 |
| WO | 2018144605 A1 | 8/2018 |
| WO | 2018154466 A1 | 8/2018 |
| WO | 2018161960 A1 | 9/2018 |
| WO | 2018181883 A1 | 10/2018 |
| WO | 2018196805 A1 | 11/2018 |
| WO | 2018198079 A1 | 11/2018 |
| WO | 2018219356 A1 | 12/2018 |
| WO | 2019069293 A1 | 4/2019 |
| WO | 2019097479 A1 | 5/2019 |
| WO | 2019100735 A1 | 5/2019 |
| WO | 2019110352 A1 | 6/2019 |
| WO | 2019123285 A1 | 6/2019 |
| WO | 2019129681 A1 | 7/2019 |
| WO | 2019143902 A2 | 7/2019 |
| WO | 2019166951 A1 | 9/2019 |
| WO | 2019206799 A1 | 10/2019 |
| WO | 2020150366 A1 | 7/2020 |
| WO | 2020190740 A1 | 9/2020 |

OTHER PUBLICATIONS

CAS registry No. 1011646-53-9; Entry Date Apr. 3, 2008.
CAS registry No. 1011895-54-7; Entry Date: Apr. 3, 2008.
CAS registry No. 1011949-47-5; Entry Date: Apr. 3, 2008.
CAS registry No. 1011949-58-8; Entry Date: Apr. 3, 2008.
Chemical Abstract Service STN CAplus [online database], Accession No. 2003:1014580. (Year: 2003).
Chemical Abstract Service STN Database Registry No. 1578268-77-5 [online][Entered STN: Apr. 1, 2014].
Chemical Abstracts Registry No. 1026741-09-2, indexed in the Registry file on Jun. 9, 2008.
Chemical Abstracts Registry No. 115280-56-3, indexed in the Registry file on STN CAS Online Jul. 16, 1988.
Chemical Abstracts Registry No. 1269203-67-9, indexed in the Registry file on STN CAS Online Mar. 21, 2011.
Chemical Abstracts Registry No. 1350251-34-1, indexed in the Registry file on STN CAS Online Dec. 7, 2011.
Chemical Abstracts Registry No. 397288-41-4, indexed in the Registry file on Mar. 1, 2002.
Chemical Abstracts Registry No. 792901-47-4, indexed in the Registry file on STN CAS Online Dec. 6, 2004.
Chemical Abstracts Registry No. 92555-24-3, indexed in the Registry file on Dec. 17, 1984.
Chemical Abstracts Registry No. 950067-32-0, indexed in the Registry file on Oct. 10, 2007.
PubChem CID 57036978, National Center for Biotechnology Information. PubChem Compound Database; CID=57036978, https://pubchem.ncbi.nlm.nih.gov/compound/57036978 (accessed May 19, 2017), create date Jun. 13, 2012.
PubChem CID 69095846 National Center for Biotechnology Information. PubChem Compound Database; CID=69095846, https://pubchem.ncbi.nlm.nih.gov/compound/69095846 (accessed May 23, 2017), create date Nov. 30, 2012.
PubChem CI D 10194182, National Center for Biotechnology Information. PubChem Compound Database; CI 0=10194182, https://pubchem.ncbi.nlm.nih.gov/compound/10194182 (accessed May 19, 2017), create date Oct. 25, 2006.
PubChem, CID 90713021, Create Date: Mar. 16, 2015.
Pubchem—'428' Create Date: Sep. 11, 2005 (Sep. 11, 2005) Date Accessed: Jun. 17, 2016.
PubChem-CID 23201920, Create Date: Dec. 5, 2007, p. 3.
PubChem-CID 63186259, Create Date: Oct. 22, 2012 (Oct. 22, 2012) p. 3.
PubChem-SID 15224030 Deposit Date: Oct. 25, 2006.
Pubchern-57224610 ('610') Create Date: Jun. 14, 2012 (Jun. 14, 2012) Date Accessed: Jun. 17, 2016.
PubChem SID 79456770 CID 10880307 , 2009.
STN search report: STN, CAPUJS,S CN109069488/PN,S CN111263586/PN Apr. 13, 2021.
"(3 'R,4R)-3-[(E)-But-2-enyl]-3'-(2-chloro-4-fluorophenyl)-4'-[1-(difluoromethyl)pyrazol-3-yl]-1'-(1,3-thiazol-2-yl)spiro[1,3-oxazolidine-4,6'-5, 7-dihydro-3H-pyrrolo[1,2-c] pyrimidine]-2-one", PubChem, CID: 138722908, Retrieved from the Internet <URL: https://pubchem.ncbi.nlm.nih.gov/compound/138722908> , 2019 , 1-10.
"8-Tert-butyl-4-[(1 E)-1-(difluoromethoxy)buta-1, 3-dienyl]-5-ethyl-12-oxo-6, 9-diazatricyclo[7.4.0.02,6]trideca-1(13),2,4, 10-tetraene-11-carboxylic acid", PubChem-CID- 134460393, CreateDate: Jun. 23, 2018 (23.06.2018), p. 2, Fig.
"N-[4-(cyanomethyl)phenyl]-5-(hexyhydro-1-H-azepine-1-yl)sulfonyl]-2-methoxy-benzamid e", Database Registry [Online] Chemical Abstracts Service, Columbus, Ohio, US; May 6, 2011 (May 6, 2011), XP55358935, accession No. RN: 1291044-81-9.
Anderson, B. D, et al. , "Part VII: Chemical issues on pharmaceutical and formulation, Section 34: Preparation of water-soluble organic compounds by salt formation", The Practice of Medicinal Chemistry, the second volume Technomics, Inc. , 1998 , 347-365.
Ballatore, C. , et al. , "Carboxylic Acid (Bio)Isosteres in Drug Design", ChemMedChem., 8( 3) , 385-395.
Blaszykowski, C. , et al. , "A Palladium-Catalyzed Alkylation/Direct Arylation Synthesis of Nitrogen-Containing Heterocycles", J. Org. Chem., 73(5) , 1888-1897.
Chowshury, C. , et al. , "A rapid and facile method for the general synthesis of 3-aryl substituted 4,5,6,7-tetrahydro[1,2,3]triazolo[1,5-a]pyrazines and their ring fused analogues", Organic & Biomolecular Chemistry, vol. 9 , 5856-5862.
Clark, M. T, et al. , "5-(alkylsulfonyl)salicylanilides as Potential Dental Antiplaque Agent", Journal of Medicinal Chemistry, 29(1) , 1986 , 25-29.
Cook, J. , et al. , "Polycyclic Aromatic Hydrocarbons. Part XXXI. Some Nitrogenous Analogues of Chrysene, Pyrene and 3:4-Benzphenanthrene", J. Chem Soc., , 395-399.

(56) References Cited

OTHER PUBLICATIONS

Das, J., et al., "Discovery of 2-Amino-heteroaryl-benzothiazole-6-anilides as Potent p56lck Inhibitors", Biorganic & Medicinal Chemistry Letters, 13, 2587-2590.

El-Hamouly, W. S, et al., "Synthesis and Antimicrobial Activity of New 3, 4-Dihydropyrimidinones", International Journal of Pharmaceutical Sciences and Research, vol. 2, 2011, 1054-1062.

Flachner, B., et al., "Rapid in silico selection of an MCHR1 antagonists' focused library from multi-million compounds' repositories: biological evaluation", Med. Chem. Res., 23, 1234-1247.

Henderson, E. A, et al., "1,4-Benzodiazepines as Inhibitors of Respiratory Syncytial Virus. The Identification of a Clinical Candidate", Journal of Medicinal Chemistry, 50(7), Apr. 2007, 1685-1692.

Ho, G., et al., "The SAR development of dihydroimidazoisoquinoline derivates as phosphodiesterase 10A inhibitors for the treatment of schizophrenia", Bioorganic & Medicinal Chemistry Letters, vol. 22, 2585-2589.

Janetka, J. W, et al., "Discovery of a novel class of 2-ureido thiophene carboxamide checkpoint kinase inhibitors", Bioorganic & Medicinal Chemistry Letters, 18, 2008, 4242-4248.

Li, X., et al., , ACS Medicinal Chemistry Letters, 8, 2017, 969-974.

Noguchi, C., et al., "G to A Hypermutation of Hepatitis B Virus", Hepatology, vol. 41, No. 3, 626-633.

Patani, G. A., et al., "Bioisosterism: A Rational Approach in Drug Design", Chem. Rev., 96, 1996, 3147-3176.

Qiu, Z., et al., "Design and Synthesis of Orally Bioavailable 4-Methyl Heteroaryldihydropyrimidine Based Hepatitis B Virus (HBV) Capsid Inhibitors", Journal of Medicinal Chemistry.

Schiff, E., et al., "Characterization of the Kinetics of the Pasive and Active Transport Mechanisms for Bile Acid Absorption in the Small Intestine and Colon of the Rat", J. of Clin. Investigation, 51(6), https://doi.org/10.1172/JCI106931, 1351-1362.

Stachulski, A. V, et al., "Thiazolides as Novel Antiviral Agensts. 1. Inhibition of Hepatistis B Virus Replication", J. Med. Chem., 54, May 9, 2011, 4119-4132.

Teuber, H., et al., "Simple indolo[2,3-a]quinolizine synthesis", Tetrahedron Letters, vol. 5(7), 325-329.

Teuber, H-J., et al., "Indolo[2,3-a]chinolizine und eine einfache Synthese von Flavoserpentin", Liebigs Ann Chem., 1988(12), 1111-1120.

Wu, et al., , Toxicology, 236, 2007, 1-6.

Yang, et al., "Enzyme-mediated hydrolytic activation of prodrugs", Acta Pharmaceutica Sinica B., vol. 1(3), Sep. 9, 2011, 143-159.

* cited by examiner

HEPATITIS B ANTIVIRAL AGENTS

RELATED APPLICATIONS

This application is a continuation of U.S. application Ser. No. 17/166,046, filed Feb. 3, 2021, which is a divisional of U.S. application Ser. No. 16/114,842, filed Aug. 28, 2018, now U.S. Pat. No. 10,952,978, issued Mar. 23, 2021, which claims the benefit of U.S. Provisional Application No. 62/550,992, filed on Aug. 28, 2017. The entire teachings of the above applications are incorporated herein by reference.

TECHNICAL FIELD

The present invention relates generally to novel antiviral agents. Specifically, the present invention relates to compounds which can inhibit the protein(s) encoded by hepatitis B virus (HBV) or interfere with the function of the HBV life cycle, compositions comprising such compounds, methods for inhibiting HBV viral replication, methods for treating or preventing HBV infection, and processes for making the compounds.

BACKGROUND OF THE INVENTION

HBV infection remains a major public health problem, affecting approximately 2 billion people worldwide. Among them, 350 million people worldwide and 1.4 million in the US develop a chronic infection, which can lead to chronic persistent hepatitis, liver cirrhosis, and hepatocellular carcinoma (HCC). Every year 500,000 to 1 million people die from the end stage of liver diseases caused by HBV infection.

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent HCC. Current therapy goals for HBV-infected patients are directed to reducing serum HBV DNA to low or undetectable levels, and to ultimately reducing or preventing the development of cirrhosis and HCC.

The HBV is an enveloped, partially double-stranded DNA (dsDNA) virus of the hepadnavirus family (Hepadnaviridae). HBV capsid or core protein (CP) plays essential roles in HBV replication. The predominant biological function of capsid protein is to act as a structural protein to encapsidate pre-genomic RNA and form immature capsid particles, which spontaneously self-assemble from many copies of core dimers in the cytoplasm. Capsid protein also regulates viral DNA synthesis through different phosphorylation status of its C-terminal phosphorylation sites. Also, capsid protein might facilitate the nuclear translocation of viral relaxed circular genome by means of the nuclear localization signals located in the Arginine-rich domain of the C-terminal region of capsid protein. In the nucleus, as a component of viral cccDNA minichromosome, capsid protein could play a structural and regulatory role in the functionality of cccDNA minichromosomes. Capsid protein also interacts with viral large envelope protein in endoplasmic reticulum (ER) and triggers the release of intact viral particles from hepatocytes.

Capsid related anti-HBV inhibitors have been reported. For example, phenylpropen-amide derivatives, including compounds named AT-61 and AT-130 (Feld J. et al. Antiviral Res. 2007, 76, 168), and a class of thiazolidin-4-ones from Valeant (WO2006/033995), have been shown to inhibit pregenomic RNA (pgRNA) packaging. Heteroaryldihydropyrimi-dines or HAPs were discovered in a tissue culture-based screening (Weber et al., Antiviral Res. 2002, 54, 69). These HAP analogs act as synthetic allosteric activators and are able to induce aberrant capsid formation that leads to degradation of the core protein. A subclass of sulphamoylarylamides shows activity against HBV (WO2013/006394, WO2013/096744, WO2014/184365, and WO2017/136403. It was also shown that the small molecule bis-ANS acts as a molecular 'wedge' and interferes with normal capsid-protein geometry and capsid formation (Zlotnick A. et al. J. Virol. 2002, 4848).

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

The present invention relates to novel antiviral compounds, pharmaceutical compositions comprising such compounds, as well as methods to treat or prevent viral (particularly HBV) infection in a subject in need of such therapy with said compounds. Compounds of the present invention inhibit the protein(s) encoded by hepatitis B virus (HBV) or interfere with the life cycle of HBV and are also useful as antiviral agents. In addition, the present invention includes the process for the preparation of the said compounds.

In its principal aspect, the present invention provides a compound of Formula (I):

or a pharmaceutically acceptable salt thereof, wherein:
X and Y are each independently selected from optionally substituted aryl or optionally substituted heteroaryl; in one embodiment one of X and Y is optionally substituted phenyl; in another embodiment, both X and Y are optionally substituted phenyl;
A is selected from the group consisting of —NHC(O)—,

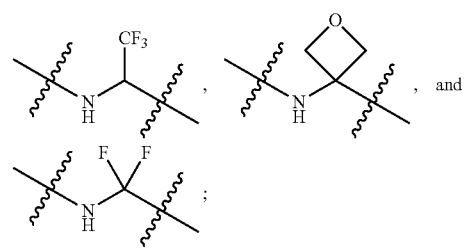

preferably A is —NHC(O)—;
L is S(O)$_2$, S(O), S or O; and
R is connected to L via a carbon atom and is independently selected from the group consisting of optionally substituted —C$_1$-C$_{10}$ alkyl, optionally substituted —C$_2$-C$_{10}$ alkenyl, optionally substituted —C$_2$-C$_{10}$ alkynyl, optionally substituted aryl, optionally substituted heteroaryl, optionally substituted —C$_3$-C$_{12}$ cycloalkyl, optionally substituted —C$_3$-C$_{12}$ cycloalkenyl, optionally substituted 3- to 12-membered heterocyclic; in one embodiment, R is optionally substituted —C$_5$-C$_{12}$ cycloalkyl or optionally substituted 5- to 12-membered heterocyclic, each optionally substituted with one or more of the following: fused rings, one or more spiro rings or one or more bridging ring moieties. In another embodiment, R is optionally substituted C$_3$-C$_{12}$ cycloalkyl-C$_1$-C$_6$-alkyl-, optionally substituted C$_3$-C$_{12}$ cycloalkenyl-C$_1$-C$_6$-alkyl-, or optionally substituted 3- to 12-membered heterocyclic-C$_1$-C$_6$-alkyl-.

Each preferred group stated above can be taken in combination with one, any or all other preferred groups.

DETAILED DESCRIPTION OF THE INVENTION

In one embodiment of the present invention is a compound of Formula (I) described above, or a pharmaceutically acceptable salt thereof.

In certain embodiments, the present invention relates to compounds of Formula (I), and their pharmaceutically acceptable salts thereof, wherein X is optionally substituted phenyl. In certain embodiments, X is phenyl substituted with one or more substituents, such as 1, 2, 3, 4 or 5 substituents. Preferably the substituents are independently selected from halogen, CN, optionally substituted —C$_1$-C$_3$ alkoxy, optionally substituted —C$_1$-C$_3$ alkyl, and optionally substituted —C$_3$-C$_6$ cycloalkyl. In certain embodiments, X is phenyl substituted with one or more substituents independently selected from fluoro, chloro, bromo, methyl, difluoromethyl, trifluoromethyl, CN and cyclopropyl. In certain embodiments, X is selected from the groups below:

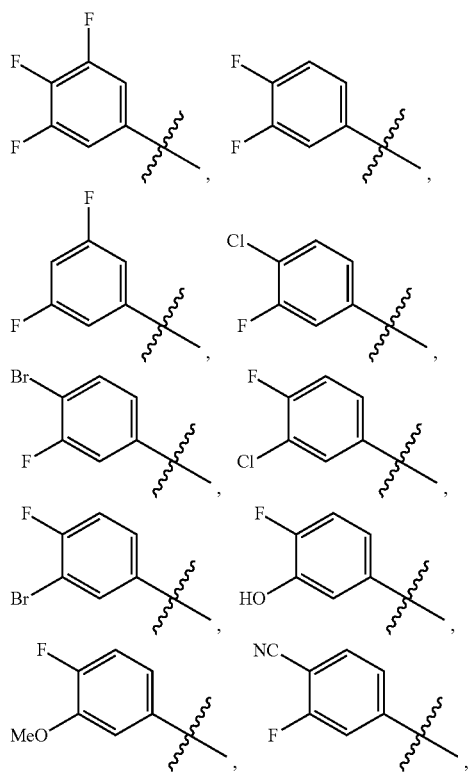

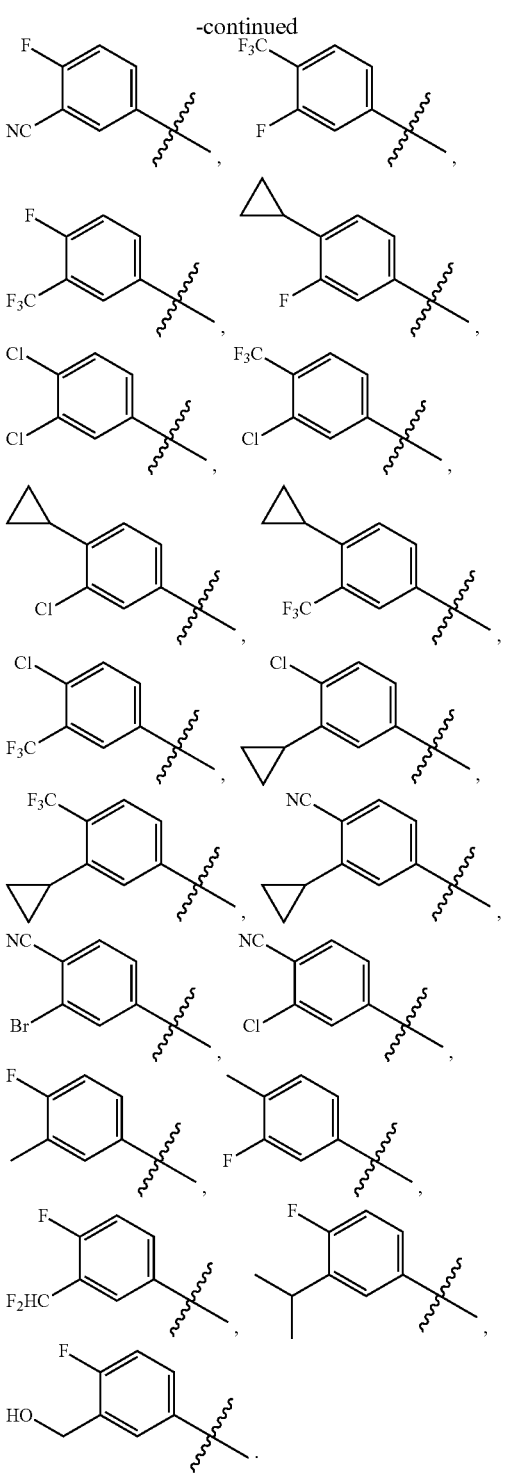

In certain embodiments, the present invention relates to compounds of Formula (I), and pharmaceutically acceptable salts thereof, wherein X is optionally substituted monocyclic heteroaryl. In certain embodiments, the present invention relates to compounds of Formula (I) or, and pharmaceutically acceptable salts thereof, wherein X is optionally substituted thiophenyl, optionally substituted thiazolyl, optionally substituted pyridyl, or optionally substituted pyrimidinyl. In certain embodiments, the present invention relates to compounds of Formula (I) or, and pharmaceutically acceptable salts thereof, wherein X is optionally substituted pyrimidinyl, optionally substituted pyridazyl, or optionally substituted pyrazyl as shown below:

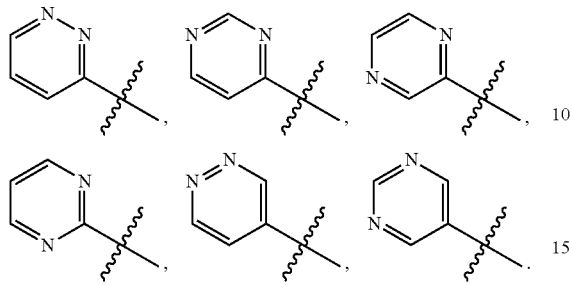

In certain embodiments, the present invention relates to compounds of Formula (I), and pharmaceutically acceptable salts thereof, wherein X is optionally substituted bicyclic heteroaryl. In certain embodiments, the present invention relates to compounds of Formula (I), and pharmaceutically acceptable salts thereof, wherein X is optionally substituted 5/6 bicyclic heteroaryl and is connected to A through either a carbon or nitrogen atom, preferably a carbon atom, of the 6-membered ring of said 5/6 bicyclic heteroaryl. In certain embodiments, the present invention relates to compounds of Formula (I), and pharmaceutically acceptable salts thereof, wherein X is optionally substituted benzimidazolyl, benzothiazolyl, benzoxazolyl, indazolyl, quinolyl, isoquinolyl or quinazolyl.

In certain embodiments, the present invention relates to compounds of Formula (I), and pharmaceutically acceptable salts thereof, wherein Y is optionally substituted phenyl. In certain embodiments, the present invention relates to compounds of Formula (I), and pharmaceutically acceptable salts thereof, wherein Y is phenyl substituted with halogen, CN, optionally substituted —$C_1$-$C_6$ alkoxy, optionally substituted —$C_1$-$C_6$ alkyl, optionally substituted —$C_1$-$C_6$ alkenyl, optionally substituted —$C_3$-$C_6$ cycloalkyl, optionally substituted aryl and optionally substituted heteroaryl. In certain embodiments, the present invention relates to compounds of Formula (I), and pharmaceutically acceptable salts thereof, wherein Y is optionally substituted 1, 3-phenylene, for example

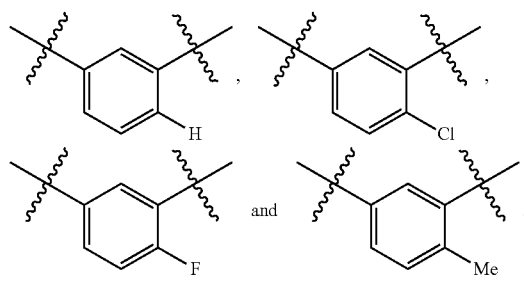

In certain embodiments, the present invention relates to compounds of Formula (I), and pharmaceutically acceptable salts thereof, wherein Y is optionally substituted 1, 3-phenylene, for example

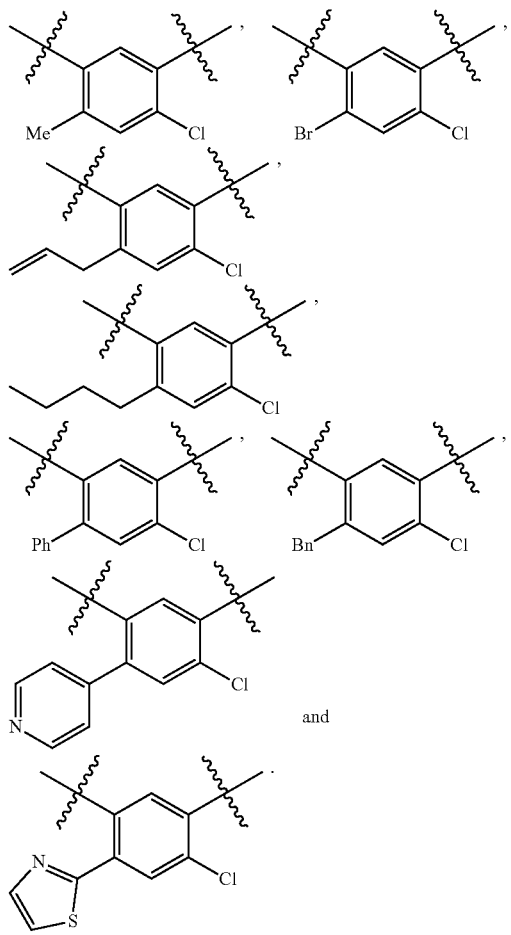

In certain embodiments, the present invention relates to compounds of Formula (I), and pharmaceutically acceptable salts thereof wherein Y is optionally substituted 2, 4-pyrrolylene, for example

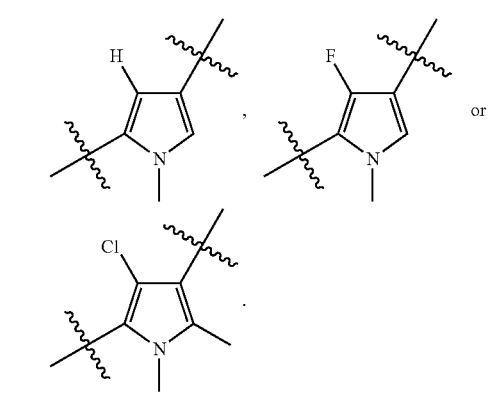

In certain embodiments, the present invention relates to compounds of Formula (I), and pharmaceutically acceptable salts thereof, wherein Y is optionally substituted monocyclic heteroaryl. In certain embodiments, the present invention relates to compounds of Formula (I) and pharmaceutically acceptable salts thereof, wherein Y is optionally substituted thiophenyl, optionally substituted thiazolyl, optionally substituted pyrrolyl, optionally substituted pyrazolyl, optionally substituted imidazolyl, optionally substituted pyridyl, or optionally substituted pyrimidinyl. In certain embodiments, the present invention relates to compounds of Formula (I) and pharmaceutically acceptable salts thereof, wherein Y is pyrrolyl optionally substituted with halogen, CN and optionally substituted —$C_1$-$C_3$ alkyl.

In certain embodiments, the present invention relates to compounds of Formula (I), and pharmaceutically acceptable salts thereof, wherein Y is optionally substituted bicyclic heteroaryl. In certain embodiments, the present invention relates to compounds of Formula (I), and pharmaceutically acceptable salts thereof, wherein Y is optionally substituted 5/6 bicyclic heteroaryl and is connected to A through either a carbon or nitrogen atom of the 5-membered ring of said 5/6 bicyclic heteroaryl. In certain embodiments, the present invention relates to compounds of Formula (I), and pharmaceutically acceptable salts thereof, wherein Y is optionally substituted benzimidazolyl, benzothiazolyl, benzoxazolyl, indazolyl, quinolyl, isoquinolyl or quinazolyl.

In certain embodiments, the present invention relates to compounds of Formula (I), and pharmaceutically acceptable salts thereof, wherein X and Y are each independently optionally substituted monocyclic heteroaryl.

In certain embodiments, the present invention relates to compounds of Formula (I), and pharmaceutically acceptable salts thereof, wherein X is optionally substituted phenyl and Y is optionally substituted monocyclic heteroaryl.

In certain embodiments, the present invention relates to compounds of Formula (I), and pharmaceutically acceptable salts thereof, wherein X is optionally substituted monocyclic heteroaryl and Y is optionally substituted phenyl.

In certain embodiments, the present invention relates to compounds of Formula (I), and pharmaceutically acceptable salts thereof, wherein X and Y are each independently phenyl or monocyclic heteroaryl, each optionally substituted with 1- to 3-substituents selected from the group consisting of halogen, CN, optionally substituted methyl, optionally substituted methoxy, and optionally substituted cyclopropyl.

In certain embodiments, the present invention relates to compounds of Formula (I), and pharmaceutically acceptable salts thereof, wherein X and Y are each independently selected from the group consisting of optionally substituted phenyl, optionally substituted thiophenyl, optionally substituted pyridyl, and optionally substituted pyrimidyl.

In certain embodiments, the present invention relates to compounds of Formula (I), and pharmaceutically acceptable salts thereof, wherein X and Y are each independently optionally substituted phenyl. In certain embodiments, the present invention relates to compounds of Formula (I), and pharmaceutically acceptable salts thereof, wherein X is optionally substituted phenyl and Y is optionally substituted pyrrolyl.

In certain embodiments, the present invention relates to compounds of Formula (I), and pharmaceutically acceptable salts thereof, wherein A is —NHC(O)—.

In certain embodiments, the present invention relates to compounds of Formula (I), and pharmaceutically acceptable salts thereof, wherein A is —NHC(O)—,

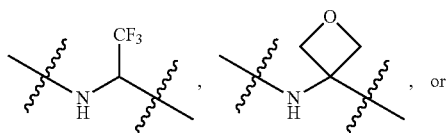

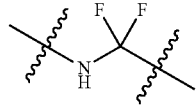

and the said nitrogen of —NHC(O)—,

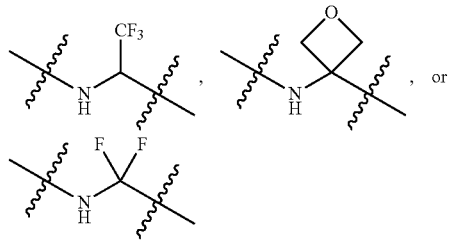

is connected to X.

In certain embodiments, the present invention relates to compounds of Formula (I), and pharmaceutically acceptable salts thereof, wherein A is —NHC(O)—,

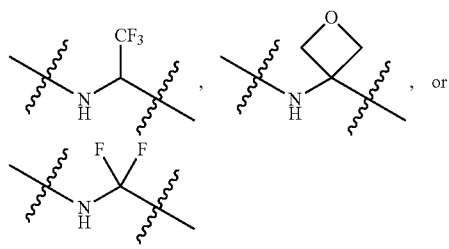

and the said nitrogen of —NHC(O)—,

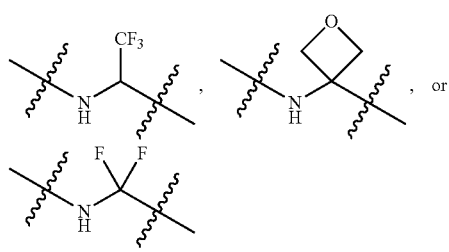

is connected to Y.

In certain embodiments, the present invention relates to compounds of Formula (I), and pharmaceutically acceptable salts thereof, wherein L is $S(O)_2$.

In certain embodiments, the present invention relates to compounds of Formula (I), and pharmaceutically acceptable salts thereof, wherein L is S(O).

In certain embodiments, the present invention relates to compounds of Formula (I), and pharmaceutically acceptable salts thereof, wherein L is S.

In certain embodiments, the present invention relates to compounds of Formula (I), and pharmaceutically acceptable salts thereof, wherein L is O.

In certain embodiments, the present invention relates to compounds of Formula (I), and pharmaceutically acceptable salts thereof, wherein R is optionally substituted —$C_1$-$C_{10}$ alkyl, optionally substituted —$C_2$-$C_{10}$ alkenyl, or optionally substituted —$C_2$-$C_{10}$ alkynyl.

In certain embodiments, the present invention relates to compounds of Formula (I), and pharmaceutically acceptable salts thereof, wherein R is optionally substituted aryl or optionally substituted heteroaryl.

In certain embodiments, the present invention relates to compounds of Formula (I), and pharmaceutically acceptable salts thereof, wherein R is optionally substituted —$C_3$-$C_{12}$ cycloalkyl or optionally substituted 3- to 12-membered heterocyclic.

In certain embodiments, the present invention relates to compounds of Formula (I), and pharmaceutically acceptable salts thereof, wherein R is optionally substituted $C_3$-$C_{12}$ cycloalkyl-$C_1$-$C_6$-alkyl-, optionally substituted $C_3$-$C_{12}$ cycloalkenyl-$C_1$-$C_6$-alkyl-, or optionally substituted 3- to 12-membered heterocyclic-$C_1$-$C_6$-alkyl-.

In certain embodiments, the present invention relates to compounds of Formula (I), and pharmaceutically acceptable salts thereof, wherein R is optionally substituted —$C_5$-$C_{12}$ cycloalkyl or optionally substituted 5- to 12-membered heterocyclic, each optionally substituted with one or more fused rings.

In certain embodiments, the present invention relates to compounds of Formula (I), and pharmaceutically acceptable salts thereof, wherein R is optionally substituted —$C_5$-$C_{12}$ cycloalkyl or optionally substituted 5- to 12-membered heterocyclic, each optionally substituted with one or more spiro rings.

In certain embodiments, the present invention relates to compounds of Formula (I), and pharmaceutically acceptable salts thereof, wherein R is optionally substituted —$C_5$-$C_{12}$ cycloalkyl or optionally substituted 5- to 12-membered, each optionally comprising a bridging moiety.

In certain embodiments, the present invention relates to compounds of Formula (I), and pharmaceutically acceptable salts thereof, wherein R is —$C(R_{10})_3$,

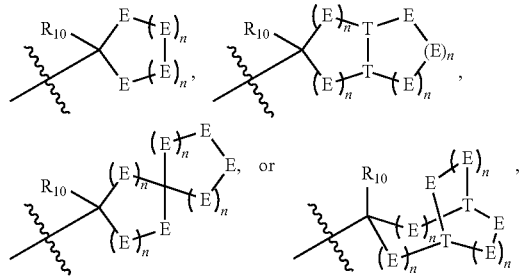

wherein n at each occurrence is independently selected from 0, 1, 2, or 3; T at each occurrence is independently selected from $C(R_{10})$ and N; E at each occurrence is independently selected from —$C(R_{10})_2$—, —$N(R_{10})$—, O, S, S(O), and $S(O)_2$; wherein $R_{10}$ at each occurrence is independently selected from the group consisting of hydrogen, halo, —CN, —$NO_2$, optionally substituted —$C_1$-$C_6$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl, optionally substituted heteroaryl, and -$L_1$-$R_1$; wherein $L_1$ is —O—, —S—, —$NR_1$—, —C(O)—, —C(O)O—, —OC(O)—, —C(O)N($R_1$)—, —N($R_1$)C(O)—, —OC(O)N($R_1$)—, —N($R_1$)C(O)O—, —N($R_1$)C(O)N($R_1$)—, —S(O)—, —$S(O)_2$—, —$S(O)_2$N($R_1$)—, —N($R_1$)$S(O)_2$—; $R_1$ at each occurrence is independently selected from the group consisting of hydrogen, optionally substituted —$C_1$-$C_6$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted aryl, and optionally substituted heteroaryl.

In certain embodiments, each $R_{10}$ is independently selected from hydrogen, halo, hydroxy, protected hydroxy, —CN, —$NO_2$, amino, protected amino, optionally substituted —$C_1$-$C_6$ alkyl, optionally substituted —$C_1$-$C_6$ alkoxy, optionally substituted aryl, optionally substituted heteroaryl and —O-(hydroxy prodrug group). In certain embodiments, the hydroxy prodrug group is phosphate or sulfamate. In certain embodiments, the said hydroxy prodrug group is an acyl group derived from an amino acid, preferably an α-amino acid.

In certain embodiments, each $R_{10}$ is independently —$C_1$-$C_6$ alkyl optionally substituted with one or more substitutents selected from the group consisting of halo, hydroxy, protected hydroxy, amino, protected amino, and optionally substituted heteroaryl.

In certain embodiments, two adjacent $R_{10}$ groups are taken together with the carbon or nitrogen atoms to which they are attached to form an olefinic or iminic double-bond or a fused ring. In certain embodiments, two geminal $R_{10}$ groups together form an oxo, an optionally substituted olefin, an optionally substituted oxime, or a spiro ring. In certain embodiments, two remote $R_{10}$ groups are taken together with the atoms to which they are attached and any intervening atoms to form a bridging moiety.

In certain embodiments, the present invention relates to compounds of Formula (I), and pharmaceutically acceptable salts thereof, wherein R is optionally substituted —$(CH_2)_{0-4}$—$C(R_{10})_3$,

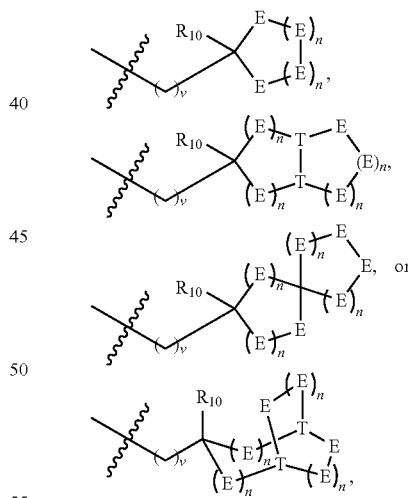

wherein n, E, T and $R_{10}$ are previously defined; v is selected from 1, 2, 3 or 4. In certain embodiments, each $R_{10}$ is independently selected from hydrogen, halo, hydroxy, protected hydroxy, —CN, —$NO_2$, amino, protected amino, optionally substituted —$C_1$-$C_6$ alkyl, optionally substituted —$C_1$-$C_6$ alkoxy, optionally substituted aryl, optionally substituted heteroaryl and —O— (hydroxy prodrug group). In certain embodiments, the hydroxy prodrug group is phosphate or sulfamate. In certain embodiments, the said hydroxy prodrug group is an acyl group derived from an amino acid, preferably an α-amino acid. In certain embodiments, each $R_{10}$ is independently —$C_1$-$C_6$ alkyl optionally substituted with one or more substitutents selected from the group consisting of halo, hydroxy, protected hydroxy, amino, protected amino, and optionally substituted heteroaryl. In certain embodiments, two adjacent $R_{10}$ groups are taken together with the carbon or nitrogen atoms to which they are attached to form an olefinic double-bond, an iminic double bond or a fused carbocyclic or heterocyclic ring. In certain embodiments, two geminal $R_{10}$ groups together form an oxo, an optionally substituted olefin, an optionally substituted oxime, or a spiro ring. In certain embodiments, two remote $R_{10}$ groups are taken together with the atoms to which they are connected and any intervening atoms to form a bridging moiety.

In certain embodiments, R is selected from the groups below, and is optionally substituted:

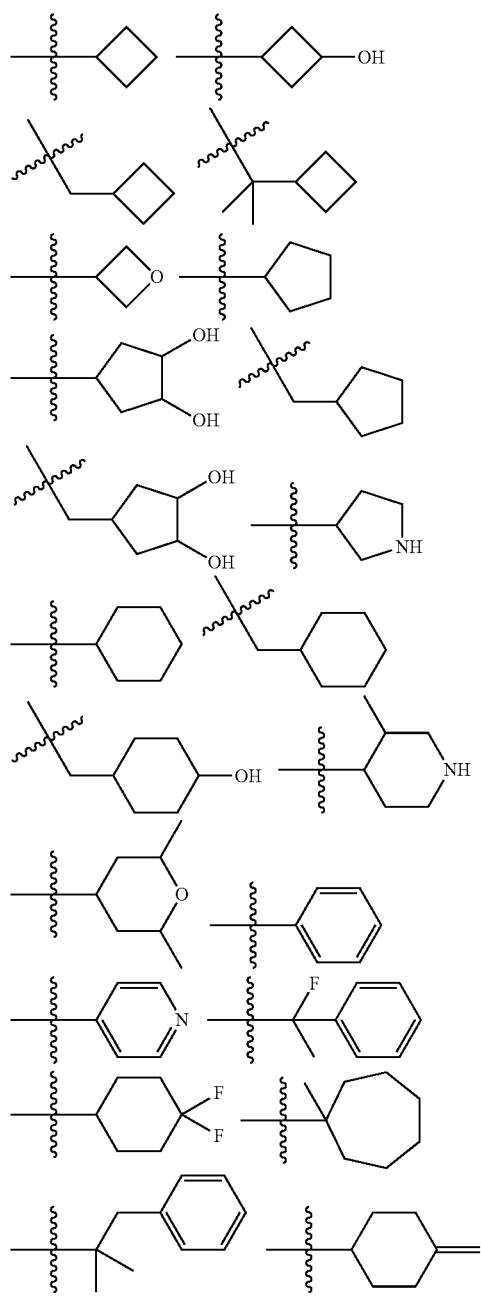

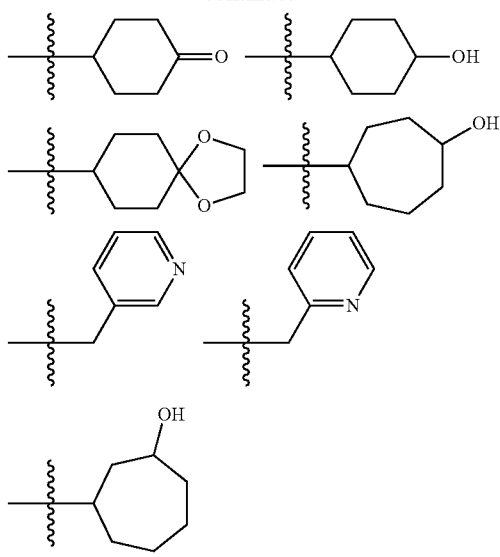

In certain embodiments, R is selected from the groups set forth below, and is optionally substituted:

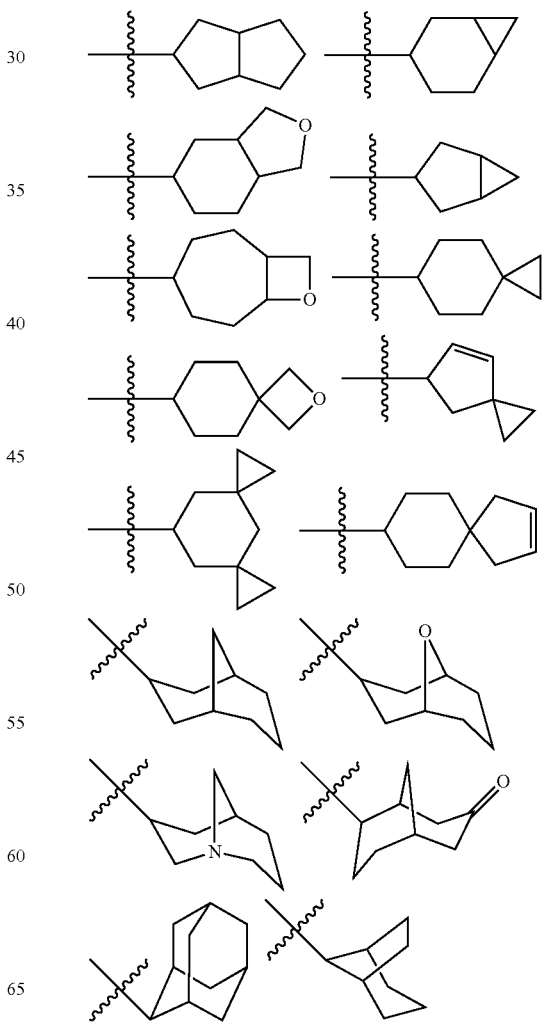

-continued

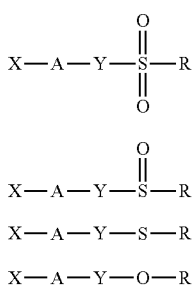

wherein X, A, Y, and R are as previously defined.

In another embodiment, the compound of Formula (I) is represented by Formula (Ia), (Tb), (Ic), or (Id) or a pharmaceutically acceptable salt thereof:

In another embodiment, the compound of Formula (I) is represented by Formula (IIa), (IIb), (IIc), (IId), (IIe), (IIf), (IIg), or (IIh), or a pharmaceutically acceptable salt thereof:

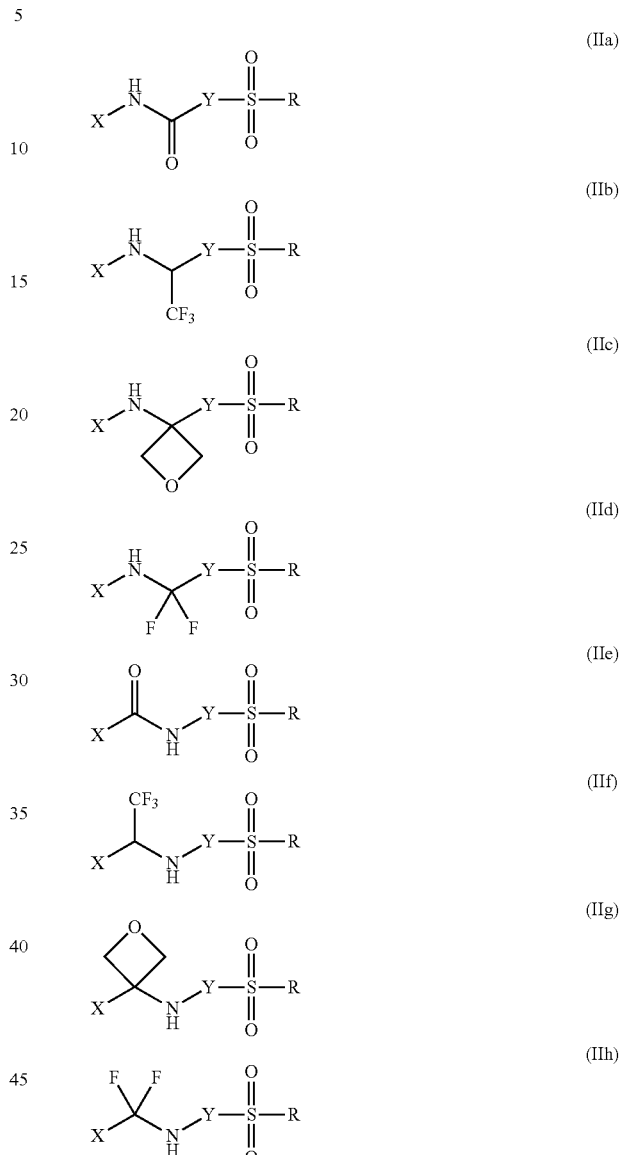

wherein X, Y, and R are as previously defined.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, wherein X and Y are each independently optionally substituted phenyl or optionally substituted monocyclic heteroaryl.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, X and Y are each independently optionally substituted phenyl.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, wherein X is optionally substituted phenyl and Y is optionally substituted 5-membered heteroaryl.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, wherein X is optionally substituted 5-membered heteroaryl and Y is optionally substituted phenyl.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, wherein X is optionally substituted phenyl and Y is optionally substituted pyrrolyl.

In certain embodiments, the present invention relates to compounds of Formula (I) represented by Formula (IIa), (IIb), (IIc), (IId), (IIe), (IIf), (IIg), or (IIh), or pharmaceutically acceptable salts thereof, wherein X and Y are each independently optionally substituted phenyl, optionally substituted naphthyl, optionally substituted pyridyl, optionally substituted pyrimidinyl, optionally substituted thiophenyl, optionally substituted pyrrolyl, optionally substituted thiazolyl, optionally substituted thiadiazolyl, optionally substituted oxazolyl, optionally substituted isoxazolyl, optionally substituted oxadiazolyl, optionally substituted imidiazolyl, optionally substituted pyrazolyl, optionally substituted triazolyl, or optionally substituted quinolinyl.

In another embodiment, the compound of Formula (I) is represented by Formula (IIIa), (IIIb), (IIIc), or (IIId), or a pharmaceutically acceptable salt thereof:

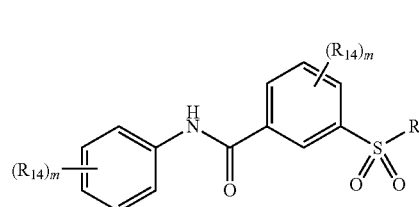

(IIIa)

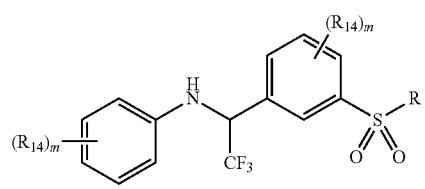

(IIIb)

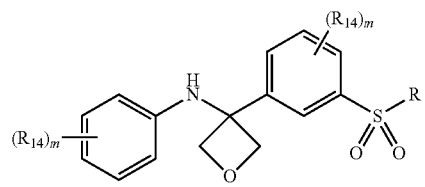

(IIIc)

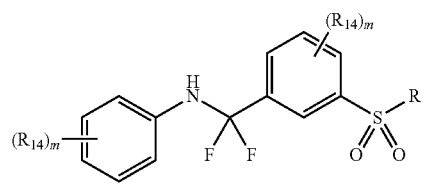

(IIId)

wherein m at each occurrence is independently 0, 1, 2, 3 or 4; $R_{14}$ at each occurrence is independently selected from the group consisting of hydroxy, protected hydroxy, halogen, —CN, —NO$_2$, optionally substituted amino, N$_3$, optionally substituted aryl, optionally substituted heteroaryl, optionally substituted —C$_1$-C$_6$ alkyl, optionally substituted —C$_2$-C$_8$ alkenyl, optionally substituted —C$_2$-C$_8$ alkynyl, optionally substituted —C$_3$-C$_8$ cycloalkyl, optionally substituted 3- to 8-membered heterocyclic, optionally substituted —C$_1$-C$_6$ alkoxy, —C(O)$_2$—C$_1$-C$_6$ alkyl, —C(O)NH—C$_1$-C$_6$ alkyl, and —C(O)—C$_1$-C$_6$ alkyl; and R is as previously defined.

In another embodiment, the compound of Formula (I) is represented by Formula (IIIa-1), (IIIb-1), (IIIc-1), or (IIId-1), or a pharmaceutically acceptable salt thereof:

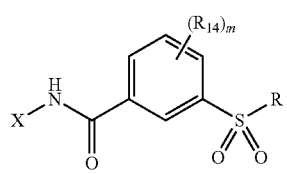

(IIIa-1)

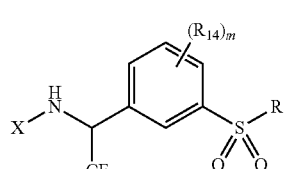

(IIIb-1)

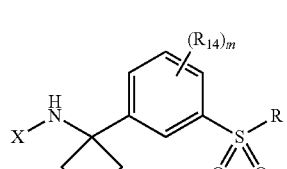

(IIIc-1)

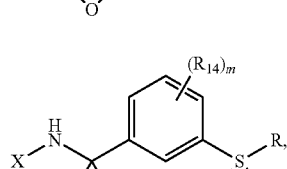

(IIId-1)

wherein X, R, $R_{14}$, and m are as previously defined.

In another embodiment, the compound of Formula (I) is represented by Formula (IIIa-2), (IIIb-2), (IIIc-2), or (IIId-2), or a pharmaceutically acceptable salt thereof:

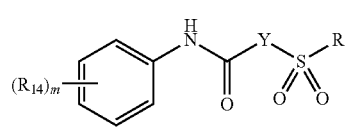

(IIIa-2)

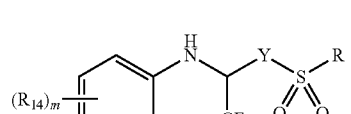

(IIIb-2)

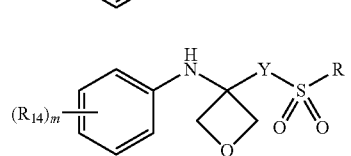

(IIIc-2)

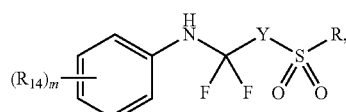
(IIId-2)

wherein Y, R, $R_{14}$, and m are as previously defined.

In another embodiment, the compound of Formula (I) is represented by Formula (IVa), (IVb), (IVc), (IVd), or (IVe) or a pharmaceutically acceptable salt thereof:

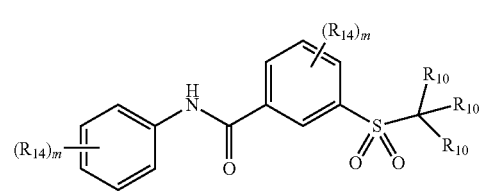
(IVa)

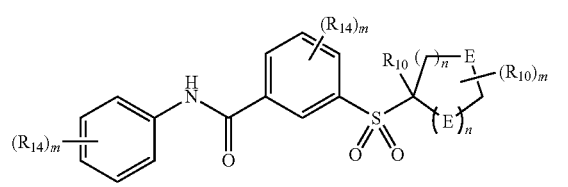
(IVb)

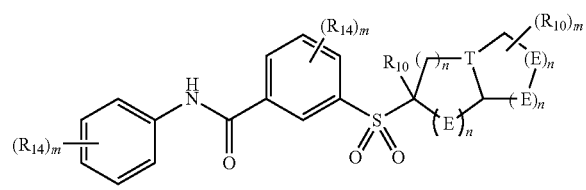
(IVc)

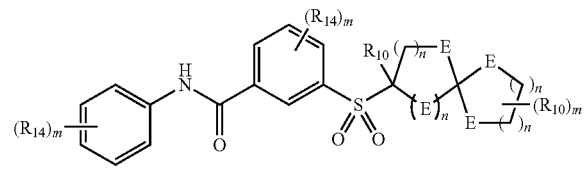
(IVd)

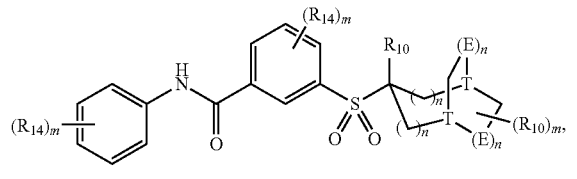
(IVe)

wherein E, T, m, n, $R_{10}$, and $R_{14}$ are as previously defined.

In another embodiment, the compound of Formula (I) is represented by Formula (Va), (Vb), (Vc), (Vd), or (Ve), or a pharmaceutically acceptable salt thereof:

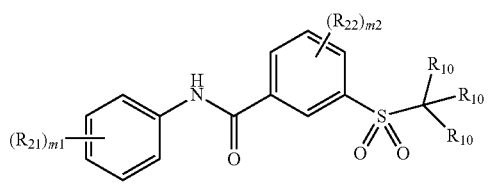
(Va)

(Vb)

(Vc)

(Vd)

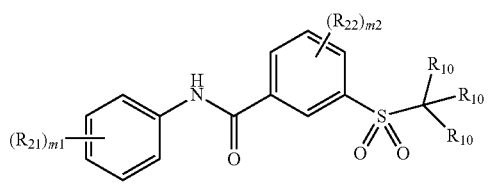
(Ve)

wherein m1 at each occurrence is independently 1, 2, or 3; m2 at each occurrence is independently 0, 1, or 2; m3 at each occurrence is independently 0, 1, 2, or 3; $R_{21}$ at each occurrence is independently selected from the group consisting of halogen, CN, optionally substituted —$C_1$-$C_6$ alkyl, optionally substituted —$C_1$-$C_6$ alkoxy, and optionally substituted $C_3$-$C_8$ cycloalkyl; $R_{22}$ at each occurrence is independently selected from the group consisting of halogen, CN, optionally substituted —$C_1$-$C_6$ alkyl, optionally substituted —$C_1$-$C_6$ alkoxy, optionally substituted aryl, and optionally substituted heteroaryl; E, n, and $R_{10}$ are as previously defined.

In another embodiment, the compound of Formula (I) is represented by Formula (Vf), (Vg), (Vh), or (Vj), or a pharmaceutically acceptable salt thereof:

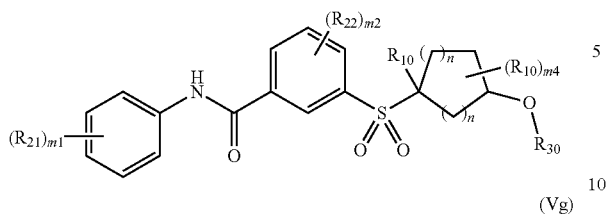
(Vf)

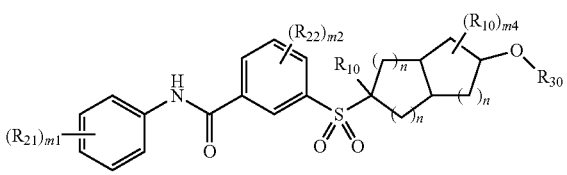
(Vg)

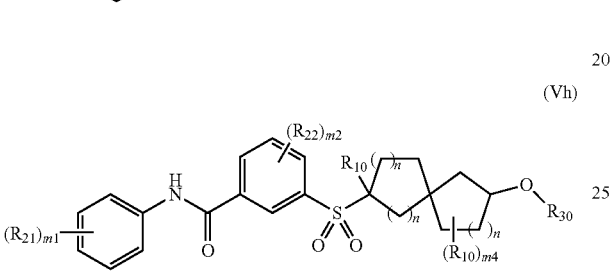
(Vh)

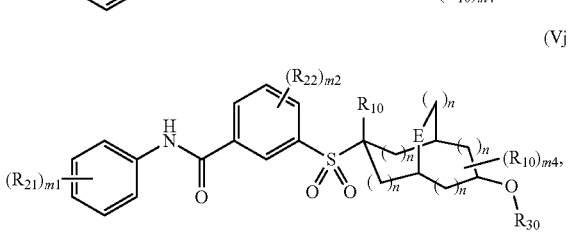
(Vj)

wherein m4 at each occurrence is independently 0, 1, or 2; $R_{30}$ is hydrogen, optionally substituted —$C_1$-$C_6$ alkyl, a hydroxy protecting group or a hydroxy prodrug group; m1, m2, n, E, $R_{10}$, $R_{21}$, and $R_{22}$ are as previously defined. In certain embodiments, $R_{30}$ is phosphate or sulfamate. In certain embodiments, $R_{30}$ is an acyl group derived from an amino acid, preferably an α-amino acid.

In another embodiment, the compound of Formula (I) is represented by Formula (VIa), (VIb), (VIc), (VId), (VIe), or (VIf), or a pharmaceutically acceptable salt thereof:

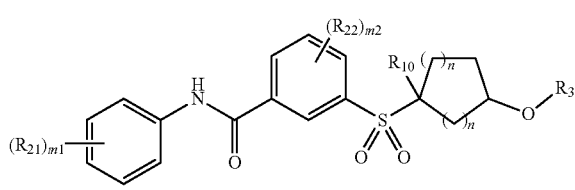
(VIa)

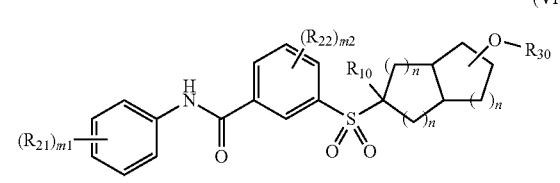
(VIb)

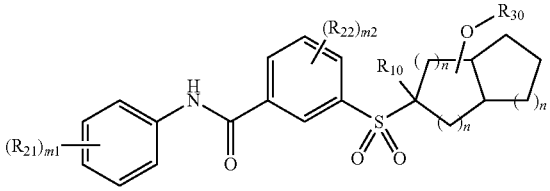
(VIc)

(VId)

(VIe)

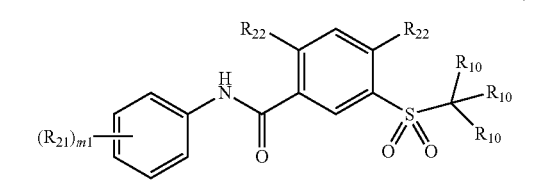
(VIf)

wherein m1 at each occurrence is independently 1, 2, or 3; m2 at each occurrence is independently 1, or 2; n, $R_{21}$, $R_{22}$, and $R_{30}$ are as previously defined. In certain embodiments, $R_{30}$ is phosphate or sulfamate. In certain embodiments, $R_{30}$ is an acyl group derived from an amino acid, preferably an α-amino acid.

In another embodiment, the compound of Formula (I) is represented by Formula (VIa), (VIb), (VIc), (VId), (VIe), or (VIf), or a pharmaceutically acceptable salt thereof, wherein m1 at each occurrence is independently 2 or 3; m2 at each occurrence is 1; n at each occurrence is independently 0, 1, or 2; $R_{21}$ is halogen, CN, optionally substituted methyl, optionally substituted methoxy, and optionally substituted cyclopropyl; $R_{22}$ is halogen, CN, optionally substituted methyl, and optionally substituted methoxy; $R_{30}$ is acyl group derived from an amino acid. In certain embodiments, $R_{30}$ is acyl group derived from an α-amino acid having an aliphatic side-chain. In certain embodiments, $R_{30}$ is acyl group derived from alaline or valine.

In another embodiment, the compound of Formula (I) is represented by Formula (VIIa), (VIIb), (VIIc), (VIId), or (VIIe), or a pharmaceutically acceptable salt thereof:

(VIIa)

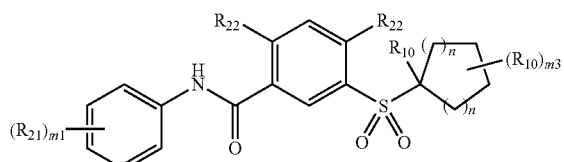
(VIIb)

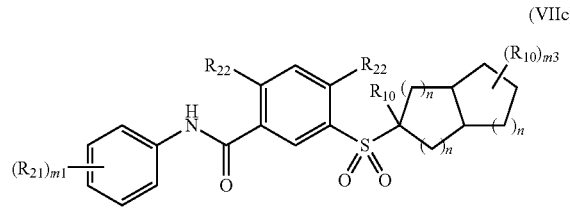
(VIIc)

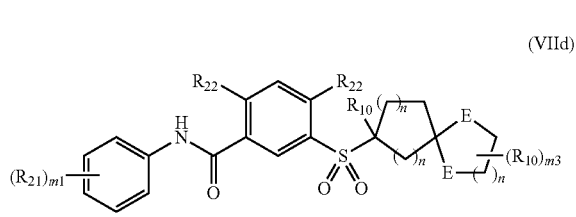
(VIId)

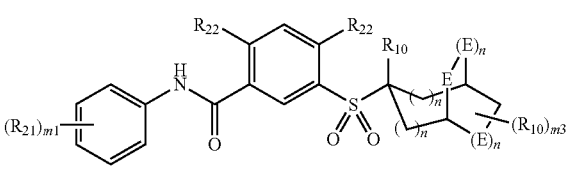
(VIIe)

wherein m1, m3, n, E, $R_{10}$, $R_{21}$, and $R_{22}$ are as previously defined.

In another embodiment, the compound of Formula (I) is represented by Formula (VIIa-1), (VIIb-1), (VIIc-1), (VIId-1), or (VIIe-1), or a pharmaceutically acceptable salt thereof:

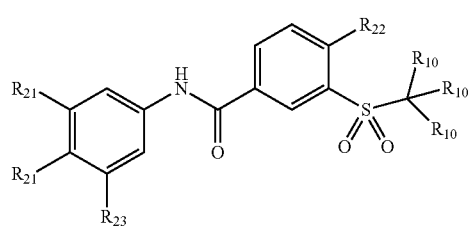
(VIIa-1)

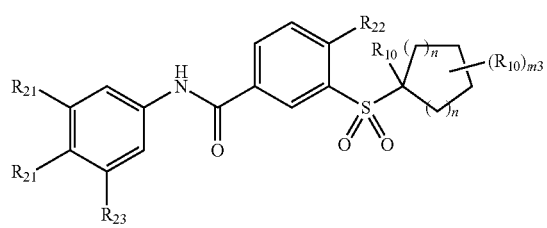
(VIIb-1)

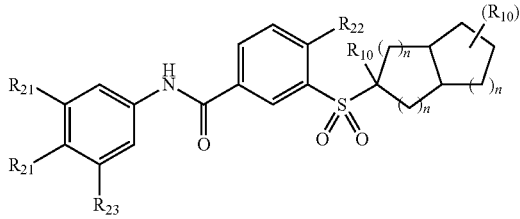
(VIIc-1)

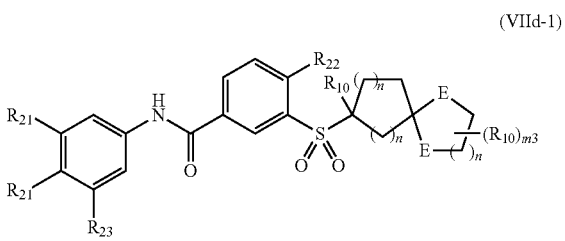
(VIId-1)

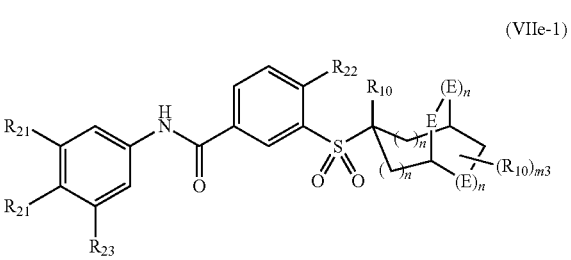
(VIIe-1)

wherein $R_{23}$ at each occurrence is independently selected from the group consisting of hydrogen, halogen, CN, optionally substituted —$C_1$-$C_6$ alkyl, optionally substituted —$C_1$-$C_6$ alkoxy, and optionally substituted $C_3$-$C_8$ cycloalkyl; m3, n, E, $R_{10}$, $R_{21}$, and $R_{22}$ are as previously defined.

In another embodiment, the compound of Formula (I) is represented by Formula (VIIa-2), (VIIb-2), (VIIc-2), or (VIId-2), or a pharmaceutically acceptable salt thereof:

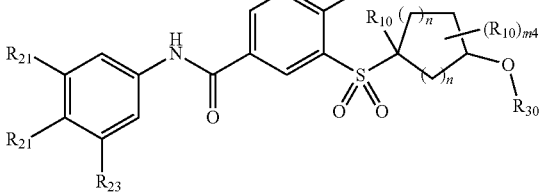
(VIIa-2)

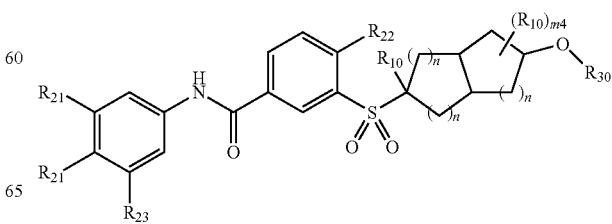
(VIIb-2)

(VIIc-2)

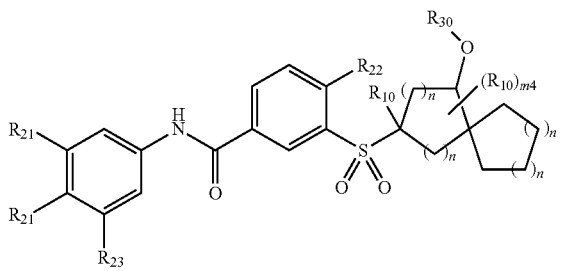

(VIId-2)

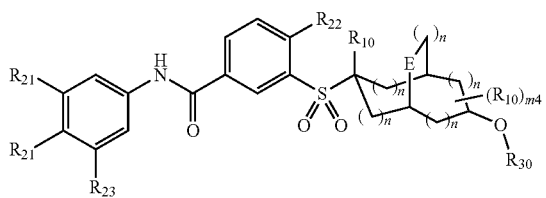

wherein m4, n, E, $R_{10}$, $R_{21}$, $R_{22}$, $R_{23}$, and $R_{30}$ are as previously defined. In certain embodiments, $R_{30}$ is hydrogen. In certain embodiments, $R_{30}$ is acyl group derived from an amino acid, preferably an α-amino acid.

In another embodiment, the compound of Formula (I) is represented by Formula (VIIa-2), (VIIb-2), (VIIc-2), or (VIId-2), or a pharmaceutically acceptable salt thereof, wherein n at each occurrence is independently 0, 1, or 2; $R_{21}$ at each occurrence is independently halogen, CN, optionally substituted methyl, optionally substituted methoxy, or optionally substituted cyclopropyl; $R_{22}$ is halogen, CN, optionally substituted methyl, or optionally substituted methoxy; $R_{23}$ is hydrogen or halogen; $R_{10}$ is hydrogen, halogen, hydroxyl, or optionally substituted $C_1$-$C_6$ alkyl; $R_{30}$ is hydrogen or acyl group derived from an amino acid. In certain embodiments, $R_{21}$ at each occurrence is fluorine. In certain embodiments, $R_{22}$ is fluorine or chlorine. In certain embodiments, $R_{10}$ is hydrogen, halogen, hydroxyl, $C_1$-$C_6$ alkyl optionally substituted with one or more groups selected from halogen, hydroxy and optionally substituted $C_1$-$C_6$ alkoxy. In certain embodiments, $R_{23}$ is hydrogen or fluorine. In certain embodiments, $R_{30}$ is an acyl group derived from alanine or valine.

In another embodiment, the compound of Formula (I) is represented by Formula (VIIIa), (VIIIb), (VIIIc), or (VIIId), or a pharmaceutically acceptable salt thereof:

(VIIIa)

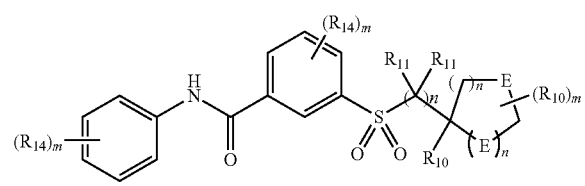

(VIIIb)

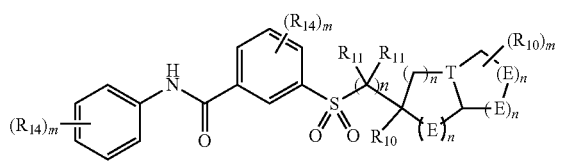

(VIIIc)

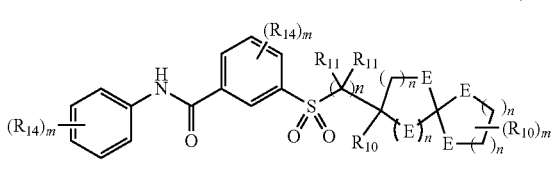

(VIIId)

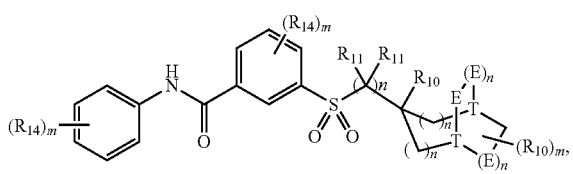

wherein $R_1$ at each occurrence is independently selected from the group consisting of hydrogen, halogen, hydroxy, protected hydroxy, —CN, amino, protected amino, optionally substituted aryl, optionally substituted heteroaryl, optionally substituted —$C_1$-$C_6$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted —$C_1$-$C_6$ alkoxy, optionally substituted —NH—$C_1$-$C_6$ alkyl, optionally substituted —N($C_1$-$C_6$ alkyl)$_2$, —$CO_2$H, optionally substituted —C(O)$_2$—$C_1$-$C_6$ alkyl, optionally substituted —C(O)NH—$C_1$-$C_6$ alkyl, and optionally substituted —C(O)—$C_1$-$C_6$ alkyl; m, n, E, T, $R_{10}$ and $R_{14}$ are as previously defined. In certain embodiments, the preferred $R_{11}$ groups include hydrogen, halogen, hydroxy, protected hydroxy, protected amino, optionally substituted aryl, optionally substituted heteroaryl, —$CO_2$H, optionally substituted —$C_1$-$C_6$ alkyl, optionally substituted NHC(O)$_2$—$C_1$-$C_6$ alkyl, and optionally substituted —$C_1$-$C_6$ alkoxy. In certain embodiments, $R_1$ is optionally substituted —$C_1$-$C_6$ alkyl, optionally substituted aryl, optionally substituted heteroaryl, and optionally substituted —$C_1$-$C_6$ alkoxy.

In another embodiment, the compound of Formula (I) is represented by Formula (VIIIa-1), (VIIIb-1), (VIIIc-1), or (VIIId-1), or a pharmaceutically acceptable salt thereof:

(VIIIa-1)

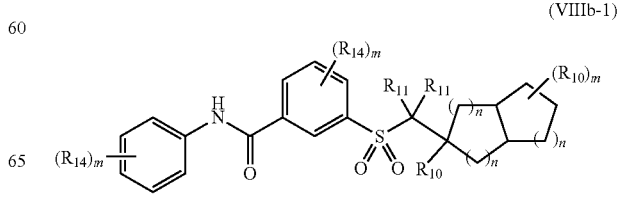

(VIIIb-1)

-continued

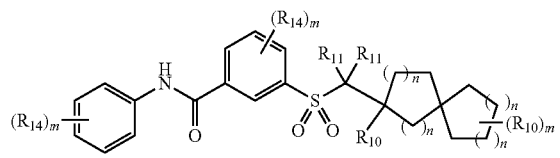

(VIIIc-1)

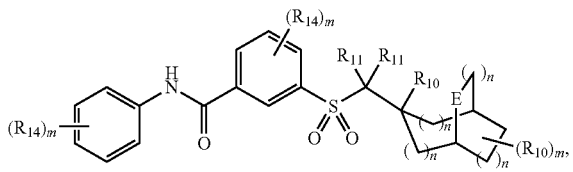

(VIIId-1)

wherein m, n, E, $R_{10}$, $R_{11}$, and $R_{14}$ are as previously defined.

In another embodiment, the compound of Formula (I) is represented by Formula (IXa), (IXb), (IXc), or (IXd), or a pharmaceutically acceptable salt thereof:

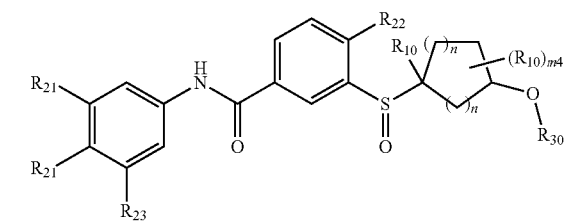

(IXa)

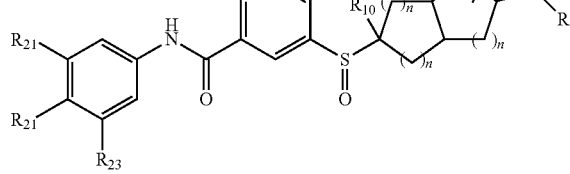

(IXb)

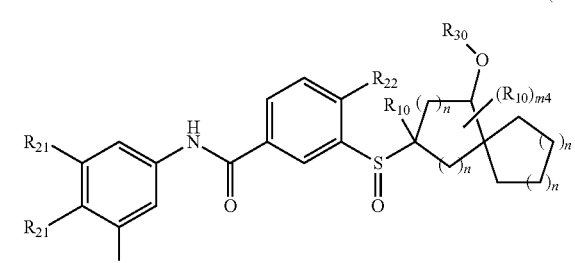

(IXc)

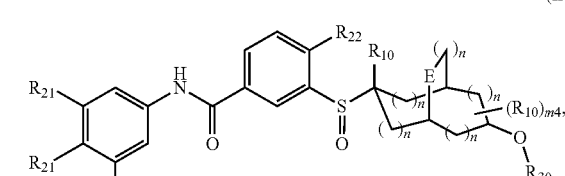

(IXd)

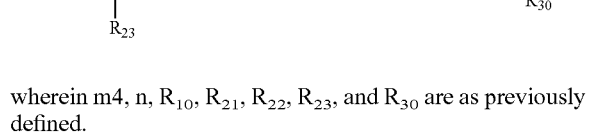

wherein m4, n, $R_{10}$, $R_{21}$, $R_{22}$, $R_{23}$, and $R_{30}$ are as previously defined.

In another embodiment, the compound of Formula (I) is represented by Formula (Xa), (Xb), (Xc), or (Xd), or a pharmaceutically acceptable salt thereof:

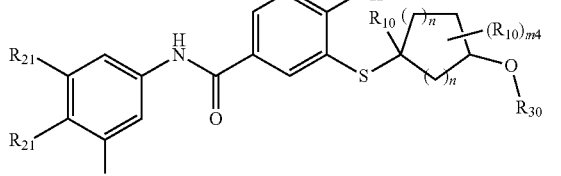

(Xa)

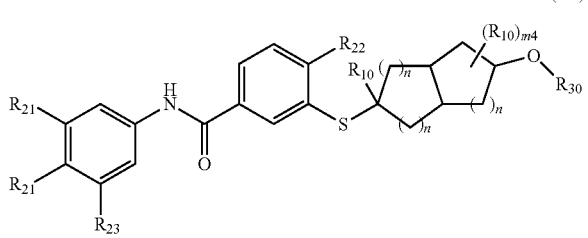

(Xb)

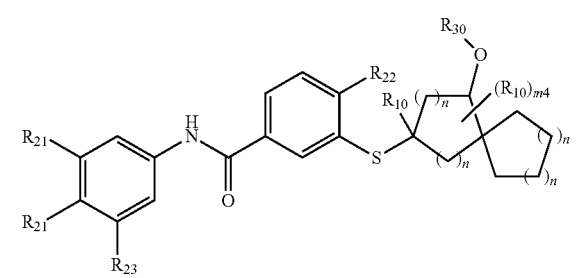

(Xc)

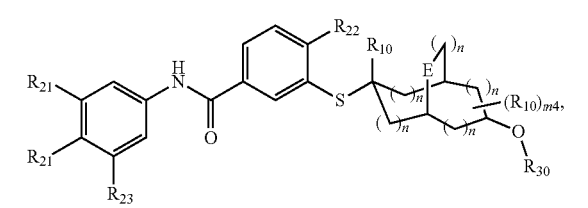

(Xd)

wherein m4, n, $R_{10}$, $R_{21}$, $R_{22}$, $R_{23}$, and $R_{30}$ are as previously defined.

In another embodiment, the compound of Formula (I) is represented by Formula (XIa), (XIb), (XIc), or (XId), or a pharmaceutically acceptable salt thereof:

(XIa)

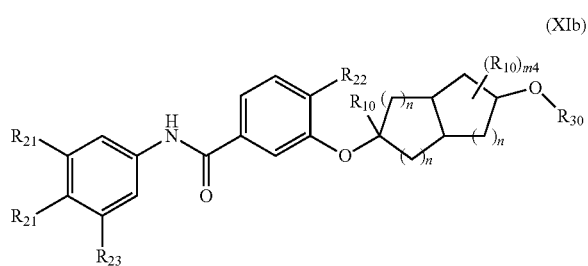
(XIb)

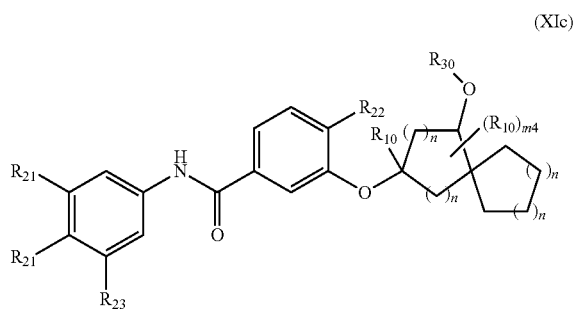
(XIc)

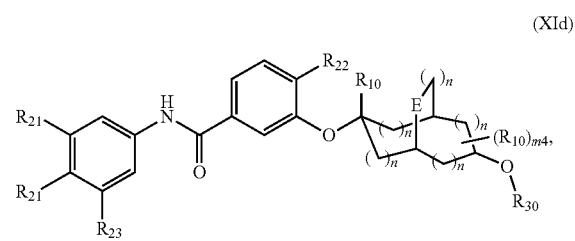
(XId)

wherein m4, n, $R_{10}$ $R_{21}$, $R_{22}$, $R_{23}$, and $R_{30}$ are as previously defined.

In another embodiment, the compound of Formula (I) is represented by Formula (XIIa), (XIIb), (XIIc), or (XIId), or a pharmaceutically acceptable salt thereof:

(XIIa)

(XIIb)

(XIIc)

(XIId)

wherein $R_{31}$ at each occurrence is independently selected from the group consisting of hydrogen, optionally substituted aryl, optionally substituted heteroaryl, optionally substituted —$C_1$-$C_6$ alkyl, optionally substituted —$C_2$-$C_8$ alkenyl, optionally substituted —$C_2$-$C_8$ alkynyl, optionally substituted —$C_3$-$C_8$ cycloalkyl, and optionally substituted 3- to 8-membered heterocyclic; m1, m2, m4, n, $R_{10}$, $R_{11}$, $R_{21}$, $R_{22}$, and $R_{30}$ are as previously defined. In certain embodiments, $R_{31}$ is —$C_1$-$C_6$ alkyl optionally substituted with one or more groups selected from halogen, hydroxy, optionally substituted $C_1$-$C_6$ alkoxy, amino, optionally substituted —NH—$C_1$-$C_6$ alkyl, optionally substituted —N($C_1$-$C_6$ alkyl)$_2$, optionally substituted —$CO_2$—$C_1$-$C_6$ alkyl, optionally substituted —C(O)NH—$C_1$-$C_6$ alkyl, optionally substituted —NHC(O)—$C_1$-$C_6$ alkyl, optionally substituted —C(O)—$C_1$-$C_6$ alkyl, and optionally substituted —NHS(O)$_2$—$C_1$-$C_6$ alkyl.

In another embodiment, the compound of Formula (I) is represented by Formula (XIIIa), (XIIIb), (XIIIc), or (XIIId), or a pharmaceutically acceptable salt thereof:

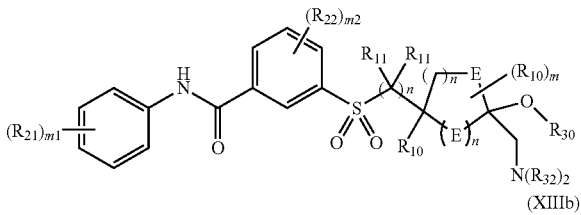
(XIIIa)

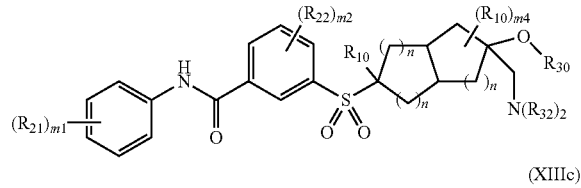
(XIIIb)

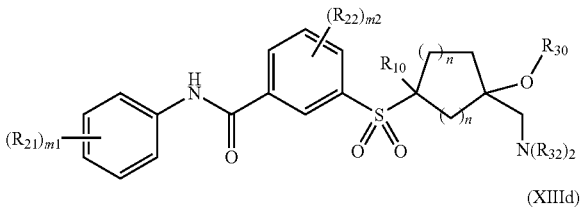
(XIIIc)

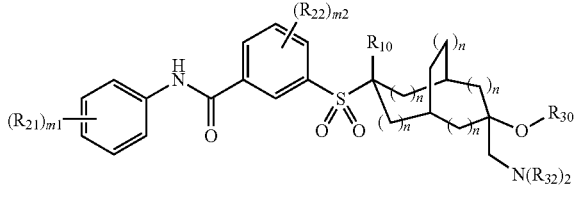
(XIIId)

wherein $R_{32}$ at each occurrence is independently selected from the group consisting of hydrogen, optionally substituted $C_1$-$C_6$ alkyl, optionally substituted —C(O)—$C_1$-$C_6$ alkyl, optionally substituted —C(O)—$C_2$-$C_8$ alkenyl, optionally substituted —C(O)—$C_2$-$C_8$ alkynyl, optionally substituted —C(O)—$C_3$-$C_8$ cycloalkyl, optionally substituted —C(O)-aryl, optionally substituted —C(O)—(3- to 8-membered heterocyclic), optionally substituted —C(O)—$C_1$-$C_6$ alkyl, optionally substituted —CO$_2$—$C_1$-$C_6$ alkyl, optionally substituted S(O)$_2$—$C_1$-$C_6$ alkyl, optionally substituted S(O)$_2$—$C_2$-$C_6$ alkenyl; preferably when one $R_{32}$ is optionally substituted —C(O)—$C_1$-$C_6$ alkyl, optionally substituted —C(O)—$C_2$-$C_8$ alkenyl, optionally substituted —C(O)—$C_2$-$C_8$ alkynyl, optionally substituted —C(O)—$C_3$-$C_8$ cycloalkyl, optionally substituted —C(O)-aryl, optionally substituted —C(O)—(3- to 8-membered heterocyclic), optionally substituted —C(O)—$C_1$-$C_6$ alkyl, optionally substituted —CO$_2$—$C_1$-$C_6$ alkyl, optionally substituted S(O)$_2$—$C_1$-$C_6$ alkyl, optionally substituted S(O)$_2$—$C_2$-$C_6$ alkenyl, the other $R_{32}$ is hydrogen or optionally substituted $C_1$-$C_6$ alkyl; m1, m2, m4, n, $R_{10}$, $R_{11}$, $R_{21}$, $R_{22}$, and $R_{30}$ are as previously defined. In certain embodiment, two $R_{32}$ groups are taken together with the nitrogen atom to which they are attached to form a 3- to 8-membered heterocyclic ring.

In another embodiment, the compound of Formula (I) is represented by Formula (XIVa), (XIVb), (XIVc), or (XIVd), or a pharmaceutically acceptable salt thereof:

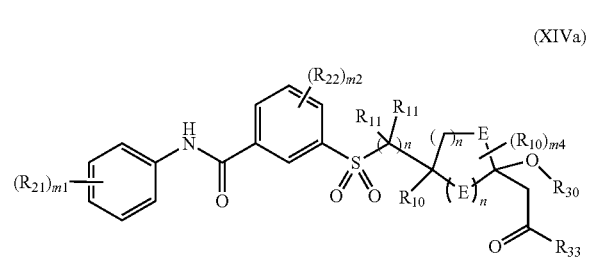
(XIVa)

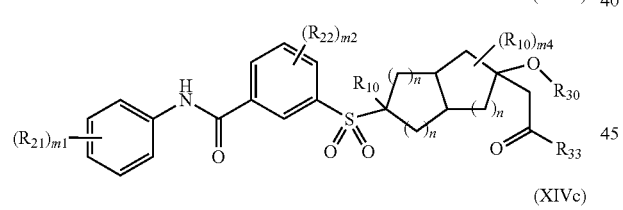
(XIVb)

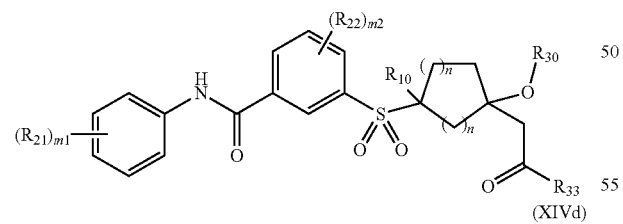
(XIVc)

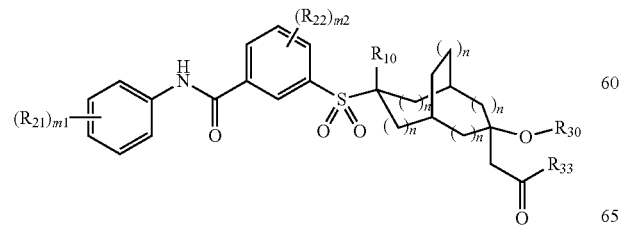
(XIVd)

wherein $R_{33}$ at each occurrence is independently selected from the group consisting of hydrogen, optionally substituted $C_1$-$C_6$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocyclic, optionally substituted —$C_1$-$C_6$ alkoxy, optionally substituted —NH—$C_1$-$C_6$ alkyl, optionally substituted —N($C_1$-$C_6$ alkyl)$_2$, optionally substituted —NH—$C_1$-$C_6$ alkenyl, optionally substituted —NH-(3- to 8-membered heterocyclic); m1, m2, m4, n, $R_{10}$, $R_{11}$, $R_{21}$, $R_{22}$, and $R_{30}$ are as previously defined.

In another embodiment, the compound of Formula (I) is represented by Formula (XVa), (XVb), (XVc), or (XVd), or a pharmaceutically acceptable salt thereof:

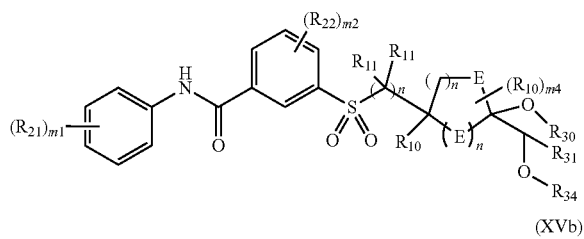
(XVa)

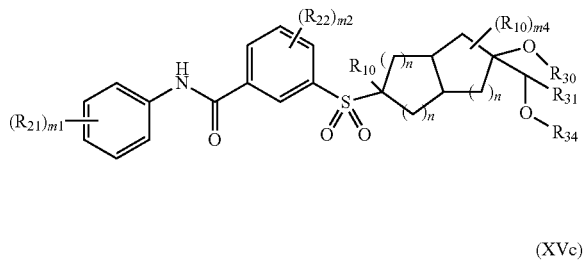
(XVb)

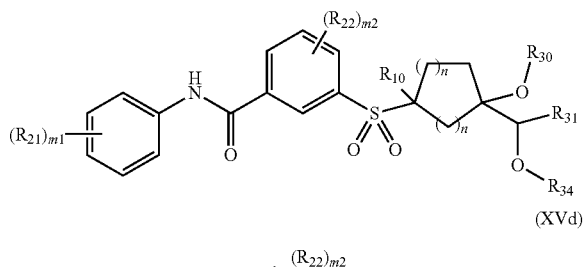
(XVc)

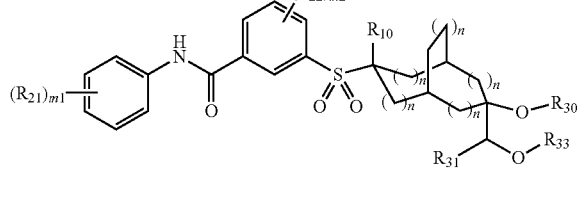
(XVd)

wherein $R_{34}$ at each occurrence is independently selected from the group consisting of hydrogen, optionally substituted $C_1$-$C_6$ alkyl, optionally substituted —$C_2$-$C_8$ alkenyl, optionally substituted —$C_2$-$C_8$ alkynyl, optionally substituted —$C_3$-$C_8$ cycloalkyl, and optionally substituted 3- to 8-membered heterocyclic; m1, m2, m4, n, $R_{10}$, $R_{11}$, $R_{21}$, $R_{22}$, $R_{30}$ and $R_{31}$ are as previously defined.

In another embodiment, the compound of Formula (I) is represented by Formula (XVI), or a pharmaceutically acceptable salt thereof:

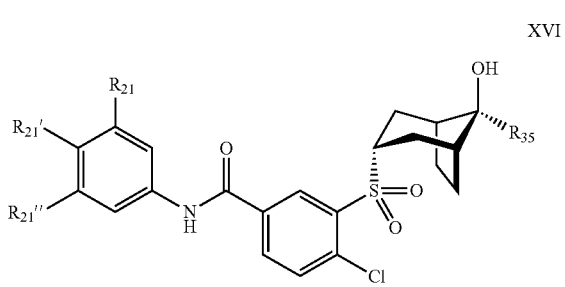

wherein $R_{21}$, $R_{21'}$ and $R_{21''}$ are independently selected from hydrogen, fluorine, methyl, difluoromethyl, and trifluoromethyl; and $R_{35}$ is —[CH($R_{36}$)]$_p$—C($R_{37}$)($R_{38}$)OH or —CH$_2$—O—CH$_2$—[CH($R_{36}$)]$_p$C($R_{37}$)($R_{38}$)OH, wherein p is 0 or 1; $R_{36}$ is hydrogen, methyl or hydroxyl; and $R_{37}$ and $R_{38}$ are independently hydrogen or methyl. Preferably, at least two of $R_{21}$, $R_{21'}$ and $R_{21''}$ are not hydrogen. More preferably, (i) none of $R_{21}$, $R_{21'}$ and $R_{21''}$ is hydrogen; or (ii) $R_{21}$ is hydrogen and $R_{21'}$ and $R_{21''}$ are not hydrogen. In preferred embodiments, at least two of $R_{21}$, $R_{21'}$ and $R_{21''}$ are fluorine. In other embodiments, each of $R_{21}$, $R_{21'}$ and $R_{21''}$ is fluorine.

In another embodiment, the compound of Formula (I) is represented by Formula (XVII), or a pharmaceutically acceptable salt thereof:

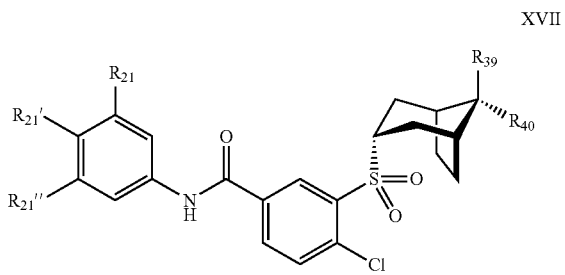

wherein $R_{21}$, $R_{21'}$ and $R_{21''}$ are independently selected from hydrogen, fluorine, methyl, difluoromethyl, and trifluoromethyl; $R_{39}$ is hydrogen or hydroxyl; and $R_{40}$ is —[C($R_{41}$)($R_{42}$)]$_q$—$R_{43}$, wherein q is 0, 1 or 2; $R_{41}$ and $R_{42}$ are each independently hydrogen, methyl, or hydroxyl; or alternatively, $R_{41}$ and $R_{42}$ can be taken together to form an oxo; and $R_{43}$ is hydrogen, hydroxyl, optionally substituted $C_1$-$C_6$ alkyl, optionally substituted $C_3$-$C_6$ cycloalkyl, optionally substituted 3- to 12-membered heterocyclic, optionally substituted aryl or optionally substituted heteroaryl. Preferably, at least two of $R_{21}$, $R_{21'}$ and $R_{21''}$ are not hydrogen. More preferably, (i) none of $R_{21}$, $R_{21'}$ and $R_{21''}$ is hydrogen; or (ii) $R_{21}$ is hydrogen and $R_{21'}$ and $R_{21''}$ are not hydrogen. In preferred embodiments, at least two of $R_{21}$, $R_{21'}$ and $R_{21''}$ are fluorine. In other embodiments, each of $R_{21}$, $R_{21'}$ and $R_{21''}$ is fluorine. Preferably, $R_{39}$ is hydroxyl; q is 1 or 2; $R_{41}$ and $R_{42}$ are each independently hydrogen or hydroxyl; and $R_{43}$ is optionally substituted $C_1$-$C_6$ alkyl, optionally substituted $C_3$-$C_6$ cycloalkyl, optionally substituted 3- to 12-membered heterocyclic, optionally substituted aryl or optionally substituted heteroaryl. More preferably, $R_{39}$ is hydroxyl; q is 1 or 2; $R_{41}$ is hydrogen; $R_{42}$ is hydroxyl; and $R_{43}$ is optionally substituted $C_1$-$C_6$ alkyl, optionally substituted $C_3$-$C_6$ cycloalkyl, optionally substituted 3- to 12-membered heterocyclic, or optionally substituted heteroaryl. In preferred embodiments, $R_{39}$ is hydrogen or hydroxyl; q is 1 or 2; $R_{41}$ is hydrogen or methyl; $R_{42}$ is hydroxyl; and $R_{43}$ is optionally substituted $C_1$-$C_6$ alkyl or optionally substituted $C_3$-$C_6$ cycloalkyl. In other embodiments, $R_{39}$ is hydrogen or hydroxyl; q is 1 or 2; $R_{41}$ is hydrogen or methyl; $R_{42}$ is hydroxyl; and $R_{43}$ is optionally substituted 3- to 12-membered heterocyclic or optionally substituted heteroaryl. In preferred embodiments, $R_{43}$ is methyl, ethyl, propyl, isopropyl, cyclopropyl, cyclobutyl, pyridyl, pyrimidinyl, oxazolyl, thiazolyl, oxazolyl, or isoxazolyl.

It will be appreciated that the description of the present invention herein should be construed in congruity with the laws and principles of chemical bonding. In some instances, it may be necessary to remove a hydrogen atom in order to accommodate a substituent at any given location.

It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

In one aspect, the compounds of the invention are useful in HBV treatment by disrupting, accelerating, reducing, delaying and/or inhibiting normal viral core protein functions including, but not limited to, direct or indirect interaction with viral relaxed circular (rc) DNA, cccDNA, or reverse transcriptase, direct or indirect interaction with host proteins such as histones or host partners such as kinase, capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, the compounds of the invention disrupt and/or modulate the interaction between core protein and viral rcDNA, cccDNA or reverse transcriptase during vial infectivity. In yet another embodiment, the compounds of the invention disrupt and/or modulate the interaction between core protein and host partners or proteins during vial infectivity. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA. In another embodiment, the additional therapeutic agent is selected from immune modulator or immune stimulator therapies, which includes T-cell response activator AIC649 and biological agents belonging to the interferon class, such as interferon alpha 2a or 2b or modified interferons such as pegylated interferon, alpha 2a, alpha 2b, lamda; or STING (stimulator of interferon genes) modulator; or TLR modulators such as TLR-7 agonists, TLR-8 agonists or TLR-9 agonists; or therapeutic vaccines to stimulate an HBV-specific immune response such as virus-like particles composed of HBcAg and HBsAg, immune complexes of HBsAg and HBsAb, or recombinant proteins comprising HBx, HBsAg and HBcAg in the context of a yeast vector; or immunity activator such as SB-9200 of certain cellular viral RNA sensors such as RIG-I, NOD2, and MDA5 protein; or RNA interence (RNAi) or small interfering RNA (siRNA) such as ARC-520, ARC-521, ARB-1467, and ALN-HBV RNAi; or another core protein inhibitor or modulator; or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence such as REP 2139 and RG7834. In an embodiment of the combination therapy, the reverse transcriptase inhibitor is at least one of Zidovudine, Didanosine, Zalcitabine, ddA, Stavudine, Lamivudine, Aba-cavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-purin-9-yl)propyl][3-(4-morpholinyl) propyl] amino Imethyl)phenyl] acetate), GS-9620 (4-Amino-2-butoxy-8-[3-(1-pyrrolidinylmethyl)benzyl]-7, 8-dihydro-6(5H)-pteridinone), and RO6864018.

In another embodiment of the combination therapy, the TLR-8 agonist is GS-9688.

In an embodiment of these combination therapies, the compound and the additional therapeutic agent are co-formulated. In another embodiment, the compound and the additional therapeutic agent are co-administered.

In another embodiment of the combination therapy, administering the compound of the invention allows for administering of the additional therapeutic agent at a lower dose or frequency as compared to the administering of the at least one additional therapeutic agent alone that is required to achieve similar results in prophylactically treating an HBV infection in an individual in need thereof.

In another embodiment of the combination therapy, before administering the therapeutically effective amount of the compound of the invention, the individual is known to be refractory to a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In still another embodiment of the method, administering the compound of the invention reduces viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another embodiment, administering of the compound of the invention causes a lower incidence of viral mutation and/or viral resistance than the administering of a compound selected from the group consisting of an HBV polymerase inhibitor, interferon, viral entry inhibitor, viral maturation inhibitor, distinct capsid assembly modulator, antiviral compounds of distinct or unknown mechanism, and combination thereof.

It should be understood that the compounds encompassed by the present invention are those that are suitably stable for use as pharmaceutical agent.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl," "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The tem "substituted heteroarylalkyl" means a heteroarylalkyl functional group in which the heteroaryl group is substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds.

Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2$NH, $S(O)_2NH_2$, $NHC(O)NH_2$, NHC(O)C(O)NH, $NHS(O)_2$NH, $NHS(O)_2NH_2$, $C(O)NHS(O)_2$, $C(O)NHS(O)_2$NH or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_8$-alkenyl, —CONH—C$_2$-C$_8$-alkynyl, —CONH—C$_3$-C$_{12}$-cycloalkyl, —CONH-aryl, —CONH-heteroaryl, —CONH-heterocycloalkyl, —OCO$_2$—C$_1$-C$_{12}$-alkyl, —OCO$_2$—C$_2$-C$_8$-alkenyl, —OCO$_2$—C$_2$-C$_8$-alkynyl, —OCO$_2$—C$_3$-C$_{12}$-cycloalkyl, —OCO$_2$-aryl, —OCO$_2$-heteroaryl, —OCO$_2$-heterocycloalkyl, —CO$_2$—C$_1$-C$_{12}$ alkyl, —CO$_2$—C$_2$-C$_8$ alkenyl, —CO$_2$—C$_2$-C$_8$ alkynyl, CO$_2$—C$_3$-C$_{12}$-cycloalkyl, —CO$_2$-aryl, CO$_2$-heteroaryl, CO$_2$-heterocyloalkyl, —OCONH$_2$, —OCONH—C$_1$-C$_{12}$-alkyl, —OCONH—C$_2$-C$_8$-alkenyl, —OCONH—C$_2$-C$_8$-alkynyl, —OCONH—C$_3$-C$_{12}$-cycloalkyl, —OCONH-aryl, —OCONH-heteroaryl, —OCONH-heterocyclo-alkyl, —NHC(O)H, —NHC(O)—C$_1$-C$_{12}$-alkyl, —NHC(O)—C$_2$-C$_8$-alkenyl, —NHC(O)—C$_2$-C$_8$-alkynyl, —NHC(O)—C$_3$-C$_{12}$-cycloalkyl, —NHC(O)-aryl, —NHC(O)— heteroaryl, —NHC(O)-heterocycloalkyl, —NHCO$_2$—C$_1$-C$_{12}$-alkyl, —NHCO$_2$—C$_2$-C$_8$-alkenyl, —NHCO$_2$— C$_2$-C$_8$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_8$-alkenyl, —NHC(O)NH—C$_2$-C$_8$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_8$-alkenyl, —NHC(S)NH—C$_2$-C$_8$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_8$-alkenyl, —NHC(NH)NH—C$_2$-C$_8$-alkynyl, —NHC(NH)NH—C$_3$-C$_{12}$-cycloalkyl, —NHC(NH)NH-aryl, —NHC(NH)NH—heteroaryl, —NHC(NH)NH-heterocycloalkyl, —NHC(NH)—C$_1$-C$_{12}$-alkyl, —NHC(NH)—C$_2$-C$_8$-alkenyl, —NHC(NH)—C$_2$-C$_8$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_8$-alkenyl, —C(NH)NH—C$_2$-C$_8$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_8$-alkenyl, S(O)—C$_2$-C$_8$-alkynyl, —S(O)—C$_3$-C$_{12}$-cycloalkyl, —S(O)-aryl, —S(O)-heteroaryl, —S(O)— heterocycloalkyl, —SO$_2$NH$_2$, —SO$_2$NH—C$_1$-C$_{12}$-alkyl, —SO$_2$NH—C$_2$-C$_8$-alkenyl, —SO$_2$NH— C$_2$-C$_8$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_8$-alkenyl, —NHSO$_2$—C$_2$-C$_8$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_8$-alkenyl, —S—C$_2$-C$_8$-alkynyl, —S—C$_3$-C$_{12}$-cycloalkyl, —S-aryl, —S— heteroaryl, —S-heterocycloalkyl, or methylthio-methyl. In certain embodiments, the substituents are independently selected from halo, preferably C$_1$ and F; C$_1$-C$_4$-alkyl, preferably methyl and ethyl; C$_2$-C$_4$-alkenyl; halo-C$_1$-C$_4$-alkyl, such as fluoromethyl, difluoromethyl, and trifluoromethyl; halo-C$_2$-C$_4$-alkenyl; C$_3$-C$_6$-cycloalkyl, such as cyclopropyl; —CN; —OH; NH$_2$; C$_1$-C$_4$-alkylamino; di(C$_1$-C$_4$-alkyl)amino; and NO$_2$. It is understood that the substituents, such as the aryls, heteroaryls, alkyls, and the like, are optionally further substituted. In some cases, each substituent in a substituted moiety is additionally optionally substituted with one or more groups, each group being independently selected from C$_1$-C$_4$-alkyl; CF$_3$, C$_1$-C$_4$-alkoxy; —OCF$_3$, —F, —C$_1$, —Br, —I, —OH, —NO$_2$, —CN, and —NH$_2$.

It is understood that the aryls, heteroaryls, alkyls, cycloalkyls and the like can be further substituted.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure (s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxycarbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in Prodrugs *Challenges and Rewards Part-2*, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "amino acid" refers to naturally occurring and synthetic a, 3, y, or 6 amino acids, and includes but is not limited to, amino acids found in proteins or intermediates in metabolism of amino acids or proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, citrulline, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from the group consisting of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl and β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is $-NR^u$-$G(S_c)$-$C(O)$-$Q^1$, wherein $Q^1$ is $-SR^v$, $-NR^vR^v$ or alkoxyl, $R^v$ is hydrogen or alkyl, S, is a side-chain of a naturally occurring or non-naturally occurring amino acid, G is $C_1$-$C_2$ alkyl, and $R^u$ is hydrogen; or $R^u$ and S, are taken together with the atoms to which they are attached to form a five-membered heterocyclic ring. In an embodiment, an amino acid derivative is provided as a substituent of a compound described herein, wherein the substituent is $-O-C(O)$-$G(S_c)$-$NH$-$Q^2$, wherein $Q^2$ is hydrogen or alkoxyl, $S_c$ is a side-chain of a naturally occurring or non-naturally occurring amino acid and G is $C_1$-$C_2$ alkyl. In certain embodiments, $Q^2$ and $S_c$ are taken together with the atoms to which they are attached to form a five-membered heterocyclic ring. In certain embodiments, G is an optionally substituted methylene and $S_c$ is selected from the group consisting of hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl and hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Prop-*

*erties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, $2^{nd}$ Ed. Wiley-VCH (1999); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)—, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus, a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

An inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections, conditions are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the compound described above may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The said "additional therapeutic or prophylactic agents" includes but not limited to, immune therapies (eg. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Combination and Alternation Therapy for HBV

It has been recognized that drug-resistant variants of HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. The compounds can be used for combinations and are selected from the group consisting of an HBV polymerase inhibitor, interferon, TLR modulators such as TLR-7 agonists or TLR-9 agonists, therapeutic vaccines, immune activator of certain cellular viral RNA sensors, viral entry inhibitor, viral maturation inhibitor, distinct capsid assembly modulator, antiviral compounds of distinct or unknown mechanism, and combination thereof. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

Preferred compounds for combination or alternation therapy for the treatment of HBV include 3TC, FTC, L-FMAU, interferon, adefovir dipivoxil, entecavir, telbivudine (L-dT), valtorcitabine (3'-valinyl L-dC), β-D-dioxolanyl-guanine (DXG), β-D-dioxolanyl-2,6-diaminopurine (DAPD), and β-D-dioxolanyl-6-chloropurine (ACP), famciclovir, penciclovir, lobucavir, ganciclovir, and ribavirin.

Although the invention has been described with respect to various preferred embodiments, it is not intended to be limited thereto, but rather those skilled in the art will recognize that variations and modifications may be made therein which are within the spirit of the invention and the scope of the appended claims.

Abbreviations

Abbreviations which may be used in the descriptions of the scheme and the examples that follow are: Ac for acetyl; AcOH for acetic acid; AIBN for azobisisobutyronitrile; BINAP for 2,2'-bis(diphenylphosphino)-1,1'-binaphthyl; $Boc_2O$ for di-tert-butyl-dicarbonate; Boc for t-butoxycarbonyl; Bpoc for 1-methyl-1-(4-biphenylyl)ethyl carbonyl; Bz for benzoyl; Bn for benzyl; BocNHOH for tert-butyl N-hydroxycarbamate; t-BuOK for potassium tert-butoxide; $Bu_3SnH$ for tributyltin hydride; BOP for (benzotriazol-1-yloxy)tris(dimethylamino)phospho-nium Hexafluorophosphate; Brine for sodium chloride solution in water; BSA for N,O-bis-(trimethylsilyl)acetamide; CDI for carbonyldiimidazole; $CH_2C_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; dppb for diphenylphos-phinobutane; DBU for 1,8-diazabicyclo[5.4.0]-undec-7-ene; DCC for N,N'-dicyclohexyl-carbodiimide; DEAD for diethylazodicarboxylate; DIAD for diisopropyl azodicarboxylate; DIPEA or $(i-Pr)_2EtN$ for N,N,-diisopropylethyl amine; Dess-Martin periodinane for 1,1,1-tris(acetyloxy)-1,1-dihydro-1,2-benziodoxol-3-(1H)-one; DMAP for 4-dimethyl-amino-pyridine; DME for 1,2-dimethoxyethane; DMF for N,N-dimethylformamide; DMSO for dimethyl sulfoxide; DMT for di(p-methoxyphenyl)-phenylmethyl or dimethoxytrityl; DPPA for diphenylphosphoryl azide; EDC for N-(3-dimethylaminopropyl)-N'-ethylcarbodiimide; EDC HCl for N-(3-dimethylaminopropyl)-N'-ethylcarbodiimide hydrochloride; EtOAc for ethyl acetate; EtOH for ethanol; $Et_2O$ for diethyl ether; HATU for O-(7-azabenzotriazol-1-yl)-N,N,N',N',-tetramethyluronium Hexafluoro-phosphate; HCl for hydrogen chloride; HOBT for 1-hydroxybenzotriazole; $K_2CO_3$ for potassium carbonate; n-BuLi for n-butyl lithium; i-BuLi for i-butyl lithium; t-BuLi for t-butyl lithium; PhLi for phenyl lithium; LDA for lithium diisopropylamide; LiTMP for lithium 2,2,6,6-tetramethyl-piperidinate; MeOH for methanol; Mg for magnesium; MOM for methoxymethyl; Ms for mesyl or $—SO_2—CH_3$; $Ms_2O$ for methanesulfonic anhydride or mesyl-anhydride; MTBE for t-butyl methyl ether; $NaN(TMS)_2$ for sodium bis(trimethylsilyl)amide; NaCl for sodium chloride; NaH for sodium hydride; $NaHCO_3$ for sodium bicarbonate or sodium hydrogen carbonate; $Na_2CO_3$ for sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4HCO_3$ for ammonium bicarbonate; $NH_4Cl$ for ammonium chloride; NMO for N-methyl-morpholine N-oxide; $NaIO_4$ for sodium periodate; Ni for nickel; NSFI for N-fluorobenzene-sulfonimide; OH for hydroxyl; o/n for overnight; $OsO_4$ for osmium tetroxide; PTSA for p-toluenesulfonic acid; PPTS for pyridinium p-toluenesulfonate; TBAF for tetrabutyl-ammonium fluoride; TEA or $Et_3N$ for triethylamine; TES for triethylsilyl; TESCI for triethylsilyl chloride; TESOTf for triethylsilyl trifluoro-methanesulfonate; TFA for trifluoroacetic acid; THF for tetrahydro-furan; TMEDA for N,N,N',N'-tetramethylethylene-diamine; TPP or $PPh_3$ for triphenylphosphine; Troc for 2,2,2-trichloroethyl carbonyl; Ts for tosyl or $—SO_2—C_6H_4CH_3$; $Ts_2O$ for tolylsulfonic anhydride or tosyl-anhydride; TsOH for p-tolylsulfonic acid; Pd for palladium; Ph for phenyl; POPd for dihydrogen dichlorobis(di-tert-butylphosphinito-xP)palladate(II); $Pd_2(dba)_3$ for tris(dibenzylideneacetone) dipalladium (0); $Pd(PPh_3)_4$ for tetrakis(triphenyl-phosphine)palladium (0); $PdCl_2$ (PPh$_3$)$_2$ for trans-dichlorobis-(triphenylphosphine)palladium (II); Pt for platinum; Rh for rhodium; rt for room temperature; Ru for ruthenium; SFC for supercritical fluid chromatography; TBS for tert-butyl dimethylsilyl; TMS for trimethylsilyl; or TMSCl for trimethylsilyl chloride.

Synthetic Methods

The compounds and processes of the present invention will be better understood in connection with the following synthetic schemes that illustrate the methods by which the compounds of the invention may be prepared. These schemes are of illustrative purpose and are not meant to limit the scope of the invention. Equivalent, similar, or suitable solvents, reagents or reaction conditions may be substituted for those particular solvents, reagents, or reaction conditions described herein without departing from the general scope of the method of synthesis. Certain reactions can be conducted as generally described in WO 2017/136403.

The compounds of the Formula I may be prepared via several different synthetic routes from a variety of optionally substituted phenyl, heteroaryl, or fused bicyclic aryl or heteroaryl precursors using the chemical transformations that are known to those skilled in the art. Strategistically, a compound of Formula I can be constructed to form the sulfonyl group at the right end followed by formation of group A at the left end. Alternatively, a compound of Formula I can be constructed to form the group A at the left end followed by formation of sulfonyl group at the right end. The preparation of sulfones can be realized by either oxidation of sulfide (reviewed by K. Schank, The Chemistry of Sulfones and Sulfoxides, Wiley, New York, 1988, Chap. 7) or alkylation/arylation of a low-valent sulfur species such as sulfinate salts (reviewed by G. Liu, C. Fan, J. Wu, Org. Biomol. Chem. 2015, 13, 1592). A sulfide can be synthesized from a thiol precursor via a nucleophilic substitution to an organic halide or sulfonate ester, or a nucleophilic addition to an epoxide, aziridine, or unsaturated substrate (reviewed by G. Solladie, Comprehensive Organic Synthesis, 1991, Vol 6, 133), or a radical addition of thiol to an unsaturated substrate. A sulfinate salt can be accessed either by reduction of a sulfonyl halide (reviewed by Schubart, R. Sulfinic Acids and Derivatives, Ullmann's Encyclopedia of Industrial Chemistry, 2000, 677) or by transition metal catalyzed reaction of aryl or hetero aryl halide (A. Shavnya, S. S. Coffey, A. C. Smith, V. Mascitti, Org. Lett., 2013, 15, 6226) or boronic acid (A. Shavnya, K. D. Hesp, V. Mascitti, A. C. Smith, Angew. Chem. Int. Ed., 2015, 54, 13571) with potassium metabisulfite. A sulfone compound may be further functionalized by deprotonation with a strong base followed by reaction of the resultant anion with an electrophile such as an organic halide, aldehyde, ketone, electrophilic halogenation reagent, or an unsaturated substrate such as a Michael addition acceptor; a tertiary sulfone may be prepared from a primary sulfone through a two-round sequential deprontonation and anionic nucleophilic reaction. An amide bond can be formed either by reaction of an acid halide or anhydride with an amine or by the direct coupling of a carboxylic acid with an amine in the presence of a coupling reagent such as DCC, EDC, or HATU.

As illustrated in Scheme 1, wherein X, Y and R are as defined previously; LG$_1$, LG$_2$ at each occurrence are leaving groups and are each independently selected from halogen, tosylate, mesylate and triflate. In one approach, an optionally substituted aryl or heteroaryl amine 1-1 can react selectively with various acid chloride 1-2 in a solvent such as but not limited to toluene, tetrahydrofuran, dichloromethane or a mixture of thereof, optionally in the presence of a base such as but not limited to triethylamine, DIPEA, or pyridine, to provide a variety of amide intermediates 1-3.1-3 is then treated with a reducing reagent such as but not limited to triphenylphosphine, SnCl$_2$, Sn/HCl, Zn/HCl, or Pd/HCOOH, to provide thiol intermediate 1-4, which reacts with intermediate 1-5 by a nucleophilic displacement fashion optionally in the presence of a base such as but not limited to potassium carbonate, sodium carbonate, triethylamine or DIPEA to afford a sulfide intermediate which is transformed to a compound of Formula IIa in a suitable solvent in the presence of a oxidizing reagent such as but not limited to hydrogen peroxide, meta-chloroperbenzoic acid, perbenzoic acid or tert-butyl peroxide. Alternatively, carboxylic ester 1-6 is converted to sulfone intermediate 1-7 using chemistry similar to that described above or by nucleophilic substitution with an organometallic agent (R-M, wherein M is a Mg- or Zn-species). 1-7 can be saponified with a base, such as but not limited to lithium hydroxide, sodium hydroxide, or potassium hydroxide, to yield carboxylic acid 1-8. The acid 1-8 can react with amine 1-1 in the presence of coupling reagent such as but not limited to DCC, EDC, or HATU, in a suitable solvent, optionally in the presence of a base such as but not limited to triethylamine, DIPEA, or pyridine, to yield the compound of Formula IIa.

Scheme 1

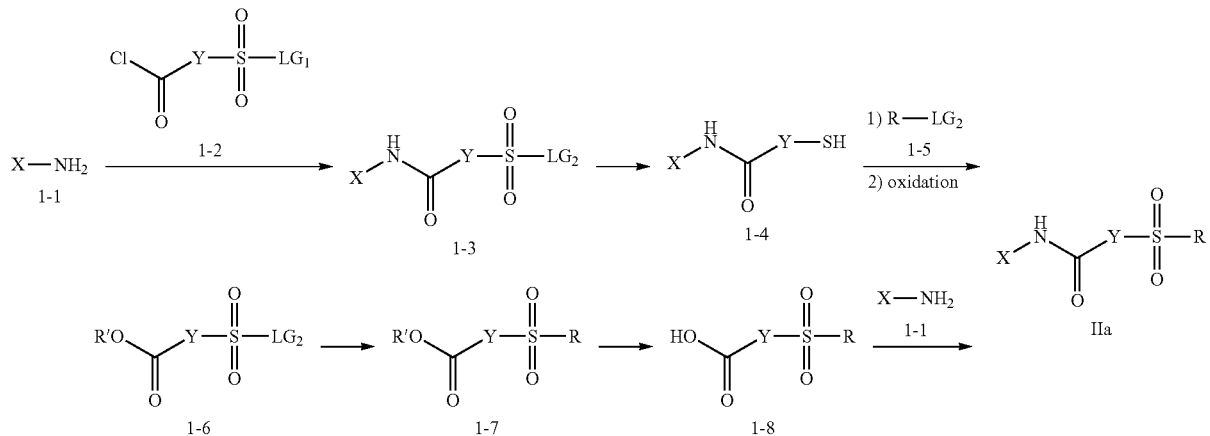

The preparation of the compound of Formula IIb is described below in Scheme 2. An aldehyde 2-1 is reacted with TMSCF$_3$ to give a trifluoroethyl alcohol 2-2, which is converted to a triflate by reacting with Tf$_2$O in the presence of base such as DIPEA, followed by displacement with amine X—NH$_2$ to afford the compound of Formula IIb.

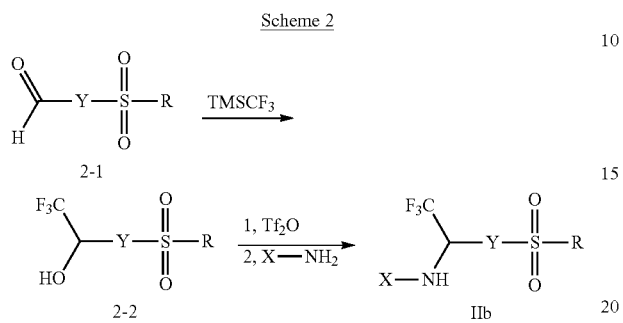

The synthesis of the compound of Formula IIc containing an aminooxetanyl moiety is exemplified in Scheme 3. An arylamine or heteroarylamine 3-1 is condensed with oxetan-3-one in the presence of an acid such as acetic acid or p-TsA to give imine 3-2, which is treated with a nucleophilic 3-3, wherein M$_1$ is an organometallic species including but not limited to that related to boronic acid/ester, organotin, organozinc, organolithium, or organomagesium moiety, to afford compound of formula IIc.

As shown in Scheme 4, the compound of Formula IId may be prepared from the compound of formula IIa. IIa may react with benzyl bromide in the presence of a base such as but not limited to NaH or LDA, to give compound 4-1, which is converted to a compound 4-2 by reacting with oxalyl chloride, followed by treatment with a fluorinating reagent such as but not limited to DAST, SF$_4$ or Et$_3$N—HF. Compound 4-2 may be treated with hydrogen gas in the presence a suitable catalyst such as but not limited to Pd/C, PtO$_2$, or Pd(OH)$_2$/C, to afford compound of Formula IId.

It will be appreciated that, with appropriate manipulation and protection of any chemical functionality, synthesis of compounds of Formula I is accomplished by methods analogous to those above and to those described in the Experimental section. Suitable protecting groups can be found, but are not restricted to, those found in T W Greene and P G M Wuts "Protective Groups in Organic Synthesis", 3rd Ed (1999), J Wiley and Sons.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Intermediate 1

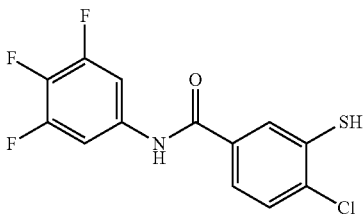 [SMILES: O=C(Nc1cc(F)c(F)c(F)c1)c1ccc(Cl)c(S)c1]

Step Int 1a.

A mixture of 4-chloro-3-(chlorosulfonyl)-benzoic acid (0.86 g, 3.4 mmol) in SOCl$_2$ (5.0 mL) was heated to reflux overnight. It was concentrated to give the desire crude product, which was used for the next step directly.

Step Int 1b.

The compound from Step Int 1a (0.91 g, 3.3 mmol) and 3,4,5-trifluoroaniline (0.49 g, 3.3 mmol) in toluene (10 mL) was stirred at 90° C. overnight. It was concentrated to give the crude desired compound, which was used for the next step directly.

Step Int 1c.

The compound from Step Int 1b (0.89 g, 2.3 mmol) and triphenylphosphine (3.4 g, 13 mmol) in toluene (12 mL) was stirred at 80° C. for 4 h. It was diluted with EtOAc and washed with sat. aq. NaHCO$_3$ and brine. The organic was dried (Na$_2$SO$_4$), filtered and concentrated. The residue was chromatographed (silica, hexanes/EtOAc) to give the desired compound as white solid (0.49 g, 71%). ESI-MS m/z=316.0, 318.0 [M−H]$^-$.

Intermediate 2

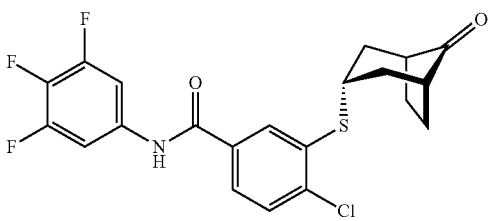

Step Int 2a.

A mixture of 2-methylenepropane-1,3-diyl diacetate (2.69 g, 15.62 mmol), Pd(OAc)$_2$ (0.210 g, 0.937 mmol), Ph$_3$P (0.983 g, 3.75 mmol), and 1-(cyclopent-1-en-1-yl)pyrrolidine (3.19 ml, 21.86 mmol) in acetonitrile (89 ml) was heated to and remained at 65° C. for 18 hours. Water (45 ml) was added and the reaction mixture was stirred for 1 hour. Saturated brine was added and it was extracted with ethyl acetate. The organic phase was dried (Na$_2$SO$_4$), filtered and concentrated. The residue was chromatographed (silica, hexanes/EtOAc) to give the desired compound (1.53 g, 71.9% yield) as a colorless oil.

Step Int 2b.

A solution of the compound from step Int 2a (41.725 g, 306 mmol) in THF (300 mL) was cooled to −78° C. followed by addition of LiAlH$_4$ (1 M in THF, 92 mL, 92 mmol). After being stirred for 15 minutes, it was quenched by water (3.4 mL), NaOH (1 M, 3.4 mL) and water (10.2 mL). The organic was dried (Na$_2$SO$_4$), filtered over Celite and concentrated to give the crude desired compound (48.4 g, 97%, contains 15% THF w/w), which was used for the following step.

Step Int 2c.

To a stirred compound from step Int 2b (50.7 g, 367 mmol) and imidazole (62.4 g, 58.8 mmol) in DMF (400 mL) at 0° C. was added TBSCl (66.3 g, 440 mmol). The resulting reaction mixture was stirred at rt for 16 h. The reaction was diluted with hexanes and the mixture was washed with water, brine. The organic layer was dried (Na$_2$SO$_4$), filtered and concentrated to give the desired compound as white solid (101.0 g, 100%).

Step Int 2d.

A suspension compound from step Int 2c (101 g, 368 mmol) in dioxane-water (1.1 L/0.36 L) at rt was added 2,6-dimethylpyridine (86 ml, 735 mmol), osmium(VIII) oxide (1.87 g, 7.35 mmol) and sodium periodate (280 g, 1.31 mol) and the mixture was stirred at rt for 20 h. It was quenched with aqueous Na$_2$S$_2$O$_3$, extracted with MBTE, washed with water, brine, dried over Na$_2$SO$_4$, filtered, concentrated to give desired product as white solid (100 g, 99%).

Step Int 2e.

To a solution of the compound of step Int 2d (118.5 g, 466 mmol) in MTBE (1.2 L) at 0° C. was added LiBH$_4$ (314 mL, 629 mmol, 2 M in THF). The resulting reaction mixture was stirred at 0° C. for 2 h. The reaction was quenched with aqueous NH$_4$Cl and the mixture was extracted with MBTE, washed with water, brine. The organic layer was dried (Na$_2$SO$_4$), filtered and concentrated. The crude product was used without further purification (117 g, 98%, 10:1 dr favoring the desired isomer).

Step Int 2f.

To a stirred solution from step Int 2e (315 mg, 1.23 mmol) and compound from step 1c (390 mg, 1.23 mmol) in toluene (5 ml) was added 2-(tributyl-15-phosphanylidene)acetonitrile (0.81 ml, 3.07 mmol), and the mixture was stirred at 100° C. for 60 h. It was cooled to rt, diluted with MBTE, washed with NaOH (0.5 N), brine, dried over Na$_2$SO$_4$, filtered, concentrated, silica column to desired compound (362 mg, 53%). ESI-MS m/z=554.15, 556.15 [M−H]$^-$.

Step Int 2g.

A suspension of compound from step Int 2f (0.53 g, 0.95 mmol) in MeOH (11 mL) at rt was added con HCl (1.0 mL) and stirred at rt for 24 h. It was concentrated under vacuum to remove majority of MeOH and the residue was extracted with EtOAc. The organic phase was washed with water, 10% K$_2$CO$_3$, brine, dried over Na$_2$SO$_4$, filtered, concentrated and recrystallized from EtOAc/hexanes to give desired product as a white solid (0.33 g, 78%). ESI-MS m/z=440.07, 442.07 [M−H]$^-$.

Step Int 2h.

A solution of compound from step Int 2g (1.8 g, 3.8 mmol) in DMSO (10 mL) at rt was added IBX (4.3 g, 15.3 mmol) and the mixture was stirred at rt for 20 h. Aqueous Na$_2$S$_2$O$_3$NaHCO$_3$ and few drops of Et$_3$N was added and stirred at rt for 1 h. It was extracted with EtOAc, washed with water, brine, dried over Na$_2$SO$_4$, filtered and concentrated to give the title compound (1.65 g, 92%). ESI-MS m/z=470.04, 472.04 [M−H]$^-$.

Intermediate 3

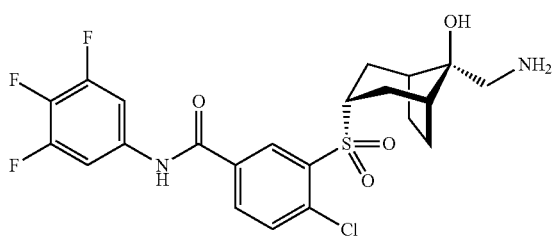

Step Int 3a.

To a solution of Int 2 (1.76 g, 4.0 mmol) and trimethylsulfoxonium iodide (1.76 g, 8.0 mmol) in DMSO (20 mL) at 0° C. was added t-BuOK (1.12 g, 10 mmol). The resulting reaction mixture was stirred at rt for 1 h. The reaction was quenched with aqueous NH₄Cl and the mixture was extracted with EtOAc, washed with water, brine. The organic layer was dried (Na₂SO₄), filtered and concentrated. The crude product was chromatographed (silica, hexanes/EtOAc) to give the desired compound as white solid (1.36 g, 75%). ESI-MS m/z=452.07, 454.07 [M−H]⁻.

Step Int 3b.

To a stirred solution of compound from step Int 3a (78 mg, 0.17 mmol) in DMF (2.5 mL) was added NH₄Cl (17 mg, 0.32 mmol) and NaN₃ (44 mg, 0.67 mmol) then stirred at 60° C. for 24 h. It was diluted with EtOAc, washed with water, brine, dried over Na₂SO₄, filtered, Con, chromatographed (silica, hexanes/EtOAc) to give the desired compound as white solid (73 mg, 88%). ESI-MS m/z=495.08, 497.08 [M−H]⁻.

Step Int 3c.

To a solution of compound from step Int 3b (0.20 g, 0.40 mmol) in NMP (2.0 mL) was added m-CPBA (0.27 g 77%, 1.2 mmol) and stirred at rt O/N. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated and chromatographed (silica, hexanes/EtOAc) to give the desired compound as white solid (0.21 g, 98%). ESI-MS m/z=527.07, 529.07 [M−H]⁻.

Step Int 3d.

Into the solution of example 257 (540 mg, 1.02 mmol) in MeOH (2 mL) and THF (1 mL), Raney nickel (washed with MeOH, 50 mg) was added. A balloon filled with hydrogen was introduced. It was stirred 2 hours at rt. The mixture was filtered through a pad of celite, washed with MeOH. The filtrated was concentrated to give the title compound (440 mg, 86%). ESI-MS m/z=501.08, 503.08 [M−H]⁻.

Intermediate 4

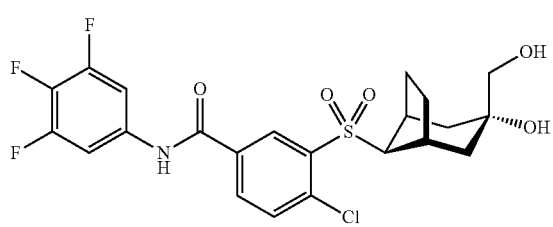 [SMILES: O=C(Nc1cc(F)c(F)c(F)c1)c1ccc(Cl)c(S(=O)(=O)[C@H]2C3CC[C@H]2C[C@](O)(CO)C3)c1]

Step Int 4a.

To a solution of compound from step Int 2b (7.7 g, 77.18% in THF, 43 mmol) in anhydrous dichloromethane (20 mL) at 0° C. was added DBU (7.9 g, 5.2 mmol) and 1,1,2,2,3,3,4,4,4-nonafluorobutane-1-sulfonyl fluoride (14.4 g, 48 mmol). The reaction was kept at 0° C. for 0.5 h before it was concentrated to dry. The residue was dissolved in hexane (70 mL). The solution was washed with HCl (0.5 M), water, NaHCO₃, brine and dried (Na₂SO₄). It was filtered through a layer of silica gel, washed with hexane (300 mL) and concentrated to give colorless oil (16.8 g 92%). ¹HNMR (400 MHz, CDCl₃) δ 5.13 (t, 1H), 4.85 (s, 2H), 2.67 (d, 2H), 2.46 (brs, 2H), 2.04 (dd, 2H), 1.72 (m, 2H), 1.58 (m, 2H).

Step Int 4b.

A mixture of compound from step Int 4a (2.101 g, 5 mmol) and 4-methylmorpho-line 4-oxide (0.703 g, 6.00 mmol) in acetone-water (4.5 mL/0.5 mL) at rt was added osmium(VIII) oxide (0.628 ml, 2.5% in t-BuOH) and stirred at rt o/n. Na₂S₂O₃ (1.58 g, 10 mmol) and water (2 mL) was added stirred at rt for 30 mins. It was partitioned (EtOAc/water). The organic was washed with 1N HCl, aq. NaHCO₃, brine and dried (Na₂SO₄). After filtered, the crude was concentrated to give the desired product (2.24 g, 99%). ¹HNMR (400 MHz, CDCl₃) δ 5.03 (t, 1H), 3.60 (s, 2H), 2.44 (brs, 2H), 1.99 (ddd, 4H), 1.82 (m, 4H), 1.61 (m, 2H).

Step Int 4c.

To a suspension of the compounds from step Int 4b (1.84 g, 5.81 mmol), triphenylphophine (0.063 g, 0.024 mmol) in THF (4 mL) at rt was degassed followed by addition of Potassium t-butoxide (1 M in THF, 5.32 mL, 5.32 mmol). In 5 minutes, the compound from step 1c (2.2 g, 4.84 mmol) in THF (9 mL) was added and stirred at 60° C. for 24 h. After being cooled, it was diluted with MBTE (60 mL), filtered and washed with MTBE. The combined solution was washed with 0.5 N NaOH, brine and dried (Na₂SO₄). It was filtered through a short silica plug (10 g silica gel) and washed with EtOAc (50 mL). The combined organic was concentrated under vacuum to give crude 2.5 g (110%).

Step Int 4d.

To the solution of the compound from step Int 4c (1.80 g, 3.81 mmol) in NMP (5 mL), m-CPBA (77 wt %, 2.14 g, 9.54 mmol) was added. It was stirred at rt for 20 hours before aq. NaS₂O₃ (3 mL) was added followed by aq. NaHCO₃ (3 mL) and MeOH (5 mL). The white solid was collected under vacuum and washed with aq. NaHCO₃, water. This mixture was further recrystallized from MeOH to give the title compound (1.7 g, 87%). ESI-MS m/z=502.07, 504.07 [M−H]⁻.

Intermediate 5

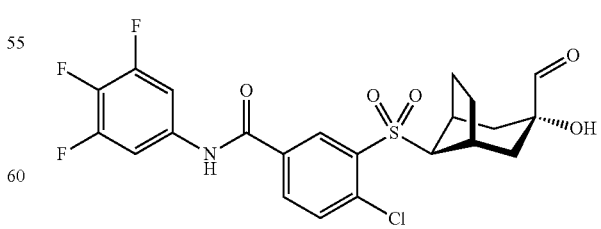

To a mixture of compound from intermediate 4 (2.00 g, 3.97 mmol), DIPEA (3.47 mL, 19.84 mmol), and DMSO (6.2 ml, 87 mmol) in DCM (12 ml) was added SO₃ pyridine complex (1.895 g, 11.9 mmol). The reaction was stirred at rt for 3 h. It was diluted with EtOAc and washed with 1 M HCl and brine. The organic was dried (Na₂SO₄), filtered and concentrated. The residue was chromatographed (silica, hexanes/acetone) to give the title compound (1.59 g, 3.18 mmol, 80% yield). ESI-MS m/z=500.05, 502.05 [M–H]⁻.

Intermediate 6

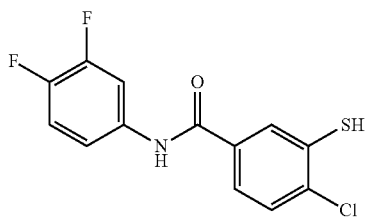 [SMILES: O=C(Nc1ccc(F)c(F)c1)c1ccc(Cl)c(S)c1]

The title compound was prepared using procedures similar to that described in Intermediate 1. ESI-MS m/z=297.99, 299.99 [M–H]⁻.

Example 1

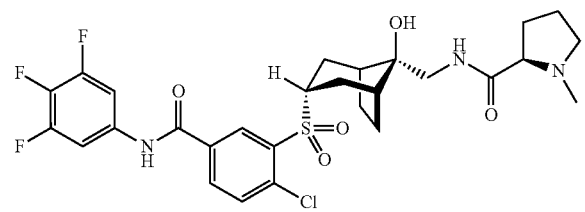

Step 1a.

Into the solution of Intermediate 3 (50 mg, 0.10 mmol) and (tert-butoxycarbonyl)-L-proline (26 mg, 0.12 mmol) in DMF (1.0 mL) was added DIPEA (0.051 mL, 0.30 mmol) and HATU (45 mg, 0.12 mmoL). It was stirred 2 hours at rt and purified on prep-HPLC (C-18, Acetonitrile/water) to afford the desired compound as a white solid (20 mg, 29%). ESI-MS m/z=698.19, 700.19 [M–H]⁻.

Step 1b

Into the solution of compound from step 1a (16 mg, 0.023 mmol) in THF (0.4 mL) was added HCl (4 M in dioxane, 0.4 mL, 1.6 mmol). It was stirred 3 hours at rt and concentrated to afford the desired compound as a white solid (14 mg, 99%). ESI-MS m/z=598.14, 600.14 [M–H]⁻.

Step 1c.

Into the solution of compound from step 1b (12 mg, 0.019 mmol), formaldehyde (0.1 mL 37% aqueous solution) and DIPEA (0.033 mL, 0.019 mmol) and a few drop of acetice acid in THE (0.5 mL) was added NaBH(OAc)₃ (12 mg, 0.057 mmoL). It was stirred 2 hours at rt and sat. aqueous NaHCO₃ was added. It was extracted with EtOAc, washed with water, brine, dry over anhydrous Na₂SO₄, filtered, concentrated and the crude was purified on prep-HPLC (C-18, Acetonitrile/water) to afford the title compound as a white solid (8.2 mg, 71%). ESI-MS m/z=612.12, 614.12 [M–H]⁻.

Example 3

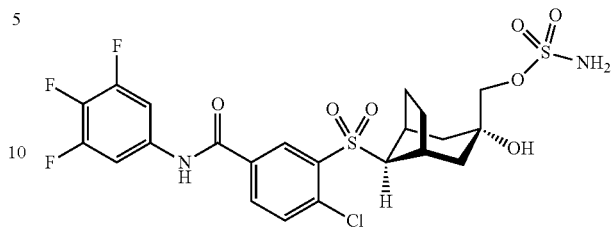

To the solution of compounds from intermediate 4 (30 mg, 0.06 mmol), sulfamoyl chloride (8.5 mg, 0.072 mmol) in THE (0.5 mL) at rt was added TEA (4 drops) and the mixture was stirred at rt for 3 hours. It was concentrated and was purified by prep-HPLC (C18 column, acetonitrile/water) eluent to give title compound (13.5 mg, 38%). ESI-MS m/z=581.04, 583.04 [M–H]⁻.

Example 4

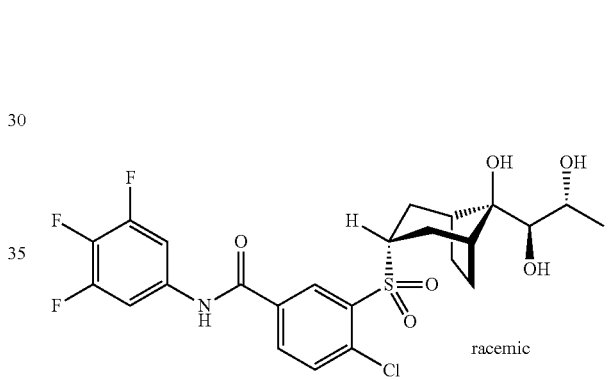

Step 4a.

To the solution of intermediate 2 (880 mg, 2.0 mmol), in THE (10 mL at 0° was added prop-1-en-1-ylmagnesium chloride 0.5 M, 12 mL) and the solution was stirred at such temperature for 30 minutes before it was quenched with a NH₄Cl (20 mL). It was extracted with EtOAc, the organic was washed with brine, dried (Na₂SO₄), filtered and concentrated. The crude was chromatographed (silica, ethyl acetate/hexanes) to give the desired compounds Z-isomer (252 mg, 26% yield) as a white solid and E-isomer (596 mg, 61%) ESI-MS m/z=502.09, 504.07 [M–H]⁻.

Step 4b.

To the solution of Z-isomer of step 4a (252 mg, 0.523 mmol) and NMO (123 mg, 1.05 mmol) in acetone (5 mL)/water (1 mL) was added OsO4 (4% in t-BuOH, 0.066 mL, 0.01 mmol) and the solution was stirred at rt o/n. It was dilute with EtOAc, wash with Na₂S₂O₃, NaHCO₃, water and brine and concentrated. This crude was dissolved in THE (3 mL). m-CPBA (77 w %, 234 mg, 1.1 mmol) was added and stirred at rt o/n. After quenched with aq. Na₂SO₃ and aq. NaHCO₃, it was extracted with EtOAc before it was dried and concentrated. The crude was crystallized from hot MeOH to give the title compound (223 mg, 78%, racemic) as white solid. ESI-MS m/z=546.06, 548.06 [M–H]⁻.

Example 5

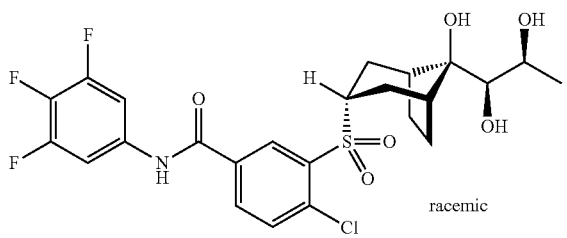

racemic

The title compound (racemic, white solid) was prepared from the E-isomer of Step 4a following similar procedures described in Step 4b. ESI-MS m/z=546.06, 548.06 [M−H]⁻.

Example 6

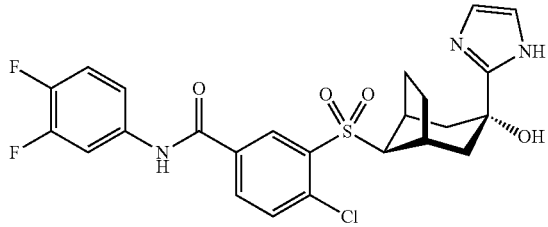 [SMILES: O=C(Nc1ccc(F)c(F)c1)c1ccc(Cl)c(S(=O)(=O)[C@H]2C3CC[C@H]2C[C@](O)(c2ncc[nH]2)C3)c1]

Step 6a.

To a mixture of the compound from Step Int 2b (1.400 g, 4.67 mmol) and Intermediate 6 (0.922 g, 5.14 mmol) in toluene (30 ml) at rt was added triphenylphosphine (1.715 g, 6.54 mmol), followed by DIAD (1.181 ml, 6.07 mmol) dropwise. The mixture was stirred at 95° C. overnight before being allowed to cool down to rt and directly purified by column chromatography (silica, hexanes/EtOAc) to afford the desired product as a white crystal (1.760 g, 90%). ESI-MS m/z=418.07, 420.06 [M−H]⁻.

Step 6b.

To a clear solution of the compound from step 6a (1.760 g, 4.19 mmol) in THF (40 ml) and water (0.5 ml) at rt was added NMO (2.455 g, 20.96 mmol), followed by osmium tetroxide (4 wt % in water, 1.644 ml, 0.210 mmol) dropwise. The mixture was stirred at rt overnight. More osmium tetroxide (4 wt % in water, 1.644 ml, 0.210 mmol) was added. The yellow solution was stirred at rt overnight. Saturated $Na_2S_2O_3$ solution was added to quench the reaction. After 20 min at rt, the mixture was diluted with THF. The aqueous layer was back-extracted with THF (*1). The combined organic layers were washed with brine (*2), dried over $Na_2SO_4$ (s), filtered and concentrated. The residual solid was recrystallized from boiling MeOH (40 ml) to afford the desired product as a white crystal (1.620 g, 80%). ESI-MS m/z=484.04, 486.04 [M−H]⁻.

Step 6c.

To a solution of the compound from step 6b (1.320 g, 2.72 mmol) and DIPEA (2.467 ml, 14.13 mmol) in DCM (8 ml) and DMSO (4.24 ml) cooled at 0° C. was added sulfur trioxide pyridine complex (1.340 g, 8.42 mmol). The resulting solution was stirred at 0° C. for 4 h. The mixture was diluted with EtOAc/THF and then washed with 0.1 N HCl aq (*2), water (*1), and brine (*1). The organic layer was dried over $Na_2SO_4$ (s), filtered and concentrated. The solid was dissolved in DCM/THF (1/1) and purified by filtering through a short column (silica, hexanes/THF) to afford the desired product as an off-white foam (1.420 g, quantitative yield). ESI-MS m/z=482.04, 484.04 [M−H]⁻.

Step 6d.

To a solution of the compound from step 6c (0.150 g, 0.310 mmol) in DMSO (3 ml) and 7 N ammonia in methanol (1.328 ml, 9.30 mmol) at rt was added glyoxal (40% in water, 0.071 ml, 0.620 mmol). The resulting solution was stirred at rt overnight. The mixture was freed of volatiles. The remaining solution was directly purified by HPLC (40~90% $CH_3CN$ in $H_2O$) to afford the title compound as a white solid (42.0 mg, 26%). ESI-MS m/z=520.07, 522.07 [M−H]⁻.

Example 7

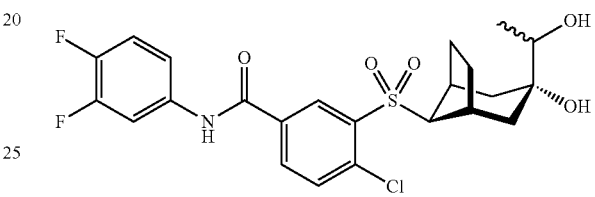

Step 7a. To a solution of the compound from step 6c (0.120 g, 0.248 mmol) in THF (4 ml) cooled at −78° C. was added methylmagnesium bromide (3 M in $Et_2O$, 0.413 ml, 1.240 mmol) dropwise. The reaction mixture was stirred at −78° C. for 30 min. More methylmagnesium bromide (3 M in $Et_2O$, 0.413 ml, 1.240 mmol) was added. The reaction mixture was stirred at −78° C. for 2 h before being allowed to warm to rt and quenched with saturated $NH_4Cl$ solution. The mixture was diluted with THF and water. The organic layer was washed with brine (*2), dried over $Na_2SO_4$ (s), filtered and concentrated. The residue was dissolved in DMSO (4 ml) and purified by HPLC (40~90% ACN in water) to afford the title compound as a white solid (39.0 mg, 31%, racemic). ESI-MS m/z=498.07, 500.07 [M−H]⁻.

Example 9

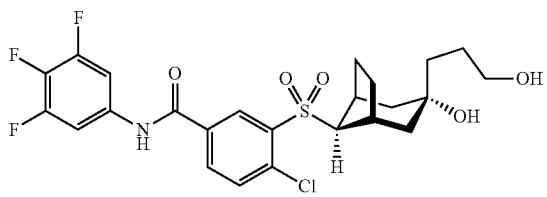 [SMILES: O=C(Nc1cc(F)c(F)c(F)c1)c1ccc(Cl)c(S(=O)(=O)[C@H]2C3CC[C@H]2C[C@](O)(CCCO)C3)c1]

Step 9a. A solution of ethyl 2-(diethoxyphosphoryl)acetate (673 mg, 3.0 mmol) in THF (10 mL) was treated with NaH (60% w/w, 120 mg, 3.0 mmol) at rt for 30 minutes before intermediate 5 (502 mg, 1.0 mmol) was added. It was stirred o/n at rt. It was diluted with EtOAc and washed with aq. $NH_4Cl$ and brine. The organic was dried ($Na_2SO_4$), filtered and concentrated. The residue was chromatographed (silica, hexanes/acetone) to give the desired compound (280 mg, 49%). ESI-MS m/z=570.09, 572.09 [M−H]⁻.

Step 9b.

Into the solution of step 9a (80 mg, 0.14 mmol) in THF (1 mL)/EtOH (1 mL), $NaBH_4$ (16 mg, 0.42 mmol) was added and stirred at rt for 2 hours before 2$^{nd}$ portion NaBH$_4$ (20 mg) was added. It was stirred for another 3 hours before it was quenched with water, extracted with EtOAc. The organic was dried (Na$_2$SO$_4$), filtered and concentrated. The crude was purified by prep-HPLC (C18 column, acetonitrile/water) to give the title compound (13.5 mg, 38%). ESI-MS m/z=530.08, 532.08 [M−H]$^-$.

Example 10

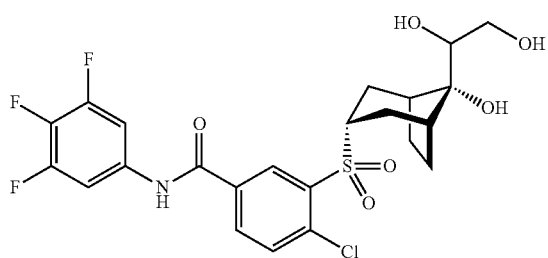

Step 10a. To a solution of triethyl phosphonoacetate (0.520 ml, 2.60 mmol) THF (5.0 mL) at 0° C. was added NaH (0.104 g 60%, 2.6 mmol). The resulting reaction mixture was stirred at 0° C. for 30 mins. A solution of intermediate 2 (0.15 g, 0.34 mmol) in THF (2.0 mL) was added and stirred at rt for 2 h. The reaction was quenched with aqueous NH$_4$Cl and the mixture was extracted with EtOAc, washed with water, brine. The organic layer was dried (Na$_2$SO$_4$), filtered and concentrated. The crude product was chromatographed (silica, hexanes/EtOAc) to give the desired compound as white solid (0.50 g, 98%). ESI-MS m/z=508.10, 510.10 [M−H]$^-$.

Step 10b.

To a solution of compounds from step 10a (0.32 g, 0.627 mmol) in THF (5.0 mL) at −78° C. was added DibAL-H (2.5 mL 1.0 M solution in hexanes, 2.5 mmol). The resulting reaction mixture was stirred at −78° C. for 1 h. The reaction was treated with aqueous potassium sodium tartrate for 3 h and the mixture was extracted with EtOAc, washed with water, brine. The organic layer was dried (Na$_2$SO$_4$), filtered and concentrated. The crude product was chromatographed (silica, hexanes/EtOAc) to give the desired compound as white solid (132 mg, 45%). ESI-MS m/z=466.06, 468.07 [M−H]$^-$.

Step 10c.

To a mixture of compound from step (43 mg, 0.092 mmol) and NMO (64 mg, 0.55 mmol) in acetone (3.0 mL) at rt was added osmium tetroxide (0.58 ml, 4% in water, 0.092 mmol) and the mixture was stirred at rt for 16 h. It was quenched with aqueous Na$_2$SO$_3$, extracted with EtOAc, washed with water, 3N HCl, NaHCO$_3$, brine, dry over Na$_2$SO$_4$, filtered, concentrated and purified by prep-HPLC (C18 column, acetonitrile/water) to give the title compound (18 mg, 37% racemic). ESI-MS m/z=578.07, 580.07 [M+HCO$_2$]$^-$.

Example 11

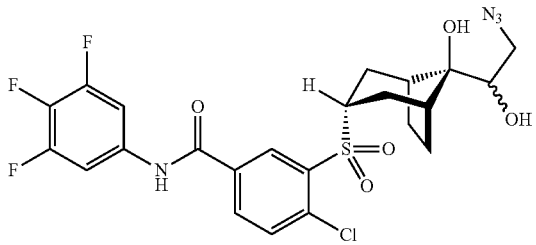

Step 11a. Into the solution of intermediate 2 (880 mg, 2.0 mmol) in THF (10 mL) vinylmagnesium chloride (1.6 M in THF 3.75 ml, 6.0 mmol) was added. It was stirred 30 minutes before aq. NH$_4$Cl was added. It was extracted with EtOAc twice. The organic was washed with brine and dried (Na$_2$SO$_4$). After being concentrated to 10 mL, the mixture was filtered under vacuum to provide the desired product (616 mg, 66%). ESI-MS m/z=466.08, 468.08 [M−H]$^-$.

Step 11b.

Into the solution of step 11a (94 mg, 0.2 mmol) in THF (2 mL) m-CPBA (77 w %, 224 mg, 1.0 mmol) was added and stirred at rt o/n. After quenched with aq. Na$_2$SO$_3$ and aq. NaHCO$_3$, it was extracted with EtOAc, dried and concentrated. The crude was chromatographed (silica, ethyl acetate/hexanes) to give the desired compounds (75 mg, 73% yield) as a white solid. ESI-MS m/z=514.08, 516.08 [M−H]$^-$.

Step 11c.

Into the solution of step 11b (75 mg, 0.14 mmol) in DMF (1 mL) NaN$_3$ (29 mg, 0.44 mmol), NH$_4$Cl (8 mg, 1.5 mmol) was added and stirred at 55° C. o/n. After cooled, it was diluted with EtOAc and was filtered. After concentrated, was purified by prep-HPLC (C18 column, acetonitrile/water) eluent to give title compound (13.5 mg, 38%, racemic) as a white solid. ESI-MS m/z=557.04, 559.04 [M−H]$^-$.

Example 14

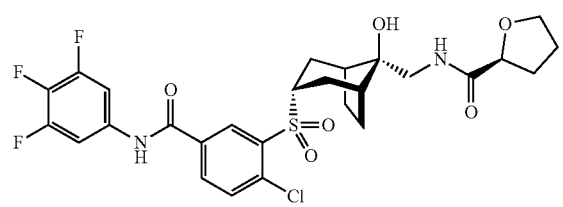

To a solution of Intermediate 3 (50 mg, 0.10 mmol) and (S)-tetrahydrofuran-2-carboxylic acid (14.43 μl, 0.149 mmol) in DMF (1 ml) was added EDC (38 mg, 0.20 mmol) and DMAP (36 mg, 0.30 mmol). The reaction was stirred at rt for 2 h. The reaction was extracted with EtOAc, washed with water and brine. The organic layer was dried (Na$_2$SO$_4$), filtered and concentrated. The crude product was chromatographed (silica, hexane/acetone) to give the title compound as white solid (14 mg, 23%, single enantiomer). ESI-MS m/z=599.125, 601.122 [M−H]$^-$.

Example 18

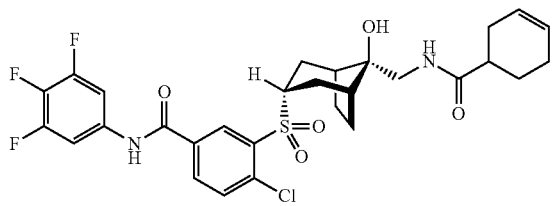

Into the solution of Intermediate 3 (75 mg, 0.15 mmol) and DIPEA (52.1 µl, 0.298 mmol) and cyclohex-3-ene-1-carboxylic acid (18.8 mg, 0.15 mmol) in DMF (1 mL) at rt was added HATU (68.0 mg, 0.18 mmol) and stirred at rt for 4 days. it was purified by prep-HPLC (C-18, Acetonitrile/water) to afford the title compound as a white solid (65 mg, 71%). ESI-MS m/z=609.14, 611.14 [M–H]⁻.

Example 19

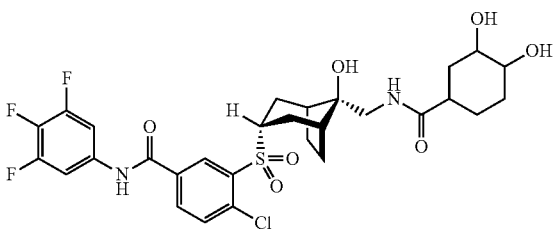

A mixture of compound from compound from example 18 (40 mg, 0.065 mmol) and NMO (23 mg, 0.196 mmol) in acetone/water (2.0/0.2 mL) at rt was treated with osmium tetroxide (0.042 ml, 4% in water, 0.0065 mmol) at rt for 16 h. It was quenched with aqueous Na₂SO₃, extracted with EtOAc, washed with water, 3N HCl, NaHCO₃, brine, dry over Na₂SO₄, filtered, concentrated and purified by prep-HPLC (C18 column, acetonitrile/water) to give the title compound (26 mg, 61%, single isomer, stereochemistry not determined). ESI-MS m/z=643.15, 645.15[M–H]⁻.

Example 20

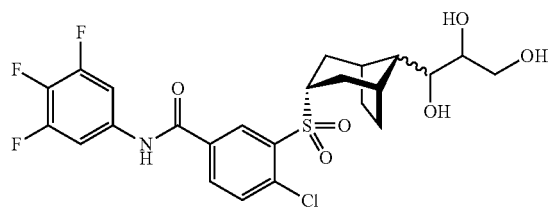

Step 20a. To a suspension of (methoxymethyl)triphenylphosphonium chloride (3.43 g, 10 mmol) THF (16 mL) at 0° C. was added t-BuOK (1.68 g, 15 mmol). The resulting mixture was stirred at rt for 30 mins. A solution of intermediate 2 (2.2 g, 5.0 mmol) in THF (4.0 mL) was added and stirred at rt for 20 h. It was quenched with aqueous NH₄Cl and the mixture was extracted with EtOAc, washed with water, brine. The organic layer was dried (Na₂SO₄), filtered and concentrated. The crude product was chromatographed (silica, hexanes/EtOAc) to give the desired compound as a white solid (2.08 g, 89%). ESI-MS m/z=466.13, 468.13 [M–H]⁻.

Step 20b.

Into a solution of the compound from step 20a (1.1 g, 2.35 mmol) in THF (10 mL) at rt was added conc. HCl (1.5 mL) and stirred at rt for 2 h. It was concentrated under vacuum to remove majority of THF and the residue was extracted with EtOAc. The organic phase was washed with water, 10% K₂CO₃, brine, dried over Na₂SO₄, filtered, concentrated to give desired compound (0.95 g, 89%). ESI-MS m/z=452.07, 454.07 [M–H]⁻.

Step 20c.

To a solution of compound from step 20b (0.27 g, 0.59 mmol) in THF (6.0 mL) at 0° C. was added vinyl magnesium bromide (2.37 mL 1 M in THF, 2.37 mmol). The resulting reaction mixture was stirred at 0° C. for 1 h. The reaction was quenched with aqueous NH₄Cl and the mixture was extracted with EtOAc, washed with water, brine. The organic layer was dried (Na₂SO₄), filtered and concentrated. The crude product was chromatographed (silica, hexanes/EtOAc) to give the desired compound as mixture of diastereomers (50 mg, 17%). ESI-MS m/z=480.08, 482.08 [M–H]⁻.

Step 20d.

To a mixture of compound from step 20c (50 mg, 0.104 mmol) and NMO (73 mg, 0.62 mmol) in acetone (3.0 mL) at rt was added osmium tetroxide (0.66 ml, 4% in water, 0.104 mmol) and the mixture was stirred at rt for 16 h. It was quenched with aqueous Na₂SO₃, extracted with EtOAc, washed with water, 3N HCl, NaHCO₃, brine, dry over Na₂SO₄, filtered, concentrated and purified by prep-HPLC using a C18 column and acetonitrile/water as eluent to give title compound as mixture of diasteromers (21 mg, 37%). ESI-MS m/z=546.06, 548.06[M–H]⁻.

Example 21

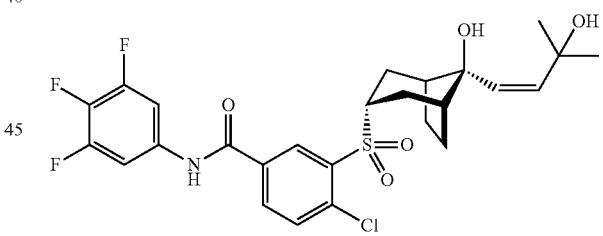

Step 21a. To a clear solution of 2-methylbut-3-yn-2-ol (0.115 g, 1.364 mmol) in THF (5 ml) at −78° C. was added BuLi (2.6 M in hexanes, 1.091 ml, 2.73 mmol) dropwise. The resulting clear solution was stirred at −78° C. for 1 h. A solution of Intermediate 2 (0.150 g, 0.341 mmol) in THF (1 ml) was added at −78° C. The mixture was stirred at −78° C. for 1 h before being allowed to warm up to rt and stirred at rt for 30 min. Saturated NH₄Cl solution was added to quench the reaction. The mixture was diluted with EtOAc and water. The organic layer was washed with brine (*2), dried over Na₂SO₄ (s), filtered and concentrated. The residue was purified by column chromatography (silica, hexanes/EtOAc) to afford the desired product as a yellow solid (0.152 g, 85%). ESI-MS m/z=522.11, 524.11 [M–H]⁻.

Step 21b.

To a solution of the compound from step 21a (140 mg, 0.267 mmol) in ethyl acetate (12 ml) at rt was added Lindlar catalyst (114 mg, 0.053 mmol). The suspension was stirred at rt with a H₂ balloon overnight. LC-MS showed ~20% conversion. The mixture was filtered through a short pad of celite. The filtrate was concentrated. The residue was purified by column chromatography (silica, hexanes/acetone) to afford the desired product as a white solid (23.5 mg, 17%). ESI-MS m/z=524.11, 526.11 [M−H]⁻.

Step 21c.

To a clear solution of the compound from step 21b (23.5 mg, 0.045 mmol) in THF (2.80 ml) and water (0.200 ml) at rt was added NMO (26.2 mg, 0.223 mmol), followed by osmium tetroxide (4% in water, 0.057 ml, 8.94 μmol). The solution was stirred at rt over the weekend before being stirred at 55° C. for 2 overnights. More osmium tetroxide (4% in water, 0.057 ml, 8.94 μmol) was added. The mixture was stirred at 55° C. overnight before being quenched with saturated Na₂S₂O₃ solution and diluted with THF. The organic layer was washed with brine (*2), dried over Na₂SO₄ (s), filtered and concentrated. The residue was dissolved in DMSO (2 ml) and purified by HPLC (40~90% ACN in water) to afford the title compound as a white solid (3.5 mg, 14%). ESI-MS m/z=556.12, 558.11 [M−H]⁻.

Example 22

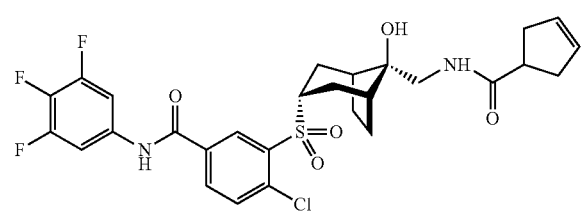

The title compound (44 mg, 84%) was prepared by following the procedure described in Example 14 from intermediate 3 and cyclopent-3-ene-1-carboxylic acid. ESI-MS m/z=641.13, 643.13 (M+HCO₂)⁻.

Example 26

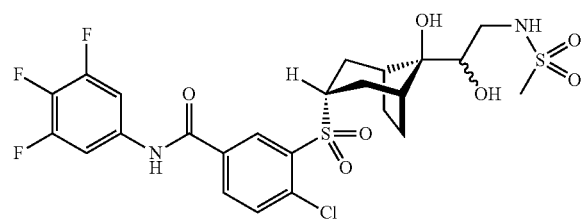

Step 26a. The desired compound was prepared from the compound of example 11 following a procedure similar to that described in step Int 3d, ESI-MS m/z=531.09, 533.09 [M−H]⁻.

Step 26b.

A solution of compound from step 26a (50 mg, 0.091 mmol) and DMAP (60 mg, 0.49 mmol) in THF-water (1.0/0.1 ml) at rt was treated with MsCl (38 mg, 0.33 mmol) at rt for 1 h. It was concentrated under vacuum and purified by prep-HPLC (C18, acetonitrile/water) to give the title compound (13 mg, 23%). ESI-MS m/z=609.07, 611.07 [M−H]⁻.

Example 27

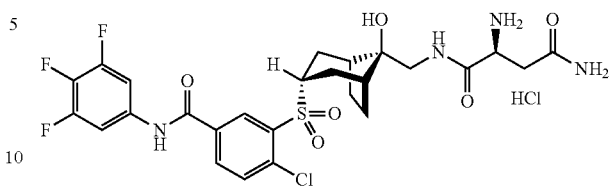

Step 27a. The desired compound was prepared using a procedure similar to that described in Example 14 from intermediate 3 and (tert-butoxycarbonyl)-L-asparagine ESI-MS. m/z=715.18, 717.18 [M−H]⁻.

Step 27b.

The compound from Step 27a was treated with HCl (4 M in dioxane) for two hours at rt. It was concentrated to give the title compound as white solid as HCl salt. ESI-MS m/z=615.12, 617.12 [M−H−56]⁻.

Example 28

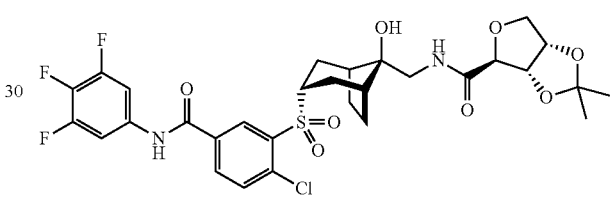

Step 28a Adonitol (1.0 g, 6.57 mmol) and pyridine hydrochloride (1.215 g, 10.52 mmol) were mixed neat and heated to 150° C. for 4 h. The crude product was chromatographed (silica, EtOAc/MeOH) to give the desired compound as colorless gum (882 mg, 100%).

Step 28b.

To a solution compound from step 28a and 2,2-dimethoxypropane (3.23 ml, 26.3 mmol) in Acetone (26.303 ml) was added PTSA (250 mg, 1.315 mmol) then stirred at rt for 30 minutes. The reaction was quenched with aqueous NaHCO₃ and the mixture was extracted with EtOAc, washed with water and brine. The organic layer was dried (Na₂SO₄), filtered and concentrated. The crude product was chromatographed (silica, dichloromethane/MeOH) to give the desired compound as colorless oil (852 mg, 74%).

Step 28c.

To a solution of compound from Step 28b (327 mg, 1.88 mmol) in acetonitrile (2 ml) and water (2 ml) was added TEMPO (59 mg, 0.375 mmol) and iodobenzene diacetate (1.21 g, 3.75 mmol). The reaction was stirred at rt for 1 h. The reaction was extracted with EtOAc, washed with water and brine. The organic layer was dried (Na₂SO₄), filtered and concentrated. The crude acid was used without further purification (454 mg, 50% purity, 64%).

Step 28d.

To a solution of Intermediate 3 (150 mg, 0.30 mmol) and compound from step 28c (168 mg, 0.447 mmol, 50% purity) in DMF (3 ml) was added EDC (114 mg, 0.60 mmol) and DMAP (109 mg, 0.90 mmol). The reaction was stirred at rt for 2 h. The reaction was extracted with EtOAc, washed with water and brine. The organic layer was dried (Na₂SO₄), filtered and concentrated. The crude product was chromatographed (silica, hexane/acetone) to give the title compound as white solid (117 mg, 58%). ESI-MS m/z=717.153, 719.151 [M+CO₂H]⁻.

Example 29

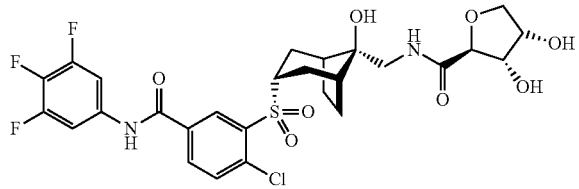

To a solution of compound from example 28 (115 mg, 0.171 mmol) in THF (5 ml) and methanol (10 ml) was added HCl (4 ml, 2 M aq, 8 mmol). The reaction was heated to 60° C. for 1 h. The reaction was extracted with EtOAc, washed with NaHCO₃, water, and brine. The organic layer was dried (Na₂SO₄), filtered and concentrated. The crude product was chromatographed (silica, hexane/acetone) to give the title compound as white solid (76 mg, 70%). ESI-MS m/z=677.119, 679.117 [M+CO₂H]⁻.

Example 32

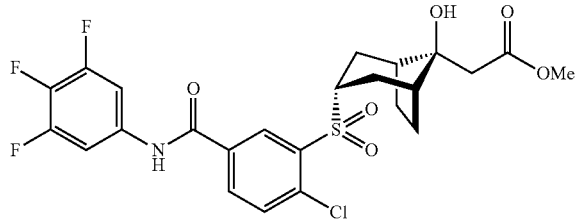

Step 32a. To solution of Intermediate 2 (3.20 g, 7.27 mmol) and tert-butyl((1-methoxyvinyl)-oxy)dimethylsilane (1.905 ml, 8.73 mmol) in THF (36 ml) at −78° C. was added BF₃ diethyletherate (1.11 ml, 8.73 mmol). Stir for 1 h at −78° C. then warm to rt over 1 h. The reaction was quenched with NaHCO₃ (aq). The crude was extracted with EtOAc, washed with water and brine. The organic layer was dried (Na₂SO₄), filtered and concentrated. The crude product was chromatographed (silica, hexane/EtOAc) to give the desired compound as white solid (2.976 g, 80%). ESI-MS m/z=511.8, 513.8 [M−H]⁻.

Step 32b.

To a solution of material from step 32a (2.976 g, 5.79 mmol) in NMP (29 ml) was added m-CPBA (3.89 g, 17.37 mmol, 77%). The reaction was stirred at rt for 18 h. The reaction was extracted with EtOAc, washed with water and brine. The organic layer was dried (Na₂SO₄), filtered and concentrated. The residue was triturated with methanol and filtered to give the title compound as a white solid (2.50 g, 4.58 mmol). ESI-MS m/z=544.076, 546.074 [M−H]⁻.

Example 33

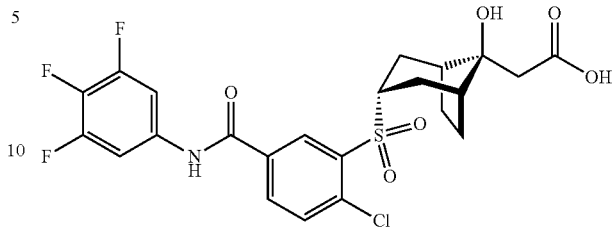

To solution of the compound of example 32 (2.50 g, 4.58 mmol) in THF (27 ml) and methanol (18 ml) was added LiOH (9.16 ml, 18.32 mmol, 2 M aq). It was stirred at rt for 6 h. The reaction was acidified to pH 3 with HCl (2 M, aq). The crude was extracted with EtOAc, washed with brine. The organic layer was dried (Na₂SO₄), filtered and concentrated to give the title compound (2.40 g, 99%). ESI-MS m/z=498.068, 500.066 [M−H]⁻.

Example 34

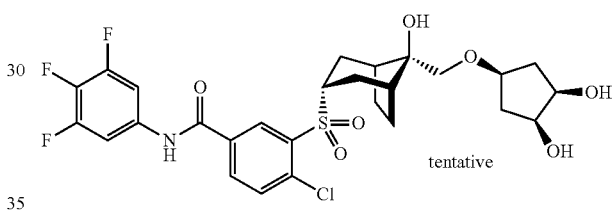

Step 34a. To a solution of compound from intermediate 2 (1.76 g, 4.0 mmol) and trimethyl-sulfoxonium iodide (1.76 g, 8.0 mmol) in DMSO (20 mL) at 0° C. was added t-BuOK (1.12 g, 10 mmol). The resulting reaction mixture was stirred at rt for 1 h. The reaction was quenched with aqueous NH₄Cl and the mixture was extracted with EtOAc, washed with water, brine. The organic layer was dried (Na₂SO₄), filtered and concentrated. The crude product was chromatographed (silica, hexanes/EtOAc) to give the desired compound as white solid (1.36 g, 75%). ESI-MS m/z=452.07, 454.07 [M−H]⁻.

Step 34b.

To a mixture of compound from step 34a (0.12 g, 0.264 mmol) and cyclopent-3-en-1-ol (0.523 mL, 6.61 mmol) was added potassium tert-butoxide (297 mg, 2.64 mmol) at rt and heated at 80° C. for 1 h then 50° C. for 16 h. The reaction was quenched with aqueous NH₄Cl and the mixture was extracted with EtOAc, washed with water, brine. The organic layer was dried (Na₂SO₄), filtered and concentrated. The crude product was chromatographed (silica, hexanes/EtOAc) to give the desired compound (82 mg, 57%). ESI-MS m/z=536.11, 538.11 [M−H]⁻.

Step 34c.

To a mixture of compound from step 34b (50 mg, 0.093 mmol) and NMO (65.3 mg, 0.558 mmol) in acetone (2.0 mL) at rt was added osmium tetroxide (0.29 ml, 4% in water, 0.046 mmol) and the mixture was stirred at rt for 2 days. It was quenched with aqueous Na₂SO₃, extracted with EtOAc, washed with water, 3N HCl, NaHCO₃, brine, dry over Na₂SO4, filtered, concentrated and purified by prep-HPLC using a C18 column and acetonitrile/water as eluent to give title compound which structure was tentatively assigned (11 mg, 19%). ESI-MS m/z=602.12, 604.12 [M–H]⁻.

Example 35

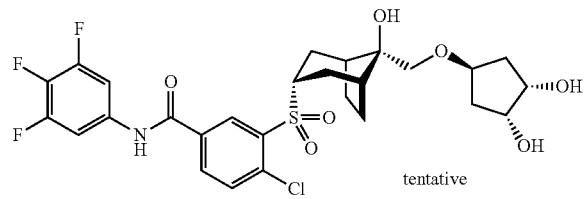

tentative

The title compound (12 mg, 21%) was isolated from example 34. ESI-MS m/z=602.12, 604.12 [M–H]⁻.

Example 36

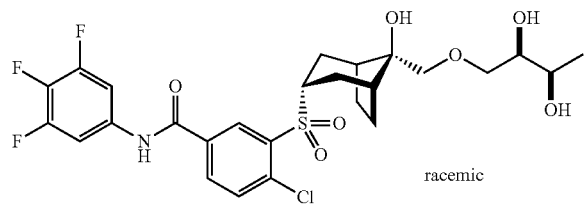

racemic

Step 36a. To a suspension of NaH (160 mg 60%, 4.00 mmol) in DMF (5.0 mL) at 0° C. was added crotyl alcohol (341 µl, 4.00 mmol) and stirred for 30 mina at rt. The compound from step 34a (182 mg, 0.40 mmol) was added and stirred at rt for 16 h. It was quenched with aqueous NH₄Cl, extracted with EtOAc, washed with water, brine, dry over Na₂SO₄. filtered, concentrated, and chromatographed (silica, hexanes/EtOAc) to give desired product (195 mg, 93%). ESI-MS m/z 524.11, 526.11 [M–H]⁻.

Step 36b.
To a mixture of compound from step 36a (190 mg, 0.36 mmol) and NMO (254 mg, 2.17 mmol) in acetone (2.5 mL) at rt was added osmium tetroxide (1.15 ml, 4% in water, 0.181 mmol) and the mixture was stirred at rt for 2 days. It was quenched with aqueous Na₂SO₃, extracted with EtOAc, washed with water, 3N HCl, NaHCO₃, brine, dry over Na₂SO₄, filtered, concentrated and purified by prep-HPLC using a C18 column and acetonitrile/water as eluent to give title compound which structure was tentatively assigned (36 mg, 17%). ESI-MS m/z=590.11, 592.11 [M–H]⁻.

Example 37

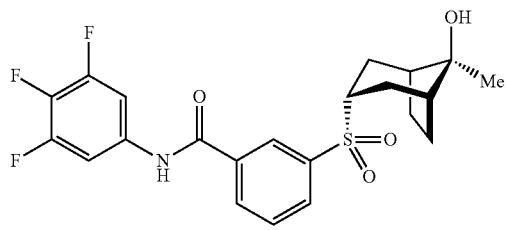

Step 37a. To a solution of the compound from Step Int 2g (1.9 g, 4.30 mmol) in NMP (12 mL) was added m-CPBA (2.89 g, 12.90 mmol) at rt. The mixture was stirred at rt overnight. It was quenched with aqueous Na₂S₂O₃ and aqueous NaHCO₃ solution with a few drops of triethylamine. The mixture was extracted with EtOAc. The organic layer was washed with water, brine, dried over Na₂SO₄, filtered and concentrated. The residual solid was recrytallized from MeOH to afford the desired product as a white solid (1.8 g, 88%). ESI-MS m/z=472.06, 474.06 [M–H]⁻.

Step 37b.
To a solution of the compound from step 37a (1.8 g, 3.8 mmol) in DMSO (10 mL) at rt was added IBX (4.3 g, 15.3 mmol). The mixture was stirred at 45° C. for 20 h. Aqueous Na₂S₂O₃ and aqueous NaHCO₃ solution with a few drops of Et₃N were added. The mixture was stirred at rt for 1 h. It was extracted with EtOAc. The organic layer was washed with water, brine, dried over Na₂SO₄, filtered and concentrated to give the desired compound (1.65 g, 92%). ESI-MS m/z=470.04, 472.04 [M–H]⁻.

Step 37c.
To a solution of the compound from step 37b (104 mg, 0.220 mmol) in THF (2 mL) at 5-10° C. was added methylmagnesium bromide (3 M in ether, 367 µl, 1.102 mmol) dropwise. More THF (2.5 mL) was added and the mixture was stirred at rt for 1 h. It was diluted with EtOAc, washed with water, aqueous Na₂SO₃ and brine. The organic layer was dried (Na₂SO₄), filtered and concentrated. The crude product was purified by Prep-TLC (silica, hexanes/EtOAc) to give the desired compound (85 mg, 79%). ESI-MS m/z=486.08, 488.08 [M–H]⁻.

Step 37d.
To a clear solution of the compound from step 37c (30.0 mg, 0.061 mmol) in THF/MeOH (1/1, 2.0 ml) rt was added 10% Pd/C (6.5 mg, 6.15 µmol) in one portion. The suspension was purged with H₂ 3 times and then stirred at rt with a H₂ balloon overnight. The suspension was then stirred at rt under H₂ (60 psi) for 4 h. More 10% Pd/C (13.0 mg, 12.3 µmol) was added. The suspension was purged with H₂ 3 times and then stirred at rt under H₂ (~15 psi) over the weekend. The mixture was filtered through a short pad of celite. The filtrate was freed of volatiles. The solid residue was triturated with DCM to afford the title compound as a white solid (20.0 mg, 72%). ESI-MS m/z=452.11, 453.11 [M–H]⁻.

Example 38

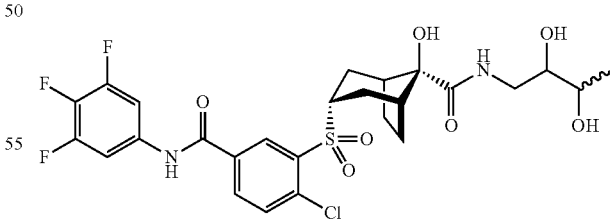

Step 38a. A solution of the compound from Step Int 3a (214 mg, 0.47 mmol) in THF/water (3.0/1.0 mL) at rt was treated with TFA (0.40 mL) at rt for 6 h. It was concentrated under vacuum to remove majority of THF. The residue was extracted with EtOAc. The organic phase was washed with water, 10% K₂CO₃, brine, dried over Na₂SO₄, filtered and concentrated to give the desired compound (0.20 g, 90%). ESI-MS m/z=470.08, 472.08 [M–H]⁻.

Step 38b.

To a solution of the compound from step 38a (0.340 g, 0.720 mmol) in DMSO (6 ml) at rt was added IBX (0.303 g, 1.081 mmol). The resulting milky mixture was stirred at rt for 2 h. The mixture was diluted with EtOAc and water. The organic layer was washed with brine (*2), dried over $Na_2SO_4$ (s), filtered and concentrated. The residue was dried under vacuum to afford the desired product as a white solid (0.324 g, 96%). ESI-MS m/z=468.05, 470.05 [M–H]$^-$.

Step 38c.

To a suspension of the compound from step 38b (0.324 g, 0.690 mmol) in t-BuOH (6.0 ml) and water (2.0 ml) at rt was added potassium phosphate, monobasic (0.657 g, 4.83 mmol), followed by 2-methyl-2-butene (1.826 ml, 17.24 mmol). Sodium chlorite (80%, 0.702 g, 6.21 mmol) was added to the suspension in one portion. The resulting clear solution was stirred at rt for 1 h. It was diluted with MTBE and 1.0 M NaOH (8 mL). The organic layer was diluted with EtOAc, washed with 0.5 M HCl aq (*1), and then brine (*1). The organics were dried over $Na_2SO_4$ (s), filtered and concentrated. The residue was dried under vacuum to afford the desired product as a white solid (0.306 g, 91%). ESI-MS m/z=484.05, 486.05 [M–H]$^-$.

Step 38d.

To a suspension of the compound from step 38c (50.0 mg, 0.103 mmol), but-2-en-1-amine hydrochloride (12.18 mg, 0.113 mmol) and DIPEA (0.054 ml, 0.309 mmol) in acetonitrile (3 ml) at rt was added HATU (47.0 mg, 0.123 mmol) in one portion. The resulting slightly milky solution was stirred at rt overnight. More DIPEA (0.054 ml, 0.309 mmol) and HATU (47.0 mg, 0.123 mmol) were added. The resulting solution was stirred at rt for 4 h and then at 55° C. for 2 h. The mixture was freed of volatiles. The residue was purified by column chromatography (silica, hexanes/EtOAc) to afford the desired product as a white solid (7.0 mg, 12%). ESI-MS m/z=583.11, 585.11 [M–H]$^-$.

Step 38e.

To a clear solution of the compound from 38d (7.0 mg, 0.013 mmol) in THF (2.0 ml) and water (0.14 ml) at rt was added NMO (7.61 mg, 0.065 mmol), followed by osmium tetroxide (0.083 ml, 0.013 mmol). The solution was stirred at 50° C. overnight. The mixture was quenched with saturated $Na_2S_2O_3$ solution and diluted with THF. The organic layer was washed with brine (*2), dried over $Na_2SO_4$ (s), filtered and concentrated. The residue was dissolved in DMSO (1 ml) and purified by HPLC (40~90% ACN in water) to afford the title compound as a white solid (3.0 mg, 38%, racemic mixture of diastereomers). ESI-MS m/z=649.13, 651.13 [M+HCO$_2$]$^-$.

Example 42

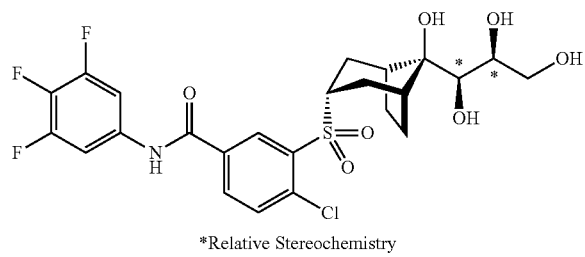

*Relative Stereochemistry

Step 42a. To a solution of the compound from Step 82a (173 mg, 0.37 mmol) in $CH_2Cl_2$ (3.7 mL) at rt was added (Z)-but-2-ene-1,4-diyl diacetate (234 µl, 1.479 mmol) and Grubbs-Hoveyda Second generation catalyst (23.1 mg, 0.037 mmol), then the mixture was degased and kept under reflux for 24 h. The mixture was concentrated, and the residue was chromatographed (silica, hexanes/EtOAc) to give the desired compound as white solid (160 mg, 80%). ESI-MS m/z=584.10, 586.10 (M+HCO$_2$)$^-$.

Step 42b.

To a solution of the compound from Step 42a (20.5 mg, 0.038 mmol) in MeOH (1.3 mL) at rt was added potassium carbonate (10.5 mg, 0.076 mmol), then the mixture was kept at rt for 1 h. The reaction mixture was diluted with water and extracted with $CH_2Cl_2$, the organic phases were dried over $Na_2SO_4$, concentrated to give the desire product (19 mg) without further purification. ESI-MS m/z=542.10, 544.10 (M+HCO$_2$)$^-$.

Step 42c.

To a solution of the compound from Step 42b (18.9 mg, 0.038 mmol) in Acetone/H$_2$O (0.8 mL, 4:1) was added NMO (26.7 mg, 0.228 mmol) and Osmium tetroxide (298 µl, 0.038 mmol). The mixture was kept at 50° C. for 2 days. It was quenched with aqueous $Na_2S_2O_3$, extracted with EtOAc, washed with water, brine, dry over $Na_2SO_4$, filtered, concentrated and purified by prep-HPLC using a C18 column and acetonitrile/water as eluent to give the title compound (3.9 mg, 18%). ESI-MS m/z=608.10, 610.10 (M+HCO$_2$)$^-$.

Example 51

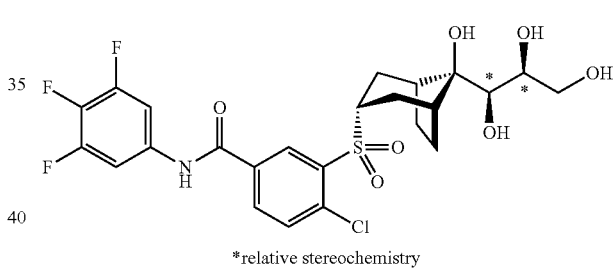

*relative stereochemistry

Step 51a. To a clear solution of 1-methoxy-4-((prop-2-yn-1-yloxy)methyl)benzene (801 mg, 4.55 mmol) in THF (15 ml) at −78° C. was added BuLi (2.6 M in hexanes, 1.819 ml, 4.55 mmol) dropwise. The resulting clear solution was stirred at −78° C. for 0.5 h. A solution of Intermediate 2 (500 mg, 1.137 mmol) in THF (3 ml) was added at −78° C. dropwise. The mixture was stirred at −78° C. for 1 h before being quenched with saturated NH$_4$Cl solution. It was allowed to warm up to rt and diluted with EtOAc and water. The organic layer was washed with brine (*1), dried over $Na_2SO_4$ (s), filtered and concentrated. The residue was purified by column chromatography (silica, hexanes/EtOAc) to afford the desired product as a white solid (0.440 g, 63%). ESI-MS m/z=614.14, 616.14 [M–H]$^-$.

Step 51b.

To a solution of the compound from step 51a (0.140 g, 0.227 mmol) in ethyl acetate (10 ml) at rt was added Lindlar catalyst (0.097 g, 0.045 mmol). The suspension was stirred at rt with a H$_2$ balloon for 2 h. The mixture was filtered through a short pad of celite. The filtrate was concentrated. The residue was purified by column chromatography (silica, hexanes/EtOAc) to afford the desired product as a white solid (96.0 mg, 68%). ESI-MS m/z=616.15, 618.15 [M–H]$^-$.

Step 51c.

To a clear solution of the compound from step 51c (46.0 mg, 0.074 mmol) in DCM (2 ml) at rt was added pH 7 buffer (0.4 ml), followed by DDQ (33.8 mg, 0.149 mmol). The biphasic mixture was stirred at rt for 3 h. It was quenched with saturated NaHCO$_3$ solution and diluted with DCM. The organic layer was dried over Na$_2$SO$_4$ (s), filtered and concentrated. The residue was purified by chromatography (silica, hexanes/EtOAc) to afford the desired product as a white solid (20.2 mg, 54%). ESI-MS m/z=496.09, 498.09 [M–H]$^-$.

Step 51d.

To a clear solution of the compound from step 51c (45.6 mg, 0.092 mmol) in THF (5.60 ml) and water (0.56 ml) at rt was added NMO (53.6 mg, 0.458 mmol), followed by osmium tetroxide in t-butanol (2.5%, 0.186 ml, 0.018 mmol). The solution was stirred at rt for 4 h and then at 50° C. for 2 overnights. The mixture was quenched with saturated Na$_2$S$_2$O$_3$ solution and diluted with THF. The organic layer was washed with brine (*2), dried over Na$_2$SO$_4$ (s), filtered and concentrated. The residue was dissolved in DMSO (2 ml) and purified by HPLC (30~90% ACN in water) to afford the title compound as a white solid (15.0 mg, 29%). ESI-MS m/z=608.09, 610.08 [M+HCO$_2$]$^-$.

Example 52

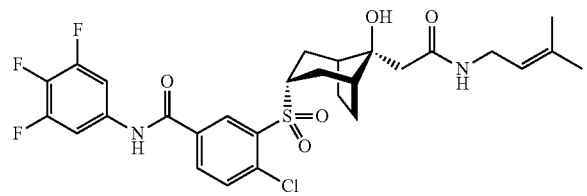

To solution of compound from Example 33 (50 mg, 0.094 mmol), 3-methylbut-2-en-1-amide hydrochloride (12.6 mg, 0.103 mmol), and DIPEA (0.5 ml, 0.282 mmol) in DMF (0.9 ml) was added a solution of HATU (54 mg, 0.141 mmol) in DMF (0.5 ml). Stir 2 h at rt. The crude reaction mixture was chromatographed (silica, hexane/acetone) to give the title compound as white solid (40 mg, 71%). ESI-MS m/z=596.8, 598.8 [M–H]$^-$.

Example 56

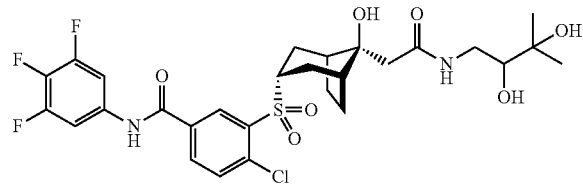

To a solution of Example 52 (40 mg, 0.067 mmol) in acetone (5 ml) was added OsO$_4$ (0.085 ml, 4% w/w water, 0.013 mmol) and NMO (19.6 mg, 0.167 mmol). It was stirred for 48 h at rt then evaporated onto silica. The residue was chromatographed (silica, hexane/acetone) to give the title compound as white solid (18 mg, 43%). ESI-MS m/z=630.8, 632.8 [M–H]$^-$.

Example 61

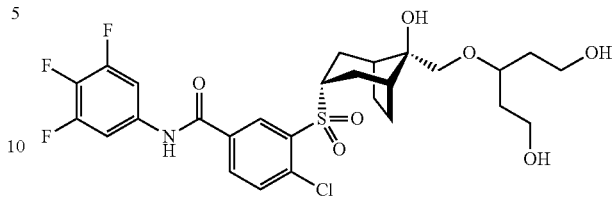

Step 61a. To a mixture of compound from example 34 (0.030 g, 0.050 mmol) and sodium bicarbonate (8.4 mg, 0.10 mmol) in THF-water (1.5/0.5 mL) was added sodium periodate (0.032 g, 0.150 mmol) and stirred at rt 16 h. It was extracted with EtOAC, washed with water, brine, dry over Na$_2$SO$_4$, filtered, concentrated and used in next step without further purification. ESI-MS m/z=600.10, 602.10 [M–H]$^-$.

Step 61b.

To a solution of compound from step 61a (30 mg, 0.050 mmol) in THF-MeOH (1.5/0.5 mL) was added NaBH$_4$ (7.57 mg, 0.20 mmol) at 0° C. then stirred at 0° C. for 30 mins. it was quenched with aqueous NH$_4$Cl, extracted with EtOAc, washed with water, brine, dry over Na$_2$SO$_4$, filtered, concentrated and purified by prep-HPLC using a C18 column and acetonitrile/water as eluent to give title compound (7.6 mg, 25%). ESI-MS m/z=604.13, 606.13 [M–H]$^-$.

Example 64

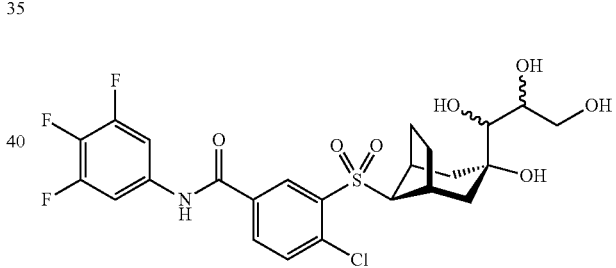

Step 64a.

To a solution of intermediate 5 (250 mg, 0.50 mmol) in THF (5 ml) in an ice-water bath was added vinylmagnesium chloride in THF (1.6 M, 1.25 mL, 2.0 mmol) and stirred at rt for 1 h before it was quenched with aq. NH$_4$Cl. It was extracted with EtOAc and washed with brine. After dried (Na$_2$SO$_4$), it was concentrated to give the crude desired compound which was used in the next step without further purification. ESI-MS m/z=528.07, 530.07 [M–H]$^-$.

Step 64b.

To a solution of crude compound of step 64a (0.3 mmol at most) in acetone (5 ml) and water (1 mL), NMO (67 mg, 0.57 mmol) and OsO$_4$ (4% in water, 0.12 mL, 0.02 mmol) was added and stirred at rt for 2 days after quenched with aq. Na$_2$S$_2$O$_3$, it was extracted with EtOAc before being dried and concentrated. The crude was chromatographed (silica, acetone/hexanes) to give the title compounds as a mixture of two pair of racemic products (122 mg, 57%, white solid). ESI-MS m/z=562.08, 564.08 [M–H]$^-$.

Example 70

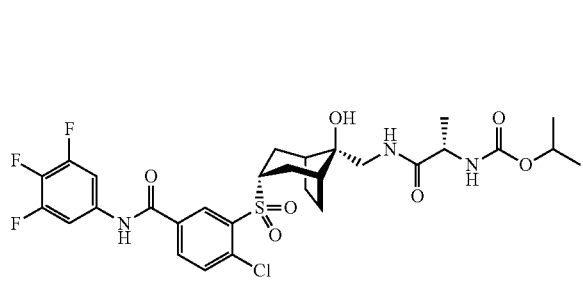

Step 70a. To a solution of Intermediate 3 (119 mg, 0.237 mmol), Boc-(L)-alanine (49 mg, 0.260 mmol) and DIPEA (0.124 ml, 0.71 mmol) in DMF (2.4 ml) was added HATU (135 mg, 0.355 mmol). The reaction was stirred at rt for 3 h. The reaction was extracted with EtOAc, washed with water and brine. The organic layer was dried ($Na_2SO_4$), filtered and concentrated. The crude product was chromatographed (silica, hexane/acetone) to give the desired product as white solid (54 mg, 34%).

Step 70b.

To a solution of compound from step 70a (54 mg, 0.08 mmol) in THF (2 ml) was added HCl (2 ml, 8 mmol, 4 M in dioxane). The reaction was stirred for 2 h then evaporated to give crude product used without further purification.

Step 70c.

To a solution of compound from step 70b (23 mg, 0.04 mmol) and DIPEA (0.017 ml, 0.1 mmol) in DMF was added isopropyl chloroformate (0.048 ml, 0.048 mmol, 1 M toluene). Stir 15 minutes at rt. The crude reaction mixture was chromatographed (prep-HPLC, acetonitrile/water) to give the title compound as white solid (3.8 mg, 14%). ESI-MS m/z=660.0, 662.0 [M+H]$^+$.

Example 74

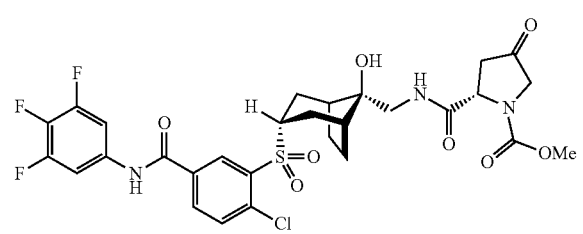

To a solution of compound from example 8 (62 mg, 0.092 mmol) in DMSO (0.6 mL) at rt was added IBX (38.6 mg, 0.138 mmol) and stirred at 45° C. for 16 h. It was quenched with MeOH and purified by prep-HPLC using a C18 column and acetonitrile/water as eluent to give title compound (11 mg, 18%). ESI-MS m/z=670.13, 672.13 [M−H]$^-$.

Example 76

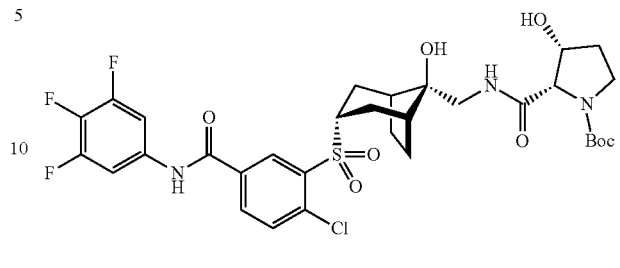

Step 76. To a solution of Intermediate 3 (95.0 mg, 0.189 mmol) and (2S,3R)-1-(tert-butoxycarbonyl)-3-hydroxypyrrolidine-2-carboxylic acid (43.7 mg, 0.189 mmol) in DMF (3 ml) at rt was added DIPEA (0.099 ml, 0.567 mmol), followed by HATU (108 mg, 0.283 mmol). The resulting clear solution was stirred at rt for 1 h. The mixture was freed of volatiles. The residue was dissolved in DCM with some THF and purified by column chromatography (silica, DCM/MeOH) to afford the title compound as a colorless sticky oil (128 mg, 95%). ESI-MS m/z=760.20, 762.20 [M+HCO$_2$]$^-$.

Example 78

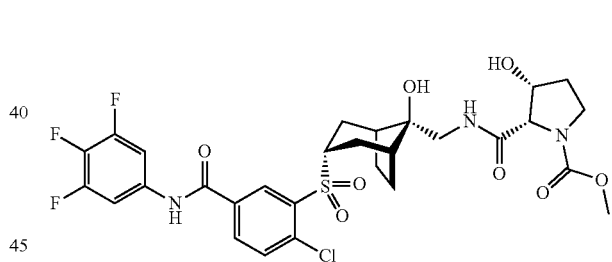

Step 78a. To a solution of compound from example 76 (0.064 g, 0.090 mmol) in THF (2 ml) at rt was added HCl (4 M in 1,4-dioxane, 0.900 ml, 3.60 mmol). The resulting clear solution was stirred at rt for 3 h. It turned into a suspension. The mixture was concentrated. The residual solid was used directly for next step. ESI-MS m/z=660.15, 662.15 [M+HCO$_2$]$^-$.

Step 78b.

To a solution of the compound from step 78a (0.090 mmol) in DMF (2.0 ml) at rt was added DIPEA (0.157 ml, 0.900 mmol), followed by a solution of methyl chloroformate (6.97 µl, 0.090 mmol) in DMF (0.1 ml). The resulting yellow solution was stirred at rt for 1 h before being freed of volatiles. The residue was dissolved in DMSO (2 ml) and purified by HPLC (40~90% ACN in water) to afford the title compound as a white solid (20.0 mg, 33% over 2 steps). ESI-MS m/z=718.16, 720.16 [M+HCO$_2$]$^-$.

Example 82

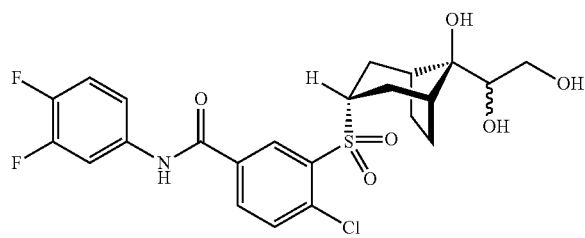

Step 82a. To a solution of the compound of step 150d (210 mg, 0.50 mmol) in THF (5 ml) in an ice-water bath was added vinylmagnesium chloride in THE (1.6 M, 0.94 mL, 1.5 mmol). It was stirred at rt for 1 h before it was quenched with aq. NH₄Cl. It was extracted with EtOAc and washed with brine. After drying (Na₂SO₄), it was concentrated and the residue was chromatographed (silica, EtOAc/hexanes) to give the desired compound (201 mg, 94%) as a white solid. ESI-MS m/z=448.08, 450.08 [M–H]⁻.

Step 82b.

To a solution of the compound of step 82a (152 mg, 0.34 mmol) in acetone (1 ml) and water (0.2 mL), NMO (79 mg, 0.68 mmol) and OsO₄ (2.5% in t-BuOH, 0.12 mL, 0.007 mmol) was added. It was stirred at rt o/n before being quenched with aq. Na₂S₂O₃. It was extracted with EtOAc, dried and concentrated. The crude was crystallized from MeOH to give the title compound (141 mg, 84%, racemic) as a white solid. ESI-MS m/z=514.08, 516.08 [M–H]–.

Example 106

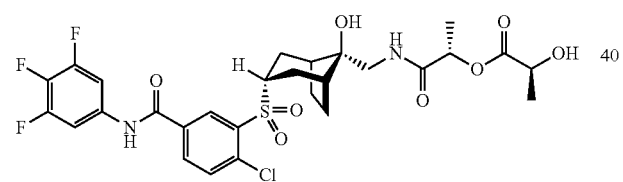

The title compound (single enantiomer) was isolated from the preparation of the compound of example 13. ESI-MS m/z=645.11, 647.11 [M–H]⁻.

Example 108

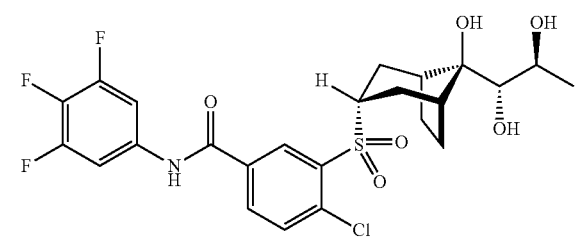

The title compound (single enantiomer, tentatively assigned) was isolated from the compound of example 4 via SFC chromatography.

Example 109

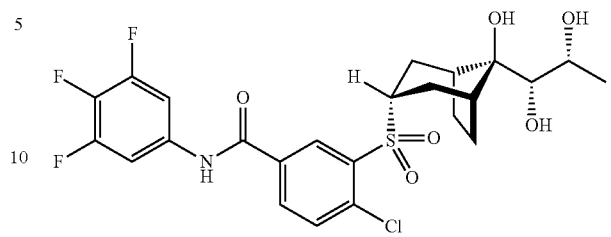

The title compound (single enantiomer, tentatively assigned) was isolated from the compound of example 5 via SFC chromatography.

Example 120

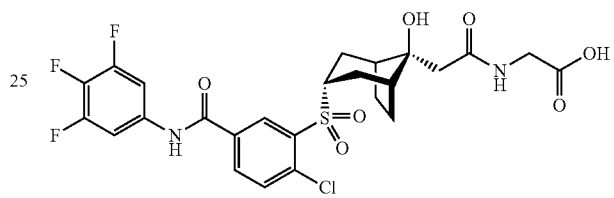

To a solution of compound from example 119 (50 mg, 0.083 mmol) in THE (1 ml) and water (0.67 ml) was added LiOH (0.33 ml, 0.67 mmol, 2 M aq) at rt. The reaction was stirred for 1 h, then acidified to pH 3 with 2 M HCl. The reaction was extracted with EtOAc, washed with water and brine. The organic layer was dried (Na₂SO₄), filtered and concentrated to give the title compound as a white solid (40 mg, 82%). ESI-MS m/z=586.8, 588.8 [M–H]⁻.

Example 121

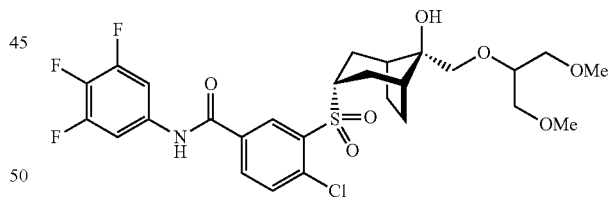

Step 121a. To a solution of compound from step 34a (170 mg, 0.375 mmol) and 1,3-dimethoxypropan-2-ol (900 mg, 7.49 mmol) in THE (2 mL) was added potassium 2-methylpropan-2-olate (630 mg, 5.62 mmol) at rt then the mixture was stirred at 60° C. for 20 h. It was cooled to rt, quenched with aqueous NH₄Cl, extracted with EtOAc, washed with water, brine, dry over Na₂SO₄, filtered, concentrated and chromatographed (silica, hexanes/EtOAc) to give desired product (98 mg, 45%). ESI-MS m/z 572.15, 574.15 [M–H]⁻.

Step 121b.

To a solution of compound from step 121a (95 mg, 0.165 mmol) in NMP (1.5 mL) was added mCPBA (0.167 g 77%, 0.745 mmol) and stirred at rt for 20 h. Aqueous Na₂S₂O₃, NaHCO₃ and few drops of Et₃N was added and stirred at rt for 1 h. It was extracted with EtOAc, washed with water, brine, dry over Na₂SO₄, filtered, concentrated and purified by prep-HPLC using a C18 column and acetonitrile/water as eluent to give title compound (44 mg, 44%). ESI-MS m/z=604.14, 606.14 [M−H]⁻.

Example 124

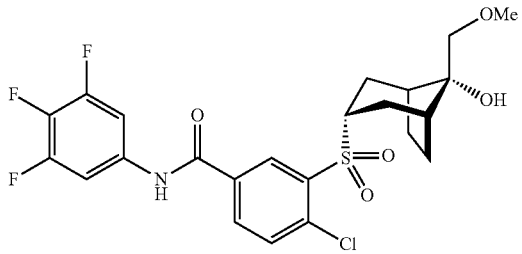

Step 124a. To a suspension of methyltriphenylphosphonium bromide (0.24 g, 0.67 mmol) THF (1.0 mL) at 0° C. was added t-BuOK (0.11 g, 1.0 mmol). The resulting reaction mixture was stirred at rt for 30 mins. A solution of compound from intermediate 2 (0.15 g, 0.34 mmol) in THF (1.0 mL) was added and stirred at rt for 24 h. The reaction was quenched with aqueous NH₄Cl and the mixture was extracted with EtOAc, washed with water, brine. The organic layer was dried (Na₂SO₄), filtered and concentrated. The crude product was chromatographed (silica, hexanes/EtOAc) to give the desired compound as white solid (1.36 g, 75%). ESI-MS m/z=436.08, 438.07 [M−H]⁻.

Step 124b.

To a suspension of compound from step 124a (0.35 g, 0.80 mmol) and NMO (0.375 g, 3.2 mmol) in acetone-water (6 mL/1 mL) at rt was added osmium tetroxide (1.0 ml, 0.080 mmol) and the mixture was stirred at rt for 18 h. It was quenched with aqueous Na₂SO₃, extracted with EtOAc, washed with water, 3N HCl, NaHCO₃, brine, dry over Na₂SO₄, filtered, concentrated to give a mixture of sulfone and sulfoxide.

Step 124c.

To a solution of compound from step 124b (156 mg, 0.32 mmol) in DMF (1.5 mL) at 0° C. was added NaH (45 mg 60%, 1.12 mmol) and MeI (45 mg, 0.32 mmol). After 1.5 h at 0° C., the reaction was quenched with aqueous NH₄Cl solution, extracted with EtOAc and the organic layer was washed with water and brine. The organic layer was dried (Na₂SO₄), filtered and concentrated, purified on prep-HPLC (C-18, Acetonitrile/water) to afford the title compound as a white solid (61 mg, 38%). ESI-MS m/z=500.09, 502.09 [M−H]⁻.

Step 124d.

To a solution of compound from step 124c (61 mg, 0.122 mmol) in NMP (1.5 mL) was added mCPBA (0.11 g 77%, 0.49 mmol) and stirred at rt for 20 h. Aqueous Na₂S₂O₃, NaHCO₃ and few drops of Et₃N was added and stirred at rt for 1 h. It was extracted with EtOAc, washed with water, brine, dry over Na₂SO₄, filtered, and concentrated to give the title compound (63 mg, 100%). ESI-MS m/z=516.08, 518.08 [M−H]⁻.

Example 125

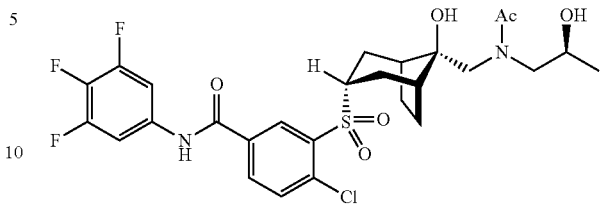

Step 125a.

To a solution of compound of step int 3a (91 mg, 0.2 mmol) in DMF (1 ml), was added (S)-1-aminopropan-2-ol (45 mg, 0.6 mmol) and stirred at 90° C. for 20 hours before being cooled. It was concentrated to give the crude desired compound which was used in the next step without further purification. ESI-MS m/z=527.12, 529.12 [M−H]⁻.

Step 125b.

To a solution of half of the compound of step 125a (~0.1 mmol) in CH₂Cl₂ (1 ml) was added TEA (3 drops) and acetic anhydride (20 mg). It was stirred 2 hours before was concentrated. NMP (1 mL) was added, followed by m-CPBA (13.5 mg, 6 mmol) and stirred at rt for 20 hours. The crude was purified by prep-HPLC (C18, acetonitrile/water) to give title compound (18 mg, 30%, three steps). ESI-MS m/z=601.13, 603.13 [M−H]⁻.

Example 130

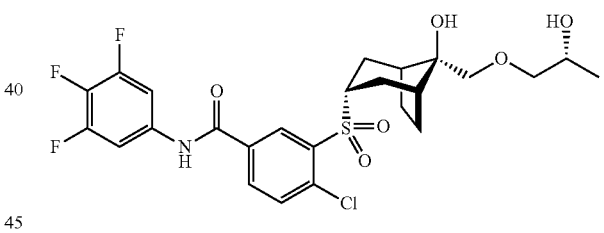

Step 130a.

To a solution of (R)-propane-1,2-diol (168 mg, 2.20 mmol) in DMF (3 mL) was added NaH (88 mg 60%, 2.20 mmol) at 0° C. and stirred at rt for 30 mins. The compound from step 34a (100 mg, 0.220 mmol) was added and heated at 55° C. for 20 h. It was cooled to rt, quenched with aqueous NH₄Cl, extracted with EtOAc, washed with water, brine, dry over Na₂SO₄, filtered, concentrated and chromatographed (silica, hexanes/EtOAc) to give desired product (65 mg, 56%). ESI-MS m/z 528.12, 530.12 [M−H]⁻.

Step 130b.

To a solution of compound from step 130a (80 mg, 0.15 mmol) in NMP (1.5 mL) was added mCPBA (0.169 g 77%, 0.75 mmol) and stirred at rt for 20 h. Aqueous Na₂S₂O₃, NaHCO₃ and few drops of Et₃N was added and stirred at rt for 1 h. It was extracted with EtOAc, washed with water, brine, dry over Na₂SO₄, filtered, concentrated and purified by prep-HPLC using a C18 column and acetonitrile/water as eluent to give title compound (65 mg, 77%, single enantiomer). ESI-MS m/z=560.11, 562.11 [M−H]⁻.

Example 136

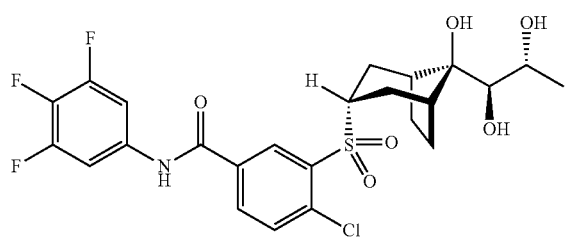

The title compound (single enantiomer, tentatively assigned) was isolated from the compound of example 4 via SFC chromatography. ESI-MS m/z=546.10 [M+H]$^+$.

Example 137

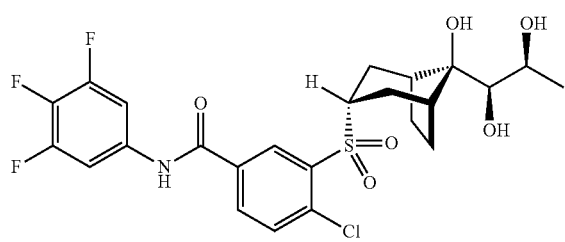

The title compound (single enantiomer, tentatively assigned) was isolated from the compound of example 5 via SFC chromatography. ESI-MS m/z=546.05[M+H]$^+$.

Example 141

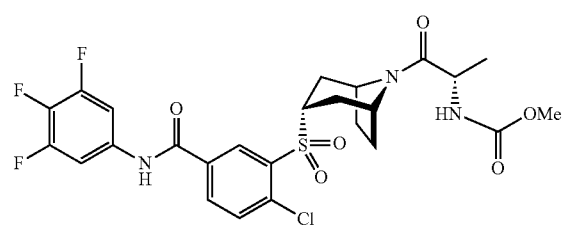

Step 141a.

A solution of Intermediate 1 (1.23 g, 3.88 mmol), 3-exo-Hydroxy-8-azabicyclo[3.2.1]octane-8-carboxylic acid tert-butyl ester (801 mg, 3.52 mmol) in 50 ml, toluene was added 2-(tributyl-15-phosphanylidene)acetonitrile (2.13 g, 8.81 mmol) then stirred at 85° C. O/N. it was diluted with methyl tert-butyl ether, washed with 0.5 N NaOH aqueous solution, water, brine, dry over Na$_2$SO$_4$, filtered, concentrated. The residue was chromatographed (silica, hexanes/EtOAc) to give the desired compound as white solid (1.63 g, 86%). ESI-MS m/z=525.12, 527.12 (M–H)$^-$.

Step 141b.

To the solution of the compound from Step 141a (1.31 g, 2.48 mmol) in N-Methyl-2-pyrrolidinone (8.29 ml) at rt was added mCPBA (1.95 g, 8.70 mmol), then the mixture was kept at rt for overnight. The reaction was quenched with Na$_2$S$_2$O$_3$ aqueous solution. The mixture was extracted with EtOAc, and the combined organic phases were dried over Na$_2$SO$_4$, filtered and concentrated. The residue was chromatographed (silica, hexanes/EtOAc) to give the desired compound as white solid (1.28 g, 92%). ESI-MS m/z=557.11, 559.11 (M–H)$^-$.

Step 141c.

To a solution of the compound from Step 141b (131 mg, 0.234 mmol) was added 2N HCl in dioxane at rt, then the mixture was kept at rt for 4 h. The solution was concentrated to give a white solid (106 mg, 99%). ESI-MS m/z=457.06, 459.06 (M–H)$^-$.

Step 141d.

To a solution of the compound from Step 141c (45 mg, 0.091 mmol) in DMF (1.8 mL) at rt was added iPr$_2$EtN (63.5 μl, 0.363 mmol), (methoxycarbonyl)-L-alanine (13.4 mg, 0.091 mmol) and HATU (51.8 mg, 0.136 mmol). The mixture was kept at rt for overnight. The mixture was partitioned between EtOAc and water. The organic phase was washed with NaHCO$_3$ aqueous solution, water and brine, dried over Na$_2$SO$_4$, filtered and concentrated. The residue was chromatographed (silica, CH$_2$Cl$_2$/MeOH) to give the title compound as white solid (37 mg, 69%, single enantiomer). ESI-MS m/z=586.10, 588.10 (M–H)$^-$.

Example 144

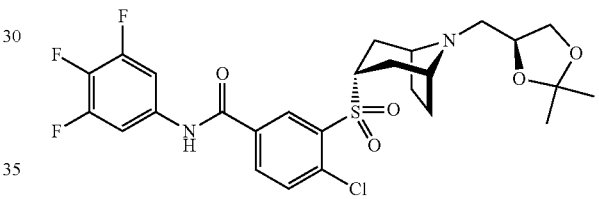

To a solution of the compound from Step 141c (49 mg, 0.099 mmol) in MeOH (0.99 mL) at rt was added (R)-2,2-dimethyl-1,3-dioxolane-4-carbaldehyde (19.31 mg, 0.148 mmol) and NaCNBH$_4$ (12.4 mg, 0.198 mmol), then the mixture was kept at rt for overnight. The reaction was quenched with NH$_4$Cl aqueous solution at rt. The reaction mixture was partition between EtOAc and water, then the organic phase was washed with water and brine, dried over Na$_2$SO$_4$, filtered and concentrated. The residue was chromatographed (silica, CH$_2$Cl$_2$/MeOH) to give the title compound as white solid (45 mg, 79%, single enantiomer). ESI-MS m/z=571.12, 573.12 (M–H)$^-$.

Example 150

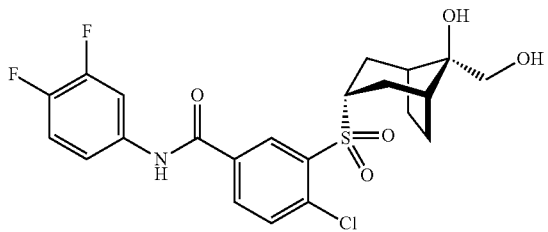

Step 150a.

To a solution of compound from step Int 2e (246 g, 959 mmol) and pyridine (155 ml, 1.92 mol) in DCM (1 L) at 0°

C. was added 3-nitrobenzenesulfonyl chloride (217 g, 978 mmol). The reaction mixture was stirred at 0° C. for 30 mins and rt for 2 days. It was quenched with water (100 mL) and stirred at rt for 1 hr followed by extraction with MBTE (4 L). The organic layer washed with water (2×1 L), 1N HCl (1 L), water (500 mL), sat NaHCO₃ (500 mL), and brine (500 mL), dried over Na₂SO₄, filtered through celite and concentrated to about (500 mL), then hexanes (500 mL) was added. The mixture was concentrated under vacuum to induce precipitation, cooled to rt and filtered, washed with cold hexanes to give desired product (321 g, 76%).

Step 150b.

To a solution of compound from step 150a (108.6 g, 246 mmol), Intermediate 4 (70 g, 234 mmol) in DMF (250 mL) was added cesium carbonate (96 g, 295 mmol). The reaction mixture was degased and slowly heated to 70° C. and stirred at 70° C. for 14 h. It was cooled to rt, diluted with MBTE, washed with water and brine, dried over Na₂SO₄, filtered and concentrated to give desired product (123 g, 98%) which was used without further purification.

Step 150c.

To a suspension of compound from step 150b (50 g, 93 mmol) in MeOH (1.6 L) in a cold water bath was added Con. HCl (200 mL) slowly to keep temperature below 30° C., then stirred at rt overnight. The reaction mixture was concentrated under vacuum to a volume of ~700 mL, cooled to 0° C., then filtered to collect the solid, which was washed with cold MeOH. Then mother liquor was concentrated to 300 mL, cooled to 0° C., filtered to collect solid. The solid was air dried for 14 h to give desired product (36 g, 91%).

Step 150d.

To a solution of compound from step 150c (36 g, 85 mmol) in DMSO (150 mL) at rt was added IBX (30.9 g, 110 mmol), then stirred at 50° C. for 2 h. The mixture was poured into 1.2 L cold water, which was extracted with EtOAc (2×500 mL). Some white solid was removed by filtration. The EtOAc extracts were washed with saturated aq. NaHCO₃ solution, brine, dried over Na₂SO₄. Filtration and concentration to ~150 mL, then cooling to 0° C. gave desired solid that was collected by filtration. The mother liquor was concentrated to 50 mL to give the second crop of desired product (34.1 g, 95%).

Step 150e.

To a suspension of trimethylsulfoxonium iodide (36.3 g, 165 mmol) in DMF (180 ml) at 0° C. was added potassium tert-butoxide (18.51 g, 165 mmol, 1.6 eq) then stirred at rt for 30 mins. A solution of compound from step 150d (43.5 g, 103 mmol) in DMF (120 ml) was added to the reaction mixture via cannula (temperature below 10° C.) and stirred at rt for 16 h. The reaction mixture was poured into cold saturated NH₄Cl (500 mL) and MBTE (1.2 L). The organic layer was washed with water (3×500 mL) and saturated NaCl (2×300 mL). The organic layer was dried with Na₂SO₄, filtered through a silica plug, washed with MBTE and concentrated to afford crude desired product that was used without further purification.

Step 150f.

To a solution of crude material from step 150e in THF/water (220/70 mL) in an ice/water bath was added TFA (30.8 ml, 400 mmol) then stirred at rt for 6.5 hours then cooled to 0° C. and 20 mL sat NaHCO₃ was added slowly and followed by solid NaOH (16.00 g, 400 mmol). EtOAc (800 mL) and water (600 mL) was added. The organic layer was washed with a mixture solution of NaHCO₃ and brine, then brine, dried (Na₂SO₄) filtered and concentrated to about 150 mL then, 450 mL cyclohexane was added cooled to 0° C., filtered, wash with cyclohexane/EtOAc (3/1) to give the desired product (39 g, 83 mmol, 81% yield for 2 steps).

Step 150g.

To a solution of compound from step 150f (5.75 g, 12.67 mmol) in NMP (40 ml) at 0° C. was added m-CPBA (8.52 g, 38.0 mmol, 77%) in one portion. Stir o/n at rt. Dilute with EtOAc, wash with Na₂S₂O₃, NaHCO₃, water and brine. Dry over Na₂SO₄ filter and concentrate. Crude product was recrystallized from MeOH. Dry at rt o/n in vacuum to give the title compound (4.10 g, 8.44 mmol, 66.6% yield). ESI-MS m/z=484.08, 486.08 [M−H]⁻.

Example 153

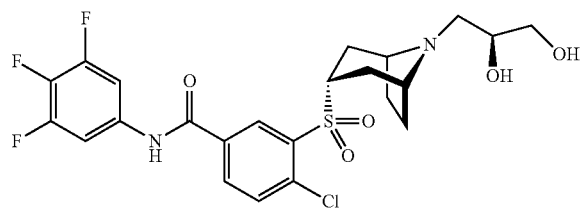

A solution of the compound from Step 144a in AcOH (500 µl, 8.73 mmol) was stirred at rt overnight. The reaction mixture was concentrated, and the residue was chromatographed (silica, CH₂Cl₂/MeOH) to give the title compound as white solid (17 mg, 88%, single enantiomer). ESI-MS m/z=577.10, 579.10 (M+HCO₂)⁻.

Example 156

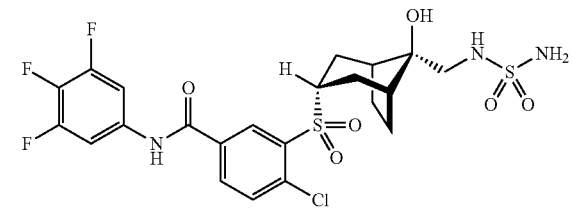

Intermediate 3 (78 mg, 0.155 mmol) and sulfuric diamide (44.7 mg, 0.465 mmol) in dioxane (0.5 mL) was stirred at 105° C. for 3 h. It was cooled to rt and purified by prep-HPLC using a C18 column and acetonitrile/water as eluent to give title compound (42 mg, 46%). ESI-MS m/z=580.06, 582.06 [M−H]⁻.

Example 163

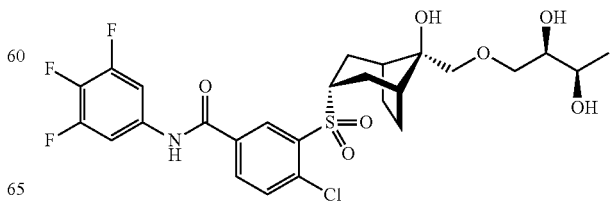

Two enantiomers of Example 36 were separated by chiral SFC. The title compound (tentatively assigned) was eluted out earlier. ESI-MS m/z=590.11, 592.11 [M−H]⁻.

Example 164

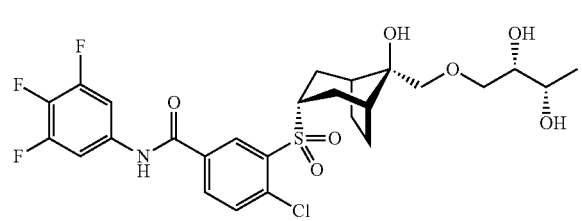

Two enantiomers of Example 36 were separated by chiral SFC. The title compound (tentatively assigned) was eluted out later. ESI-MS m/z=590.11, 592.11 [M−H]⁻.

Example 174

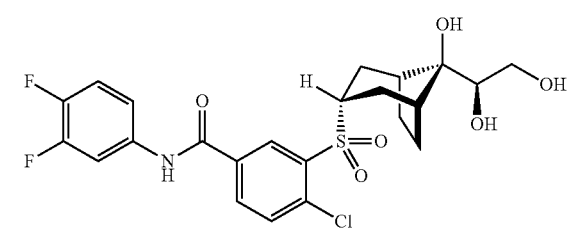

The title compound (single enantiomer, tentatively assigned, eluted out earlier) was isolated from the compound of example 82 via SFC chromatography. ESI-MS m/z=514.09, 516.09 [M−H]⁻.

Example 175

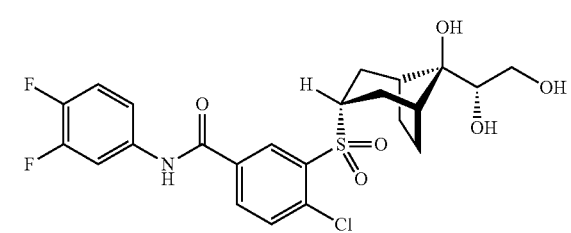

The title compound (single enantiomer, tentatively assigned, eluted out later) was isolated from the compound of example 82 via SFC chromatography. ESI-MS m/z=514.09, 516.09 [M−H]⁻.

Example 180

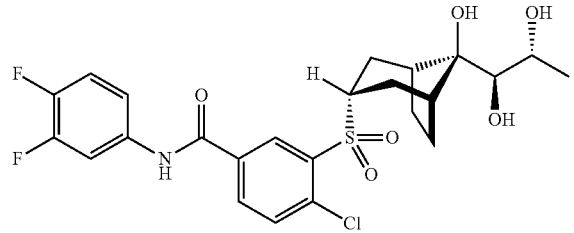

The title compound (single enantiomer, tentatively assigned, eluted out earlier) was isolated from the compound of example 172 via SFC chromatography. ESI-MS m/z=528.10, 530.10[M−H]⁻.

Example 181

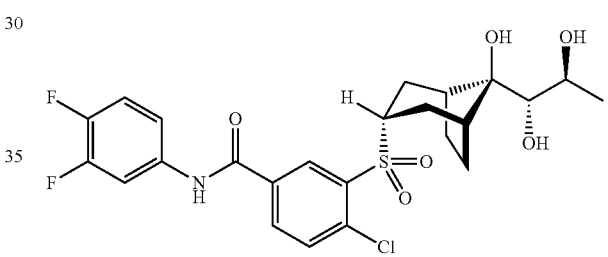

The title compound (single enantiomer, tentatively assigned, eluted out later) was isolated from the compound of example 172 via SFC chromatography. ESI-MS m/z=528.10, 530.10[M−H]⁻.

Example 182

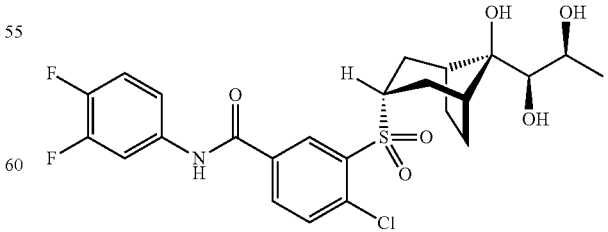

The title compound (single enantiomereluted out earlier) was isolated from the compound of example 173 via SFC chromatography. ESI-MS m/z=528.10, 530.10[M−H]⁻.

Example 183

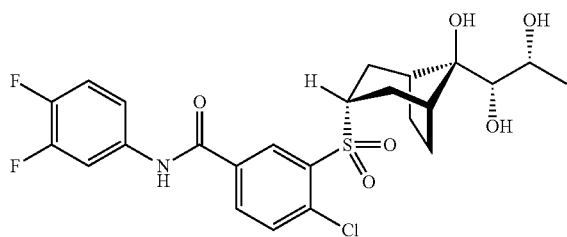

The title compound (single enantiomer, eluted out later) was isolated from the compound of example 173 via SFC chromatography. ESI-MS m/z=528.10, 530.10[M−H]⁻.

Example 202

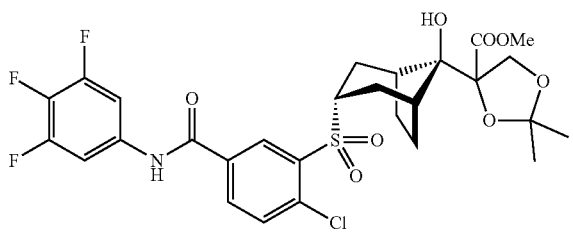

Step 202a.

To a solution of methyl (R)-2,2-dimethyl-1,3-dioxolane-4-carboxylate (55 mg, 0.35 mmol) in THF (1 ml), was added LDA (0.34 mmol) freshly prepared in THF at −78° C. and stirred at same temperature for 15 minutes before a solution of intermediate 2 (100 mg, 0.23 mmol) in THF (1 mL) was added. It was raised to 0° C. in one hour and quenched by aq. NH₄Cl. It was extracted with EtOAc and washed with brine and dried (Na₂SO₄). After being concentrated, the crude was chromatographed (silica, EtOAc/hexanes) to give the desired compound (79 mg, contaminated with intermediate 2). ESI-MS m/z=598.12, 600.12[M−H]⁻.

Step 125b.

To a solution of compound of step 202a (79 mg, 0.13 mmol) in THF (2 ml), was added m-CPBA (112 mg, 0.5 mmol) and stirred at rt. o/n. The crude was purified by prep-HPLC (C18, acetonitrile/water) to give title compound (13 mg, 10%, two steps). ESI-MS m/z=630.11, 632.11 [M−H]⁻.

Example 203

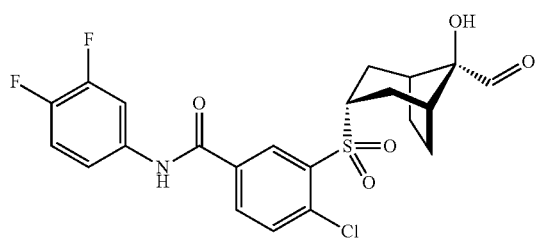

To a solution of the compound of example 150 (207 mg, 0.426 mmol) in DMSO (2.1 ml) was added IBX (179 mg, 0.639 mmol). The reaction stirred at rt for 2 h. The reaction was extracted with EtOAc, washed with water and brine. The organic layer was dried (Na₂SO₄), filtered and concentrated. The crude product was chromatographed (silica, hexane/acetone) to give the title compound as white solid (175 mg, 85%). ESI-MS m/z=481.6, 483.6 [M−H]⁻.

Example 204

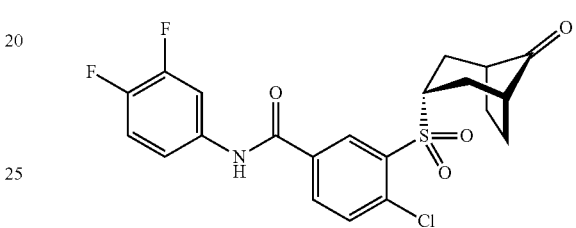

To a solution of the compound of example 150 (103 mg, 0.212 mmol) in THF (2 ml) and NaHCO₃ (aq sat. 1 ml) was added NaIO₄ (140 mg, 0.655 mmol). The reaction stirred at rt for 2 h. The reaction was extracted with EtOAc, washed with water and brine. The organic layer was dried (Na₂SO₄), filtered and concentrated. The crude product was chromatographed (silica, hexane/acetone) to give the title compound as white solid (60 mg, 62%). ESI-MS m/z=452.05, 454.05 [M−H]⁻.

Example 205

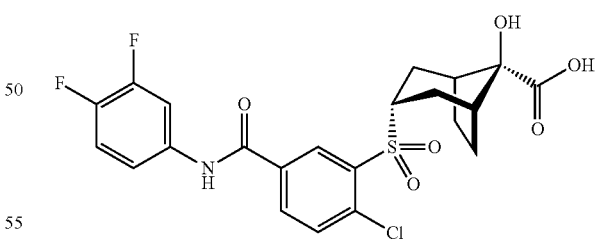

To a solution of the compound of example 203 (140 mg, 0.289 mmol), 2-methyl-2-butene (0.77 ml, 7.23 mmol), KH₂PO₄ (276 mg, 2.025 mmol) in THF (3 ml) and water (1 ml) was added NaClO₂ (294 mg, 2.60 mmol). The reaction stirred at rt for 1 h. The reaction acidified to pH 4 with 1 M HCl then extracted with EtOAc, washed with water and brine. The organic layer was dried (Na₂SO₄), filtered and concentrated. The crude product was chromatographed (silica, hexane/acetone) to give the title compound as white solid (109 mg, 75%). ESI-MS m/z=497.7, 499.6 [M−H]⁻.

Example 206

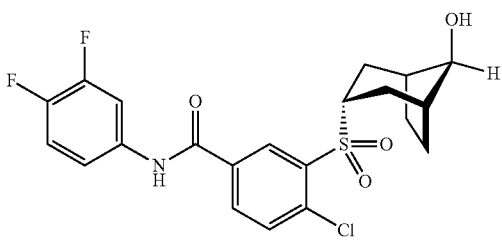

To a solution of the compound of example 204 (22 mg, 0.048 mmol) in THF (0.5 ml) and MeOH (0.5 ml) was added NaBH₄ (9 mg, 0.244 mmol). The reaction stirred at rt for 15 minutes. The reaction was extracted with EtOAc, washed with water and brine. The organic layer was dried (Na₂SO₄), filtered and concentrated to give the title compound as white solid (21 mg, 95%, stereochemistry not determined). ESI-MS m/z=453.6, 455.6 [M–H]⁻.

Example 210

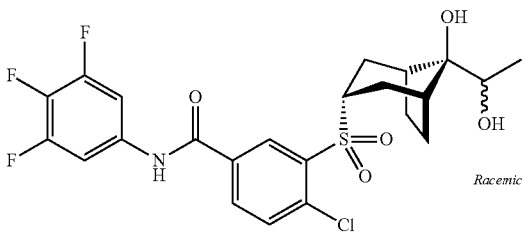

To a solution of the compound from Step 11b (47 mg, 0.091 mmol) in THF (911 μl) was added 2N LiBH₄ solution (22.77 μl, 0.046 mmol) at rt, then the mixture was kept at rt for overnight. The reaction was quenched with NH₄Cl aqueous solution, and the mixture was extracted with EtOAc. The combined organic phases were washed with water and brine, dried over Na₂SO₄, filtered and concentrated. The residue was chromatographed (silica, CH₂Cl₂/MeOH) to give the title compound as white solid (14 mg, 30%). ESI-MS m/z=562.09, 564.09, (M+HCO₂)⁻.

Example 272

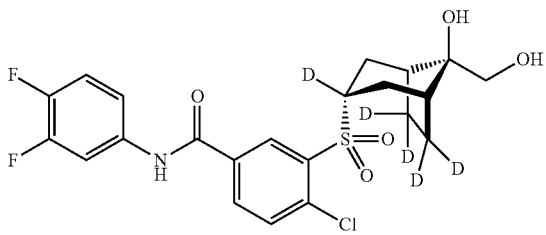

Step 272a.

To a suspension of Me₃SOI (1.98 g, 9.0 mmol.) in DMF (5.0 mL) at 0° C. was added t-BuOK (1.01 g, 9.0 mmol.) and stirred at rt for one hour. The reaction was cooled to 0° C. (1R,5S)-3-methylenebicyclo[3.2.1]octan-8-one-6,6,7,7-d4 (in DMF (2.0 mL), which was prepared using procedures similar to those described in step intermediate 2a, was charged drop-wise to the reaction mixture. The reaction was stirred for 2 hours. To the reaction mixture was added 15% NH₄Cl drop-wise and extracted with MTBE. The aqueous phase was re-extracted by MTBE. Then all the organic phase was combined and washed with water and brine. The organic phase was dried over Na₂SO₄, filtered and concentrated to dryness to give the desired product (0.59 g, 64%).

Step 272b.

To a solution of compound from step 272a (0.59 g, 3.83 mmol) in THF/water (3.9/1.3 mL) at 0° C. was added TFA (0.589 mL, 7.65 mmol). The reaction was stirred at rt for 20 hours. The reaction was cooled to 0° C. and Na₂CO₃ was added slowly and adjusted pH to 7-8. EtOAc and water were added. The two layers were separated (brine was added to assist separation), the organic layer was washed with water and brine. The organic phase was dried over Na₂SO₄, filtered and concentrated to dryness to give desired product (0.50 g, 76%).

Step 272c.

To a solution of compound from step 272b (0.48 g, 2.8 mmol), imidazole (0.57 g, 8.4 mmol) in DMF (4.0 mL) was added TBSCl (0.63 g, 4.2 mmol) and stirred at rt for 18 h. It was quenched by pouring into cold water. The product was extracted with hexanes. The organic phase was washed with brine, dried over Na₂SO₄, filtered and concentrated to give crude product (0.97 g, 100%).

Step 272d.

To a solution of compound from step 272c. (1.43 g, 5.0 mmol) in dioxane-water (18/6.0 mL) was added 2, 6-lutidine (1.16 mL, 10 mmol.), and OsO₄ (0.78 mL, 2.5% solution in t-butanol, 0.05 mmol). The mixture was cooled to 0° C. and NaIO₄ (3.21 g, 15 mmol) was added. The suspension was stirred at rt for 16 hours. Aq. Na₂S₂O₃ solution was added. The mixture was stirred for 1 hour and filtered through celite. The mixture was extracted with MBTE/Hexanes. The organic phase was washed with water, 1 N HCl, Sat.NaHCO₃ and brine. The organic phase was separated, dried over Na₂SO₄, filtered and concentrated to give the crude product (1.0 g, 69%).

Step 272e.

To a solution of LiBD₄ (0.108 g, 4.2 mmol) was added compound from step 272d (0.577 g, 2.0 mmol) in MBTE (12 mL) dropwise at 0° C. The resulting solution was stirred for 2 hours at 0° C. The reaction was quenched by slowly addition of aq.NH₄Cl keeping the temperature below 15° C. The reaction mixture was diluted with MBTE and water. The mixture was separated, and the organic layer was washed with brine. The mixture was dried over Na₂SO₄, filtered and concentrated under vacuum. The crude product was chromatographed (silica, hexanes/EtOAc) to give the desired compound as white solid (0.39, 67%).

Step 272f.

To a solution of compound from step 272e (0.39 g, 1.34 mmol) and pyridine (0.216 mL, 2.68 mmol) in DCM (2 mL) at rt was added TsCl (0.306 g, 1.60 mmol) and stirred at rt for 40 h. It was quenched with H₂O and extracted with EtOAc. The mixture was washed with H₂O, 1 M HCl, Sat.NaHCO₃ and brine. The organic phase was collected, dried over Na₂SO₄, filtered and concentrated. The crude product was chromatographed (silica, hexanes/EtOAc) to give the desired compound as white solid (0.59, 99%).

Step 272g.

To a solution of compound from step 272f (1.7 g, 3.81 mmol) in MeOH (22 mL) was added conc. HCl (1.0 mL) and stirred at rt for 16 h. It was diluted with EtOAc and the mixture washed with water, sat.NaHCO₃, brine, dried over Na₂SO₄, filtered and concentrated. The crude product was recrystallized from hexanes/MBTE to give desired product (1.1 g, 87%).

Step 272h.

A solution of compound from step 272g (0.16 g, 0.48 mmol), intermediate 6 (0.12 g, 0.40 mmol) and Cs₂CO₃ (0.128 g, 0.392 mmol) in DMF (1.0 mL) was stirred at 75° C. for 16 h. It was diluted with EtOAc and the mixture washed with water, brine, dried over Na₂SO₄, filtered and concentrated. The crude product was chromatographed (silica, hexanes/EtOAc) to give the desired compound as white solid (0.162 g, 88%). ESI-MS m/z=457.12, 459.12 [M−H]⁻.

Step 272i.

A solution of compound from step 272h (0.16 g, 0.35 mmol) and m-CPBA (253 mg, 1.13 mmol, 77%) in NMP (2.0 mL) was stirred at rt for 24 h. Aqueous Na₂S₂O₃, NaHCO₃ and few drops of Et₃N was added and stirred at rt for 1 h. It was extracted with EtOAc, washed with water, brine, dry over Na₂SO₄, filtered, recrystallized from MeOH to give title compound (118 mg, 68%). ESI-MS m/z=489.11, 491.11 [M−H]⁻.

Example 279

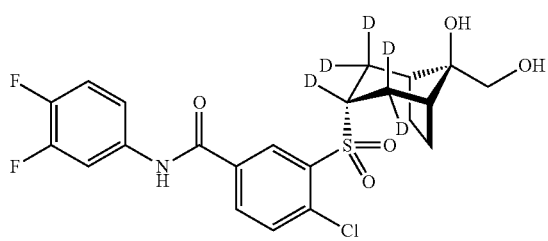

Step 279a.

To a suspension of Me₃SOI (48.5 g, 220 mmol.) in DMF (120 mL) at 0° C. was added t-BuOK (24.72 g, 220 mmol) and stirred at rt for one hour. The reaction was cooled to 0° C. Intermediate 2a (20 g, 147 mmol) in DMF (80 mL) was charged drop-wise to the reaction mixture. The reaction was stirred for 2 hours. To the reaction mixture was added 15% NH₄Cl drop-wise and extracted with MTBE. The aqueous phase was re-extracted by MTBE. The combined organic layer was washed with water and brine, dried over Na₂SO₄, filtered and concentrated to give the desired product (19.9 g, 90%).

Step 279b.

To a solution of compound from step 279a (20 g, 133 mmol) in THF/water (150/50 mL) at 0° C. was added TFA (30.8 mL, 399 mmol). The reaction was stirred at rt for 3 hours, then cooled to 0° C. and Na₂CO₃ was added slowly and adjusted pH to 7-8. EtOAc and water were added. The two layers were separated (brine was added to assist separation), the organic layer was washed with water and brine, dried over Na₂SO₄, filtered and concentrated to provide desired product (17.7 g, 79%).

Step 279c.

To a solution of compound from step 279b (10 g, 59.4 mmol), imidazole (10.2 g, 148 mmol) in DMF (80 mL) was added TBSCl (10.7 g, 71.3 mmol) and stirred at rt for 18 h. It was quenched by pouring into cold water. The product was extracted with hexanes. The organic phase was washed with brine, dried over Na₂SO₄, filtered and concentrated to give crude product (18.1 g, 100%).

Step 279d.

To a solution of compound from step 279c. (16.8 g, 59.4 mmol) in dioxane-water (170/60 mL) was added 2, 6-lutidine (13.8 mL, 119 mmol.), and OsO₄ (9.3 mL 2.5% solution in t-butanol, 0.59 mmol). The mixture was cooled and NaIO₄ (37.1 g, 178.2 mmol) was added. The suspension was stirred at rt for 16 hours. Aq. Na₂S₂O₃ solution was added. The mixture was stirred for 1 hour and filtered through celite. The mixture was extracted with MBTE/Hexanes. The organic phase was washed with water, 1 N HCl, Sat.NaHCO₃ and brine. The organic phase was separated, dried over Na₂SO₄, filtered and concentrated to give the crude product (16.6 g, 94%).

Step 279f.

To a solution of compound from step 279d (143 mg, 0.503 mmol) in CD₃OD (3.0 mL) was added MeONa (5.4 mg, 0.10 mmol) and the mixture was stirred at rt for 3 h. It was concentrated and the residue was redissolved in CD₃OD (3.0 mL) and stirred for 3 h. The same reaction cycle was repeated two more times and the solution was cooled to 0° C. and NaBD₄ (0.10 g, 2.4 mmol) was added portionwise. After 1 h, it was quenched by slowly addition of aq.NH₄Cl. MBTE and water were added. The mixture was separated, and the organic layer was washed with brine. The mixture was dried over Na₂SO₄, filtered and concentrated under vacuum. The crude product was chromatographed (silica, hexanes/EtOAc) to give the desired compound as white solid (0.070 g, 50%).

Step 279g.

To a mixture of intermediate 6 (73 mg, 0.24 mmol) and compounds from step 279f (71 mg, 0.24 mmol) in toluene (1.5 mL) at rt was added cyanomethylenetributyl-phosphorane (176 mg, 0.73 mmol) and stirred at 75° C. for 16 h. The mixture was cooled to rt and was chromatographed (silica, hexanes/EtOAc) to give the desired compound as white solid (0.11 g, 79%). ESI-MS m/z=571.21, 573.21 [M−H]⁻.

Step 279h.

To a solution of compound from step 279g (0.11 g, 0.19 mmol) in MeOH (3.0 mL) was added con. HCl (0.3 mL) and stirred at rt for 2 h. It was diluted with EtOAc and the mixture washed with water, Sat.NaHCO₃, brine, dried over Na₂SO₄, filtered and concentrated. The crude product was recrystallized from hexanes/MBTE to give desired product (0.083 g, 94%). ESI-MS m/z=457.12, 459.12 [M−H]⁻.

Step 279i.

A solution of compound from step 279h (0.083 g, 0.18 mmol) and m-CPBA (0.14 g, 0.63 mmol, 77%) in NMP (2.0 mL) was stirred at rt for 24 h. Aqueous Na₂S₂O₃, NaHCO₃ and few drops of Et₃N was added and stirred at rt for 1 h. It was extracted with EtOAc, washed with water, brine, dried over Na₂SO₄, filtered, concentrated purified by prep-HPLC (C18, acetonitrile/water) to give title compound (48 mg, 54%). ESI-MS m/z=489.11, 491.11 [M−H]⁻.

Example 281

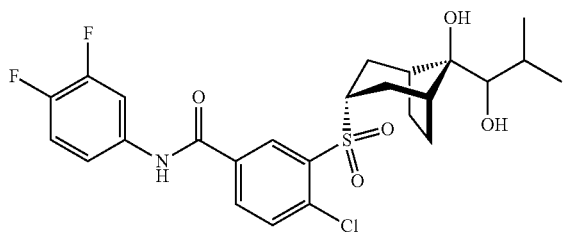

Step 281a.

To a solution of compound from step 150f (4.0 g, 8.11 mmol) in DMSO (22 mL) was added IBX (3.70 g, 13.22 mmol). The reaction mixture was heated to 50° C. for 3 h. The reaction mixture was then cooled to rt and diluted with EtOAc. The reaction mixture was filtered, the solid discarded and the filtrate was washed with water and saturated NaCl. The organic layer was dried with $Na_2SO_4$, filtered and concentrated to afford crude desired product that was used without further purification (3.90 g, 98%).

Step 281b.

To a solution of compound from step 281a (50 mg, 0.111 mmol) in THF (0.53 mL) at −78° C. was added isopropylmagnesium chloride, lithium chloride complex (237 μL, 0.243 mmol, 1.3 M in THF). The reaction mixture was stirred for 30 minutes and quenched by aq. $NH_4Cl$. It was extracted with EtOAc and washed with brine and dried ($Na_2SO_4$). After being concentrated, the crude was chromatographed (silica, EtOAc/hexanes) to give the desired compound (18 mg, 33%). ESI-MS m/z=540.14, 542.14[M+$HCO_2$]$^-$.

Step 281c.

To a solution of compound from step 281b (18 mg, 0.01 mmol) in NMP (0.5 ml), was added m-CPBA (24 mg, 0.096 mmol, 77%) and stirred at rt o/n. The reaction was extracted with EtOAc, washed with water and brine. The organic layer was dried ($Na_2SO_4$), filtered and concentrated. The crude product was chromatographed (silica, hexane/acetone) to give the title compound as white solid (14 mg, 73%). ESI-MS m/z=572.13, 574.13[M+$HCO_2$]$^-$.

Example 283

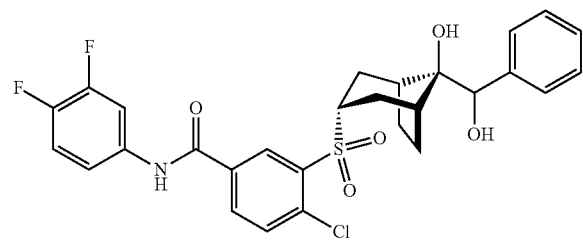

Step 283a.

To a solution of compound from step 281a (50 mg, 0.111 mmol) in THF (0.53 mL) at −78° C. was added phenylmagnesium bromide (237 μL, 0.243 mmol, 1 M in THF). The reaction mixture was stirred for 30 minutes and quenched by aq. $NH_4Cl$. It was extracted with EtOAc and washed with brine and dried ($Na_2SO_4$). After being concentrated, the crude was chromatographed (silica, EtOAc/hexanes) to give the desired compound (17 mg, 29%). ESI-MS m/z=574.13, 576.13[M+$HCO_2$]$^-$.

Step 283b.

To a solution of compound from step 283a (17 mg, 0.03 mmol) in NMP (0.5 ml), was added m-CPBA (22 mg, 0.096 mmol, 77%) and stirred at rt o/n. The crude was purified by prep-HPLC (C18, acetonitrile/water) to give title compound (3 mg, 17%). ESI-MS m/z=606.12, 608.12 [M+$HCO_2$]$^-$.

Example 284

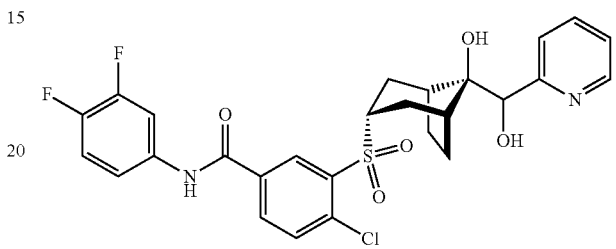

Step 284a.

To a solution of 2-bromopyridine (46 μL, 0.49 mmol) in THF (1 mL) at 0° C. was added isopropylmagnesium chloride, lithium chloride complex (0.49 mL, 0.49 mmol, 1.3 M in THF). The reaction mixture was warmed to rt and stirred for 30 minutes, then cooled to −78° C. followed by addition of a solution of compound from step 281a (100 mg, 0.221 mmol) in THF (1 mL). The reaction mixture was stirred for 18 h, slowly warming to rt and quenched by aq. $NH_4Cl$. It was extracted with EtOAc and washed with brine and dried ($Na_2SO_4$). After being concentrated, the crude was chromatographed (silica, acetone/hexanes) to give the desired compound (11 mg, 9%). ESI-MS m/z=575.12, 577.12 [M+$HCO_2$]$^-$.

Step 284b.

To a solution of compound of step 284a (11 mg, 0.02 mmol) in NMP (1 ml), was added p-TSA (20 mg, 0.105 mmol) and m-CPBA (20 mg, 0.089 mmol, 77%) and stirred at rt o/n. The reaction was extracted with EtOAc, washed with water and brine. The organic layer was dried ($Na_2SO_4$), filtered and concentrated. The crude product was chromatographed (silica, hexane/acetone) to give the title compound as white solid (6 mg, 51%). ESI-MS m/z=607.13, 609.13 [M+$HCO_2$]$^-$.

Example 284a

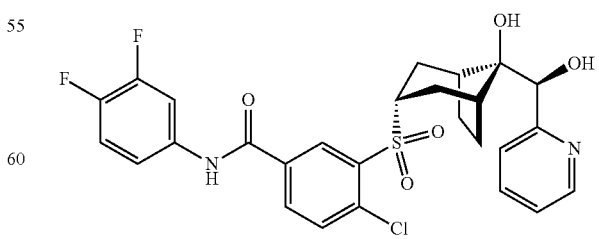

The title compound (single enantiomer, tentatively assigned) was isolated from the compound of example 284 via SFC chromatography, earlier eluting compound.

Example 284b

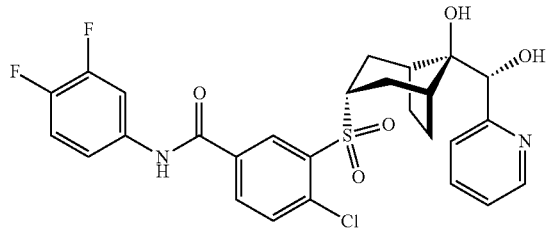

The title compound (single enantiomer, tentatively assigned) was isolated from the compound of example 284 via SFC chromatography, later eluting compound.

Example 285

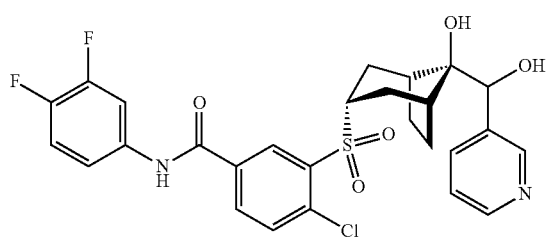

Step 285a.

To a solution of 3-bromopyridine (46 µL, 0.49 mmol) in THF (1 mL) at 0° C. was added isopropylmagnesium chloride, lithium chloride complex (0.49 mL, 0.49 mmol, 1.3 M in THF). The reaction mixture was warmed to rt and stirred for 30 minutes, then cooled to −78° C. followed by addition of a solution of compound from step 281a (100 mg, 0.221 mmol) in THF (1 mL). The reaction mixture was stirred for 18 h, slowly warming to rt and quenched by aq. NH$_4$Cl. It was extracted with EtOAc and washed with brine and dried (Na$_2$SO$_4$). After being concentrated, the crude was chromatographed (silica, acetone/hexanes) to give the desired compound (15 mg, 13%). ESI-MS m/z=575.12, 577.12 [M+HCO$_2$]$^-$.

Step 285b.

To a solution of compound of step 285a (15 mg, 0.028 mmol) in NMP (1 ml), was added p-TSA (20 mg, 0.105 mmol) and m-CPBA (20 mg, 0.089 mmol, 77%) and stirred at rt o/n. The reaction was extracted with EtOAc, washed with water and brine. The organic layer was dried (Na$_2$SO$_4$), filtered and concentrated. The crude product was chromatographed (silica, hexane/acetone) to give the title compound as white solid (8 mg, 50%). ESI-MS m/z=607.13, 609.13 [M+HCO$_2$]$^-$.

Example 285a

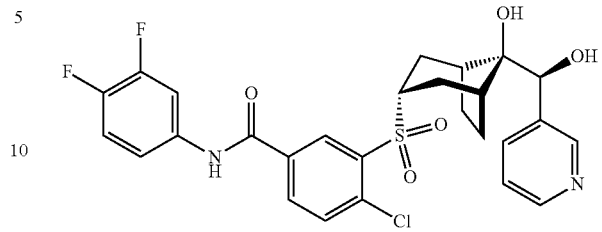

The title compound (single enantiomer, tentatively assigned) was isolated from the compound of example 285 via SFC chromatography, earlier eluting compound.

Example 285b

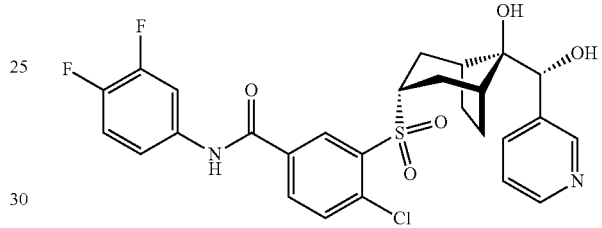

The title compound (single enantiomer, tentatively assigned) was isolated from the compound of example 285 via SFC chromatography, later eluting compound.

Example 286

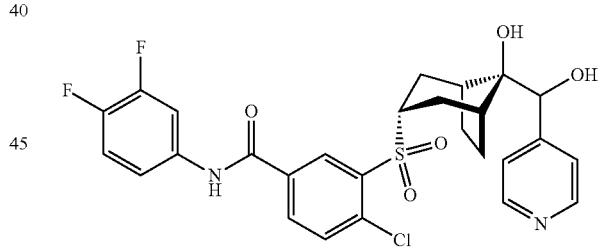

Step 286a.

To a solution of 4-iodopyridine (159 mg, 0.774 mmol) in THF (1.5 mL) at 0° C. was added n-butyllithium (0.31 mL, 0.774 mmol, 2.5 M in hexanes). This reaction mixture was warmed to rt and stirred for 30 minutes, then cooled to −78° C. followed by addition of a solution of compound from step 281a (100 mg, 0.221 mmol) in THF (1 mL). The reaction mixture was stirred for 18 h, slowly warming to rt and quenched by aq. NH$_4$Cl. It was extracted with EtOAc and washed with brine and dried (Na$_2$SO$_4$). After being concentrated, the crude was chromatographed (silica, acetone/hexanes) to give the desired compound (45 mg, 38%). ESI-MS m/z=575.30, 577.30[M+HCO$_2$]$^-$.

Step 286b.

To a solution of compound of step 286a (45 mg, 0.085 mmol) in NMP (2 ml), was added p-TSA (48 mg, 0.254 mmol) and m-CPBA (57 mg, 0.254 mmol, 77%) and stirred at rt o/n. The reaction was extracted with EtOAc, washed with water and brine. The organic layer was dried (Na₂SO₄), filtered and concentrated. The crude product was chromatographed (silica, hexane/acetone) to give the title compound as white solid (8 mg, 17%). ESI-MS m/z=607.29, 609.29 [M+HCO₂]⁻.

Example 287

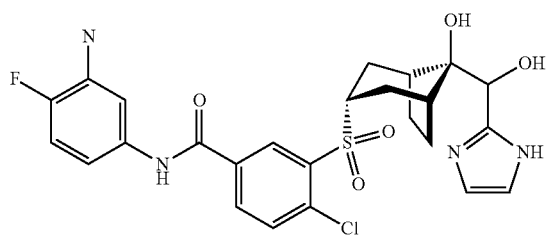

Step 287a.
To a solution of 1-(diethoxy)-1H-imidazole (159 mg, 0.487 mmol) in THE (1 mL) at −78° C. was added n-butyllithium (0.195 mL, 0.487 mmol, 2.5 M in hexanes). The reaction mixture stirred for 30 minutes followed by addition of a solution of compound from step 281a (100 mg, 0.221 mmol) in THE (1 mL). The reaction mixture was stirred for 18 h, slowly warming to rt and quenched by aq. NH₄Cl. It was extracted with EtOAc and washed with brine and dried (Na₂SO₄). After being concentrated, the crude was chromatographed (silica, acetone/hexanes) to give the desired compound (22 mg, 38%). ESI-MS m/z=564.29, 566.29[M+HCO₂]⁻.

Step 287b.
To a solution of compound of step 287a (22 mg, 0.042 mmol) in NMP (2 ml), was added p-TSA (50 mg, 0.263 mmol) and m-CPBA (50 mg, 0.223 mmol, 77%) and stirred at rt o/n. The reaction was extracted with EtOAc, washed with water and brine. The organic layer was dried (Na₂SO₄), filtered and concentrated. The crude product was chromatographed via prep-HPLC (C18, acetonitrile/water) to give the title compound as white solid (6 mg, 26%). ESI-MS m/z=596.28, 598.28 [M+HCO₂]⁻.

Example 288

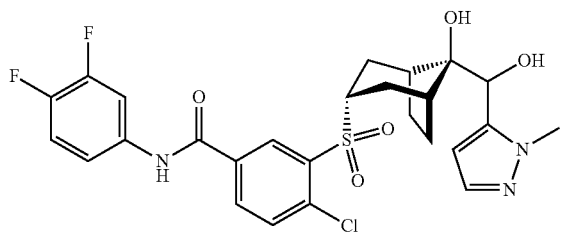

Step 288a.
To a solution of 1-methyl-1H-pyrazole (64 μL, 0.774 mmol) in THE (1.5 mL) at 0° C. was added n-butyllithium (0.31 mL, 0.774 mmol, 2.5 M in hexanes). The reaction mixture stirred for 30 minutes followed by addition of a solution of compound from step 281a (100 mg, 0.221 mmol) in THE (1 mL). The reaction mixture was stirred for 18 h, slowly warming to rt and quenched by aq. NH₄Cl. It was extracted with EtOAc and washed with brine and dried (Na₂SO₄). After being concentrated, the crude was chromatographed (silica, acetone/hexanes) to give the desired compound (79 mg, 67%). ESI-MS m/z=578.32, 580.31 [M+HCO₂]⁻.

Step 288b.
To a solution of compound of step 288a (79 mg, 0.148 mmol) in NMP (2 ml), was added m-CPBA (99 mg, 0.444 mmol, 77%) and stirred at rt o/n. The reaction was extracted with EtOAc, washed with water and brine. The organic layer was dried (Na₂SO₄), filtered and concentrated. The crude product was chromatographed (silica, acetone/hexanes) to give the title compound as white solid (65 mg, 78%). ESI-MS m/z=610.30, 612.30 [M+HCO₂]⁻.

Example 289

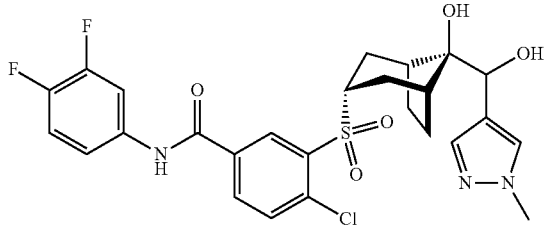

Step 289a.
To a solution of 4-bromo-1-methyl-1H-pyrazole (69 μL, 0.664 mmol) in THE (2 mL) at −78° C. was added n-butyllithium (0.266 mL, 0.664 mmol, 2.5 M in hexanes). The reaction mixture stirred for 30 minutes followed by addition of a solution of compound from step 281a (100 mg, 0.221 mmol) in THE (1 mL). The reaction mixture was stirred for 18 h, slowly warming to rt and quenched by aq. NH₄Cl. It was extracted with EtOAc and washed with brine and dried (Na₂SO₄). After being concentrated, the crude was chromatographed (silica, acetone/hexanes) to give the desired compound (23 mg, 19%). ESI-MS m/z=578.31, 580.31 [M+HCO₂]⁻.

Step 289b.
To a solution of compound of step 289a (23 mg, 0.148 mmol) in NMP (2 ml), was added m-CPBA (29 mg, 0.444 mmol, 77%) and stirred at rt o/n. The reaction was extracted with EtOAc, washed with water and brine. The organic layer was dried (Na₂SO₄), filtered and concentrated. The crude product was chromatographed (silica, acetone/hexanes) to give the title compound as white solid (22 mg, 90%). ESI-MS m/z=610.30, 612.31 [M+HCO₂]⁻.

Example 290

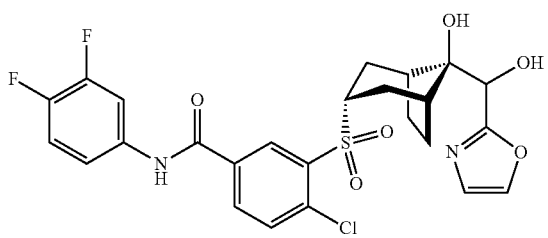

Step 290a.

To a solution of oxazole (76 μL, 1.162 mmol) in THF (1.5 mL) at 0° C. was added i-PrMgCl—LiCl (0.894 mL, 1.162 mmol, 1.3 M in THF). The reaction mixture stirred for 30 minutes followed by addition of a solution of compound from step 281a (150 mg, 0.332 mmol) in THE (1.5 mL). The reaction mixture was stirred for 3 h, slowly warming to rt and quenched by aq. NH₄Cl. It was extracted with EtOAc and washed with brine and dried (Na₂SO₄). After being concentrated, the crude was chromatographed (silica, acetone/hexanes) to give the desired compound (22 mg, 38%). ESI-MS m/z=565.28, 567.28 [M+HCO₂]⁻.

Step 290b.

To a solution of compound of step 290a (133 mg, 0.042 mmol) in NMP (2.5 ml), was added p-TSA (243 mg, 1.276 mmol) and m-CPBA (172 mg, 0.766 mmol, 77%) and stirred at rt o/n. The reaction was extracted with EtOAc, washed with water and brine. The organic layer was dried (Na₂SO₄), filtered and concentrated. The crude product was chromatographed via prep-HPLC (C18, acetonitrile/water) to give the title compound as white solid (20 mg, 14%). ESI-MS m/z=597.26, 599.26 [M+HCO₂]⁻.

Example 291

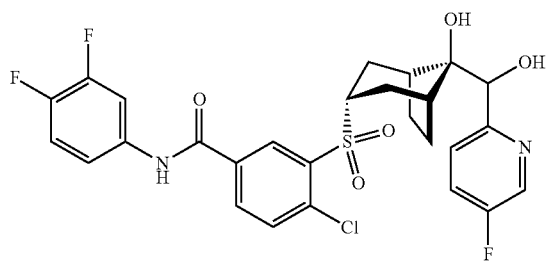

Step 291a.

To a solution of 2-bromo-5-fluoropyridine (302 mg, 1.715 mmol) in THE (3 mL) was added n-butyllithium (0.730 ml, 1.826 mmol, 2.5 M in THF) dropwise at −78° C. After being stirred for 1 h at the same temperature, a solution of the compound from step 281a (250 mg, 0.553 mmol) in THE (1.5 mL) was added into the mixture at −78° C. The reaction was slowly warmed to rt and stirred for 16 h. Sat. NH₄Cl solution was added. The mixture was extracted with EtOAc, dried over Na₂SO₄, and purified by column chromatography (silica. MeOH/DCM) to give the desired compound (70 mg, 0.128 mmol, 23% yield) as pale brown solid.

Step 291b.

To a solution of the compound from step 291a (70 mg, 0.128 mmol), p-TSA (72.8 mg, 0.383 mmol) in NMP (1 mL) was added m-CPBA (86 mg, 0.383 mmol, 77%) at 0° C. The reaction was slowly warmed to rt and stirred for 16 h. Sat. Na₂S₂O₃ solution and NaHCO₃ solution were added and the resulting mixture was stirred for 1 h at rt. The mixture was extracted with EtOAc, washed with sat. Na₂S₂O₃ solution and NaHCO₃ solution (×2), brine, and dried over Na₂SO₄. The crude material was purified by column chromatography (silica, MeOH/DCM) to give the title compound (17.0 mg, 0.128 mmol, 23% yield) as light brown solid. ESI-MS m/z=580.00, 582.01 [M−H]⁻.

Example 291a

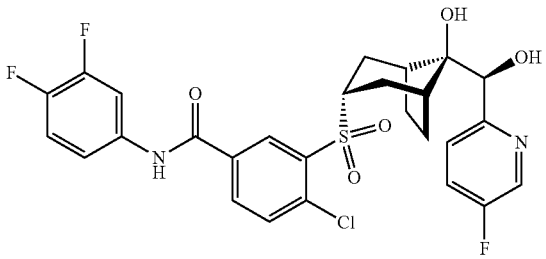

The title compound (single enantiomer, tentatively assigned) was isolated from the compound of example 291 via SFC chromatography, earlier eluting compound.

Example 291b

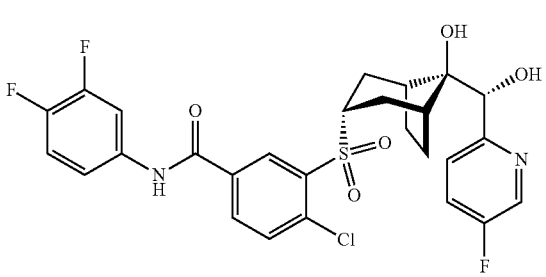

The title compound (single enantiomer, tentatively assigned) was isolated from the compound of example 291 via SFC chromatography, later eluting compound.

Example 292

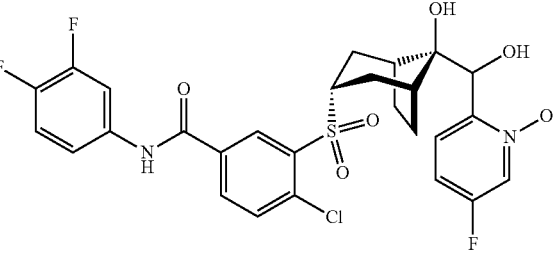

The crude material from step 291b was purified by column chromatography (0-20% MeOH in DCM) to give the title compound (9.3 mg, 0.016 mmol, 12% yield) as light brown solid. ESI-MS m/z=596.00, 598.01 [M−H]⁻.

Example 293

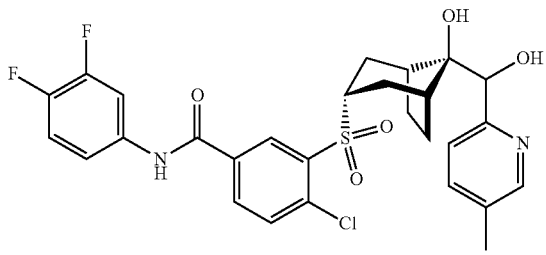

Step 293a.

To a solution of 2-bromo-5-methylpyridine (200 mg, 1.16 mmol) in THF (1.5 mL) at −78° C. was added n-butyllithium (0.465 mL, 1.16 mmol, 2.5 M in hexane). The reaction mixture stirred for 30 minutes followed by addition of a solution of compound from step 281a (150 mg, 0.332 mmol) in THF (1.5 mL). The reaction mixture was stirred for 1 h, slowly warming to rt and quenched by aq. NH$_4$Cl. It was extracted with EtOAc and washed with brine and dried (Na$_2$SO$_4$). After being concentrated, the crude was chromatographed (silica, acetone/hexanes) to give the desired compound (129 mg, 71%). ESI-MS m/z=589.14, 591.14 [M+HCO$_2$]−.

Step 293b.

To a solution of compound of step 293a (129 mg, 0.24 mmol) in NMP (2.4 ml), was added p-TSA (225 mg, 1.18 mmol) and m-CPBA (159 mg, 0.71 mmol, 77%) and stirred at rt o/n. The reaction was extracted with EtOAc, washed with water and brine. The organic layer was dried (Na$_2$SO$_4$), filtered and concentrated. The crude product was chromatographed (silica, hexane/acetone) to give the title compound as white solid (109 mg, 80%). ESI-MS m/z=621.13, 623.13 [M+HCO$_2$]−.

Example 297

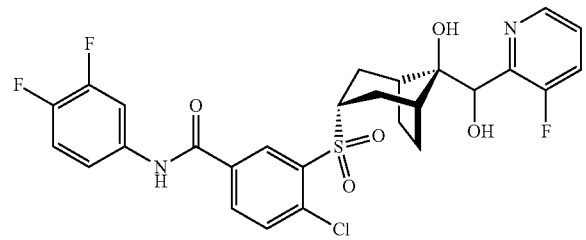

Step 297a.

To a solution of 2-bromo-3-fluoropyridine (204 mg, 1.16 mmol) in THF (1.5 mL) at −78° C. was added n-butyllithium (0.465 mL, 1.16 mmol, 2.5 M in hexane). The reaction mixture stirred for 30 minutes followed by addition of a solution of compound from step 281a (150 mg, 0.332 mmol) in THF (1.5 mL). The reaction mixture was stirred for 1 h, slowly warming to rt and quenched by aq. NH$_4$Cl. It was extracted with EtOAc and washed with brine and dried (Na$_2$SO$_4$). After being concentrated, the crude was chromatographed (silica, acetone/hexanes) to give the desired compound (10 mg, 5.5%). ESI-MS m/z=563.12, 565.10 [M+HCO$_2$]. Also isolated was 3-(((1R,3r,5S,8r)-8-((2-bromo-3-fluoropyridin-4-yl)(hydroxy)methyl)-8-hydroxybicyclo[3.2.1]octan-3-yl)thio)-4-chloro-N-(3,4-difluorophenyl)benzamide (77 mg, 37%). ESI-MS m/z=671.03, 673.04 [M+HCO$_2$]-Step 297b. To a solution of compound of step 297a (10 mg, 0.018 mmol) in NMP (0.2 ml), was added p-TSA (17 mg, 0.09 mmol) and m-CPBA (12 mg, 0.055 mmol, 77%) and stirred at rt. o/n. The reaction was extracted with EtOAc, washed with water and brine. The organic layer was dried (Na$_2$SO$_4$), filtered and concentrated. The crude product was chromatographed (silica, hexane/acetone) to give the title compound as white solid (4.7 mg, 44%). ESI-MS m/z=625.11, 627.11 [M+HCO$_2$]−.

Example 298

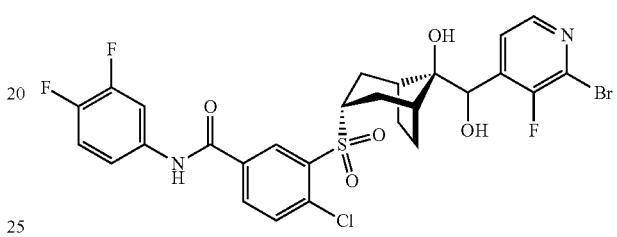

Step 298.

To a solution of side-product from step 297a (3-(((1R,3r,5S,8r)-8-((2-bromo-3-fluoropyridin-4-yl)(hydroxy)methyl)-8-hydroxybicyclo[3.2.1]octan-3-yl)thio)-4-chloro-N-(3,4-difluorophenyl)benzamide (77 mg, 0.123 mmol) in NMP (1.3 ml), was added p-TSA (117 mg, 0.613 mmol) and m-CPBA (82 mg, 0.368 mmol, 77%) and stirred at rt o/n. The reaction was extracted with EtOAc, washed with water and brine. The organic layer was dried (Na$_2$SO$_4$), filtered and concentrated. The crude product was chromatographed (silica, hexane/acetone) to give the title compound as white solid (64 mg, 79%). ESI-MS m/z=703.01, 705.12 [M+HCO$_2$]−.

Example 307

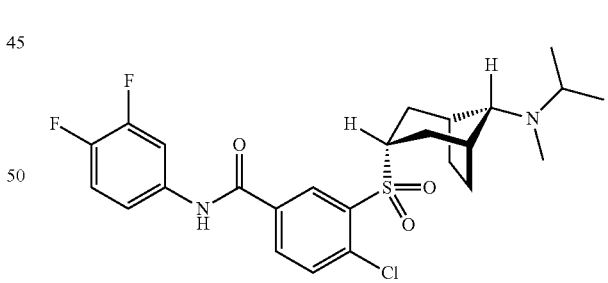

Step 307a.

To the mixture of compound from example 150d (7.04 g, 16.61 mmol) in ACN (70 ml) and DBU (3.25 ml, 21.59 mmol) at 0° C. Nonafluorobutane-1-sulfonyl fluoride (5.52 g, 18.27 mmol) was added via a pippete in one min and stirred at such temperature for 1 h. When it was still cooled, MTBE 200 mL was added. The solution was washed with water, with 1 N HCl twice, then water, aq. NaHCO$_3$ twice, brine twice. After being dried (Na$_2$SO$_4$) and concentrated, 13.5 g light yellow solid was obtained. To it MTBE/Hexanes ~ 1:10 (200 mL) was added and stirred at rt for 30 mins before filtered under vacuum. The solid collected was washed with MTBE/hexanes (1:10, 100 mL) to give (10.1 g, 86%) off white solid. ESI-MS m/z=704.02, 706.02 [M−H]⁻.

Step 307b.

To the solution of compound from step 307a (200 mg, 0.283 mmol) in DMF (2 mL), methyl isopropylamine (0.15 mL) was added stirred at 75° C. for two days. The crude was diluted with EtOAc, washed with water twice, brine twice and dried (Na₂SO₄) and concentrated. The crude was chromatographed (silica, MeOH/DCM) to give desired compound as a mixture with other impurities. ESI-MS m/z=477.15, 479.15 [M−H]⁻.

Step 307c.

The title compound was obtained from the compound of step 307b following the procedure described in example 284b and purified by prep-HPLC. ESI-MS m/z=509.14, 511.14 [M−H]⁻.

Example 308

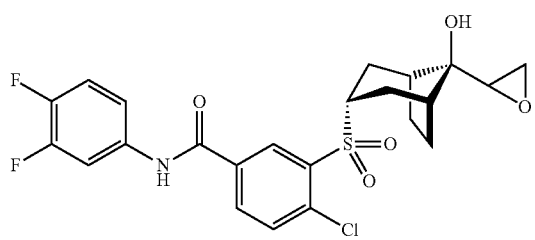

To the compound form step 82a (570 mg, 1.27 mmol) in THF (10 mL), m-CPBA (77% w/w, 1.42 g, 6.33 mmol) was added and stirred at rt o/n. To it, aq. Na₂S₂O₃ (10 mL) and NaHCO₃ (10 mL) were added, followed by 4 drops TEA and EtOAc (50 mL). It was stirred at rt for 1.5 hour before being separated. The aq. phase was extracted with EtOAc. The combined organic was washed with NaHCO₃, brine and dried (Na₂SO₄). After concentrated, the crude light yellow solid was dissolved in MeOH (50 mL) under heating (heat gun) and cooled to rt slowly before kept at 0° C. fro 30 mins. The formed crystals were collected under vacuum to afford the title compound (510 mg, 81%) as white solid. ESI-MS m/z=496.20, 498.20 [M−H]⁻.

Example 309

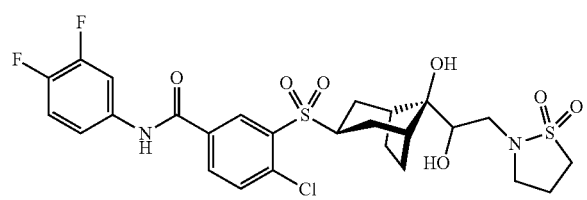

To a solution of compound from example 308 (50 mg, 0.10 mmol) in DMF (0.5 mL), 1,1-Dioxoisothiazolidine (18.3 mg, 0.15 mmol) was added followed by K₂CO₃ (14 mg, 0.1 mmol) and stirred at 50° C. o/n. The crude was purified on prep-HPLC (C-18, Acetonitrile/water) to give the title compound (16 mg, 26%) as a white solid. ESI-MS m/z=617.25, 619.25 [M−H]⁻.

Example 314

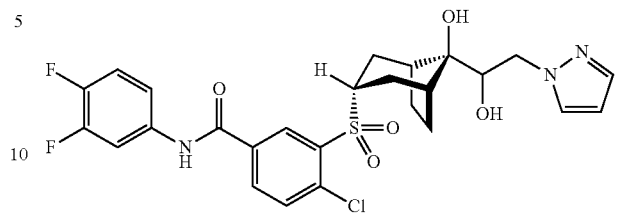

Step 314a.

To a slurry of Me₃SOI (365 mg, 1.66 mmol) in DMF (1 mL) was added potassium tert-butoxide (186 mg, 1.66 mmol) at 0° C. The mixture was warmed to rt and stirred for 45 min. The compound from step 281a (150 mg, 0.33 mmol) in DMF (2 mL) was added dropwise into the reaction mixture. After stirring for 4 h at rt, the reaction mixture was cooled to 0° C., sat. NH₄Cl solution was added, extracted with MTBE, and dried over Na₂SO₄. The crude product was purified by column chromatography (0-50% EtOAc in Hex) to give the desired compound (42.0 mg, 0.090 mmol, 27% yield) as white solid.

Step 314b.

To a solution of the compound from step 314a (42 mg, 0.090 mmol) in DMF (2 mL) was added 1H-pyrazole (12.27 mg, 0.180 mmol), potassium carbonate (18.69 mg, 0.135 mmol). The reaction was stirred at 65° C. for 15 h. The mixture was extracted with EtOAc, dried over Na₂SO₄, and purified by column chromatography (0-70% EtOAc in Hex) to give the desired compound (30.0 mg, 0.056 mmol, 62% yield) as off-white solid.

Step 314c.

To a solution of the compound from step 314b (30 mg, 0.056 mmol) and 10-camphorsulfonic acid (CSA) (19.57 mg, 0.084 mmol) in NMP (0.2 mL) was added m-CPBA (37.8 mg, 0.169 mmol, 77%) at 0° C. The reaction was slowly warmed to rt and stirred for 15 h. Sat. Na₂S₂O₃ solution and NaHCO₃ solution were added into the mixture and stirred for 1 h. The reaction was extracted with EtOAc, washed with sat. Na₂S₂O₃ solution and NaHCO₃ solution (×2), brine, and dried over Na₂SO₄. The crude material was purified by column chromatography (silica, hexanes/acetone) to give the title compound (20 mg, 0.035 mmol, 63% yield) as off-white solid. ESI-MS m/z=565.30, 567.29 [M−H]⁻.

Example 315

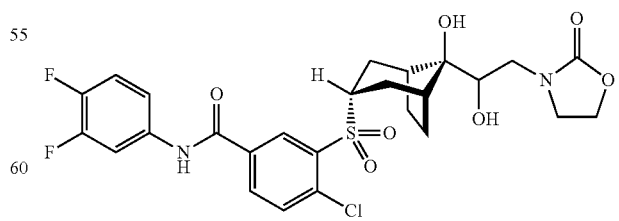

Step 315a.

To a solution of oxazolidin-2-one (42.0 mg, 0.483 mmol) in DMF (1 mL) was added sodium hydride (17.38 mg, 0.435 mmol) at 0° C. The mixture was stirred for 1 h at rt, and cooled to 0° C. The compound from step 314a (45 mg, 0.097 mmol) in DMF (1 mL) was added into the reaction. The mixture was heated to 55° C. for 15 h. The reaction was cooled to rt and sat. NH₄Cl solution was added. The mixture was extracted with EtOAc, dried over Na₂SO₄, and purified by column chromatography (silica, hexanes/EtOAc) to give the desired compound (40 mg, 0.072 mmol, 75% yield) as white solid.

Step 315b.

To a solution of the compound from step 315a (38 mg, 0.069 mmol) in NMP (1 mL) was added m-CPBA (46.2 mg, 0.206 mmol, 77%) at 0° C. The reaction was slowly warmed to rt and stirred for 16 h. The mixture was extracted with EtOAc, washed with sat. Na₂S₂O₃ solution and NaHCO₃ solution (×2), brine, and dried over Na₂SO₄. The crude material was purified by column chromatography (silica, MeOH/DCM) to give the title compound (14.0 mg, 0.024 mmol, 35% yield) as off-white solid. ESI-MS m/z=584.02, 586.02 [M−H]⁻.

Example 316

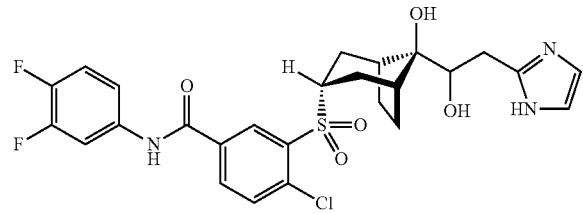

Step 316a.

To a solution of 1-(diethoxymethyl)-1H-imidazole (0.053 ml, 0.322 mmol) in THF (2 mL) was added n-butyllithium (0.116 ml, 0.290 mmol, 2.5 M in THF) at −78° C. The mixture was warmed to 0° C. and stirred for 45 min, and then cooled to −78° C. The compound from step 314a (30 mg, 0.064 mmol) in THF (1 mL) was added into the reaction mixture. The reaction was heated to 50° C. and stirred for 16 h. The reaction was cooled to rt and sat. NH₄Cl solution was added. The mixture was extracted with EtOAc, dried over Na₂SO₄, and purified by column chromatography (silica, hexanes/acetone) to give the desired compound (13 mg, 0.024 mmol, 38% yield) as an off-white solid.

Step 316b.

To a solution of the compound from step 316a (13 mg, 0.024 mmol), CSA (8.48 mg, 0.037 mmol) in NMP (1 mL) was added m-CPBA (16.37 mg, 0.073 mmol, 77%) at 0° C. The reaction was slowly warmed to rt and stirred for 15 h. The mixture was extracted with EtOAc, washed with sat. Na₂S₂O₃ solution and NaHCO₃ solution (×2), brine, and dried over Na₂SO₄. The crude material was purified by column chromatography (silica, hexanes/acetone) to give the title compound (5.8 mg, 0.010 mmol, 42% yield) as an off-white solid. ESI-MS m/z=565.02, 566.02 [M−H]⁻.

Example 317

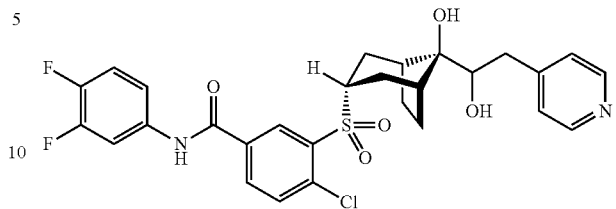

Step 317a.

To a solution of 4-methylpyridine (0.134 ml, 1.372 mmol) in THF (3 mL) was added lithium diisopropylamide (1.372 ml, 1.372 mmol, 1 M in THF) dropwise at −78° C. The mixture was stirred for 1 h at the same temperature. A solution of the compound from step 281a (200 mg, 0.443 mmol) in THF (1.5 mL) was added into the mixture at −78° C. The reaction was slowly warmed to rt and stirred for 16 h. Sat. NH₄Cl solution was added. The mixture was extracted with EtOAc, dried over Na₂SO₄, and purified by column chromatography (silica, MeOH/DCM) to give the desired compound (91 mg, 0.167 mmol, 38% yield) as a sticky oil.

Step 317b.

To a solution of the compound from step 317a (91 mg, 0.167 mmol), p-TSA (95 mg, 0.501 mmol) in NMP (1 mL) was added m-CPBA (112 mg, 0.501 mmol, 77%) at 0° C. The reaction was slowly warmed to rt and stirred for 16 h. The mixture was extracted with EtOAc, washed with sat. Na₂S₂O₃ solution and NaHCO₃ solution (×2), brine, and dried over Na₂SO₄. The crude material was purified by column chromatography (silica, hexanes/acetone) to give the title compound (61.0 mg, 0.106 mmol, 63% yield) as white solid. ESI-MS m/z=576.04, 578.04 [M−H]⁻.

Example 318

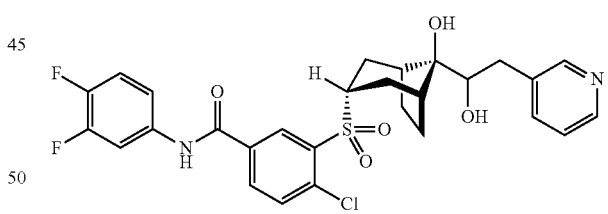

Step 318a.

To a solution of 3-methylpyridine (0.134 ml, 1.372 mmol) in THF (3 mL) was added lithium diisopropylamide (1.372 ml, 1.372 mmol, 1 M in THF) dropwise at −78° C. After being stirred for 30 min at the same temperature, the mixture was warmed to 0° C. and stirred for 30 min and cooled down to −78° C. A solution of the compound from step 281a (200 mg, 0.443 mmol) in THF (1.5 mL) was added into the mixture at −78° C. The reaction was slowly warmed to rt and stirred for 15 h. Sat. NH₄Cl solution was added. The mixture was extracted with EtOAc, dried over Na₂SO₄, and purified by column chromatography (silica, MeOH/DCM) to give the desired compound (70 mg, 0.128 mmol, 29% yield) as a pale yellow solid.

Step 318b.

To a solution of the compound from step 318a (70 mg, 0.128 mmol), p-TSA (73.3 mg, 0.385 mmol) in NMP (1 mL) was added m-CPBA (86 mg, 0.385 mmol, 77%) at 0° C. The reaction was slowly warmed to rt and stirred for 16 h. Sat Na$_2$S$_2$O$_3$ solution and NaHCO$_3$ solution were added and the resulting mixture was stirred for 1 h at rt. The mixture was extracted with EtOAc, washed with sat. Na$_2$S$_2$O$_3$ solution and NaHCO$_3$ solution (×2), brine, and dried over Na$_2$SO$_4$. The crude material was purified by column chromatography (silica, hexanes/acetone) to give the title compound (27.0 mg, 0.047 mmol, 36% yield) as a white solid. ESI-MS m/z=576.04, 578.04 [M−H]$^-$.

Example 319

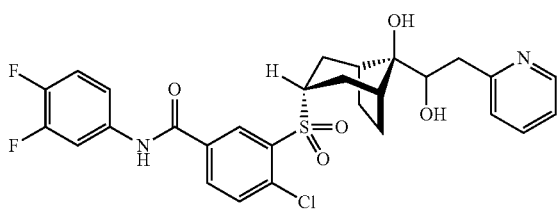

Step 319a.

To a solution of 2-methylpyridine (0.135 ml, 1.372 mmol) in THF (3 mL) was added lithium diisopropylamide (0.549 ml, 1.372 mmol, 1 M in THF) dropwise at −78° C. After being stirred for 1 h min at the same temperature, a solution of the compound from step 281a (200 mg, 0.443 mmol) in THF (1.5 mL) was added into the mixture at −78° C. The reaction was slowly warmed to rt and stirred for 16 h. Sat. NH$_4$Cl solution was added. The mixture was extracted with EtOAc, dried over Na$_2$SO$_4$, and purified by column chromatography (silica, MeOH/DCM) to give the desired compound (130 mg, 0.239 mmol, 54% yield) as pale yellow solid.

Step 319b.

To a solution of the compound from step 319a (130 mg, 0.239 mmol), p-TSA (136 mg, 0.716 mmol) in NMP (1 mL) was added m-CPBA (160 mg, 0.716 mmol, 77%) at 0° C. The reaction was slowly warmed to rt and stirred for 16 h. Sat. Na$_2$S$_2$O$_3$ solution and NaHCO$_3$ solution were added and the resulting mixture was stirred for 1 h at rt. The mixture was extracted with EtOAc, washed with sat. Na$_2$S$_2$O$_3$ solution and NaHCO$_3$ solution (×2), brine, and dried over Na$_2$SO$_4$. The crude material was purified by column chromatography (silica, hexanes/acetone) to give the title compound (80.0 mg, 0.139 mmol, 58% yield) as white solid. ESI-MS m/z=576.04, 578.04 [M−H]$^-$.

Example 320

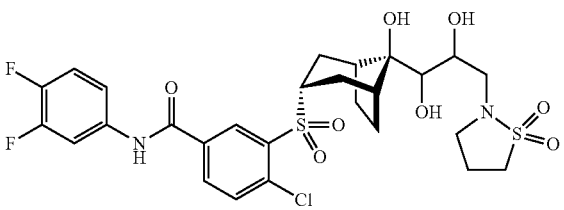

Step 320a.

To a solution of compound from example 82a (450 mg, 1.00 mmol) in DCM (5 mL), allylbromide (363 mg, 3.0 mmol) was added followed by Hoveyda-Grubbs 2$^{nd}$ generation catalyst (12.5 mg, 0.2 mmol) and stirred at rt o/n. The reaction was concentrated.

The crude was chromatographed (silica, EtOAc/hexanes) to give desired compound (410 mg, a mixture of desired and starting material in a ratio 1.1:1) as an off-white solid. ESI-MS m/z=542.16, 544.16[M−H]$^-$.

Step 320b.

To a solution of compound from step 320a (170 mg, 0.31 mmol) in DMF (2 mL), Dioxoisothiazolidine (38 mg, 0.31 mmol) was added followed by K$_2$CO$_3$ (44 mg, 0.31 mmol) and stirred at 65° C. o/n. The crude was diluted with EtOAc, washed with water twice, brine twice and dried (Na$_2$SO$_4$) and concentrated. The crude was chromatographed (silica, MTBE/hexanes) to give desired compound (59 mg, 32%) off-white solid. ESI-MS m/z=627.12, 629.12 [M−H+HCOOH]$^-$.

Step 320c.

The title compound was obtained from the compound of step 320b following the procedure described in example 4b. ESI-MS m/z=693.30, 695.30 [M−H+HCOOH]$^-$.

Example 321

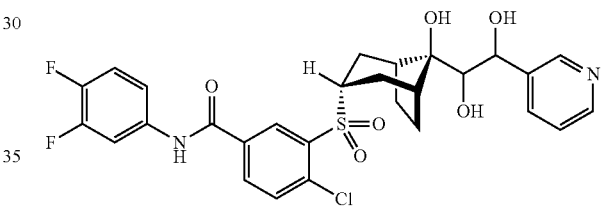

Step 321a.

To a solution of compound from step 82a (100 mg, 0.222 mmol) and 3-bromopyridine (26 μL, 0.267 mmol) in DMF (2 mL) was added Et$_3$N (62 μL, 0.445 mmol), tri-o-tolylphosphine (6.8 mg, 0.022 mmol), and palladium acetate (2.5 mg, 0.011 mmol). The reaction mixture was stirred at 120° C. for 18 h. The reaction mixture was cooled, then extracted with EtOAc, washed with water and brine, dried over Na$_2$SO$_4$ filtered and concentrated. The crude material was purified by column chromatography (silica, hexane/acetone) to give the desired compound (100 mg, 0.190 mmol, 85% yield). ESI-MS m/z=571.30, 573.30 [M−H]$^-$.

Step 321b.

To a solution compound from step 321a (52 mg, 0.099 mmol) in acetone (1 mL) and water (0.2 mL) was added OsO$_4$ (25 μL, 4.93 μmol, 5% in water) and NMO (58 mg, 0.493 mmol). The reaction mixture was stirred at rt for 72 h. The reaction mixture was diluted with ethyl acetate and then washed with saturated Na$_2$S$_2$O$_3$ and saturated NaCl. The organic layer was dried with Na$_2$SO$_4$, filtered and concentrated. The crude material was used without further purification.

Step 321c.

To a solution of crude material from step 321b in NMP (2 mL) was added p-TSA (56 mg, 0.294 mmol) and m-CPBA (110 mg, 0.49 mmol, 77%) and stirred at rt. o/n. The reaction was extracted with EtOAc, washed with water and brine. The organic layer was dried (Na$_2$SO$_4$), filtered and concentrated. The crude product was chromatographed (silica,

Example 322

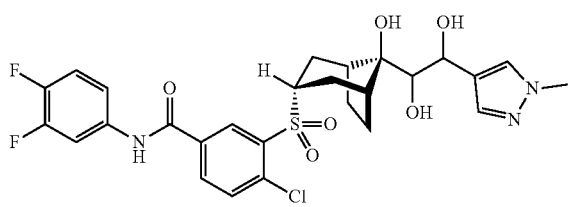

Step 322a.

To a solution of compound from step 82a (100 mg, 0.222 mmol) and 4-bromo-1-methyl-1H-pyrazole (28 μL, 0.267 mmol) in DMF (2 mL) was added Et₃N (62 μL, 0.445 mmol), tri-o-tolylphosphine (6.8 mg, 0.022 mmol), and palladium acetate (2.5 mg, 0.011 mmol). The reaction mixture was stirred at 120° C. for 18 h. The reaction mixture was cooled then extracted with EtOAc, washed with water and brine, dried over Na₂SO₄ filtered and concentrated. The crude material was purified by column chromatography (silica, hexane/acetone) to give the desired compound (12 mg, 0.023 mmol, 10% yield). ESI-MS m/z=574.32, 576.32 [M–H]⁻.

Step 322b.

To a solution compound from step 322a (12 mg, 0.099 mmol) in acetone (0.5 mL) and water (0.1 mL) was added OsO₄ (6 μL, 1.13 μmol, 5% in water) and NMO (13 mg, 0.113 mmol). The reaction mixture was stirred at rt for 72 h. The reaction mixture was diluted with ethyl acetate and then washed with saturated Na₂S₂O₃ and saturated NaCl. The organic layer was dried with Na₂SO₄, filtered and concentrated. The crude mixture was used without further purification.

Step 322c.

To a solution of crude material from step 322b in NMP (1 mL) was added m-CPBA (16 mg, 0.069 mmol, 77%) and stirred at rt. o/n. The reaction was extracted with EtOAc, washed with water and brine. The organic layer was dried (Na₂SO₄), filtered and concentrated. The crude product was chromatographed (silica, hexane/acetone) to give the title compound as a white solid. ESI-MS m/z=640.33, 642.33 [M+HCO₂]⁻.

Example 323

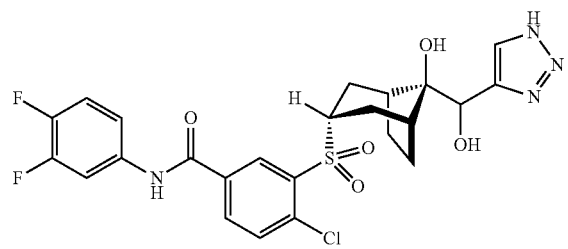

Step 323a.

To a solution of trimethylsilylacetylene (0.50 ml, 3.56 mmol) in THF (1.66 ml) was added n-BuLi (1.426 ml, 3.56 mmol, 2.5 M in THF) at –78° C. The resulting mixture was stirred for 1 h at the same temperature. A solution of compound from step 281a (0.3 g, 0.664 mmol) in THF (1.66 mL) was added into the reaction at –78° C. The resulting light yellow solution was slowly warmed up to rt and stirred for 3 h. Sat. NH₄Cl solution was added. The mixture was extracted with EtOAc, dried over Na₂SO₄, and used without further purification.

Step 323b.

To a solution of the compound from step 323a (365 mg, 0.664 mmol) in MeOH (3 ml) and water (0.3 ml) was added potassium carbonate (459 mg, 3.32 mmol) at rt. The mixture was stirred for 15 h at rt. Solvent removed in vacuo, and the resulting mixture was extracted with EtOAc, dried over Na₂SO₄, and then purified by column chromatography (silica, hexanes/EtOAc) to give the desired compound (204.9 mg, 0.429 mmol, 65% yield) as a white solid.

Step 323c.

A mixture of formaldehyde (109 μl, 1.465 mmol), acetic acid (12.58 μl, 0.220 mmol) and THF (1 mL) was stirred for 15 min at rt. Sodium azide (14.28 mg, 0.220 mmol) was added, followed by the compound from step 323b (70 mg, 0.146 mmol). The mixture was stirred for 10 min, and sodium ascorbate (5.80 mg, 0.029 mmol) was added, followed by copper(II) sulfate (1.169 mg, 7.32 μmol) in 150 uL of water. The reaction was heated to 50° C. and stirred for 16 h, and then extracted with EtOAc, dried over Na₂SO₄, and then purified by column chromatography (silica, MeOH/DCM) to give the desired compound (53.4 mg, 0.103 mmol, 70% yield) as greenish solid.

Step 323d.

To a solution of the compound from step 323c (53.4 mg, 0.102 mmol) and p-TsOH (97 mg, 0.512 mmol) in NMP (1 mL) was added m-CPBA (68.9 mg, 0.307 mmol, 77%) at 0° C. The reaction was slowly warmed to rt and stirred for 15 h. Sat. Na₂S₂O₃ solution and NaHCO₃ solution were added and the resulting mixture was stirred for 1 h at rt. The mixture was extracted with EtOAc, washed with sat. Na₂S₂O₃ solution and NaHCO₃ solution (×2), brine, and dried over Na₂SO₄. The crude material was purified by column chromatography (silica, MeOH/DCM with 0.1% NH₃) to give the title compound (15.0 mg, 0.027 mmol, 27% yield) as an off-white solid. ESI-MS m/z=549.95, 551.97 [M–H]⁻.

Example 327

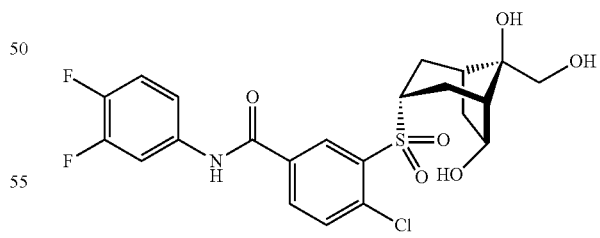

Step 327a.

Treatment of the compound from step 279d with the condition described in step Int 2e gave the desired product. H NMR (400 MHz, Chloroform-d) δ 3.90 (m, 1H), 3.43 (s, 2H), 2.69 (s, 1H), 1.84 (m, 4H), 1.70 (m 2H), 1.57 (m, 2H), 1.45 (t, J=6.7 Hz, 3H), 0.83 (m, 9H), 0.00 (s, 6H).

Step 327b.

To a solution of compound of step 327a (10.6 g, 37.0 mmol) in CH₂C₂ (74.0 ml) at 0° C. was added pyridine (8.98 ml, 111 mmol), DMAP (0.226 g, 1.850 mmol) and benzenesulfonyl chloride (5.19 ml, 40.7 mmol). After being stirred at rt o/n, water (15 mL) was added and stirred 30 mins. It was concentrated then diluted with EtOAc (400 mL) and washed with saturated aq. $NaHCO_3$, water, 1 M HCl, water, brine. The organic layer was dried ($Na_2SO_4$) and concentrated to give the crude product that was used for the next step without further purification.

Step 327c.

To a solution of step 327b (15.60 g, 36.6 mmol) in 2-methyl-THF (58.5 ml) at rt was added conc. HCl (11.70 ml, 140 mmol). The resulting clear solution was stirred at rt for 3 h. The mixture was poured portion-wise into a mixture of saturated aq. $NaHCO_3$ and DCM. The aqueous layer was extracted with DCM twice. The combined organic phase was washed with brine, dried ($Na_2SO_4$), filtered and concentrated. The residue was dried under vacuum to afford a white solid which was used directly for next step.

Step 327d.

To a solution of compound of step 327c (11.42 g, 36.6 mmol) in $CH_2Cl_2$ (122 ml) at 0° C. was added DMAP (0.447 g, 3.66 mmol), pyridine (8.87 ml, 110 mmol) and acetic anhydride (3.79 ml, 40.2 mmol). The reaction was stirred at rt overnight. Saturated aq. $NaHCO_3$ (30 mL) was added and stirred 15 mins. After separated, the aq. phase was extracted with $CH_2Cl_2$ (100 mL×2), the combined organic phases were dried ($Na_2SO_4$) and concentrated. The crude was chromatographed to give the desired compound (11.4 g, 93% three steps) as off-white solid.

Step 327e.

To a solution of compound from step 327d (4.000 g, 11.29 mmol) in acetic acid (45 ml) at rt was added manganese bis(trifluoromethanesulfonate) (0.91 ml, 0.011 mmol) (0.0125 M in acetic acid/water 9/1) and 2,2'-bipyridine (0.018 g, 0.113 mmol). After being stirred 10 min at rt, peracetic acid/KOH mixture (prepared by adding 10% KOH (3.0 ml) to 35% peracetic acid (10.0 ml), 11.79 ml, 39.5 mmol) was added dropwise over ~10 min. It was further stirred 15 mins at rt followed by addition of acetone (130 ml). After 1 min at rt, the slightly cloudy solution was filtered through a short pad of celite, washed with acetone. The filtrate was concentrated. The crude residue was chromatographed (silica, EtOAc/hexanes) to afford desired compound (2.130 g, 51%) as colorless oil.

Step 327f.

To a clear solution of step 327e (2.130 g, 5.78 mmol) and intermediate 6 (1.820 g, 6.07 mmol) in DMF (5.78 ml) at rt was added potassium carbonate (0.799 g, 5.78 mmol). The mixture was stirred at 70° C. for 12 h before being cooled. The mixture was diluted with EtOAc and saturated $NH_4Cl$ solution. The organic layer was washed with water/brine (1/1, *2), brine (*1), dried and concentrated. The crude residue was chromatographed (silica, EtOAc/DCM) to afford desired compound (2.10 g, 70%). ESI-MS m/z=508.07, 510.07 [M−H]$^-$.

Step 327g.

To a solution of compound from step 327f (40 mg, 0.078 mmol) in EtOH at 0° C. was added $NaBH_4$ (6 mg, 0.16 mmol). 30 mins later 2nd portion 2 eq. $NaBH_4$ was added and stirred at rt for 3 hours. total ~10 eq. $NaBH_4$ was added. It was concentrated to remove the volatile. The crude was dissolved in EtOAc and washed with $NH_4Cl$ and brine, dried concentrated to give the crude desire compound (60 mg) as white solid. This material was used in the next step without further purification. ESI-MS m/z=468.08, 470.08 [M−H]$^-$.

Step 327h.

The title compound was obtained from step 327g, by followed the procedure described in example 130b. ESI-MS m/z=500.07, 502.07 [M−H]$^-$.

Example 328

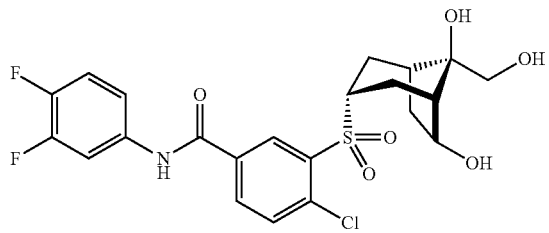 [SMILES: O=C(Nc1ccc(F)c(F)c1)c1ccc(Cl)c(S(=O)(=O)[C@@H]2CC3C[C@@H](O)[C@@H](C2)[C@@]3(O)CO)c1]

Step 328a.

To the compound from step 327f (610 mg, 1.2 mmol) in EtOH (50 mL)/MeOH (15 mL) at 0° C., $NaBH_4$ (360 mg, 9.6 mmol) was added. 15 mins later $2^{nd}$ portion $NaBH_4$ (200 mg) was added. 10 mins later, $3^{rd}$ portion $NaBH_4$ (100 mg) was added, stirred another 10 mins. When still cooled, diluted HCl (0.5 M) was added dropwise until no more bubbling. EtOAc (200 mL) was added, followed by water 50 mL. The organic was washed with water, brine, dried ($Na_2SO_4$) and concentrated. The crude residue was chromatographed (silica, EtOAc/hexanes) to afford desired compound (410 mg, 67%) as a white solid. ESI-MS m/z=510.09, 512.09[M−H]$^-$.

Step 328b.

To solution of the compound of step 328a (382 mg, 0.77 mmol) in toluene (1 mL), 2-(tributyl-15-phosphaneylidene)acetonitrile (647 mg, 2.68 mmol) in toluene (3 mL) was added. it was heated at 95 to 100° C. for 1 h, $2^{nd}$ portion 2-(tributyl-15-phosphaneylidene)acetonitrile (400 mg) was added and heated another 1.5 h. $3^{rd}$ portion 2-(tributyl-15-phosphaneylidene)acetonitrile (500 mg) the was added, and heated another 1.5 h before being cooled and concentrated, the crude product was chromatographed (silica, MTBE/hexanes) to give desired compound (302 mg 80%) as white solid. ESI-MS m/z=492.08, 494.08[M−H]$^-$.

Step 328c.

To the compound form step 328b (295 mg, 0.60 mmol) in acetic anhydride (5 mL), $BF_3$etherate (0.6 mL, 4.8 mmol) was added and stirred at rt for 30 mins. The reaction was added into an aq. $NaHCO_3$ (40 mL) in an ice water bath slowly. It was extracted with EtOAc twice. The combined organic was washed with water, brine and dried ($Na_2SO_4$). After being concentrated, the crude residue was chromatographed (silica, EtOAc/hexanes) to afford desired compound (245 mg, 69%) as a white solid, a mixture of bis-acetates and tri-acetates. ESI-MS m/z=552.10, 554.10[M−H]$^-$ (bis-acetates), m/z=594.11, 596.11[M−H]$^-$ (tri-acetates).

Step 328d.

$K_2CO_3$ (183 mg, 1.33 mmol) was added into the solution of the compound from step 328c (245 mg, 0.44 mmol) in MeOH (3 mL). 2 hours later extra $K_2CO_3$ (25 mg) was added and stirred for another 1 h before being diluted with EtOAc and washed with water. The aqueous phase was extracted with EtOAc. The combined organic phase was washed with brine, dried ($Na_2SO_4$) and concentrated. The crude was chromatographed (silica, MTBE/hexanes) to give desired compound (148 mg, 71%) off-white solid. ESI-MS m/z=468.08, 470.08[M−H]$^-$.

Step 328e.

The title compound was obtained from compound of step 328d following the procedure described in example 130b. ESI-MS m/z=500.07, 502.07 [M−H]⁻.

Example 329

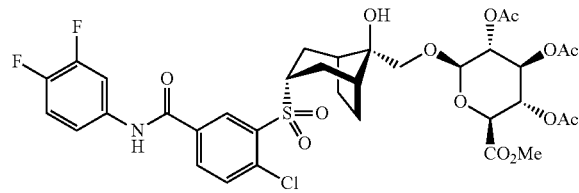

To a solution of compound from example 150 (250 mg, 0.514 mmol) in acetonitrile (5 mL) was added (2R,3R,4S,5S,6S)-2-bromo-6-(methoxycarbonyl)tetrahydro-2H-pyran-3,4,5-triyl triacetate (613 mg, 1.543 mmol) and Ag$_2$CO$_3$ (1.42 g, 2.57 mmol, 50% w/w on celite). The reaction mixture was heated at 80° C. for 18 h. The crude reaction mixture was filtered through celite, concentrated and purified via chromatography (silica, acetone/hexanes) to give title compound (195 mg, 47%). ESI-MS m/z=846.17, 848.16 (M+HCO$_2$)⁻.

Example 330

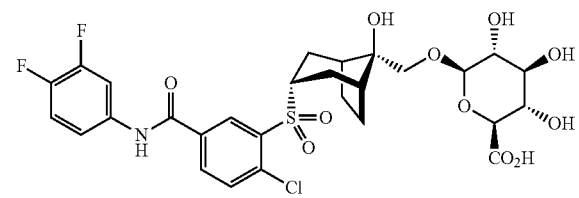

To a solution of compound from example 329 (195 mg, 0.243 mmol) in THF (3 mL), methanol (1 mL), and water (2 mL) was added LiOH (50 mg, 2.09 mmol). The reaction mixture was heated at 40° C. for 1 h. The crude reaction mixture was diluted with EtOAc and acidified to pH 4 with 1 M HCl. The organic layer was washed with brine, dried over Na$_2$SO$_4$ filtered and concentrated. The crude product was purified via prep-HPLC (C18, acetonitrile/water) to give title compound (10 mg, 6%). ESI-MS m/z=660.11, 662.11 (M−H)⁻.

Example 331

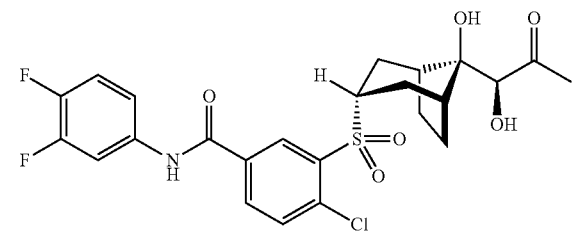

A mixture of example 182 (159 mg, 0.30 mmol) and IBX (101 mg, 0.36 mmol) in DMSO (1.5 mL) was stirred at rt for 4 h. Aq. Na$_2$S$_2$O$_3$ solution was added and the mixture was extracted with EtOAc. The organic layer was washed with water, brine, dried over Na$_2$SO$_4$, filtered, concentrated and purified by prep-HPLC (C18 column, acetonitrile/water) to give title compound (58 mg, 36%). ESI-MS m/z=572.27, 574.27 (M+HCO$_2$)⁻.

Example 332

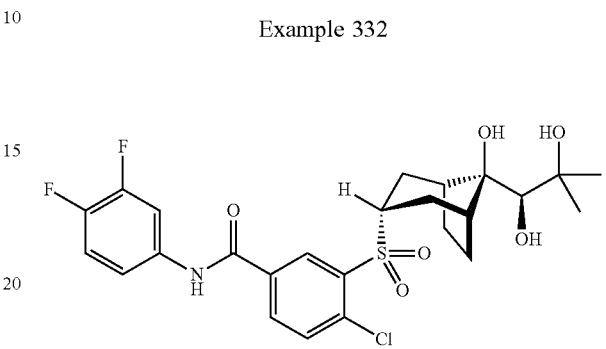

To a solution of the compound from step 331 (230 mg, 0.436 mmol) in THF (5 ml) was added methylmagnesium bromide (0.508 ml, 1.525 mmol) at −78° C. It was stirred for 3 h at the same temperature. Water was added, and the mixture was extracted with EtOAc, dried over Na$_2$SO$_4$. The crude material was purified by column chromatography (silica, hexanes/acetone) to the title compound (34.3 mg, 0.063 mmol, 15% yield) as white solid. ESI-MS m/z=541.01, 543.01 [M−H]⁻.

Example 333

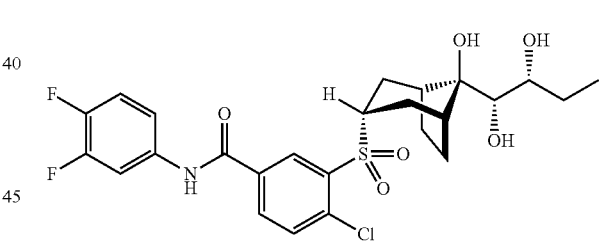

Step 333a.

A mixture of compound from step 82a (112 mg, 0.25 mmol), E-hex-3-ene (630 mg, 7.5 mmol) and Hoveyda-Grubbs catalyst 2$^{nd}$ Generation (15.7 mg, 0.025 mmol) in DCM (2.0 mL) was stirred at rt for 20 h. The mixture was purified by column chromatography (silica, hexanes/EtOAc) to give the desired compound as white solid (78 mg, 65%). ESI-MS m/z=476.13, 478.13 [M−H]⁻.

Step 333b.

To a suspension of compound from step 333a (78 mg, 0.163 mmol) and NMO (0.115 g, 0.98 mmol) in acetone-water (2.1 mL/0.3 mL) at rt was added osmium tetroxide (0.205 ml, 2.5% in t-butanol, 0.016 mmol) and the mixture was stirred at rt for 20 h. It was quenched with aqueous Na$_2$SO$_3$, extracted with EtOAc, washed with water, 3N HCl, NaHCO$_3$, brine, dried over Na$_2$SO$_4$, filtered and concentrated to give a mixture of sulfone and sulfoxide, used without further purification.

Step 333c.

To a solution of compound from step 333b in NMP (2 mL) was added m-CPBA (0.183 g, 0.85 mmol, 77%) and stirred at rt for 20 h. Aqueous $Na_2S_2O_3$, $NaHCO_3$ and few drops of $Et_3N$ was added and stirred at rt for 1 h. It was extracted with EtOAc, washed with water, brine, dried over $Na_2SO_4$, filtered, concentrated and purified by prep-HPLC (C18, acetonitrile/water) to give racemic product. The racemic product was separated by chiral SFC using MeOH as eluent to give the title compound (18 mg, 20%). ESI-MS m/z=542.29, 544.29 [M−H]⁻.

Example 334

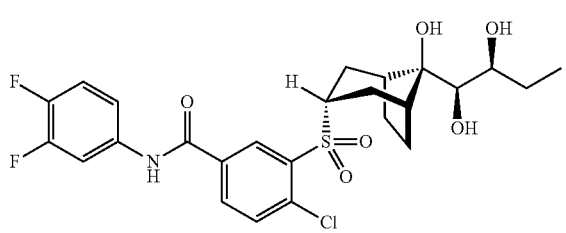

Step 334.

The title compound (18 mg, 20%) was isolated from example 333. ESI-MS m/z=542.29, 544.29 [M−H]⁻.

Example 336

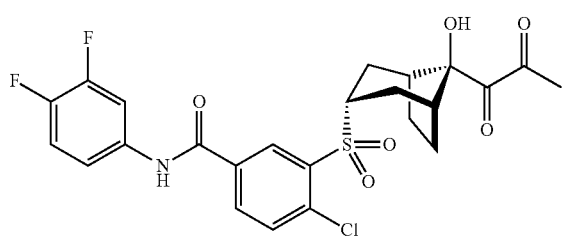

A solution of the compound of Example 182 (1.05 g, 1.98 mmol) and IBX (0.777 g, 2.77 mmol) in DMSO (5 mL) was stirred at rt for overnight. It was quenched with $Na_2S_2O_3$ aqueous solution and $NaHCO_3$ aqueous solution. The reaction mixture was extracted with EtOAc, washed with water and brine, dried over $Na_2SO_4$, filtered, and concentrated. The resulting crude product was purified by prep-HPLC (C18, acetonitrile/water) to give the title compound (32 mg, 3.1%) as a white solid. ESI-MS m/z=570.26, 572.26 [M+HCO₂]⁻.

Example 337

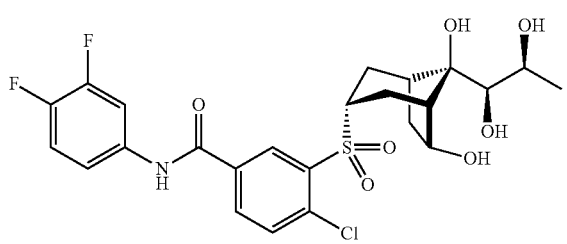

Step 337a.

To a solution of compound from step int 2a (92.0 g, 676 mmol) in THF (135 ml) at 0° C. was added a solution of prop-1-yn-1-ylmagnesium bromide (1554 ml, 777 mmol) via cannula 30 minutes. It was stirred 5 mins before the ice bath was removed. The mixture was warmed up to rt and kept at rt for 30 mins. The reaction mixture cooled to 0° C., saturated aq. $NH_4Cl$ (500 mL) was added, followed by MTBE (500 mL). The aqueous phase was separated and extracted with MTBE (500 mL). The combined organic phases were washed with brine and dried ($Na_2SO_4$). The solution past through a short column of silica gel and concentrated to give a yellow oil (125 g, 105% yield).

Step 337b.

To a solution of compound from step 337a (50.0 g, 284 mmol) in dioxane (400 mL) and water (133 mL) at 0° C. was added 2,6-lutidine (66.1 ml, 567 mmol) and sodium periodate (212 g, 993 mmol), followed by the addition of a solution of $OsO_4$ (1.803 ml, 0.284 mmol, 4% in water). This mixture was warmed up to rt and stirred at rt for 2 days, then cooled to 0° C. and quenched with saturated $Na_2S_2O_3$ aq solution. The mixture was stirred at 0° C. for 1 h, then diluted with 1 L water, extracted with MTBE (1 L×3). The combined organic phases were washed with 1N HCl twice, water, $NaHCO_3$ aq solution, water and brine, dried ($Na_2SO_4$), and concentrated. The crude residue was chromatographed to afford the desired product (40.2 g, 80%) off-white solid.

Step 337c.

A solution of LAH (1 M in THF, 265 mL, 265 mmol) and DME (430 mL) was cooled at 0° C. A solution of compound form step 337b (18.9 g, 106 mmol) in DME (80 mL) was added dropwise in about 0.5 h and stirred one more hour. It was heated to and kept at 80° C. for 2 h before being cooled to 0° C. It was quenched carefully with 10 mL water and 10 mL 15% NaOH solution, 30 mL water, followed by the addition of 72 g of $Na_2SO_4$ solid and stirred for 1 h before being filtered. After concentration, the crude residue was chromatographed to afford the desired product (12.6 g, 65%) off-white solid.

Step 337d.

Into a solution of step 337c (4.58 g, 25.1 mmol) in dichloromethane (50 mL) at rt was added pyridine (4.1 mL, 50 mmol) and benzenesulfonyl chloride (5.33 g, 30.2 mmol). The reaction was stirred o/n at rt before water (30 mL) was added. The mixture was stirred for 1 h. After separation, the aqueous phase was extracted with DCM (100 mL). The combined organic phase was washed with HCl (1 M, 20 mL*2), water, $NaHCO_3$, brine and dried ($Na_2SO_4$). After being concentrated, the crude residue was chromatographed to afford the desired product (6.67 g, 82%) off-white solid.

Step 337e.

To a solution of $K_2OsO_6·2H_2O$ (381 mg, 1.03 mmol), (DHQ)₂PHAL (1.61 mg, 2.07 mmol), $K_2CO_3$ (8.58 g, 62.1 mmol), and $K_3FeCN_6$ (20.4 g, 62.1 mmol) in t-BuOH (40 mL)/water (40 mL) at 0° C. was added compound from step 337d (6.67 g, 20.69 mmol) and $MeSO_2NH_2$ (5.90 g, 62.1 mmol). The reaction was warmed to rt and stirred one day. It was cooled to 0° C. and $Na_2SO_3$ (30 g) was added. The mixture was stirred 15 mins at 0° C., then 1 hour at rt before partition with EtOAc (50 mL). The aq. phase was back extracted with EtOAc. The combined organic was washed with aq. $Na_2S_2O_3$, water, 1 N HCl (20 mL*2), water, 2 M KOH (10 mL*2), water, brine*2. It was dried ($Na_2SO_4$) and concentrated to give the desired product (7.20 g, 97%) as an off-white solid. This material was used in the next step without further purification.

Step 337f.

To a solution of compound of step 337e (7.20 g, 20.20 mmol) in $CH_2Cl_2$ (50 ml) at 0° C. was added DIPEA (14.11 ml, 81 mmol) and acetic anhydride (5.72 ml, 60.6 mmol). The reaction was stirred at rt overnight. Saturated aq. $NaHCO_3$ (30 mL) was added and stirred 15 mins. After separation, the aq. phase was extracted with $CH_2Cl_2$ (100 mL×2), the combined organic phases were dried ($Na_2SO_4$) and concentrated. The crude was chromatographed to give the desired compound (8.2 g, 100%) as off-white solid.

Step 337g.

To a clear solution of compound from step 337f (5.09 g, 11.55 mmol) in hexfluoroisopropanol (40 ml) at rt was added manganese bis(trifluoromethanesulfonate) (20 mg ml, 0.058 mmol) and 2,2'-bipyridine (0.09 g, 0.58 mmol). After being stirred 10 min at rt, peracetic acid/KOH mixture (prepared by adding 10% KOH (3.0 ml) to 35% peracetic acid (10.0 ml), 11.79 ml, 39.5 mmol)) was added via a syringe pump over 1 h. Acetone (100 ml) was added. After stirring 10 mins, it was concentrated. The crude residue was chromatographed (silica, EtOAc/hexanes) to afford recovered starting material 3.1 g and the higher polar mixture 1.79 g. This high polar mixture was used in the next step directly.

Step 337h.

To a solution of the high polar mixture from step 337g was added intermediate 6 by following the step 327f to afford two set mixtures. One set mixture contains the ketone product; ESI-MS m/z=640.31, 642.31 [M+HCOO−]−. The other set contains the alcohol product. ESI-MS m/z=642.32, 644.32 [M+HCOO−]−.

Step 337i.

The alcohol product from step 337h was treated with the conditions described in steps 328d and 328e sequentially and purified by prep-HPLC (C-18, Acetonitrile/water) to offer the title compound as a white solid. ESI-MS m/z=590.27, 592.27 [M+HCOO−]−.

Example 339

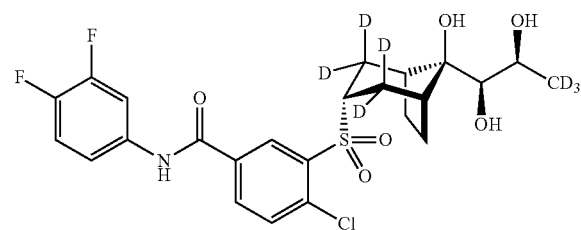

Step 339a.

To a solution of intermediate 2a (2.29 g, 16.8 mmol) in THF (18 mL) at 0° C. was added ethynylmagnesium bromide (40.4 mL, 20.2 mmol, 0.5 M in THF) and stirred at 0° C. for 30 mins. The reaction was quenched by slowly addition of aq.$NH_4Cl$. MBTE and water were added. The mixture was separated and the organic layer was washed with water and brine. The mixture was dried over $Na_2SO_4$, filtered and concentrated under vacuum to give desired product (2.73 g, 100%).

Step 339b.

To a solution of compound from step 339a (1.7 g, 8.38 mmol) in THF (12 mL) at 0° C. was added n-BuLi (7.38 mL, 18.4 mmol, 2.5 M in hexanes) dropwise. After 20 mins at 0° C. $CD_3I$ (0.69 mL, 10.9 mmol) was added and the mixture was stirred at rt for 20 h. The reaction was quenched by slowly addition of aq.$NH_4Cl$. MBTE and water were added. The mixture was separated, and the organic layer was washed with water and brine. The mixture was dried over $Na_2SO_4$, filtered, concentrated under vacuum. The crude product was chromatographed (silica, hexanes/MBTE) to give the desired product (1.09 g, 65%).

Step 339c.

To a solution of compound from step 339b. (0.986 g, 5.5 mmol) in dioxane-water (12/4 mL), 2, 6-lutidine (1.45 mL, 11 mmol.), and $OsO_4$ (0.18 mL 2.5% solution in t-butanol, 0.017 mmol) were added. The mixture was cooled and $NaIO_4$ (4.12 g, 19.25 mmol) was added. The suspension was stirred at rt for 16 hours. Aq. $Na_2S_2O_3$ solution was added. The mixture was stirred for 1 hour and filtered through celite. The mixture was extracted with MBTE/Hexanes. The organic phase was washed with water, 1 N HCl, Sat-.$NaHCO_3$ and brine, dried over $Na_2SO_4$, filtered and concentrated to give the crude product (0.64 g, 64.2%). Step 339d. To a solution of compound from step 339c (0.64 g, 3.53 mmol) in $CD_3OD$ (10 mL) was added MeONa (23 mg, 0.42 mmol) and the mixture was stirred at rt for 3 h. It was concentrated, and the residue was redissolved in $CD_3OD$ (5 mL) and stirred for 3 h. The same reaction cycle was repeated two more times and the solution was quenched with D20. The mixture was extracted with MBTE. The organic layer was washed with D20 and sat. NaCl solution in D20, dried over $Na_2SO_4$, filtered and concentrated under vacuum to give the desired compound (0.62 g, 95%).

Step 339e.

To a solution of $LiBH_4$ (3.35 mL, 6.70 mmol, 2 M solution in THF) at −40° C. was added compound from step 339d (0.62 g, 3.35 mmol) in MBTE (20 mL). The resulting solution was warmed up to 0° C. in 1 h. The reaction was quenched by slowly addition of aq.$NH_4Cl$. MBTE and water were added. The mixture was separated, and the organic layer was washed with brine. The mixture was dried over $Na_2SO_4$, filtered and concentrated under vacuum. The crude product was chromatographed (silica, hexanes/MBTE) to give the desired compound as white solid (0.45 g, 72%).

Step 339f.

A solution of compound from step 339e (0.45 g, 2.40 mmol), LAH (6.01 mL, 6.01 mmol, 1 M in THF) and MeONa (26 mg, 0.48 mmol) in DME (12 mL) was heated to and kept at 80° C. for 2 h. The reaction mixture was cooled to 0° C., quenched carefully with 0.23 mL water and 0.23 mL 15% NaOH solution, kept for 10 min, then 0.69 mL water, followed by the addition of 5 g of $Na_2SO_4$ solid and stirred for 1 h before filtration. The filtrate was concentrated. The crude product chromatographed (silica, hexanes/ MBTE) to give the desired compound (0.32 g, 70%).

Step 339g.

To a solution of compound from step 339f (0.32 g, 1.69 mmol) in dichloromethane (3.5 mL) at rt was added pyridine (0.33 mL, 4.3 mmol) and 4-toluenesulfonyl chloride (0.387 g, 2.02 mmol). The reaction was stirred at rt o/n the water was added. The mixture was stirred for 1 h. After separation, the aqueous phase was extracted with DCM. The combined organic phase was washed with 1N HCl, water, $NaHCO_3$, brine, dried over $Na_2SO_4$ and concentrated. The crude product chromatographed (silica, hexanes/MBTE) to give the desired compound (0.52 g, 90%).

Step 339h.

To a solution of $K_2OsO_6 \cdot 2H_2O$ (27 mg, 0.073 mmol), $(DHQ)_2PHAL$ (85 mg, 0.109 mmol), $K_2CO_3$ (0.604 g, 4.37 mmol), and K$_3$FeCN$_6$ (1.44 g, 4.37 mmol) in t-BuOH (7.0 mL)/water (7.0 mL) at 0° C. was added compound from step 339g (0.50 g, 1.46 mmol) and MeSO$_2$NH$_2$ (0.277 g, 2.91 mmol). The reaction was allowed to slowly warm to rt and stirred for 3 days. The mixture was cooled to 0° C. followed by addition of Na$_2$SO$_3$. The mixture was stirred 15 mins at 0° C. then 1 hour at rt before partition with EtOAc. The aq. phase was back extracted with EtOAc. The combined organic was washed with aq. Na$_2$S$_2$O$_3$, water, 1 N HCl, water, 2 M KOH, water, brine, dried (Na$_2$SO$_4$), filtered and concentrated. The crude product chromatographed (silica, hexanes/EtOAc), then suspended in MeOH (5.6 mL) for 16 h and filtered to collect the desired product as a white solid (0.39 g, 70%).

Step 339i.

A solution of compound from step 339 h (0.39 g, 1.03 mmol), intermediate 6 (0.316 g, 1.06 mmol) and K$_2$CO$_3$ (0.143 g, 1.03 mmol) in DMF (1.1 mL) was stirred at 70° C. for 16 h. It was diluted with EtOAc and the mixture washed with water, brine, dried over Na$_2$SO$_4$, filtered and concentrated. The crude product was chromatographed (silica, hexanes/EtOAc) to give the desired compound as white solid (0.37 g, 71%). ESI-MS m/z=503.16, 505.16 [M−H]$^−$.

Step 339j.

A solution of compound from step 339i (0.37 g, 0.73 mmol) and m-CPBA (0.575 g, 2.56 mmol, 77%) in NMP (3.0 mL) was stirred at rt for 24 h. Aqueous Na$_2$S$_2$O$_3$, NaHCO$_3$ and few drops of Et$_3$N was added and stirred at rt for 1 h. It was extracted with EtOAc, washed with water, brine, dry over Na$_2$SO$_4$, filtered, recrystallized from MeOH to give title compound (0.33 g, 84%). ESI-MS m/z=535.15, 537.15 [M−H]$^−$.

Example 340

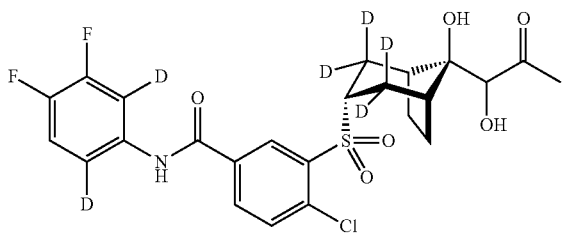

Step 340a.

A mixture of compound from step 337c. (3.2 g, 17.6 mmol) and IBX (6.8 g, 24.3 mmol) in DMSO (20 mL) was stirred at 45° C. for 14 h. Aq. Na$_2$S$_2$O$_3$ solution was added at rt and the mixture was extracted with EtOAc. The organic layer was washed with water, brine, dried over Na$_2$SO$_4$, filtered and concentrated. The crude product was chromatographed (silica, hexanes/MBTE) to give desired product (2.3 g, 72%).

Step 340b.

To a solution of compound from step 340a (2.3 g, 12.8 mmol) in CD$_3$OD (20 mL) was added MeONa (138 mg, 2.55 mmol) and the mixture was stirred at rt for 3 h. It was concentrated, and the residue was redissolved in CD$_3$OD (20 mL) and stirred for 3 h. The same reaction cycle was repeated two more times and the solution was quenched with D2O. The mixture was extracted with MBTE. The organic layer was washed with D2O and sat. NaCl solution in D2O, dried over Na$_2$SO$_4$, filtered and concentrated under vacuum to give the desired compound (2.0 g, 85%).

Step 340c.

To a solution of LiBH$_4$ (10.8 mL, 21.6 mmol, 2 M solution in THF) at −40° C. was added compound from step 340b (2.0 g, 10.8 mmol) in MBTE (60 mL). The resulting solution was warmed to 0° C. in 1 h. The reaction was quenched by slow addition of aq.NH$_4$Cl then diluted with MBTE and water. The mixture was separated, and the organic layer was washed with brine. The mixture was dried over Na$_2$SO$_4$, filtered and concentrated. The crude product was chromatographed (silica, hexanes/MBTE) to give the desired compound as white solid (1.4 g, 69%).

Step 340d.

To a solution of compound from step 340c (0.216 g, 1.16 mmol) in dichloromethane (1.5 mL) at rt was added pyridine (0.28 mL, 3.48 mmol) and 3-nitrobenzenesulfonyl chloride (0.385 g, 1.74 mmol). The reaction was stirred at rt o/n. Water was added then stirred for 1 h. After separation, the aqueous phase was extracted with DCM. The combined organic phase was washed with 1N HCl, water, NaHCO$_3$, and brine, dried over Na$_2$SO$_4$ filtered and concentrated. The crude product chromatographed (silica, hexanes/MBTE) to give the desired compound (0.37 g, 86%).

Step 340e.

A solution of compound from step 340d (0.36 g, 0.97 mmol), methyl 4-chloro-3-mercaptobenzoate (0.206 g, 1.02 mmol) and Cs$_2$CO$_3$ (0.316 g, 0.97 mmol) in DMF (1.1 mL) was stirred at 80° C. for 16 h. It was diluted with EtOAc and the mixture washed with water, brine, dried over Na$_2$SO$_4$, filtered and concentrated. The crude product was chromatographed (silica, hexanes/EtOAc) to give the desired compound as white solid (0.25 g, 69%).

Step 340f.

To a solution of compound from step 340e (0.25 g, 0.674 mmol) in THF (3.0 mL) was added LiOH (2.7 mL, 1.35 mmol, 0.5 M solution in water) and the mixture was stirred at rt for 3 h. The reaction was quenched by addition of 1 N. HCl. EtOAc and water was added. The mixture was separated, and the organic layer was washed with brine. The mixture was dried over Na$_2$SO$_4$, filtered and concentrated under vacuum to give the desired compound as white solid (0.23 g, 96%). ESI-MS m/z=355.24, 357.24 [M−H]$^−$.

Step 340g.

To a solution of compound from step 340f (0.23 g, 0.644 mmol), 3, 4-difluorobenzene-2,6-D2-amine (0.127 g, 0.967 mmol), DMAP (0.039 g, 0.322 mmol) in DMF (2.5 mL) was added EDC (0.185 g, 0.967 mmol) in and stirred at rt for 16 h. It was diluted with EtOAc and the mixture washed with water, brine, dried over Na$_2$SO$_4$, filtered and concentrated. The crude product was chromatographed (silica, hexanes/EtOAc) to give the desired compound (0.26 g, 86%). ESI-MS m/z=468.31, 470.31 [M−H]$^−$.

Step 340h.

To a suspension of compound from step 340g (260 mg, 0.553 mmol) and NMO (0.324 g, 2.77 mmol) in acetone-water (2.1 mL/0.3 mL) at rt was added osmium tetroxide (0.28 ml, 0.055 mmol, 5% in water) and the mixture was stirred at rt for 20 h. It was quenched with aqueous Na$_2$SO$_3$, extracted with EtOAc, washed with water, 1N HCl, NaHCO$_3$, brine, dry over Na$_2$SO$_4$, filtered and concentrated to give a mixture of sulfone and sulfoxide used without further purification.

Step 340i.

To a solution of compound from step 340h in NMP (2.5 mL) was added m-CPBA (0.41 g, 1.83 mmol, 77%) and stirred at rt for 20 h. Aqueous Na$_2$S$_2$O$_3$, NaHCO$_3$ and few drops of Et$_3$N was added and stirred at rt for 1 h. It was extracted with EtOAc, washed with water, brine, dried over Na$_2$SO$_4$, filtered and concentrated to five the desired product (0.27 g, 96%). ESI-MS m/z=580.33, 582.33 (M+HCO$_2$)$^-$.

Step 340j.

A mixture of compound from step 340i (362 mg, 0.675 mmol) and IBX (227 mg, 0.81 mmol) in DMSO (5.0 mL) was stirred at rt for 4 h. Aq. Na$_2$S$_2$O$_3$ solution was added and the mixture was extracted with EtOAc. The organic layer was washed with water, brine, dried over Na$_2$SO$_4$, filtered, concentrated and purified by prep-HPLC (C18 column, acetonitrile/water) to give title compound (150 mg, 41%). ESI-MS m/z=578.32, 580.32 (M+HCO$_2$)$^-$.

Example 341

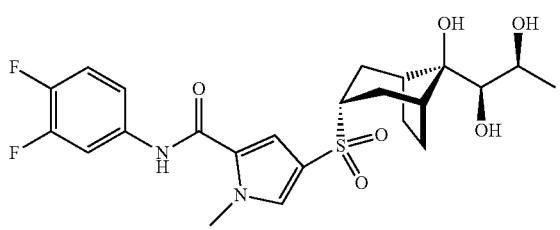

Step 341a.

1-methyl-1H-pyrrole-2-carboxylic acid (3 g, 23.98 mmol) was dissolved portionwise in chlorosulfonic acid (12 ml, 179 mmol) in an ice bath. The reaction was stirred for 70 min at the same temperature. The mixture was quenched slowly by adding ice/water (100 mL) (very reactive!!) and stirred for 15 min. The precipitate was filtered, rinsed with water and the resulting solid was dissolved in EtOAc, dried over NaSO$_4$. Solvent was removed in vacuo and dried overnight in vacuo to give the desired compound (3.60 g, 16.10 mmol, 67% yield) as an off-white solid.

Step 341b.

To a mixture of the compound from step 341a (1 g, 4.47 mmol) in DCM (20 mL) and DMF (0.02 mL) was added oxalyl chloride (11.18 ml, 22.36 mmol). The reaction was stirred for 5 h at rt. Solvent was removed in vacuo then chased with benzene (×3) to give the desired compound (1.08 g, 100% yield) as pale yellow solid.

Step 341c.

To a solution of the compound from step 341b (400 mg, 1.652 mmol) in toluene (15 mL) was added 3,4-difluoroaniline (0.164 ml, 1.652 mmol) in toluene (1 mL) at rt. The mixture was heated at 110° C. and stirred for 1 h, and then cooled down to rt and stirred for 16 h. Solid was filtered off and the resulting filtrate was removed in vacuo, which was used without further purification (553 mg, 100% yield).

Step 341d.

To a suspension of the compound from step 341c (550 mg, 1.643 mmol) in toluene (10 mL) was added triphenylphosphine (2.16 g, 8.22 mmol). The reaction was heated to 85° C. and stirred for 6 h. The reaction was cooled to rt and 10 mL of H$_2$O was added. Organic layer was washed with water (5 mL) twice, followed by 1N NaOH. Aq layer was collected. Aq layer was acidified by 1N HCl to pH4. It turned to a white emulsion as HCl was added. It was extracted with EtOAc and the resulting mixture became clear colorless solution. Organic layer was collected, dried over Na$_2$SO$_4$ to give desired compound (220 mg, 0.820 mmol, 50% yield) as white solid.

Step 341e.

To a solution of the compound from step 341d (130 mg, 0.485 mmol) and compound from step 337d (187 mg, 0.505 mmol) in DMF (0.5 mL) was added cesium carbonate (197 mg, 0.606 mmol). The reaction was heated to 70° C. and stirred for 17 h. The mixture was extracted with EtOAc, dried over Na$_2$SO$_4$, and then purified by column chromatography (silica, hexanes/EtOAc) to give desired compound (170 mg, 0.364 mmol, 72% yield) as a white solid.

Step 341f.

To a solution of the compound from step 341e (35 mg, 0.075 mmol) in NMP (0.3 mL) was added m-CPBA (50.4 mg, 0.225 mmol, 77%) at 0° C. The reaction was slowly warmed to rt and stirred for 15 h. Sat. Na$_2$S$_2$O$_3$ solution and NaHCO$_3$ solution were added and the resulting mixture was stirred for 1 h at rt. The mixture was extracted with EtOAc, washed with sat. Na$_2$S$_2$O$_3$ solution and NaHCO$_3$ solution (×2), brine, and dried over Na$_2$SO$_4$. The crude material was purified by column chromatography (silica, hexanes/EtOAc) to give the title compound (24.0 mg, 0.048 mmol, 64% yield) as a white solid. ESI-MS m/z=497.52, 499.53 [M−H]$^-$.

Example 344

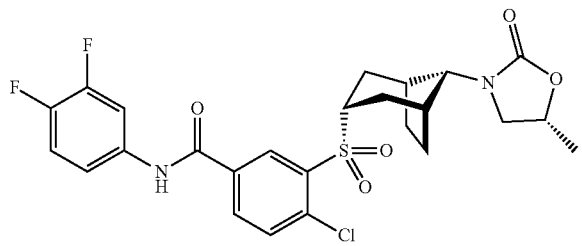

Step 344a.

To the solution of compound from step 307a (500 mg, 0.71 mmol) in 2-methyl-tetrahydrofuran (3 mL) was added (R)-1-aminopropan-2-ol (160 mg, 2.12 mmol) then stirred at 75° C. for one day. The crude was diluted with EtOAc, washed with water twice, brine twice and dried (Na$_2$SO$_4$) and concentrated. The crude was chromatographed (silica, MeOH/DC) to give desired compound (255 mg) as a mixture of desired with other impurities. ESI-MS m/z=479.27, 481.27[M−H]$^-$.

Step 344b.

To the solution of mixture from step 344a (255 mg, 0.53 mmol) in 2-methyl-tetrahydrofuran (2 mL) was added, CDI (112 mg, 0.69 mmol) and TEA (0.15 mL, 1.06 mmol). The reaction mixture was heated to 50° C. for 1 h before being cooled and concentrated. The crude was chromatographed (silica, EtOAc/hexanes) to give desired compound as a mixture with other impurities. ESI-MS m/z=505.26, 507.26 [M−H]$^-$.

Step 344c.

The compound from step 344b was treated with the conditions described in 130b and purified by prep-HPLC (C-18, Acetonitrile/water) to offer the title compound as a white solid. ESI-MS m/z=537.26. 539.26 [M−H]$^-$.

Example 345

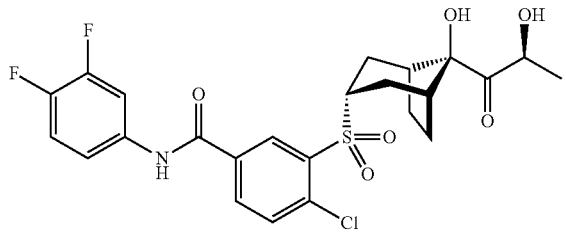

Step 345a.

To a solution of the compound from step 182 (1.046 g, 2.100 mmol) in CH$_2$C$_2$ (21 mL) at rt was added triethylamine (0.586 ml, 4.20 mmol) and Ac$_2$O (0.238 ml, 2.52 mmol), then the mixture was kept at rt for overnight. Then the reaction mixture was partitioned between NaHCO$_3$ aqueous solution and CH$_2$C$_2$. The combined organic phases were dried over Na$_2$SO$_4$, concentrated and the crude product was purified by flash column chromatography to give a mixture (415 mg) of two inseparable mono acylated products. ESI-MS m/z=584.13, 586.13 [M+HCO$_2$]$^-$.

Step 345b.

To a solution of the compound from step 345a (415 mg, 0.768 mmol) in CH$_2$C$_2$ was added 2-iodoxylbenzoic acid (430 mg, 1.54 mmol). The mixture was kept at rt overnight then saturated Na$_2$S$_2$O$_3$ aqueous solution was added. The mixture was partition between EtOAc and water. The combined organic phases were washed with brine, dried over Na$_2$SO$_4$ and concentrated. The resulting crude product was chromatograped (silica, hexanes/EtOAc) to give the desired product (39 mg, 8.2% over 2 steps) as a white solid. ESI-MS m/z=582.12, 584.12 [M+HCO$_2$]$^-$.

Step 345c.

To a solution of the compound from Step 345b (39.1 mg, 0.073 mmol) in THF (0.3 mL) and MeOH (1.1 mL) at rt was added K$_2$CO$_3$ (10 mg, 0.073 mmol). Then the mixture was kept at rt for 1 h. The reaction mixture was diluted with MTBE, washed with water, dried over Na$_2$SO$_4$ and concentrated to give the desired crude product (19 mg, 53%) as a white solid, which was taken into next step without further purification. ESI-MS m/z=540.11, 542.11 [M+HCO$_2$]$^-$.

Step 345d.

To a solution of the compound from Step 345c (19 mg, 0.038 mmol) in CH$_2$C$_2$ (1.9 mL) at rt was added m-CPBA (34.3 mg, 0.153 mmol, 77%) and stirred at rt overnight. The reaction was quenched with saturated Na$_2$S$_2$O$_3$ aqueous solution and NaHCO$_3$ aqueous solution. The reaction mixture was partitioned between EtOAc and aqueous phase. The combined organic phases were washed with brine, dried over Na$_2$SO$_4$ and concentrated. The resulting crude product was chromatographed to give the desired product (11 mg, 29% over 2 steps) as a white solid. ESI-MS m/z=572.09, 574.09 [M+HCO$_2$]$^-$.

Example 346

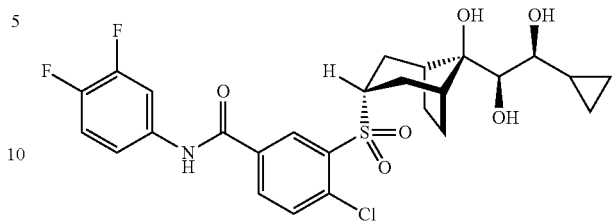

Step 346a.

To a solution of ethynylcyclopropane (1.864 ml, 22.03 mmol) in THF (4.50 ml) was added n-BuLi (8.81 ml, 22.03 mmol, 2.5 M in THF) at −78° C. The resulting mixture was stirred for 1 h at the same temperature. A solution of compound from step int 2a (2.0 g, 14.68 mmol) in THF (9 ml) was added into the reaction at −78° C. The resulting light yellow solution was slowly warmed to rt and stirred for 2 h. Sat. NH$_4$Cl solution was added. The mixture was extracted with MTBE, dried over Na$_2$SO$_4$ to give 2.95 g (99% yield) of the desired compound as yellow oil, which was used without further purification.

Step 346b.

To a solution of the compound from step 346a (2.97 g, 14.68 mmol) in dioxane (122 mL) and water (25 mL) at 5° C. were added 2,6-lutidine (3.42 ml, 29.4 mmol), sodium periodate (10.99 g, 51.4 mmol). OsO$_4$ (0.921 ml, 0.073 mmol, 2.5% in t-BuOH) was added and the resulting mixture was stirred for 15 h at rt. Na$_2$S$_2$O$_3$ (50 mL) and EtOAc (100 mL) were added. The mixture was stirred for 30 min then filtered. Solid was washed with EtOAc (×3). Filtrate was collected and washed with 0.5N HCl (×4). Aq layer was back extracted with EtOAc and the combined organic layer was dried over Na$_2$SO$_4$. The crude material was chromatographed (silica, hexanes/acetone) to give the desired compound (2.25 g, 11.01 mmol, 75% yield) as a light yellow oil.

Step 346c.

To a solution of LiBH$_4$ (13.77 ml, 27.5 mmol, 2 M in THF) in MTBE (22.03 ml) at −50° C. was added a solution of the compound from step 346b (2.25 g, 11.01 mmol) in MTBE (5 mL). The reaction was stirred at −50° C. for 3 h. NH$_4$Cl (50 mL) was added. The mixture was extracted with EtOAc (100 mL), washed with brine, dried over Na$_2$SO$_4$ and chromatographed (silica, hexanes/EtOAc) to give the desired compound (1.62 g, 7.85 mmol, 71% yield) as a white solid.

Step 346d.

To a mixture of LAH (13.77 ml, 13.77 mmol, 1 M in THF) and NaOMe (0.074 g, 1.377 mmol) in DME (15 mL) at rt was added a solution of the compound from step 346c (1.42 g, 6.88 mmol) in DME (2 mL). The reaction was heated to 80° C. and stirred for 3 h. The reaction was cooled down to 0° C., quenched with water and 1N NaOH solution carefully. The mixture was filtered. The filtrate was extracted with MTBE, dried over Na$_2$SO$_4$. Recrystallization of the resulting material with MTBE and Hex to give the desired compound (1.30 g, 6.24 mmol, 91% yield) as a white solid.

Step 346e.

To a solution of the compound from step 346d (1.6 g, 7.68 mmol) in DCM (10 ml) was added pyridine (1.243 ml, 15.36 mmol) at 0° C. 4-methylbenzenesulfonyl chloride (1.904 g, 9.99 mmol) was added. The mixture was slowly warmed to rt and stirred for 16 h. Water was added, and the mixture was extracted with DCM, dried over Na$_2$SO$_4$. The crude material was purified by column chromatography (silica, hexanes, EtOAc) to give the desired compound (2.10 g, 5.79 mmol, 75% yield) as a colorless oil.

Step 346f.

To a mixture of t-BuOH (29.0 ml) and water (29.0 ml) at 0° C. was added potassium osmate dihydrate (0.064 g, 0.174 mmol), (DHQ)$_2$PHAL (0.203 g, 0.261 mmol), potassium hexacyanoferrate(III) (5.72 g, 17.38 mmol) and potassium carbonate (2.402 g, 17.38 mmol), followed by methanesulfonamide (3.31 g, 34.8 mmol) and the compound from step 346e (2.1 g, 5.79 mmol). The reaction was warmed to rt slowly and stirred for 50 h. Na$_2$SO$_3$ (3.7 g) was added at 0° C. and the resulting mixture was stirred for 1 h at rt. EtOAc was added, solid was filtered through Celite, and washed with EtOAc (×2). Organic layer was extracted with EtOAc, and washed with 1N HCl (×3), followed by 2N K$_2$CO$_3$ solution and brine, and dried over Na$_2$SO$_4$ to give 1.85 g (4.67 mmol, 81% yield) of the desired product as an off-white solid, which was used without further purification.

Step 346g.

To a solution of the compound from step 346f (1.85 g, 4.67 mmol) in DMF (15.55 ml) was added K$_2$CO$_3$ (0.632 g, 4.57 mmol) at rt. 4-chloro-N-(3,4-difluorophenyl)-3-mercaptobenzamide (1.468 g, 4.90 mmol) was added. The resulting mixture was heated to 75° C. and stirred for 15 h. The reaction was cooled to rt, water was added, and extracted with EtOAc (×3), washed with brine, dried over Na$_2$SO$_4$. The crude material was chromatographed (silica, hexanes/EtOAc) to give the desired compound (1.91 g, 3.64 mmol, 75% yield) as an off-white solid.

Step 346h.

To a solution of the compound from step 346g (1.91 g, 3.64 mmol) in NMP (10 mL) was added m-CPBA (2.451 g, 10.93 mmol, 77%) at 0° C. The mixture was warmed to rt and stirred for 15 h. The reaction was quenched with sat. Na$_2$S$_2$O$_3$ solution and NaHCO$_3$ solution, stirred for 1 h. The mixture was extracted with EtOAc, washed with sat. Na$_2$S$_2$O$_3$ solution and NaHCO$_3$ solution (×2), brine, dried over Na$_2$SO$_4$. The crude material was chromatographed (silica, hexanes/acetone) to give the desired compound (1.26 g, 2.27 mmol, 42% yield) as white solid. ESI-MS m/z=555.02, 557.02 [M−H]$^-$.

Example 347

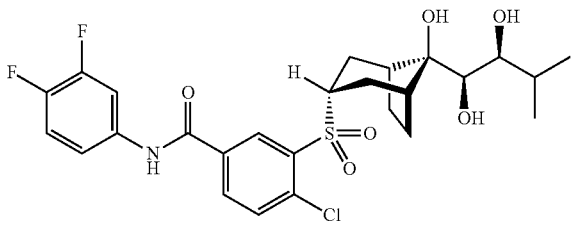

Step 347a.

To a solution of 3-methylbut-1-yne (2.253 ml, 22.03 mmol) in THF (4.50 ml) was added n-BuLi (8.81 ml, 22.03 mmol, 2.5 M in THF) at −78° C. The resulting mixture was stirred for 1 h at the same temperature. A solution of compound from step int 2a (2.0 g, 14.68 mmol) in THF (10 ml) was added into the reaction at −78° C. The resulting light yellow solution was slowly warmed to rt and stirred for 2 h. Sat. NH$_4$Cl solution was added. The mixture was extracted with MTBE, dried over Na$_2$SO$_4$ to give 3.0 g (99% yield) of the desired compound as a yellow oil, which was used without further purification.

Step 347b.

To a solution of the compound from step 347a (3.0 g, 14.68 mmol) in dioxane (122 mL) and water (25 mL) at 5° C. were added 2,6-lutidine (3.42 ml, 29.4 mmol), sodium periodate (10.99 g, 51.4 mmol). Osmium tetroxide (0.921 ml, 0.073 mmol, 2.5% in tBuOH) was added and the resulting mixture was stirred for 16 h at rt. Na$_2$S$_2$O$_3$ (50 mL) and EtOAc (100 mL) were added. The mixture was stirred for 30 min then filtered. Solid was washed with EtOAc (×3). Filtrate was collected, washed with 0.5N HCl (×4). Aq layer was back extracted with EtOAc and combined organic layer was dried over Na$_2$SO$_4$. The crude material was chromatographed (silica, hexanes/acetone) to give the desired compound (1.60 g, 7.76 mmol, 53% yield) as a light yellow oil.

Step 347c.

To a solution of LiBH$_4$ (9.70 ml, 19.39 mmol, 2 M in THF) in MTBE (15.51 ml) at −50° C. was added a solution of the compound from step 347b (1.60 g, 7.76 mmol) in MTBE (5 mL). The reaction was stirred at −50° C. for 3 h. NH$_4$Cl (50 mL) was added. The mixture was extracted with EtOAc (100 mL), washed with brine, dried over Na$_2$SO$_4$. The crude material was chromatographed (silica, hexanes/EtOAc) to give the desired compound (1.16 g, 5.58 mmol, 72% yield) as a white foaming solid.

Step 347d.

To a mixture of LAH (11.16 ml, 11.16 mmol, 1 M in THF) and sodium methoxide (0.060 g, 1.116 mmol) in DME (15 mL) at rt was added a solution of the compound from step 347c (1.162 g, 5.58 mmol) in DME (2 mL). The reaction was heated to 80° C. and stirred for 3 h. The reaction was cooled down to 0° C., quenched with water and 1N NaOH solution carefully. The mixture was filtered. The filtrate was extracted with MTBE, dried over Na$_2$SO$_4$. Recrystallization of the resulting material with MTBE and Hex to give the desired compound (1.06 g, 5.02 mmol, 90% yield) as a white solid.

Step 347e.

The desired compound was obtained from the compound of step 347d following the procedure described in example 346e as cloudy oil (1.51 g, 4.14 mmol, 87% yield).

Step 347f.

The desired compound was obtained from the compound of step 347e following the procedure described in example 346f as off-white solid (1.01 g, 2.53 mmol, 61% yield).

Step 347g.

The desired compound was obtained from the compound of step 347f following the procedure described in example 346g as off-white solid (0.87 g, 1.65 mmol, 65% yield).

Step 347h.

The desired compound was obtained from the compound of step 347g following the procedure described in example 346h as white solid (0.74 g, 1.32 mmol, 80% yield). ESI-MS m/z=557.03, 559.02 [M−H]$^-$.

Example 348

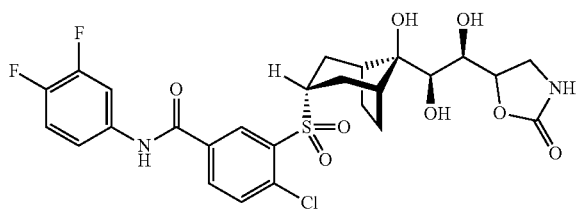

Step 348a.

To a solution of compound from example 82a (50 mg, 0.111 mmol) in DCE (2 ml) at rt were added tert-butyl 2-oxo-5-vinyloxazolidine-3-carboxylate (71.1 mg, 0.333 mmol) and Grubbs-Hoveyda 2$^{nd}$ generation catalyst (6.96 mg, 0.011 mmol). The mixture was degased with bubbling N$_2$ for 5 min and heated to 60° C. and stirred for 15 h. The reaction was cooled to rt. Water was added. The mixture was extracted with DCM, dried over Na$_2$SO$_4$. The crude material was chromatographed (silica, hexanes/EtOAc) to give the desired compound (45 mg, 0.071 mmol, 64% yield) as an off-white solid.

Step 348b.

To a solution of the compound from step 348a (45 mg, 0.071 mmol) in acetone (3 ml) and water (0.8 ml) was added NMO (33.2 mg, 0.283 mmol), OsO$_4$ (178 µl, 0.014 mmol, 2.5% in t-BuOH) at rt. The reaction was stirred for 16 h. It was quenched with sat. Na$_2$S$_2$O$_3$ solution and extracted with EtOAc, washed with brine, and dried over Na$_2$SO$_4$. The crude material was used without further purification.

Step 348c.

To a solution of the compound from step 348b (50 mg, 0.071 mmol) in DCM (1 ml) was added TFA (0.027 ml, 0.355 mmol) at rt. The reaction was stirred for 2 h. Solvent removed. The mixture was extracted with DCM, washed with sat. NaHCO$_3$ solution, dried over Na$_2$SO$_4$. The crude material was purified by column chromatography (silica, MeOH/DCM) to give the desired compound (2:1 isomeric mixture, 14.5 mg, 0.024 mmol, 34% yield) as off-white solid. ESI-MS m/z=600.02, 602.02 [M−H]$^-$.

The following examples were prepared using procedures similar to those described above:

| Example | Structure | ESIMS (M − H)$^-$ or (M + H)$^+$ |
|---|---|---|
| 2 | 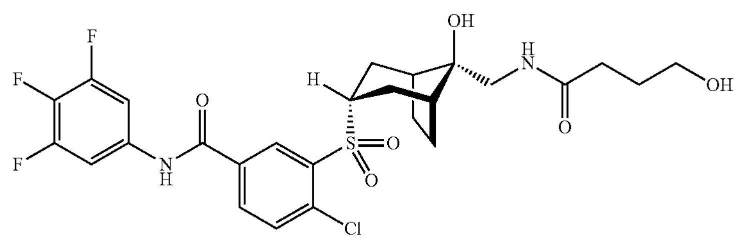 | 587.12, 589.12 |
| 8 | 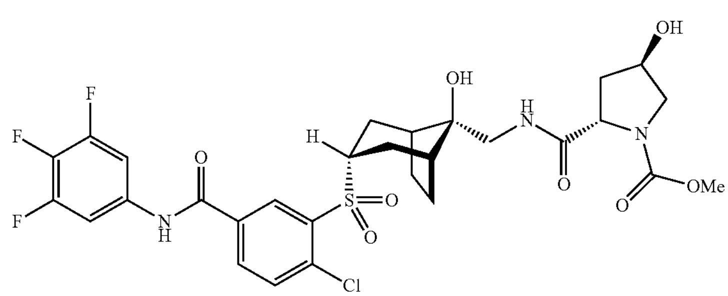 | 672.13, 674.13 |
| 12 | 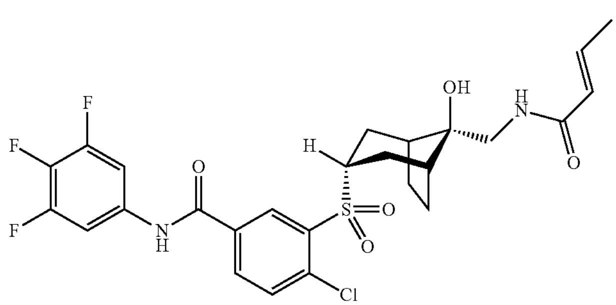 | 569.09, 571.09 |

-continued

| Example | Structure | ESIMS (M − H)− or (M + H)+ |
|---|---|---|
| 13 | 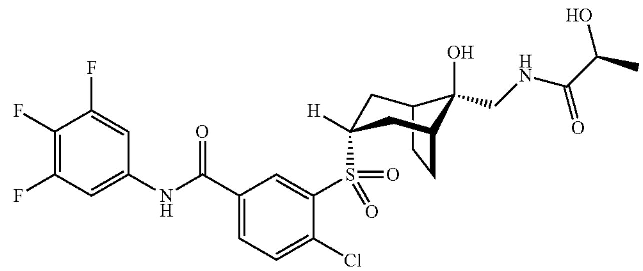 | 573.09, 575.09 |
| 15 | 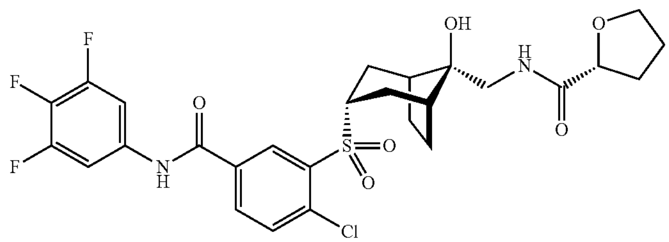 | 599.123, 601.121 |
| 16 | 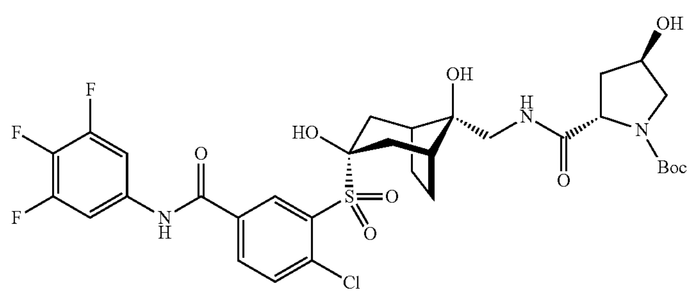 | 714.19, 716.19 |
| 17 | 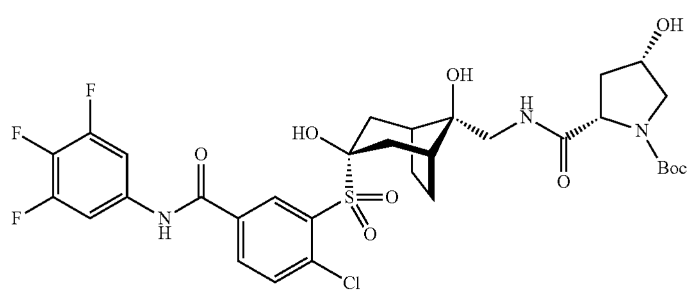 | 714.19, 716.18 |
| 22 | 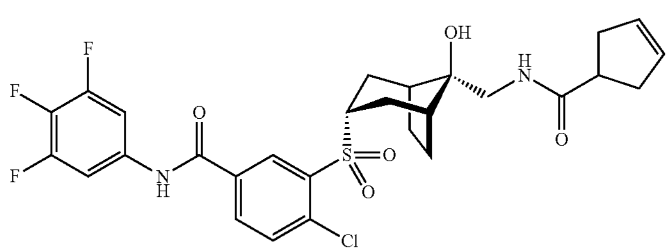 | 641.13, 643.13 (M + HCO2)−. |

-continued
| Example | Structure | ESIMS (M − H)⁻ or (M + H)⁺ |
|---|---|---|
| 23 | 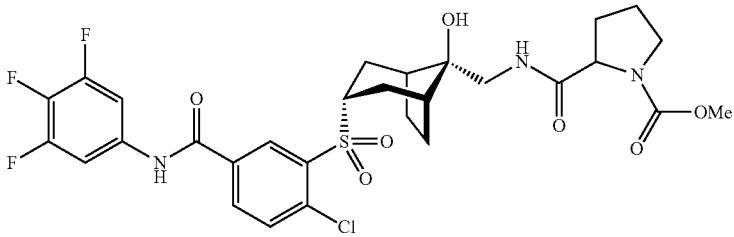 | 702.15, 704.15 (M + HCO₂)⁻ |
| 24 | 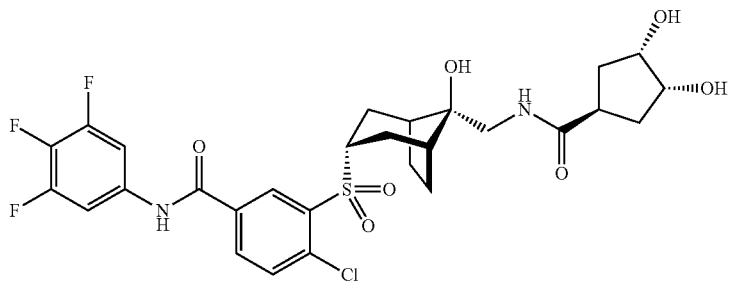 | 675.13, 677.13 (M + HCO₂)⁻ |
| 25 | 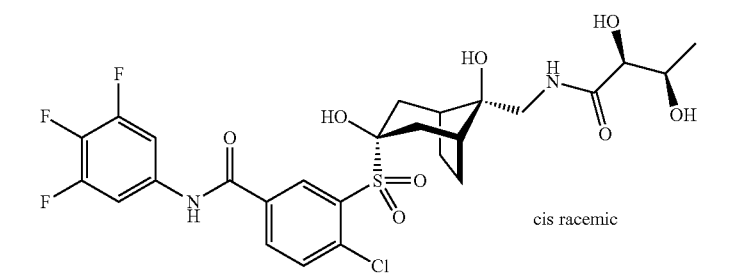 cis racemic | 603.10, 605.10 |
| 30 | 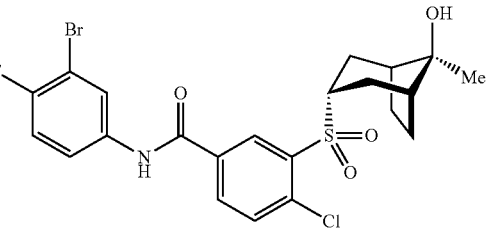 | 532.05 |
| 31 | 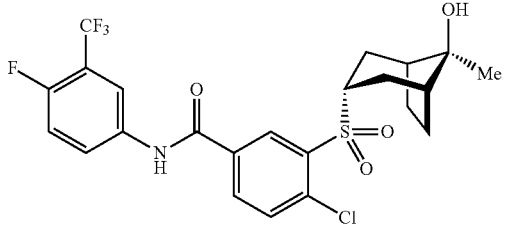 | 444.08, 446.06 537.20 [M + NH₄]⁺. |
| 39 | 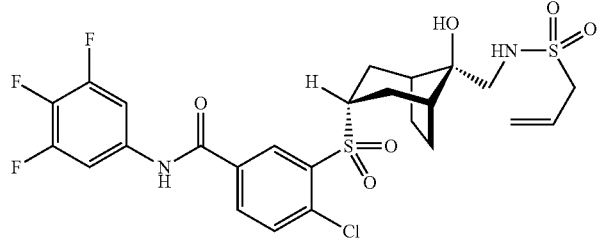 | 605.07, 607.07 |

-continued

| Example | Structure | ESIMS (M − H)⁻ or (M + H)⁺ |
|---|---|---|
| 40 | 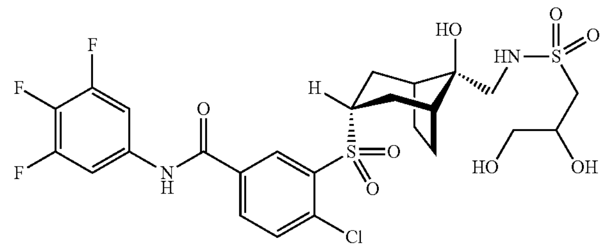 | 639.08, 641.08 |
| 41 | 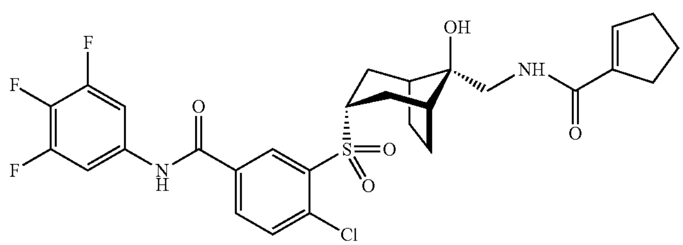 | 641.13, 643.13 (M + NCO₂)⁻ |
| 43 | 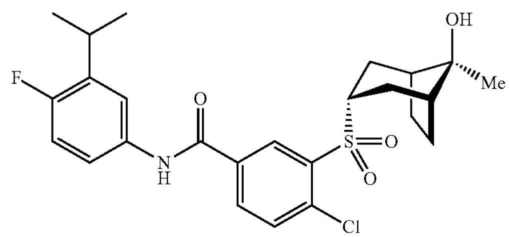 | 494.20 |
| 44 | 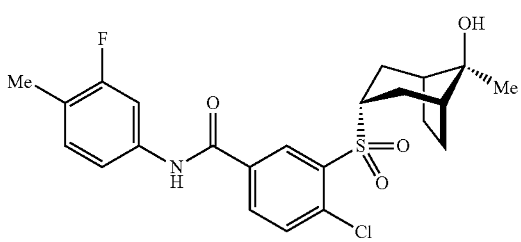 | 466.20 |
| 45 | 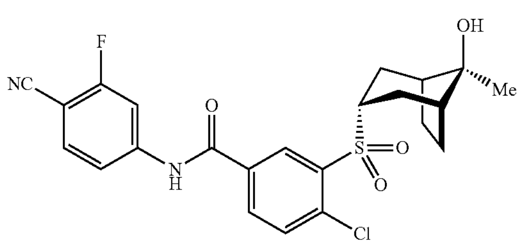 | 494.20 [M + NH₄]⁺ |
| 46 | 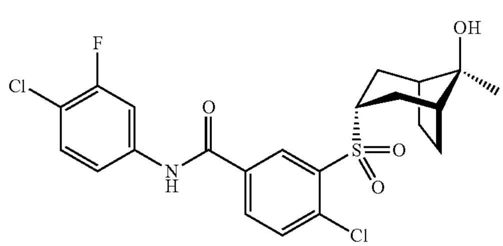 | 486.15 [M + H]⁺, 503.15 [M + NH₄]⁺. |

-continued

| Example | Structure | ESIMS (M − H)⁻ or (M + H)⁺ |
|---|---|---|
| 47 | 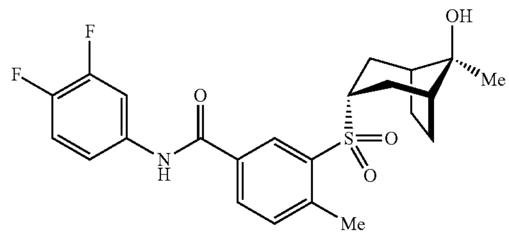 | 450.20 |
| 48 | 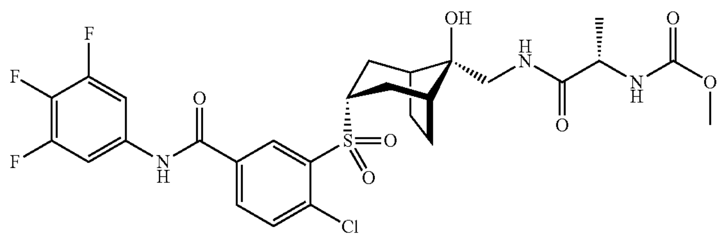 | 630.12, 632.12 |
| 49 | 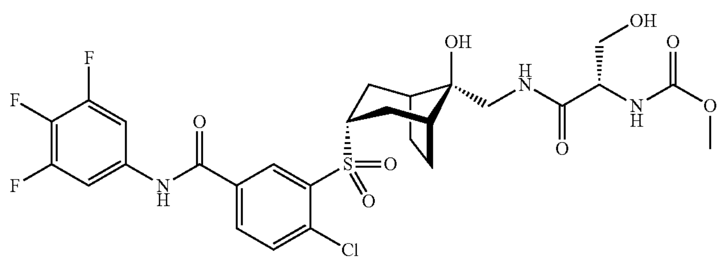 | 646.11, 648.11 |
| 50 | 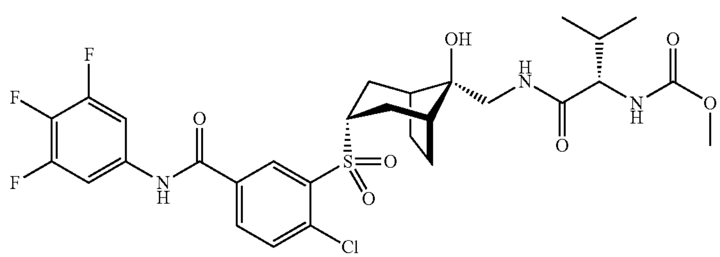 | 658.16, 660.16 |
| 53 | 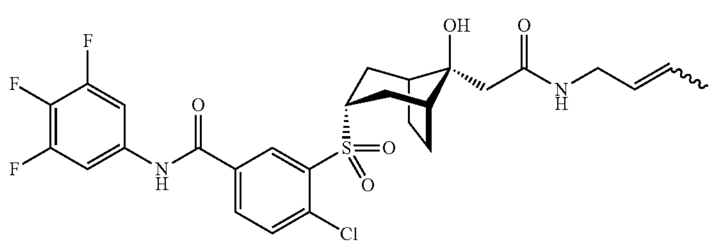 | 584.8, 586.8 |
| 54 | 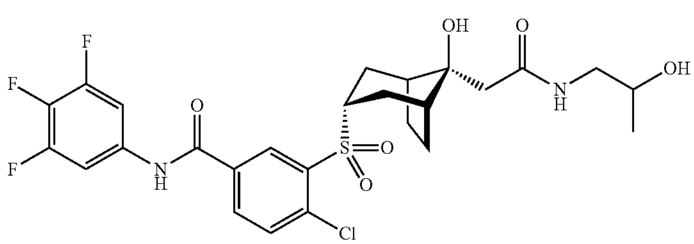 | 586.8, 588.8 |

| Example | Structure | ESIMS (M − H)⁻ or (M + H)⁺ |
|---|---|---|
| 55 | 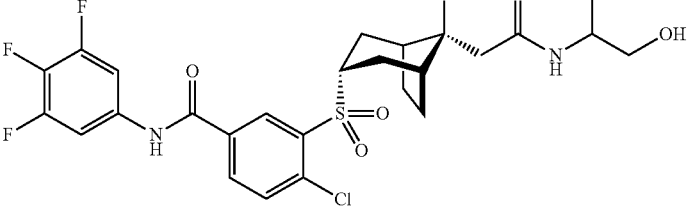 | 586.8, 588.8 |
| 57 | 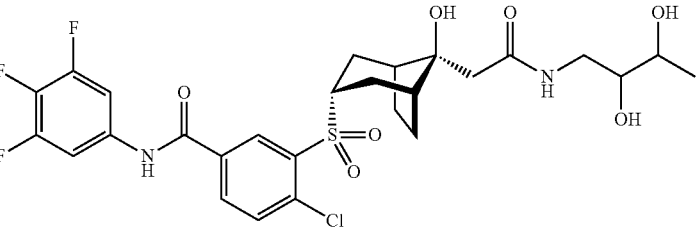 | 616.8, 618.8 |
| 58 | 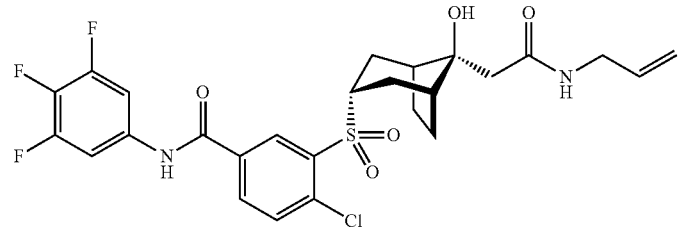 | 568.8, 570.8 |
| 59 | 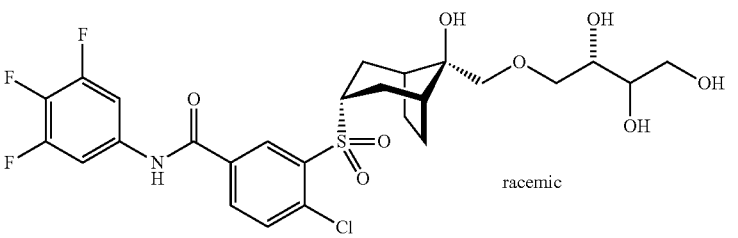 *Relative Stereochemistry | 675.13, 677.13 (M + NCO$_2$)⁻ |
| 60 | 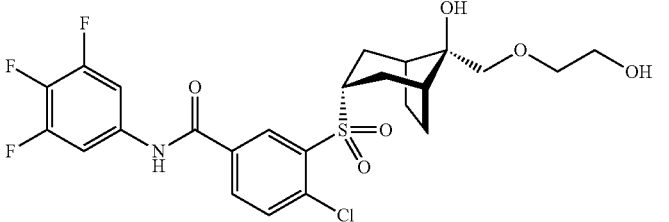 racemic | 606.11, 608.11 |
| 62 | 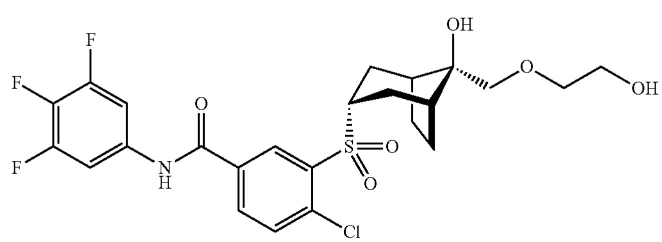 | 546.08, 548.08 |

-continued
| Example | Structure | ESIMS (M − H)⁻ or (M + H)⁺ |
|---|---|---|
| 63 | 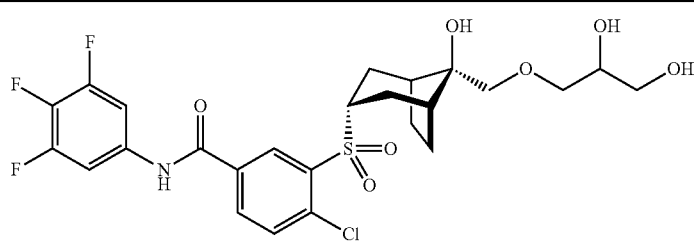 | 576.09, 578.09 |
| 65 | 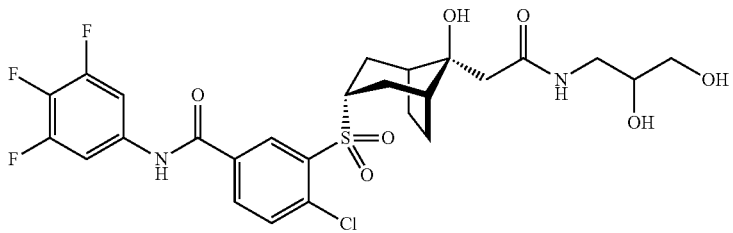 | 602.8, 604.8 |
| 66 | 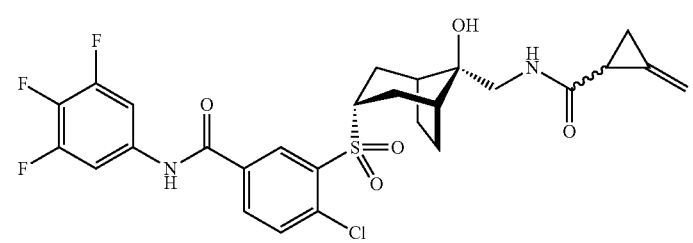 | 627.11, 629.11 (M + NCO$_2$)⁻ |
| 67 | 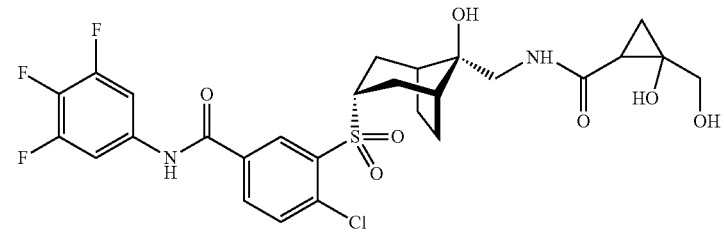 | 661.12, 663.12 (M + HCO$_2$)⁻ |
| 68 | 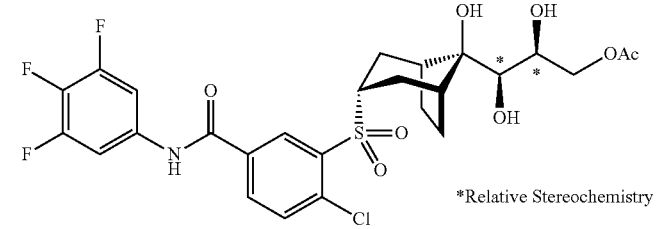 *Relative Stereochemistry | 650.11, 651.11 (M + HCO$_2$)⁻ |
| 69 | 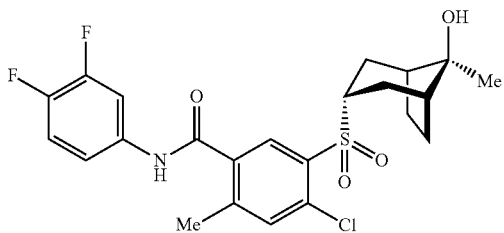 | 484.20 [M + H]⁺, 501.20 [M + NH$_4$]⁺ |

-continued

| Example | Structure | ESIMS (M − H)⁻ or (M + H)⁺ |
|---|---|---|
| 71 | 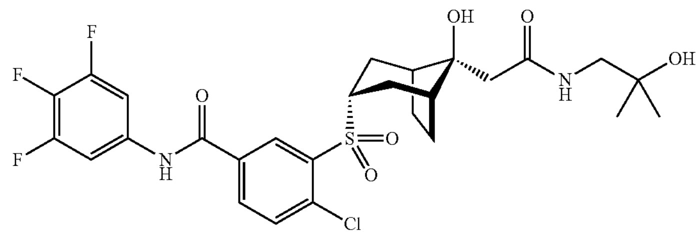 | 600.8, 602.8 |
| 72 | 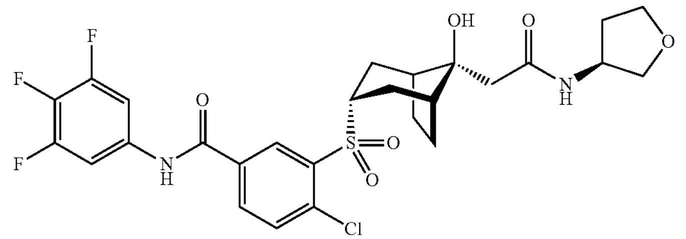 | 598.8, 600.8 |
| 73 | 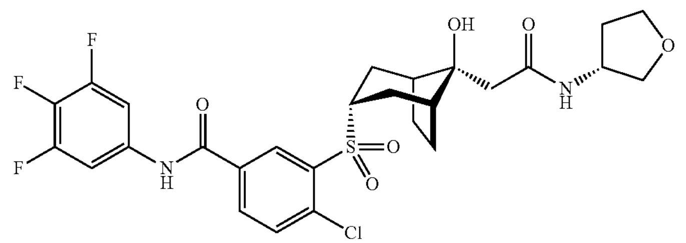 | 598.8, 600.8 |
| 75 | 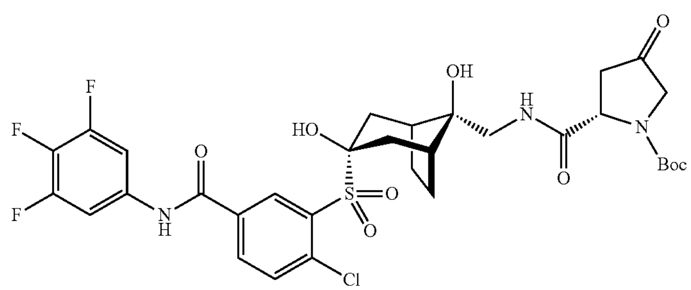 | 712.18, 714.18 |
| 77 | 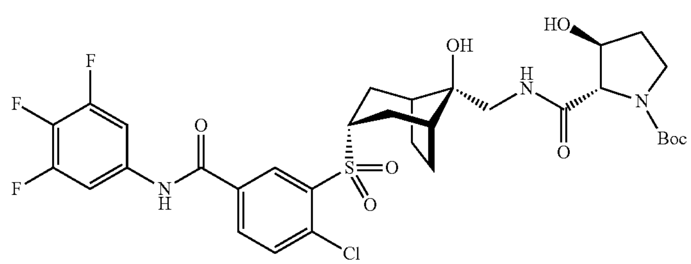 | 760.20, 762.20 [M + NCO₂]⁻ |
| 79 | 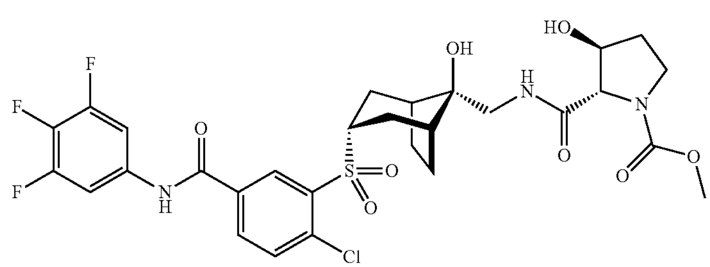 | 718.16, 720.16 [M + HCO₂]⁻ |

| Example | Structure | ESIMS (M − H)⁻ or (M + H)⁺ |
|---|---|---|
| 80 | 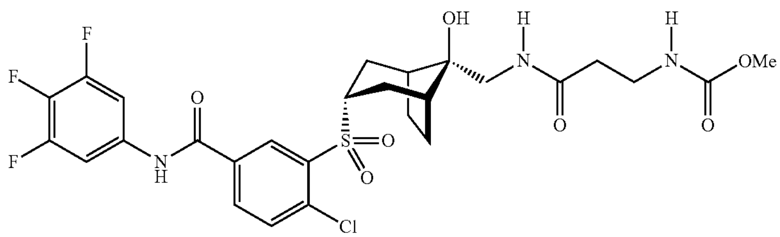 | 676.14, 678.14 (M + HCO₂)⁻ |
| 81 | 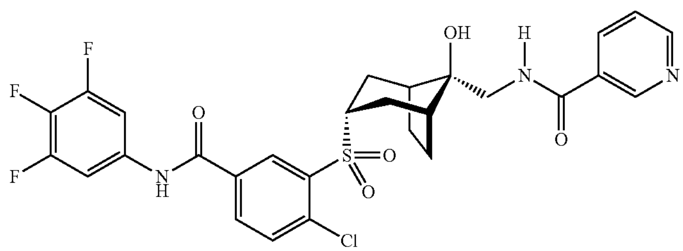 | 676.14, 678.14 (M + HCO₂)⁻ |
| 83 | 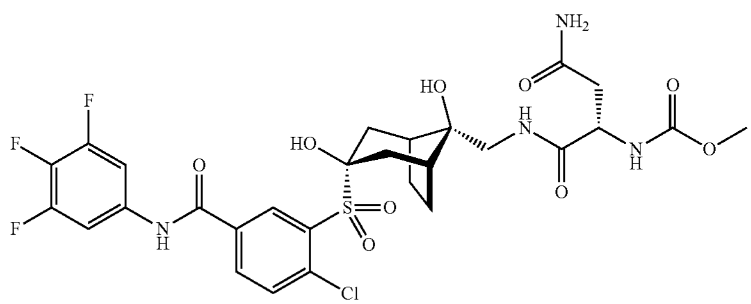 | 673.13, 675.13 |
| 84 | 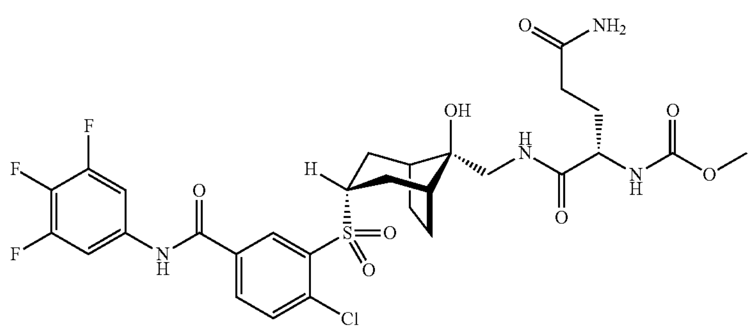 | 687.15, 689.15 |
| 85 | 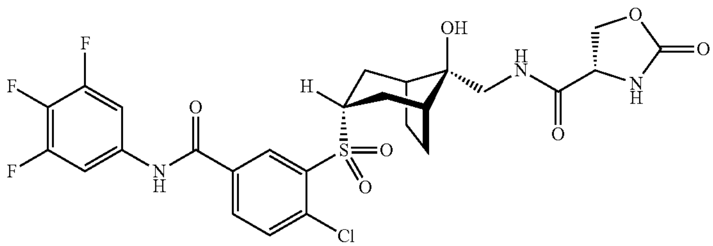 | 614.09, 616.09 |

-continued

| Example | Structure | ESIMS (M − H)⁻ or (M + H)⁺ |
|---|---|---|
| 86 | 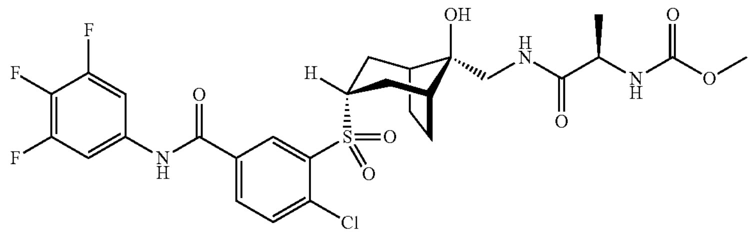 | 630.13, 632.13 |
| 87 | 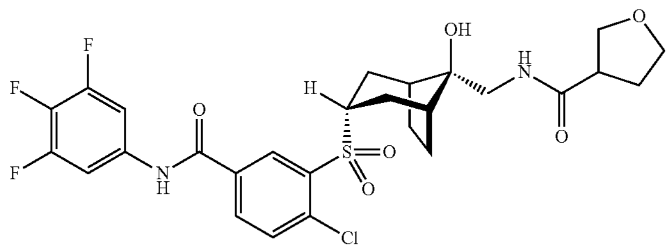 | 598.8, 600.8 |
| 88 | 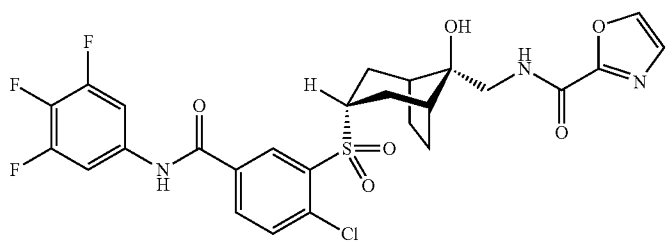 | 595.8, 597.8 |
| 89 | 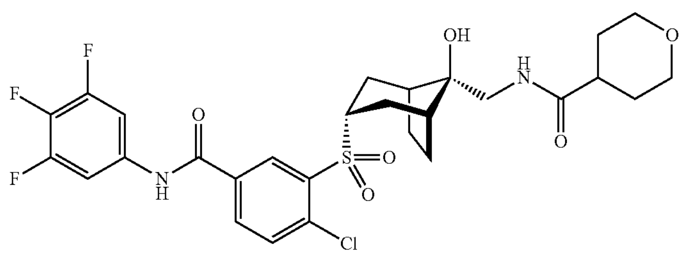 | 612.8, 614.8 |
| 90 | 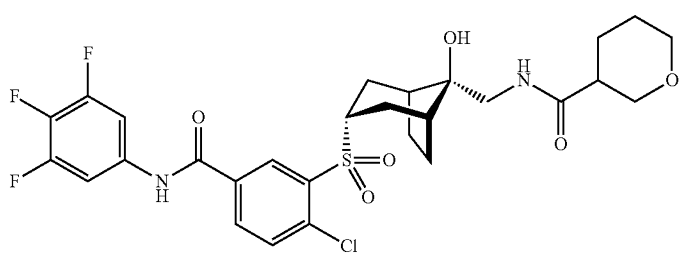 | 612.8, 614.8 |
| 91 | 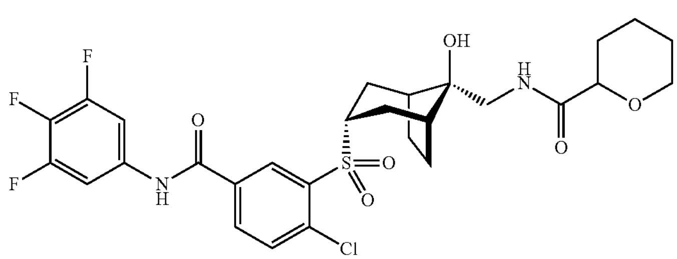 | 612.8, 614.8 |

| Example | Structure | ESIMS (M − H)⁻ or (M + H)⁺ |
|---|---|---|
| 92 | 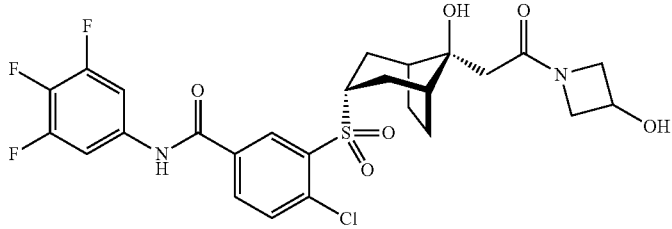 | 584.7, 586.7 |
| 93 | 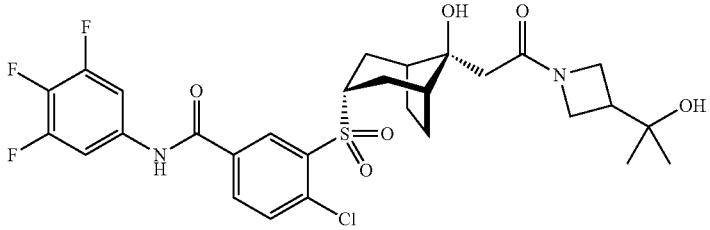 | 626.8, 628.8 |
| 94 | 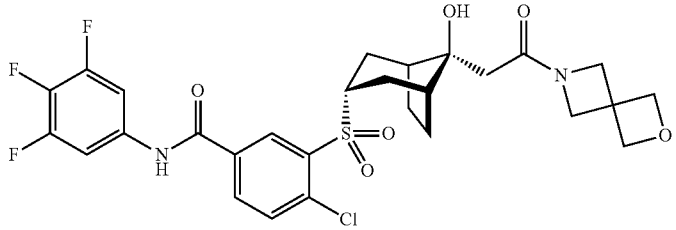 | 610.8, 612.8 |
| 95 | 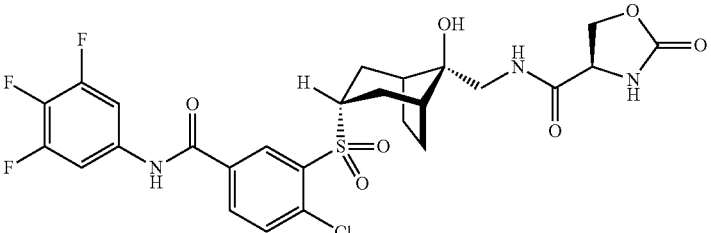 | 614.09, 616.09 |
| 96 | 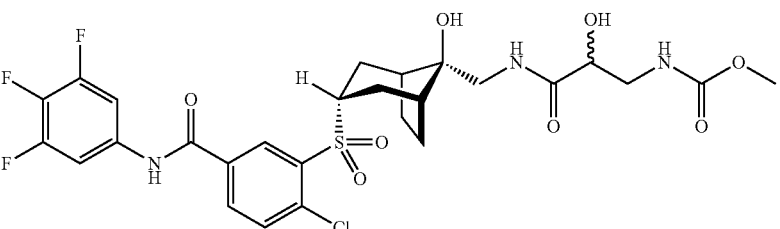 | 646.12, 648.12 |
| 97 | 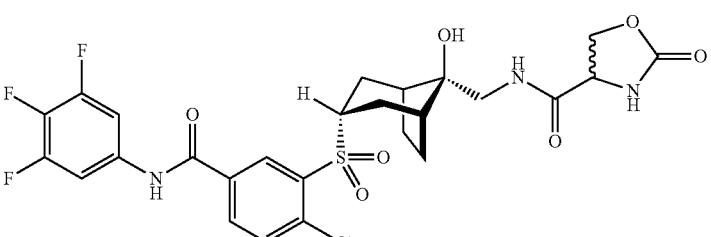 | 614.10, 616.10 |

-continued
| Example | Structure | ESIMS (M − H)− or (M + H)+ |
|---|---|---|
| 98 | 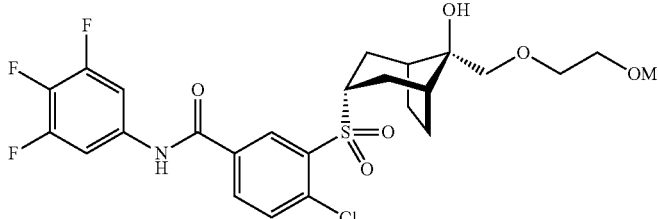 | 560.11, 562.11 |
| 99 | 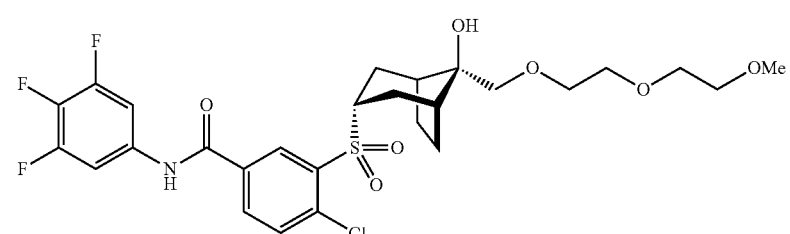 | 605.15, 606.15 |
| 100 | 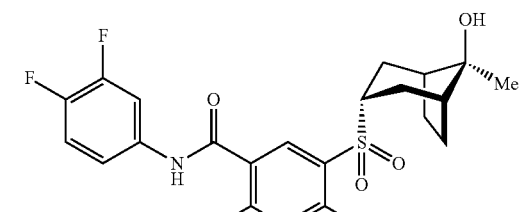 | 548.00 |
| 101 | 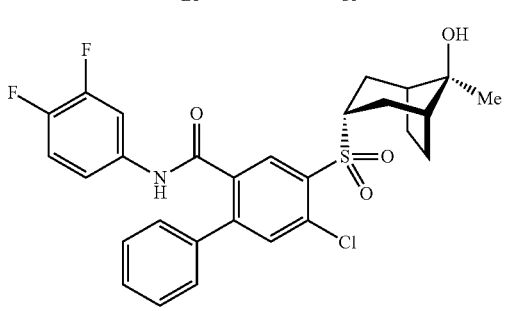 | 546.15 |
| 102 | 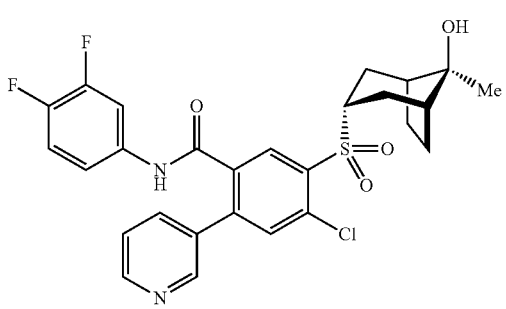 | 547.20 |
| 103 | 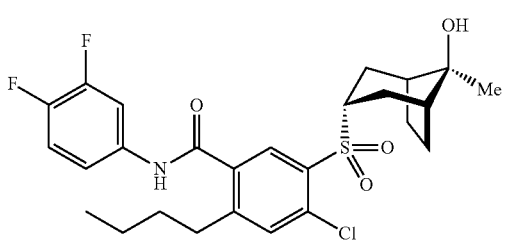 | 526.15 |

-continued

| Example | Structure | ESIMS (M − H)⁻ or (M + H)⁺ |
|---|---|---|
| 104 | 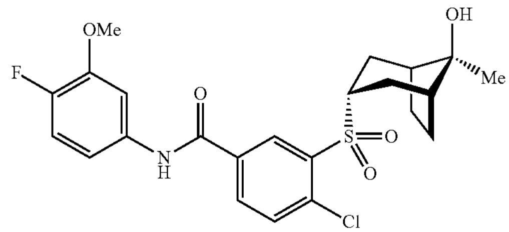 | 482.15 |
| 105 | 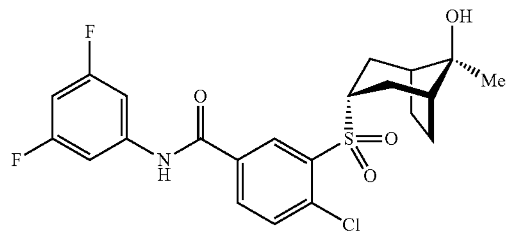 | 487.15 [M + NH₄]⁺ |
| 107 | 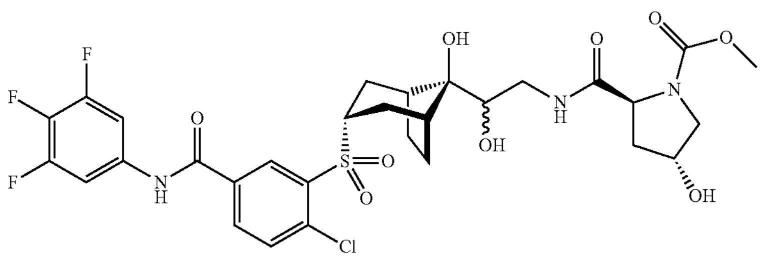 | 702.15, 704.15 |
| 110 | 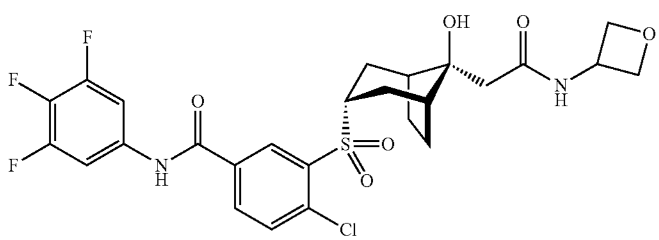 | 584.8, 586.8 |
| 111 | 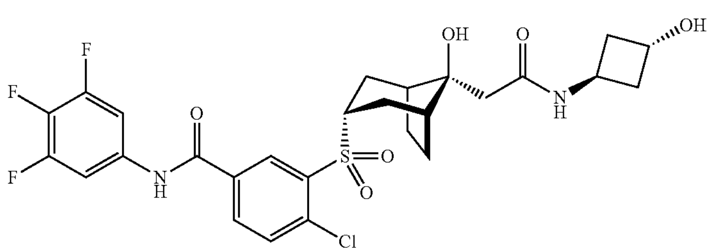 | 598.8, 600.8 |
| 112 | 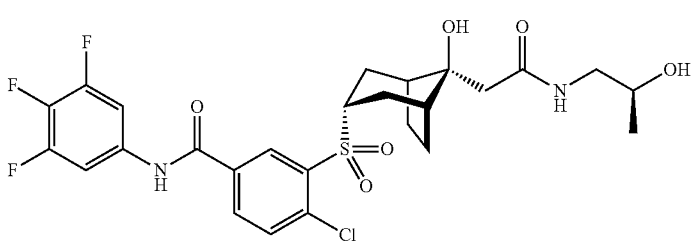 | 586.8, 588.8 |

-continued

| Example | Structure | ESIMS (M − H)⁻ or (M + H)⁺ |
|---|---|---|
| 113 | 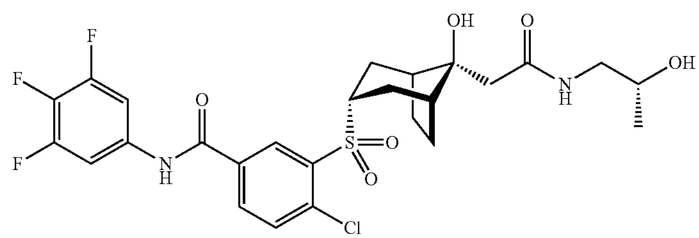 | 586.8, 588.8 |
| 114 | 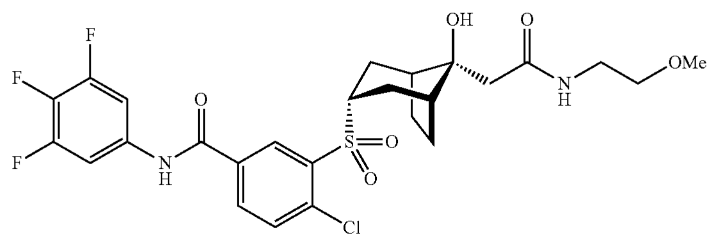 | 586.8, 588.8 |
| 115 | 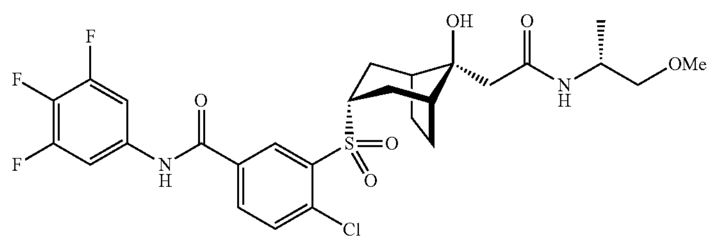 | 600.8, 602.8 |
| 116 | 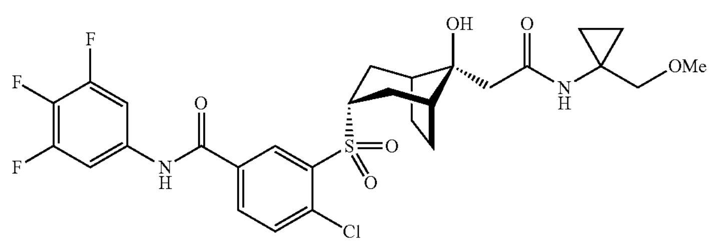 | 612.8, 614.8 |
| 117 | 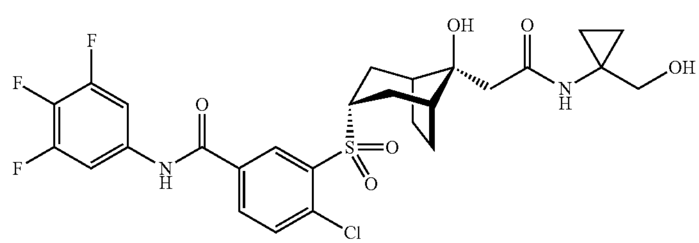 | 598.8, 600.8 |
| 118 | 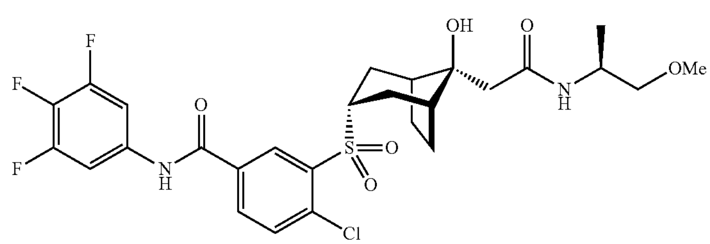 | 600.8, 602.8 |

-continued
| Example | Structure | ESIMS (M − H)⁻ or (M + H)⁺ |
|---|---|---|
| 119 | 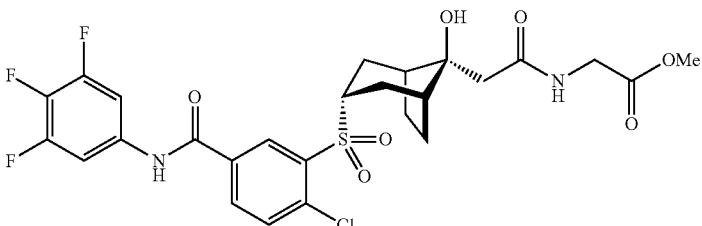 | 600.8, 602.8 |
| 122 | 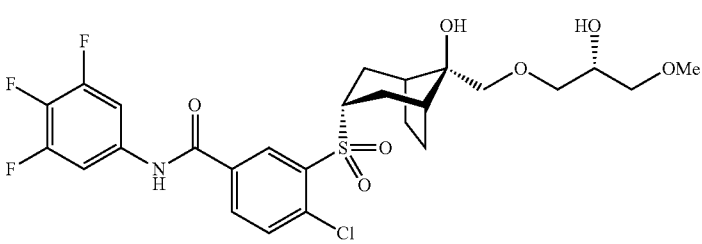 | 590.12, 592.12 |
| 123 | 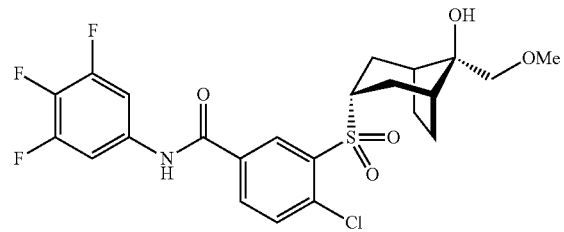 | 516.08, 518.08 |
| 126 | 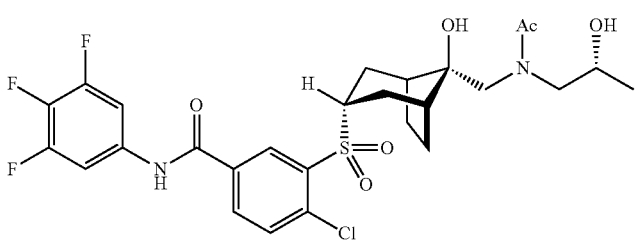 | 601.13, 603.13 |
| 127 | 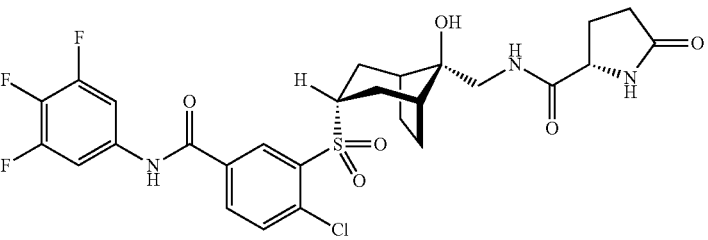 | 612.11, 614.11 |
| 128 | 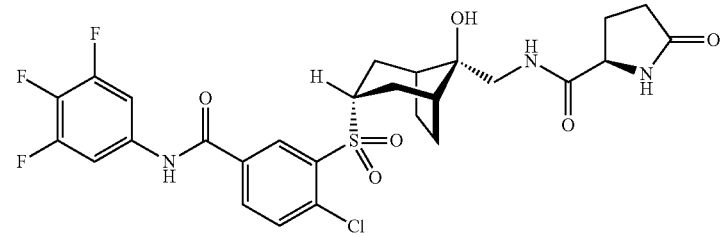 | 658.12, 660.12 [M − HCO₂]⁻ |

-continued

| Example | Structure | ESIMS (M − H)− or (M + H)+ |
|---|---|---|
| 129 | 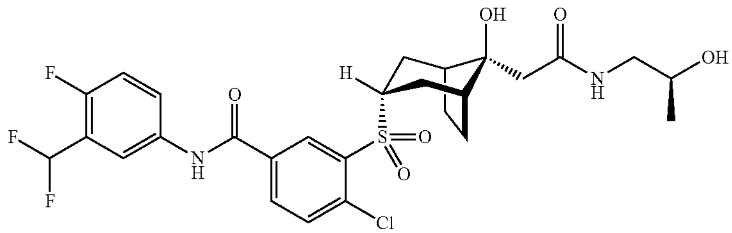 | 601.13, 603.12 |
| 131 | 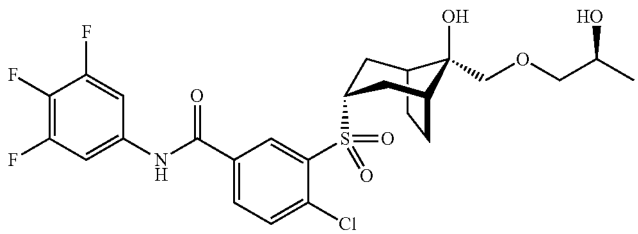 | 560.11, 562.11 |
| 132 | 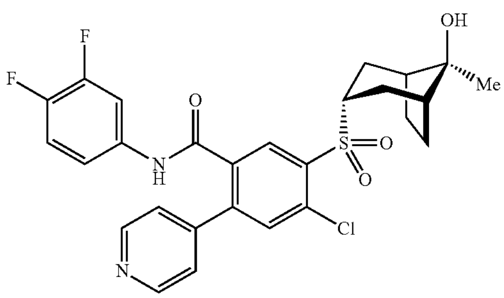 | 673.0, 675.0547.05 |
| 133 | 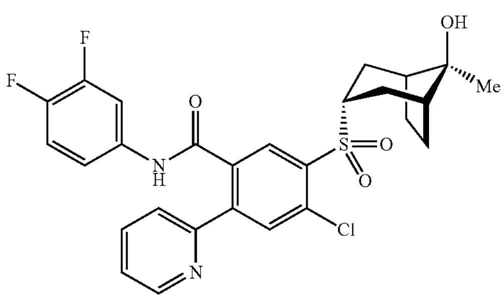 | 547.20 |
| 134 | 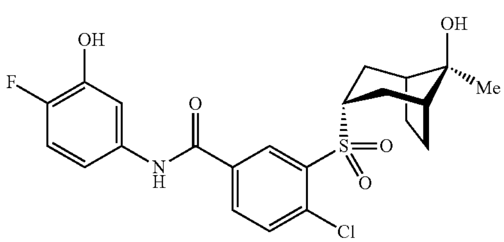 | 468.15 |
| 135 | 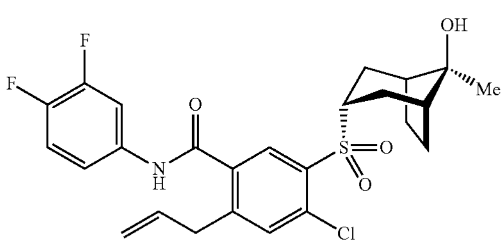 | 510.15 |

-continued

| Example | Structure | ESIMS (M − H)⁻ or (M + H)⁺ |
|---|---|---|
| 138 | 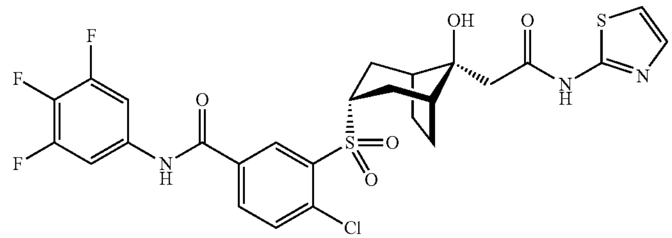 | 611.8, 613.8 |
| 139 | 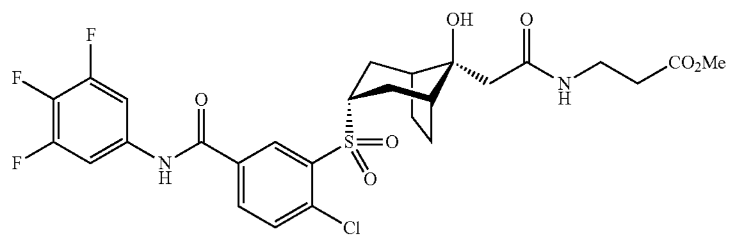 | 614.8, 616.8 |
| 140 | 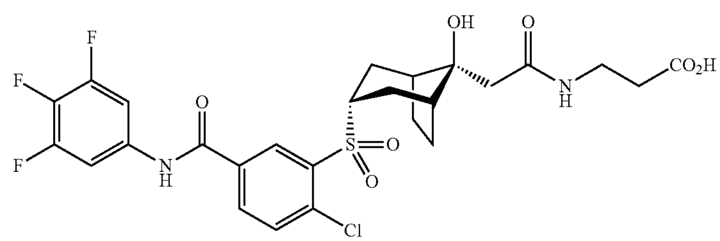 | 600.8, 602.8 |
| 142 | 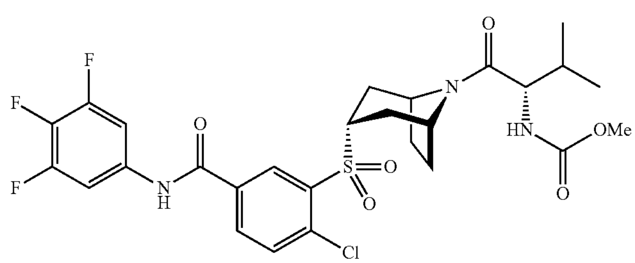 | 614.13, 616.13 |
| 143 | 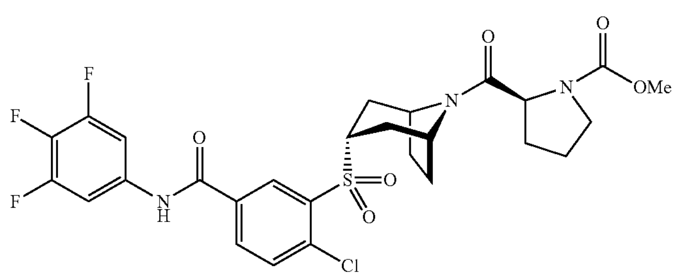 | 612.11, 614.11 |
| 145 | 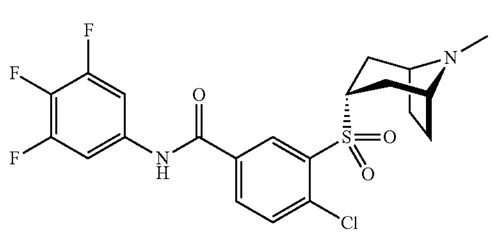 | 471.07, 473.07 |

-continued
| Example | Structure | ESIMS (M − H)⁻ or (M + H)⁺ |
|---|---|---|
| 146 | 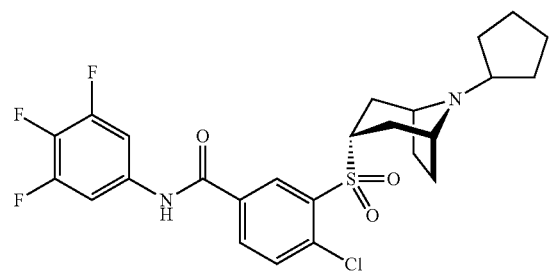 | 525.12, 527.12 |
| 147 | 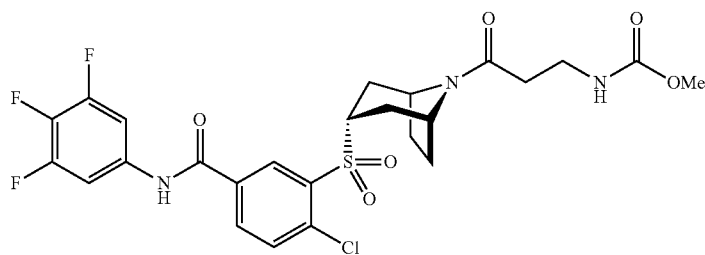 | 586.10, 588.10 |
| 148 | 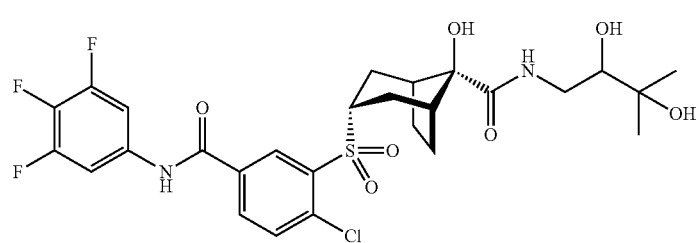 | 663.14, 665.14 [M + HCO₂]⁻ |
| 149 | 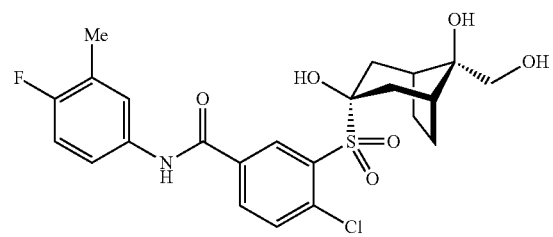 | 480.10, 482.10 |
| 151 | 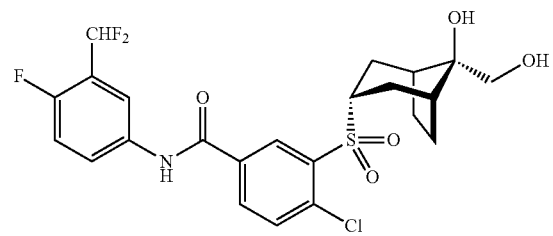 | 516.08, 518.08 |

| Example | Structure | ESIMS (M − H)⁻ or (M + H)⁺ |
|---|---|---|
| 152 | 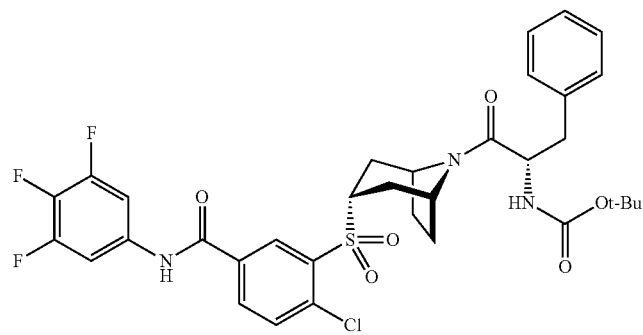 | 704.18, 706.18 |
| 154 | 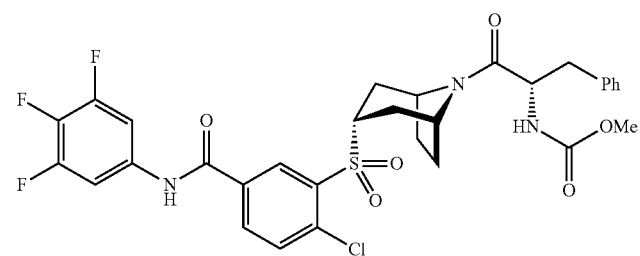 | 662.13, 664.13 |
| 155 | 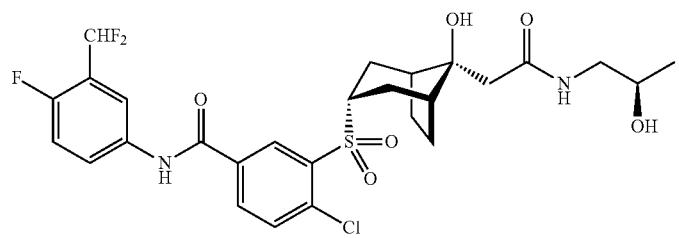 | 601.14, 603.14 |
| 157 | 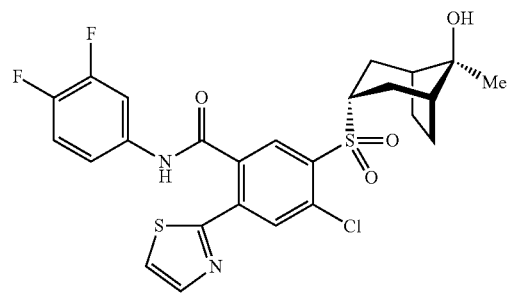 | 553.15 |
| 158 | 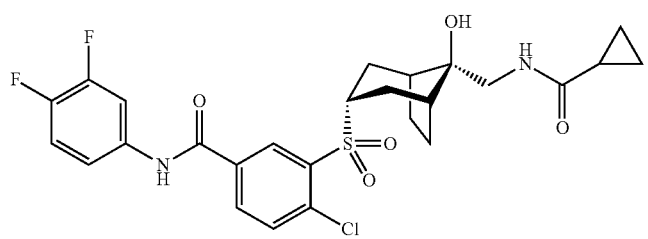 | 553.05 |

-continued

| Example | Structure | ESIMS (M − H)⁻ or (M + H)⁺ |
|---|---|---|
| 159 | 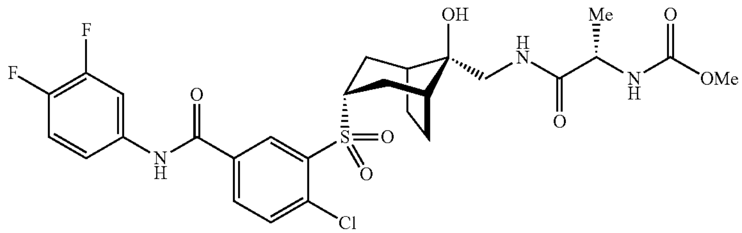 | 614.10 |
| 160 | 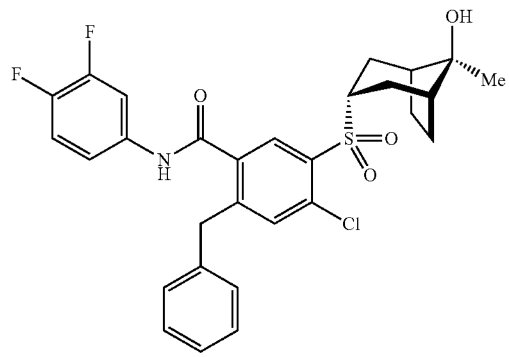 | 558.15 |
| 161 | 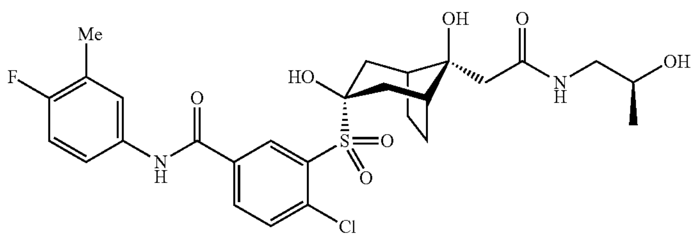 | 565.15, 567.15 |
| 162 | 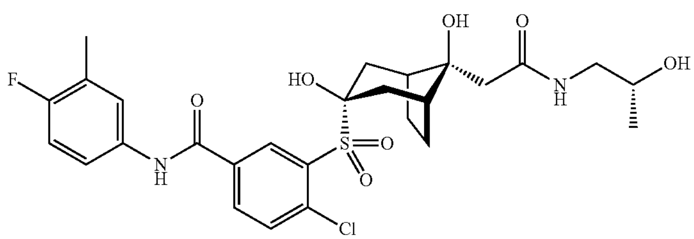 | 565.15, 567.15 |
| 165 | 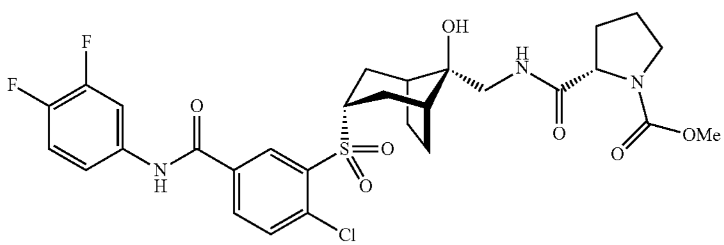 | 540.30 |
| 166 | 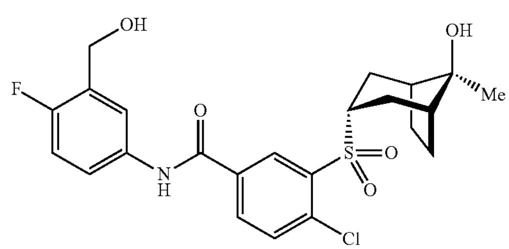 | 482.20 |

-continued

| Example | Structure | ESIMS (M − H)⁻ or (M + H)⁺ |
|---|---|---|
| 167 | 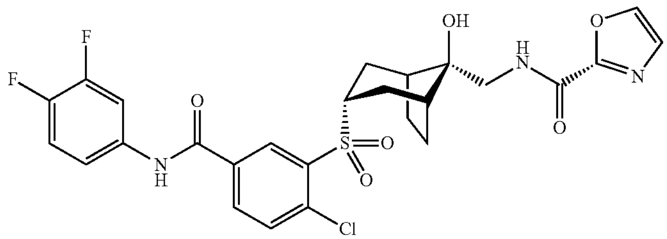 | 580.2 |
| 168 | 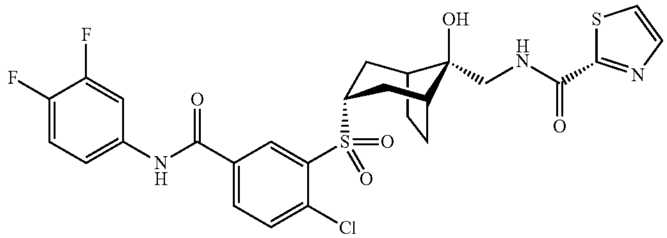 | 596.2 |
| 169 | 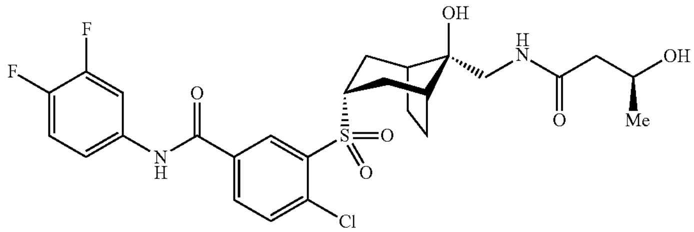 | 571.2 |
| 170 | 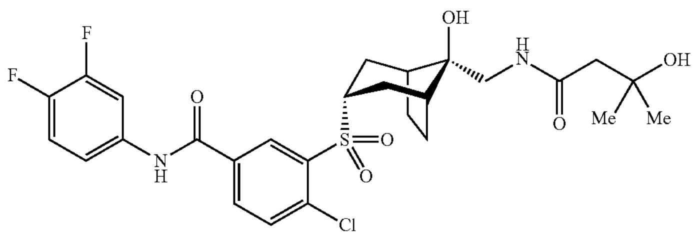 | 585.2 |
| 171 | 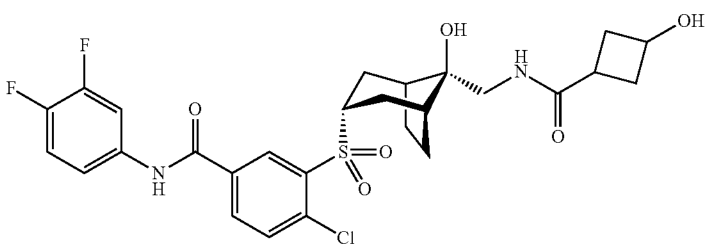 | 583.2 |
| 172 | racemic | 528.10, 530.10 |

-continued
| Example | Structure | ESIMS (M − H)− or (M + H)+ |
|---|---|---|
| 173 | 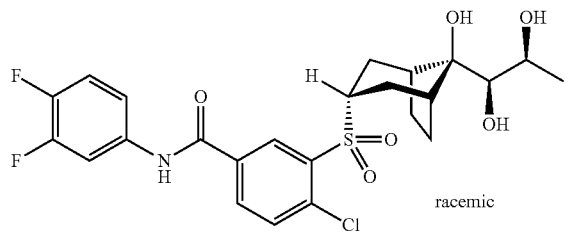 racemic | 528.10, 530.10 |
| 176 | 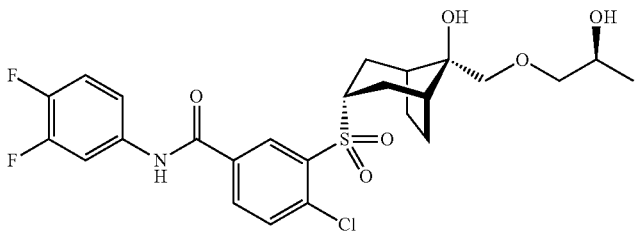 | 542.12, 544.12 |
| 177 | 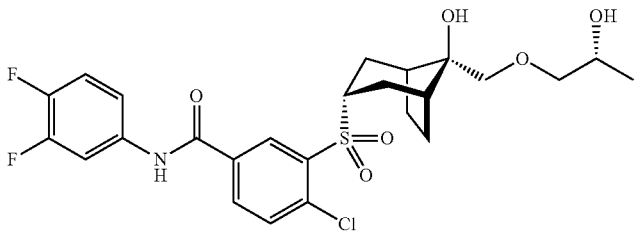 | 542.12, 544.12 |
| 178 | 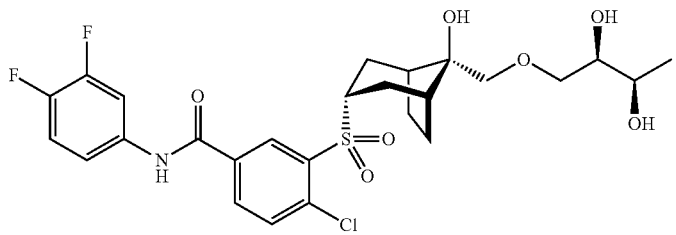 | 572.13, 574.13 |
| 179 | 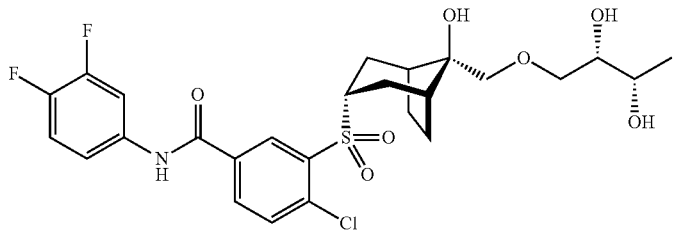 | 572.13, 574.13 |
| 184 | 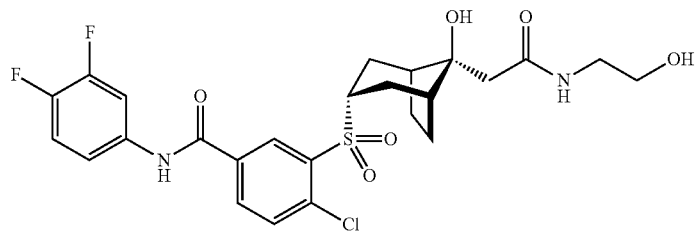 | 557.15 |

-continued

| Example | Structure | ESIMS (M − H)⁻ or (M + H)⁺ |
|---|---|---|
| 185 | 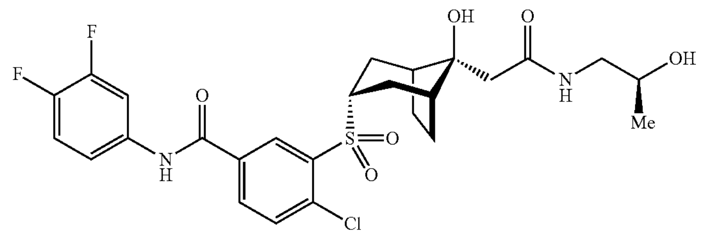 | 571.25 |
| 186 | 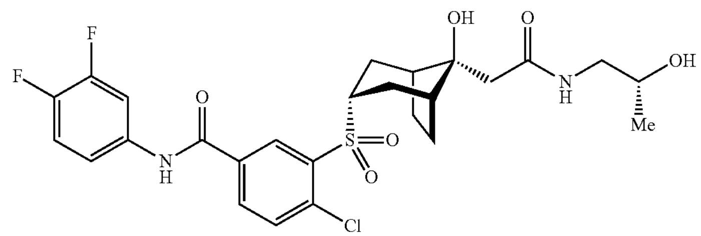 | 571.20 |
| 187 | 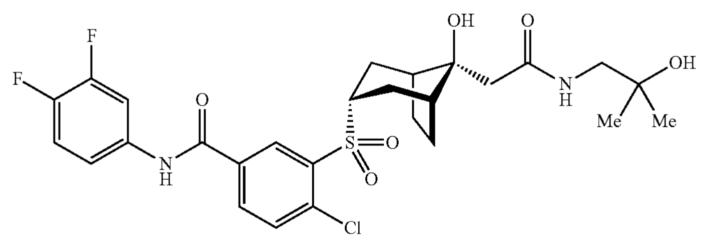 | 585.20, 587.15 |
| 188 | 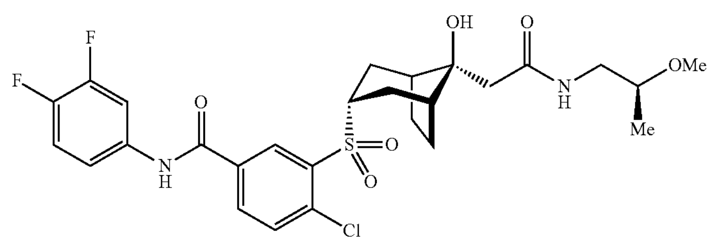 | 585.20, 587.15 |
| 189 | 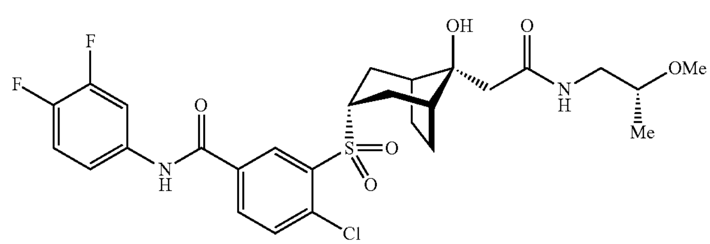 | 585.20, 587.15 |
| 190 | 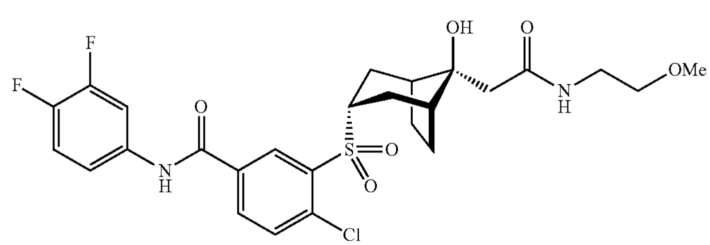 | 571.20 |

-continued

| Example | Structure | ESIMS (M − H)⁻ or (M + H)⁺ |
|---|---|---|
| 191 | 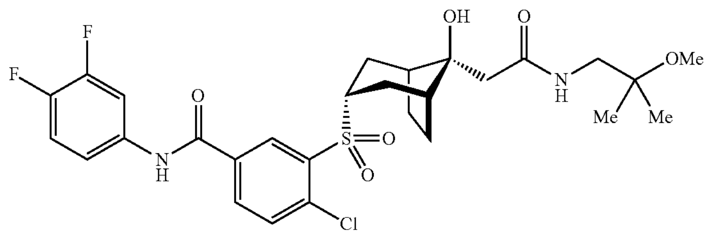 | 599.30 |
| 192 | 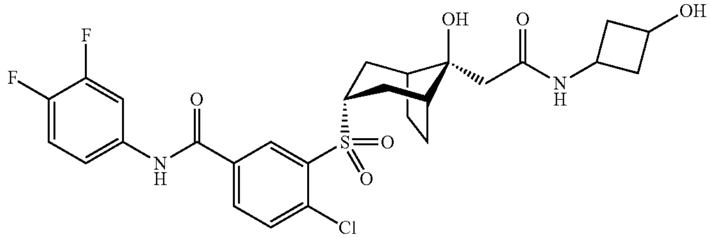 | 583.20 |
| 193 | 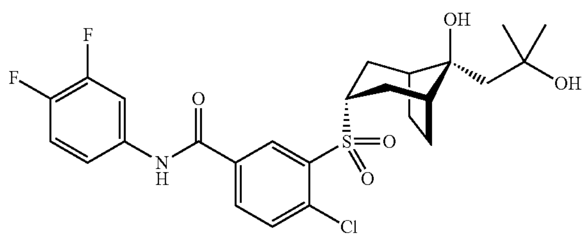 | 526.05 |
| 194 | 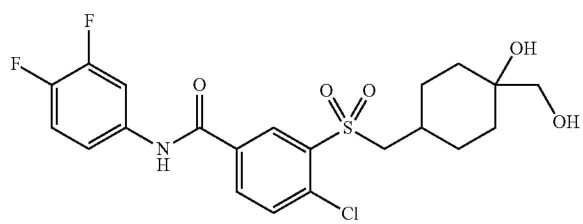 [SMILES: O=C(Nc1ccc(F)c(F)c1)c1ccc(Cl)c(S(=O)(=O)CC2CCC(O)(CO)CC2)c1] | 471.95 |
| 195 | 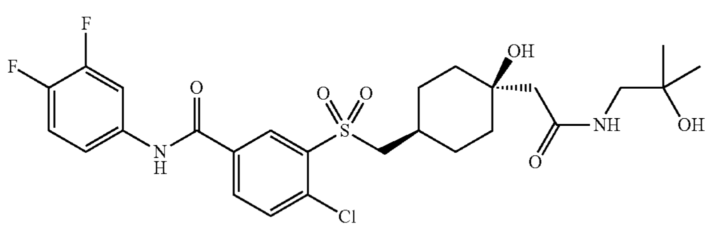 [SMILES: CC(C)(O)CNC(=O)C[C@]1(O)CC[C@@H](CS(=O)(=O)c2cc(C(=O)Nc3ccc(F)c(F)c3)ccc2Cl)CC1] | 571.00 |
| 196 | 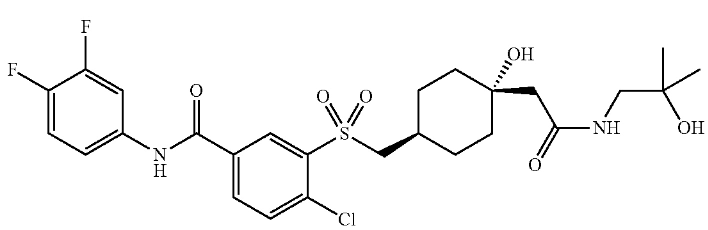 [SMILES: CC(C)(O)CNC(=O)C[C@]1(O)CC[C@H](CS(=O)(=O)c2cc(C(=O)Nc3ccc(F)c(F)c3)ccc2Cl)CC1] | 571.00 |

-continued

| Example | Structure | ESIMS (M − H)⁻ or (M + H)⁺ |
|---|---|---|
| 197 | 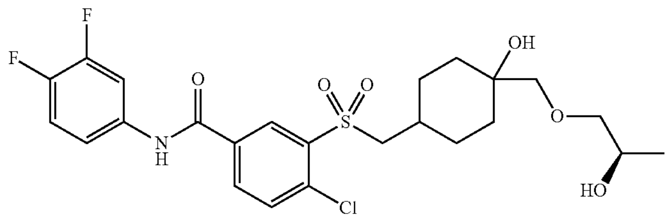 [SMILES: C[C@@H](O)COCC1(O)CCC(CS(=O)(=O)c2cc(C(=O)Nc3ccc(F)c(F)c3)ccc2Cl)CC1] | 530.10 |
| 198 | 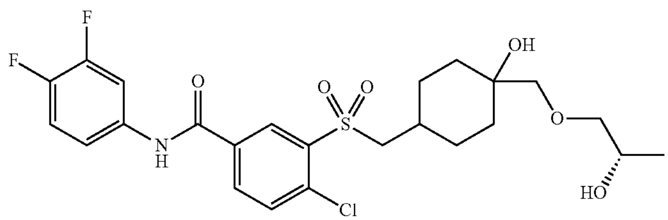 [SMILES: C[C@H](O)COCC1(O)CCC(CS(=O)(=O)c2cc(C(=O)Nc3ccc(F)c(F)c3)ccc2Cl)CC1] | 530.00 |
| 199 | 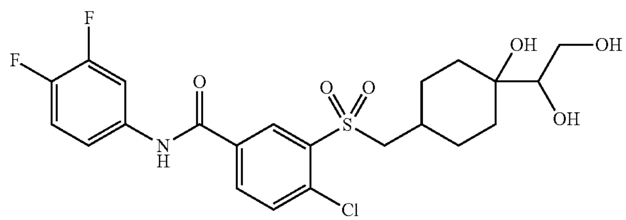 [SMILES: O=C(Nc1ccc(F)c(F)c1)c1ccc(Cl)c(S(=O)(=O)CC2CCC(O)(C(O)CO)CC2)c1] | 502.05, 504.05 |
| 200 | 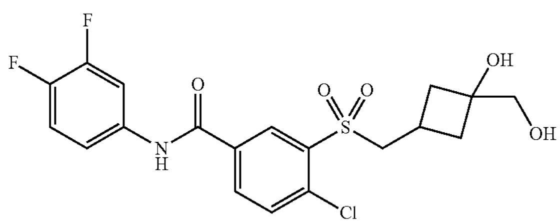 [SMILES: O=C(Nc1ccc(F)c(F)c1)c1ccc(Cl)c(S(=O)(=O)CC2CC(O)(CO)C2)c1] | 443.95 |
| 201 | 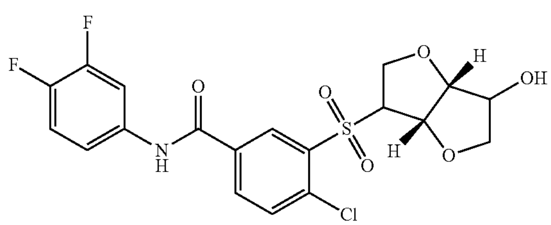 [SMILES: O=C(Nc1ccc(F)c(F)c1)c1ccc(Cl)c(S(=O)(=O)C2CO[C@@H]3C(O)CO[C@H]23)c1] | 458.00, 460.00 |
| 207 | 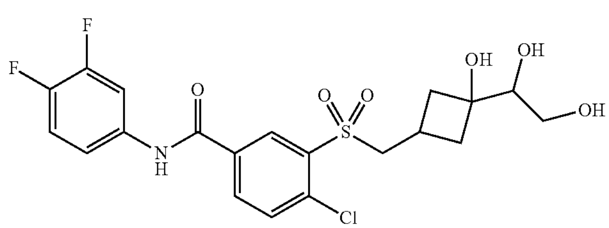 [SMILES: O=C(Nc1ccc(F)c(F)c1)c1ccc(Cl)c(S(=O)(=O)CC2CC(O)(C(O)CO)C2)c1] | 473.95 |
| 208 | 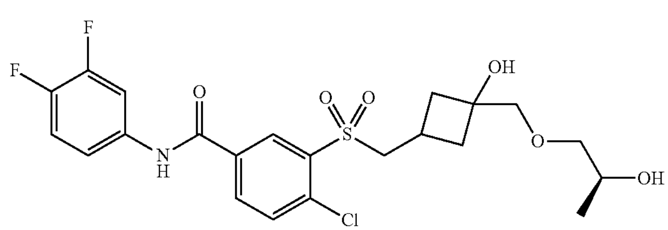 [SMILES: C[C@H](O)COCC1(O)CC(CS(=O)(=O)c2cc(C(=O)Nc3ccc(F)c(F)c3)ccc2Cl)C1] | 501.95 |

-continued
| Example | Structure | ESIMS (M − H)⁻ or (M + H)⁺ |
|---|---|---|
| 209 | 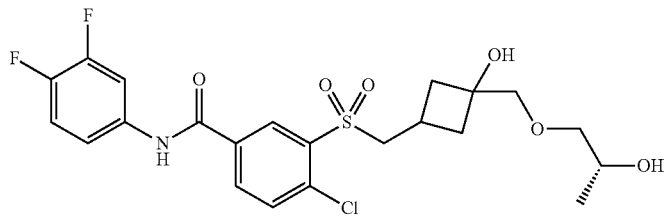 [SMILES: C[C@@H](O)COCC1(O)CC(CS(=O)(=O)c2cc(C(=O)Nc3ccc(F)c(F)c3)ccc2Cl)C1] | 501.95 |
| 211 | 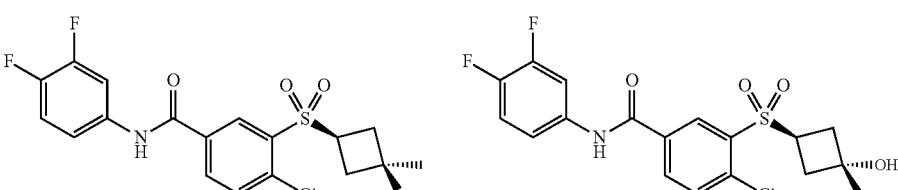<br>4:1 mixture | 413.95 |
| 212 | 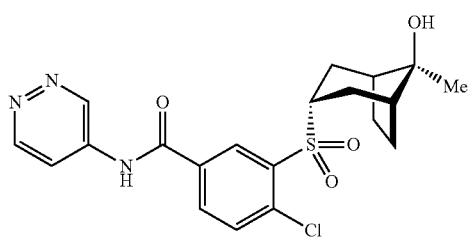 | 436.05 |
| 213 | 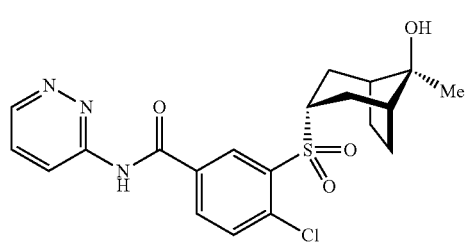 | 436.30 |
| 214 | 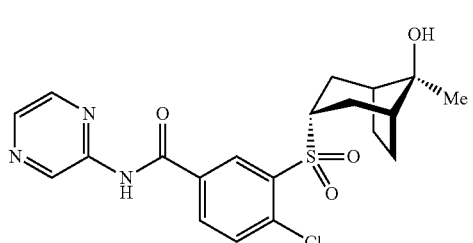 | 434.20 |
| 215 | 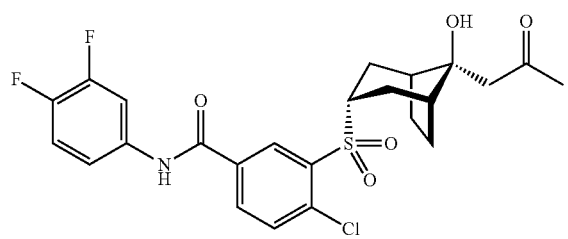 | 510.00 |

-continued

| Example | Structure | ESIMS (M − H)⁻ or (M + H)⁺ |
|---|---|---|
| 216 | 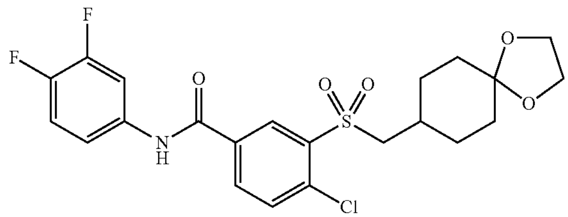 [SMILES: O=C(Nc1ccc(F)c(F)c1)c1ccc(Cl)c(S(=O)(=O)CC2CCC3(CC2)OCCO3)c1] | 484.00 |
| 217 | 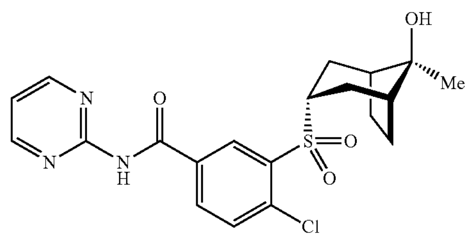 | 436.05 |
| 218 | 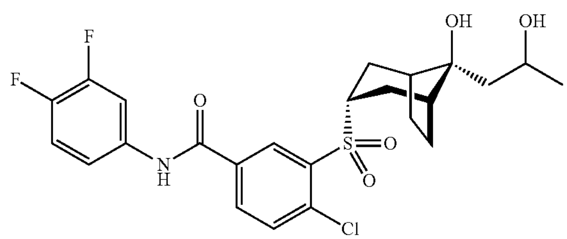 | 512.05 |
| 219 | 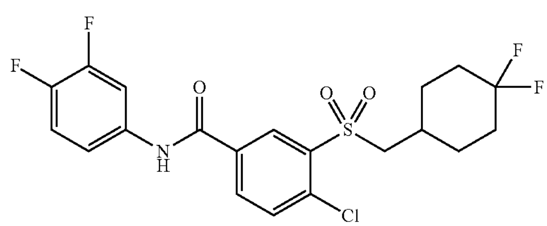 [SMILES: O=C(Nc1ccc(F)c(F)c1)c1ccc(Cl)c(S(=O)(=O)CC2CCC(F)(F)CC2)c1] | 462.00 |
| 220 | 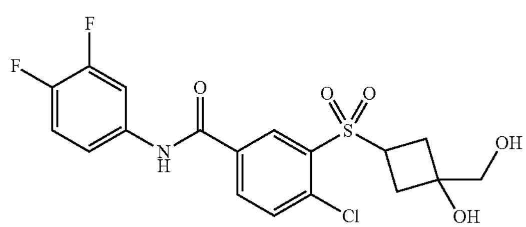 [SMILES: O=C(Nc1ccc(F)c(F)c1)c1ccc(Cl)c(S(=O)(=O)C2CC(O)(CO)C2)c1] | 429.95 |
| 221 | 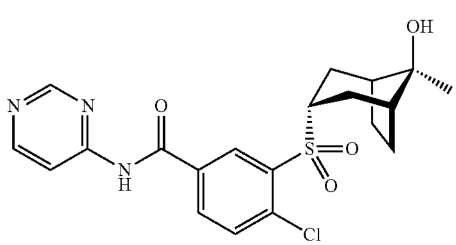 | 436.25 |

| Example | Structure | ESIMS (M − H)⁻ or (M + H)⁺ |
|---|---|---|
| 222 | 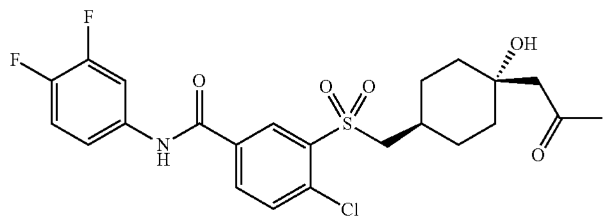 [SMILES: CC(=O)C[C@]1(O)CC[C@H](CS(=O)(=O)c2cc(C(=O)Nc3ccc(F)c(F)c3)ccc2Cl)CC1] | 498.05 |
| 223 | 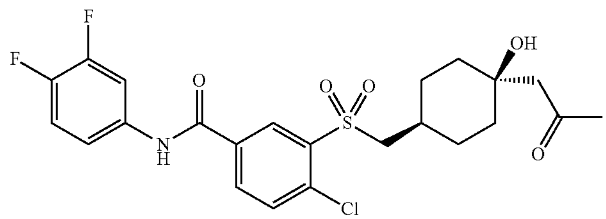 [SMILES: CC(=O)C[C@]1(O)CC[C@@H](CS(=O)(=O)c2cc(C(=O)Nc3ccc(F)c(F)c3)ccc2Cl)CC1] | 498.00 |
| 224 | 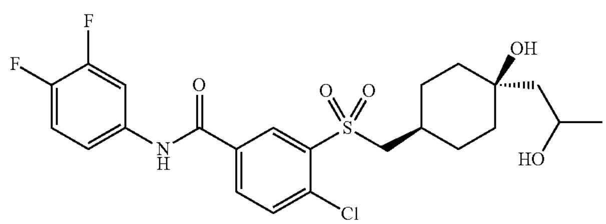 [SMILES: CC(O)C[C@]1(O)CC[C@@H](CS(=O)(=O)c2cc(C(=O)Nc3ccc(F)c(F)c3)ccc2Cl)CC1] | 500.05 |
| 225 | 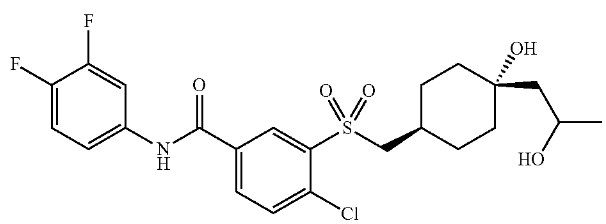 [SMILES: CC(O)C[C@]1(O)CC[C@H](CS(=O)(=O)c2cc(C(=O)Nc3ccc(F)c(F)c3)ccc2Cl)CC1] | 500.05, 502.05 |
| 226 | 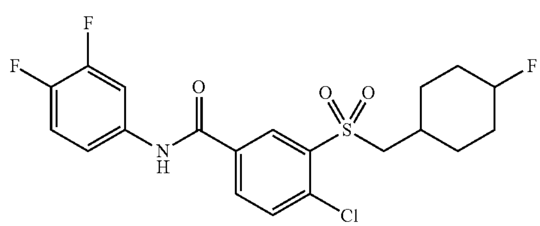 [SMILES: O=C(Nc1ccc(F)c(F)c1)c1ccc(Cl)c(S(=O)(=O)CC2CCC(F)CC2)c1] | 444.00 |
| 227 | 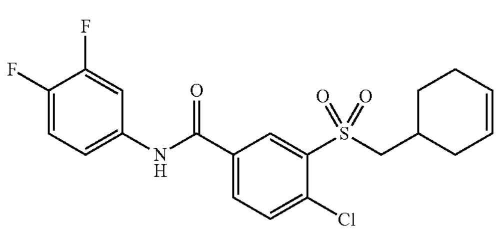 [SMILES: O=C(Nc1ccc(F)c(F)c1)c1ccc(Cl)c(S(=O)(=O)CC2CC=CCC2)c1] | 424.00 |

-continued

| Example | Structure | ESIMS (M − H)⁻ or (M + H)⁺ |
|---|---|---|
| 228 | 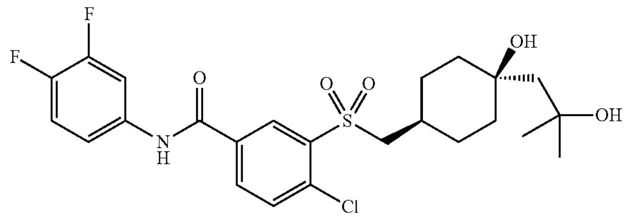 [SMILES: CC(C)(O)C[C@]1(O)CC[C@@H](CS(=O)(=O)c2cc(C(=O)Nc3ccc(F)c(F)c3)ccc2Cl)CC1] | 514.05 |
| 229 | 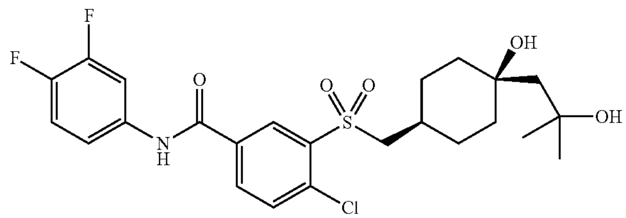 [SMILES: CC(C)(O)C[C@]1(O)CC[C@@H](CS(=O)(=O)c2cc(C(=O)Nc3ccc(F)c(F)c3)ccc2Cl)CC1] | 514.10 |
| 230 | 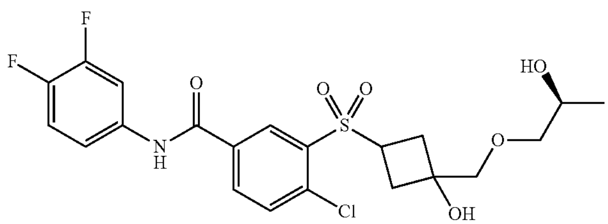 [SMILES: C[C@H](O)COCC1(O)CC(S(=O)(=O)c2cc(C(=O)Nc3ccc(F)c(F)c3)ccc2Cl)C1] | 488.00 |
| 231 | 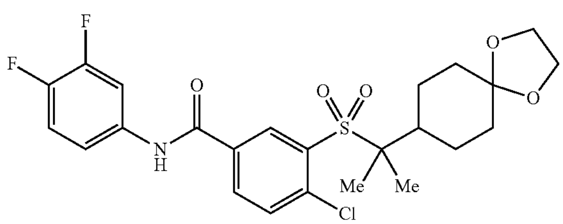 [SMILES: CC(C)(C1CCC2(CC1)OCCO2)S(=O)(=O)c1cc(C(=O)Nc2ccc(F)c(F)c2)ccc1Cl] | 512.05 |
| 232 | 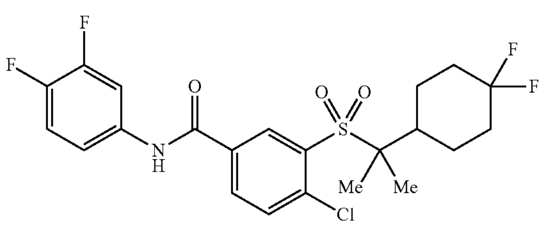 [SMILES: CC(C)(C1CCC(F)(F)CC1)S(=O)(=O)c1cc(C(=O)Nc2ccc(F)c(F)c2)ccc1Cl] | 490.05 |
| 233 | 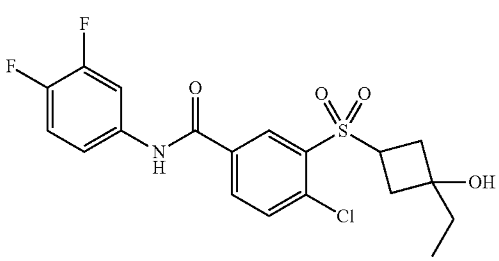 [SMILES: CCC1(O)CC(S(=O)(=O)c2cc(C(=O)Nc3ccc(F)c(F)c3)ccc2Cl)C1] | 428.00 |

-continued

| Example | Structure | ESIMS (M − H)⁻ or (M + H)⁺ |
|---|---|---|
| 234 | 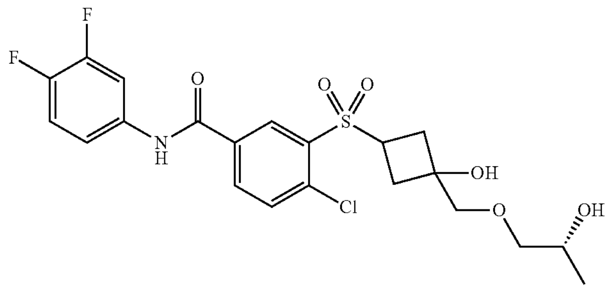 [SMILES: C[C@@H](O)COCC1(O)CC(S(=O)(=O)c2cc(C(=O)Nc3ccc(F)c(F)c3)ccc2Cl)C1] | 488.00 |
| 235 | 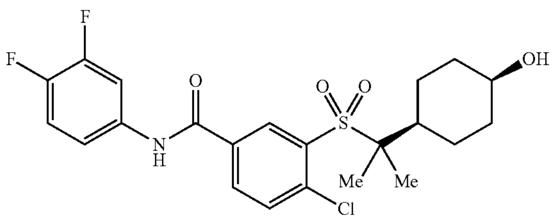 [SMILES: CC(C)([C@H]1CC[C@@H](O)CC1)S(=O)(=O)c1cc(C(=O)Nc2ccc(F)c(F)c2)ccc1Cl] | 470.00 |
| 236 | 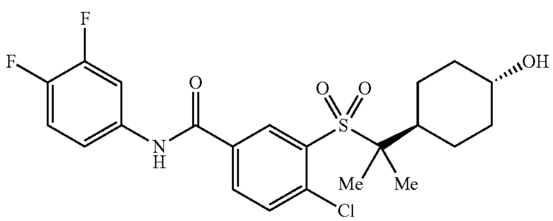 [SMILES: CC(C)([C@H]1CC[C@H](O)CC1)S(=O)(=O)c1cc(C(=O)Nc2ccc(F)c(F)c2)ccc1Cl] | 470.00 |
| 237 | 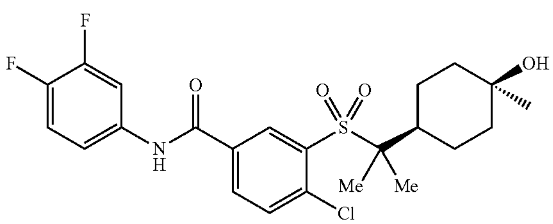 [SMILES: CC(C)([C@H]1CC[C@@](C)(O)CC1)S(=O)(=O)c1cc(C(=O)Nc2ccc(F)c(F)c2)ccc1Cl] | 484.05 |
| 238 | 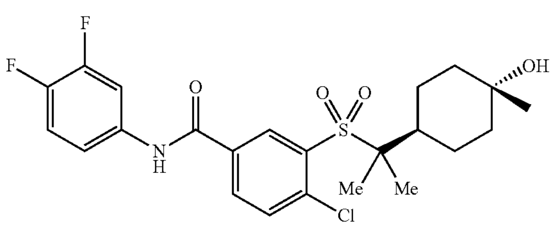 [SMILES: CC(C)([C@H]1CC[C@](C)(O)CC1)S(=O)(=O)c1cc(C(=O)Nc2ccc(F)c(F)c2)ccc1Cl] | 484.05 |
| 239 | 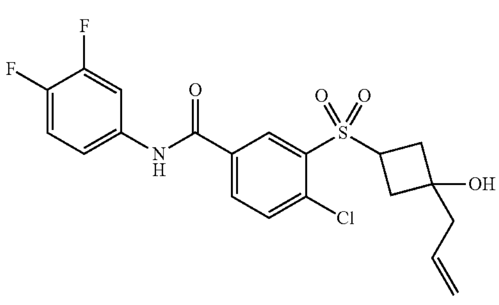 [SMILES: C=CCC1(O)CC(S(=O)(=O)c2cc(C(=O)Nc3ccc(F)c(F)c3)ccc2Cl)C1] | 440.00 |

| Example | Structure | ESIMS (M − H)⁻ or (M + H)⁺ |
|---|---|---|
| 240 | 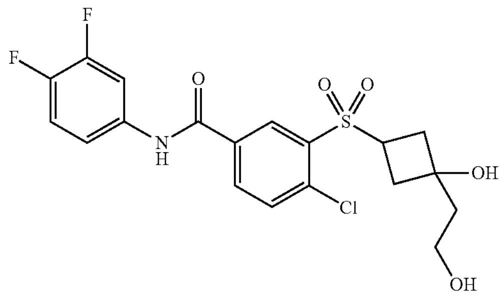 [SMILES: O=C(Nc1ccc(F)c(F)c1)c1ccc(Cl)c(S(=O)(=O)C2CC(O)(CCO)C2)c1] | 444.00 |
| 241 | 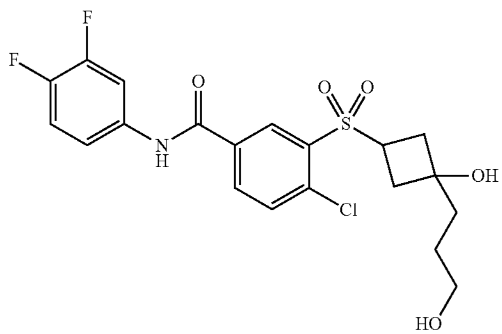 [SMILES: O=C(Nc1ccc(F)c(F)c1)c1ccc(Cl)c(S(=O)(=O)C2CC(O)(CCCO)C2)c1] | 258.00 |
| 242 | 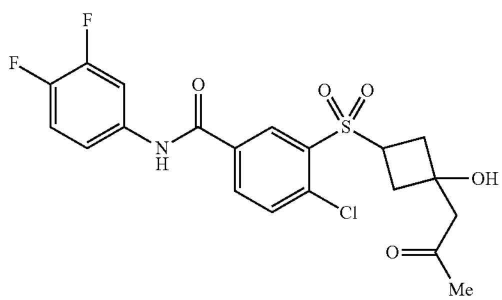 [SMILES: CC(=O)CC1(O)CC(S(=O)(=O)c2cc(C(=O)Nc3ccc(F)c(F)c3)ccc2Cl)C1] | 471.95 |
| 243 | 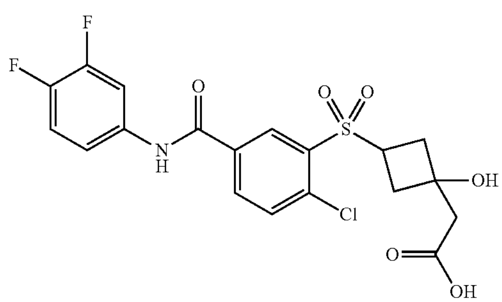 [SMILES: O=C(O)CC1(O)CC(S(=O)(=O)c2cc(C(=O)Nc3ccc(F)c(F)c3)ccc2Cl)C1] | 458.00 |
| 244 | 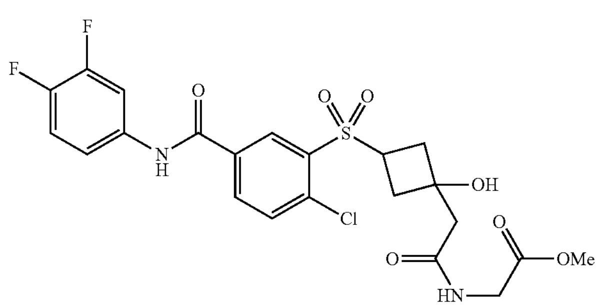 [SMILES: COC(=O)CNC(=O)CC1(O)CC(S(=O)(=O)c2cc(C(=O)Nc3ccc(F)c(F)c3)ccc2Cl)C1] | 529.00 |

| Example | Structure | ESIMS (M − H)⁻ or (M + H)⁺ |
|---|---|---|
| 245 | 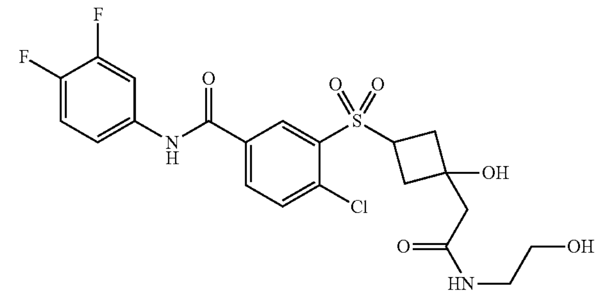 [SMILES: O=C(CC1(O)CC(S(=O)(=O)c2cc(C(=O)Nc3ccc(F)c(F)c3)ccc2Cl)C1)NCCO] | 503.10 |
| 246 | 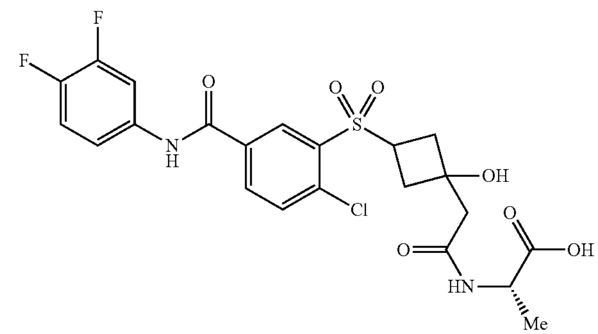 [SMILES: C[C@H](NC(=O)CC1(O)CC(S(=O)(=O)c2cc(C(=O)Nc3ccc(F)c(F)c3)ccc2Cl)C1)C(=O)O] | 543.00 |
| 247 | 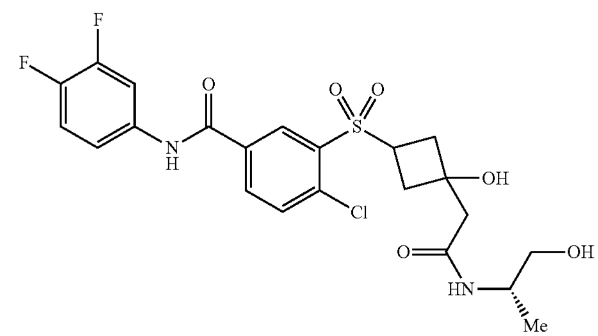 [SMILES: C[C@@H](CO)NC(=O)CC1(O)CC(S(=O)(=O)c2cc(C(=O)Nc3ccc(F)c(F)c3)ccc2Cl)C1] | 517.15 |
| 248 | 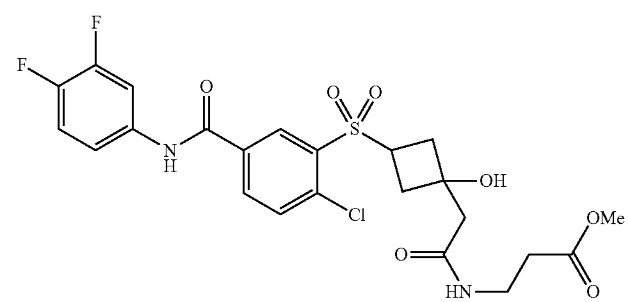 [SMILES: COC(=O)CCNC(=O)CC1(O)CC(S(=O)(=O)c2cc(C(=O)Nc3ccc(F)c(F)c3)ccc2Cl)C1] | 542.95 |
| 249 | 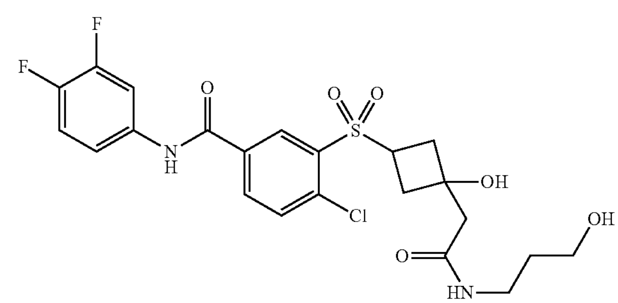 [SMILES: O=C(CC1(O)CC(S(=O)(=O)c2cc(C(=O)Nc3ccc(F)c(F)c3)ccc2Cl)C1)NCCCO] | 517.15 |

| Example | Structure | ESIMS (M − H)⁻ or (M + H)⁺ |
|---|---|---|
| 250a | 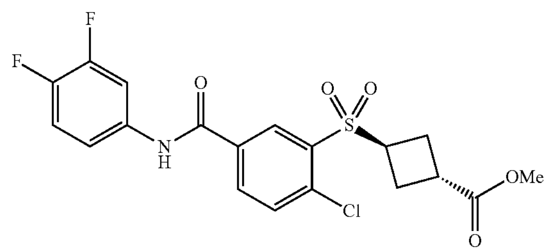 [SMILES: COC(=O)[C@H]1C[C@H](S(=O)(=O)c2cc(C(=O)Nc3ccc(F)c(F)c3)ccc2Cl)C1] | 442.05 |
| 250b | 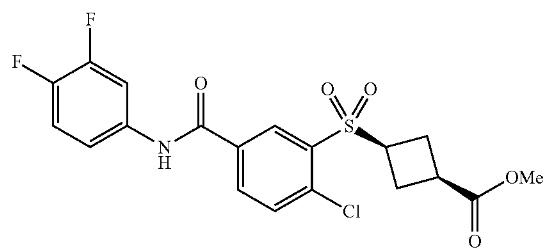 [SMILES: COC(=O)[C@H]1C[C@@H](S(=O)(=O)c2cc(C(=O)Nc3ccc(F)c(F)c3)ccc2Cl)C1] | 444.05 |
| 251 | 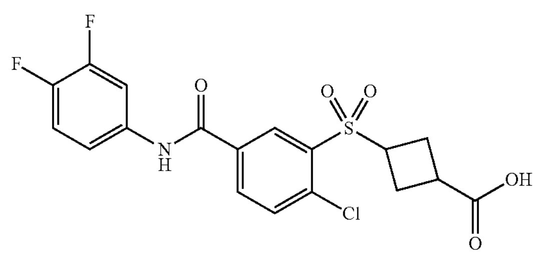 [SMILES: O=C(Nc1ccc(F)c(F)c1)c1ccc(Cl)c(S(=O)(=O)C2CC(C(=O)O)C2)c1] | 430.05 |
| 252a | 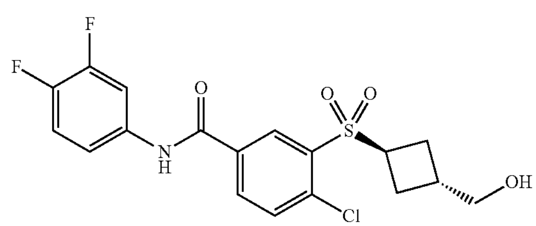 [SMILES: O=C(Nc1ccc(F)c(F)c1)c1ccc(Cl)c(S(=O)(=O)[C@H]2C[C@H](CO)C2)c1] | 414.05 |
| 252b | 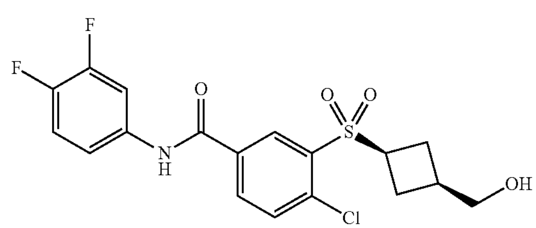 [SMILES: O=C(Nc1ccc(F)c(F)c1)c1ccc(Cl)c(S(=O)(=O)[C@H]2C[C@@H](CO)C2)c1] | 414.05 |
| 253a | 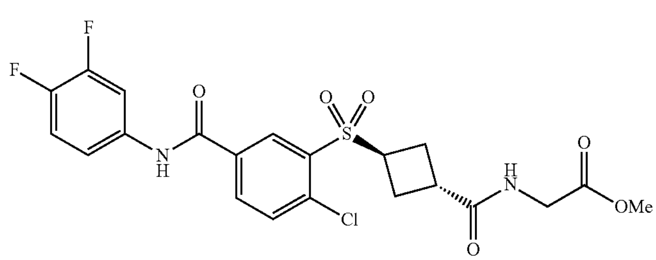 [SMILES: COC(=O)CNC(=O)[C@H]1C[C@H](S(=O)(=O)c2cc(C(=O)Nc3ccc(F)c(F)c3)ccc2Cl)C1] | 499.10 |

-continued

| Example | Structure | ESIMS (M − H)⁻ or (M + H)⁺ |
|---|---|---|
| 253b | 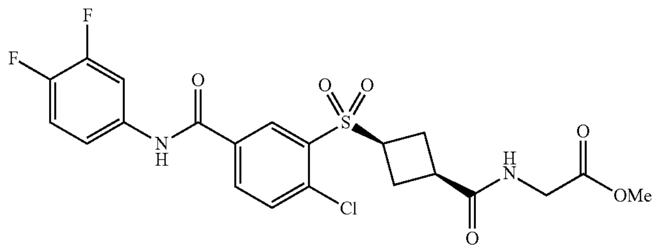 [SMILES: COC(=O)CNC(=O)[C@H]1C[C@@H](S(=O)(=O)c2cc(C(=O)Nc3ccc(F)c(F)c3)ccc2Cl)C1] | 499.10 |
| 254 | 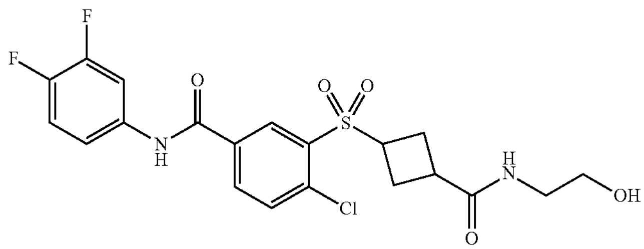 [SMILES: O=C(Nc1ccc(F)c(F)c1)c1ccc(Cl)c(S(=O)(=O)C2CC(C(=O)NCCO)C2)c1] | 473.10 |
| 255 | 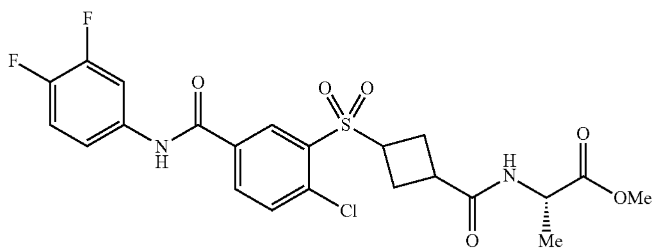 [SMILES: COC(=O)[C@H](C)NC(=O)C1CC(S(=O)(=O)c2cc(C(=O)Nc3ccc(F)c(F)c3)ccc2Cl)C1] | 515.05 |
| 256a | 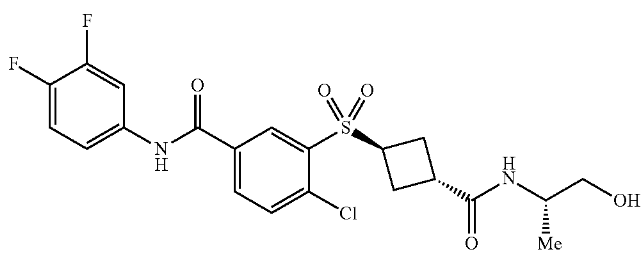 [SMILES: C[C@@H](CO)NC(=O)[C@H]1C[C@H](S(=O)(=O)c2cc(C(=O)Nc3ccc(F)c(F)c3)ccc2Cl)C1] | 485.15 |
| 256b | 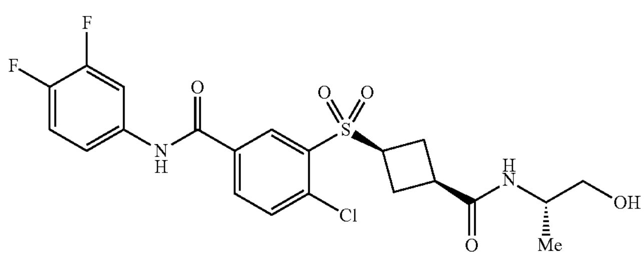 [SMILES: C[C@@H](CO)NC(=O)[C@H]1C[C@@H](S(=O)(=O)c2cc(C(=O)Nc3ccc(F)c(F)c3)ccc2Cl)C1] | 485.15 |
| 257a | 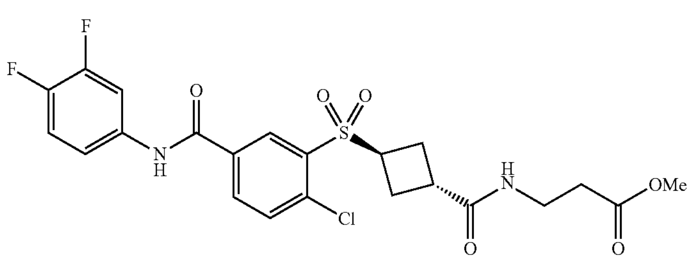 [SMILES: COC(=O)CCNC(=O)[C@H]1C[C@H](S(=O)(=O)c2cc(C(=O)Nc3ccc(F)c(F)c3)ccc2Cl)C1] | 513.10 |

-continued

| Example | Structure | ESIMS (M − H)⁻ or (M + H)⁺ |
|---|---|---|
| 257b | 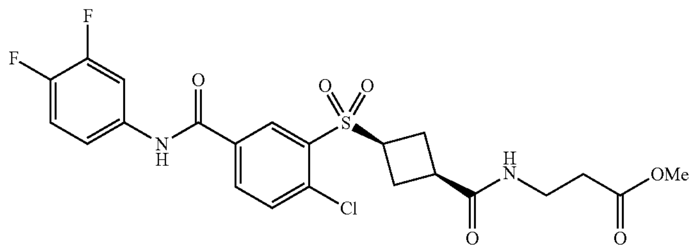 [SMILES: COC(=O)CCNC(=O)[C@H]1C[C@@H](S(=O)(=O)c2cc(C(=O)Nc3ccc(F)c(F)c3)ccc2Cl)C1] | 513.15 |
| 258 | 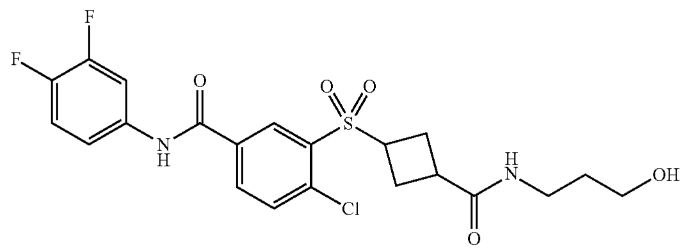 [SMILES: O=C(Nc1ccc(F)c(F)c1)c1ccc(Cl)c(S(=O)(=O)C2CC(C(=O)NCCCO)C2)c1] | 487.15 |
| 260 | 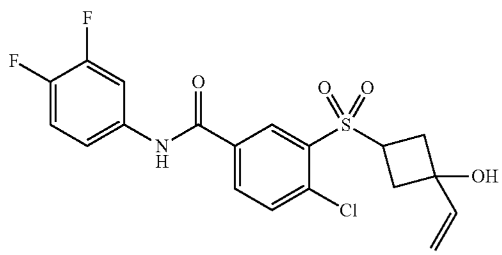 [SMILES: C=CC1(O)CC(S(=O)(=O)c2cc(C(=O)Nc3ccc(F)c(F)c3)ccc2Cl)C1] | 425.95 |
| 280 | 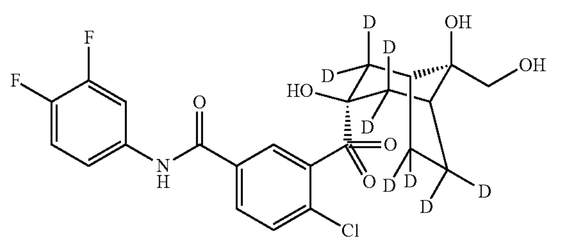 | 292.13, 294.13 [M − H]⁻ |
| 282 | 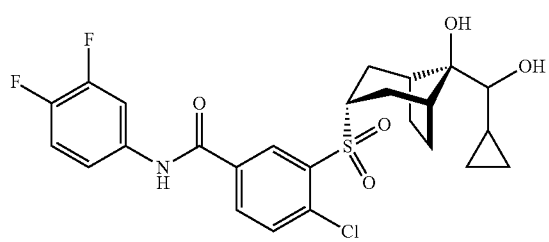 | 564.29, 566.29 |
| 294 | 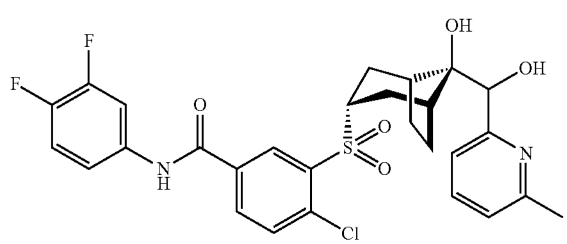 | 621.13, 623.13 [M + HCO₂]⁻ |

| Example | Structure | ESIMS (M − H)⁻ or (M + H)⁺ |
|---|---|---|
| 294a | 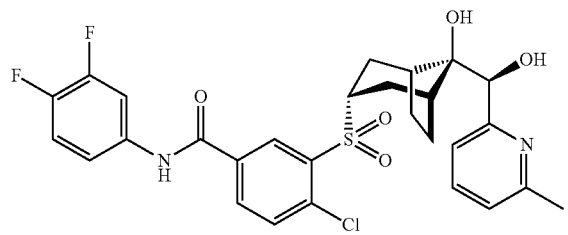 | 621.13, 623.13 [M + HCO$_2$]⁻ |
| 294b | 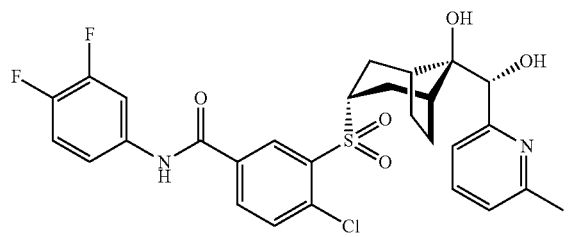 | 621.13, 623.13 [M + HCO$_2$]⁻ |
| 295 | 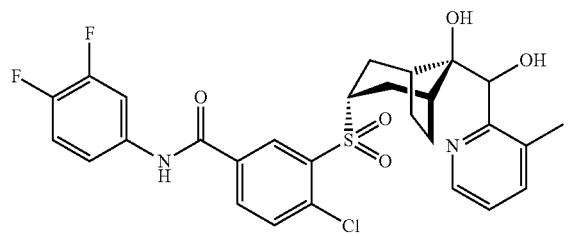 | 621.13, 623.13 [M + HCO$_2$]⁻ |
| 295a | 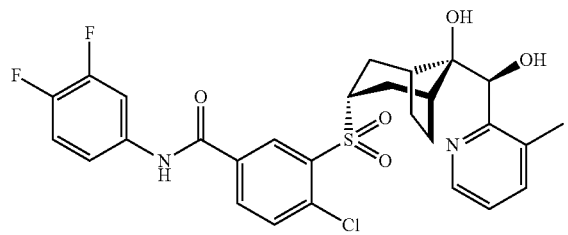 | 621.13, 623.13 [M + HCO$_2$]⁻ |
| 295b | 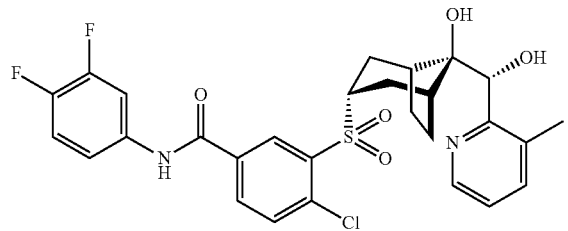 | 621.13, 623.13 [M + HCO$_2$]⁻ |
| 296 | 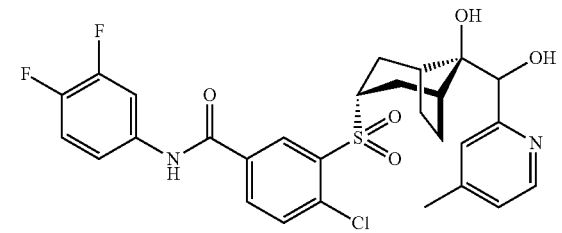 | 621.13, 623.13 [M + HCO$_2$]⁻ |

-continued

| Example | Structure | ESIMS (M − H)⁻ or (M + H)⁺ |
|---|---|---|
| 296a | 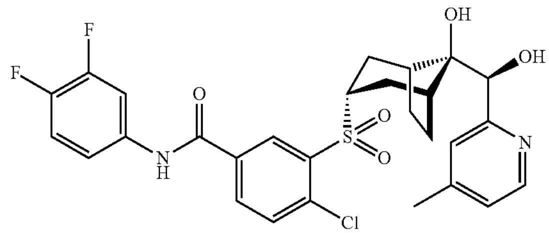 | 621.13, 623.13 [M + HCO₂]⁻ |
| 296b | 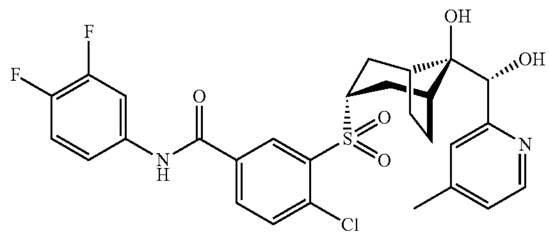 | 621.13, 623.13 [M + HCO₂]⁻ |
| 297a | 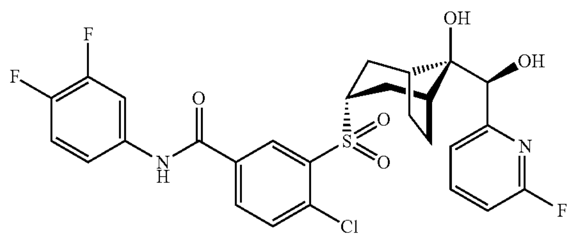 | 625.11, 627.11 [M + HCO₂]⁻ |
| 297b | 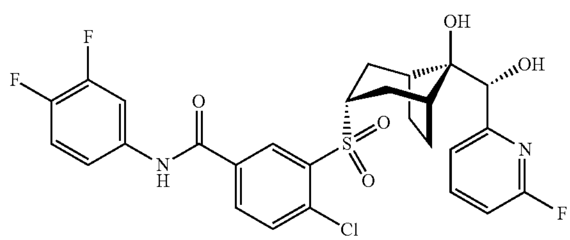 | 625.11, 627.11 [M + HCO₂]⁻ |
| 299 | 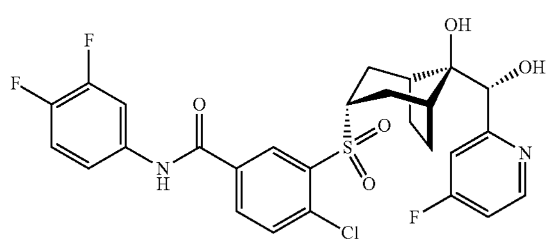 | 625.11, 627.10 [M + HCO₂]⁻ |
| 300 | 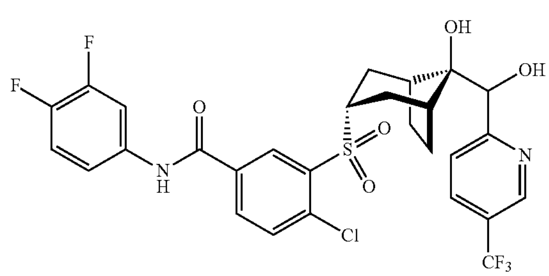 | 675.10, 677.10 [M + HCO₂]⁻ |

-continued

| Example | Structure | ESIMS (M − H)⁻ or (M + H)⁺ |
|---|---|---|
| 301 | 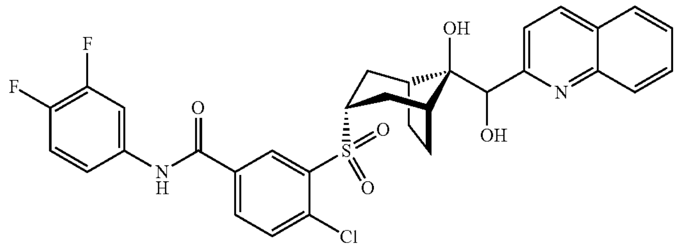 | 657.32, 659.32 [M + HCO₂]⁻ |
| 302 | 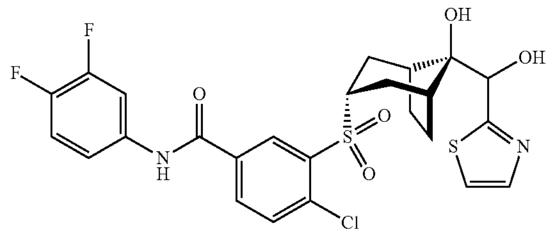 | 613.24, 615.23 [M + HCO₂]⁻ |
| 302a | 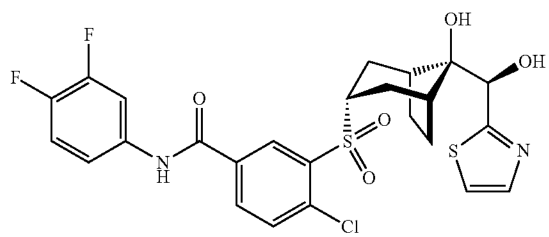 | 613.24, 615.23 [M + HCO₂]⁻ |
| 302b | 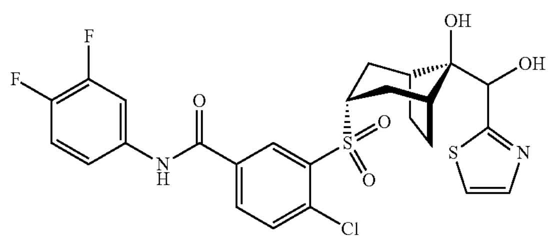 | 613.24, 615.23 [M + HCO₂]⁻ |
| 303 | 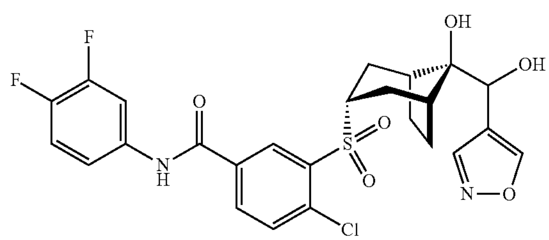 | 597.27, 599.26 [M + HCO₂]⁻ |
| 304 | 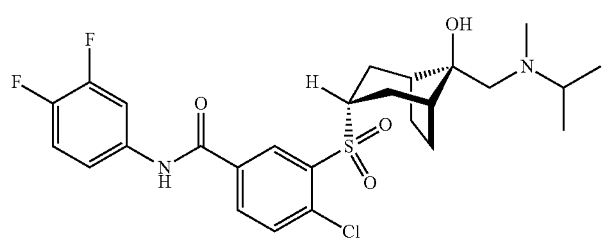 | 539.16, 541.16 [M − H]⁻ |

-continued
| Example | Structure | ESIMS (M − H)⁻ or (M + H)⁺ |
|---|---|---|
| 305 | 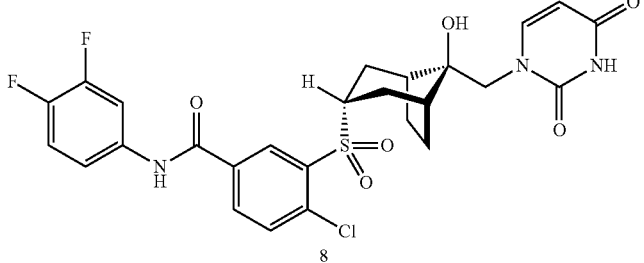 | 624.10, 626.10 [M + CO₂]⁻ |
| 306 | 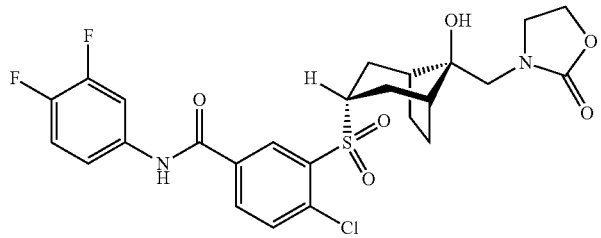 | 553.26, 5552.6 [M − H]⁻ |
| 310 | 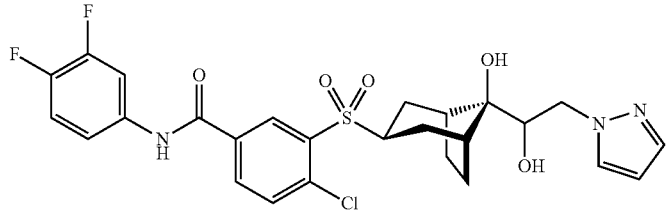 | 610.12, 612.12 [M + HCO₂]⁻ |
| 311 | 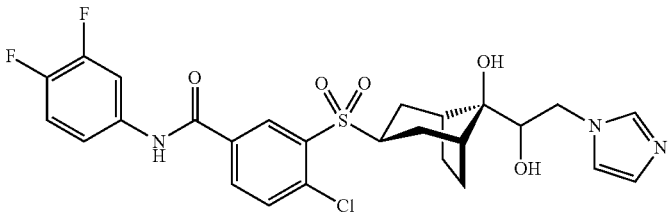 | 610.12, 612.12 [M + HCO₂]⁻ |
| 312 | 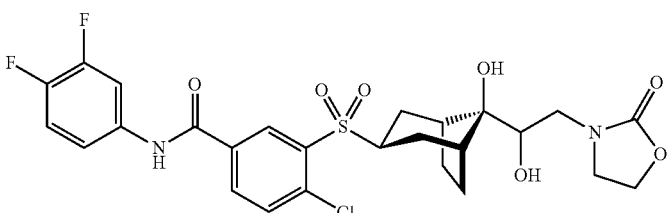 | 629.11, 31.11 [M + HCO₂]⁻ |
| 313 | 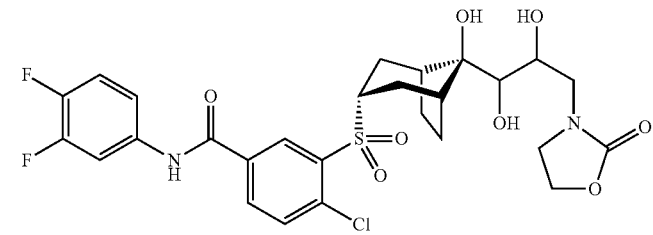 | 659.31, 661.31 [M + HCO₂]⁻ |

| Example | Structure | ESIMS (M − H)⁻ or (M + H)⁺ |
|---|---|---|
| 324 | 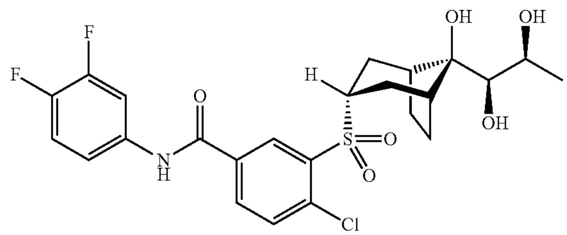 | 558.14 [M + HCO₂]⁻ |
| 325 | 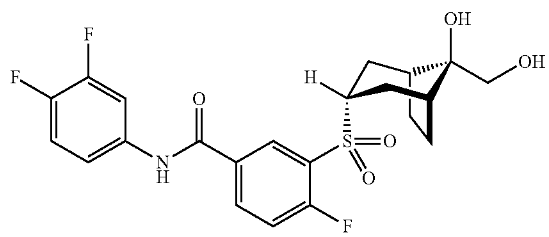 | 514.11 [M − H]⁻ |
| 326 | 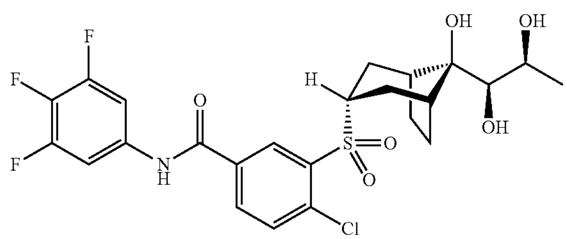 | 576.13 [M + HCO₂]⁻ |
| 335 | 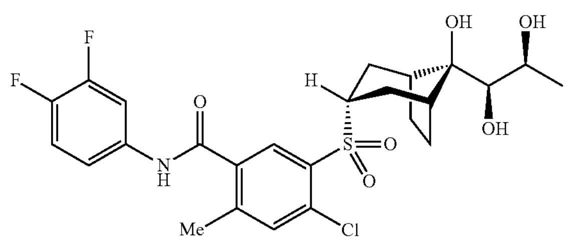 | 588.30, 590.30 [M + HCO₂]⁻ |
| 338 | 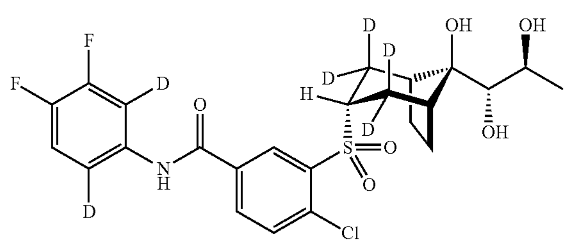 | 580.15, 582.15 [M + HCO₂]⁻ |
| 342 | 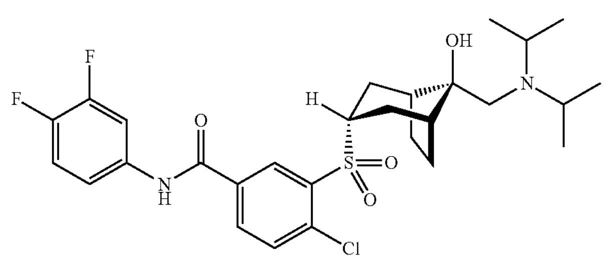 | 567.19, 569.19 [M − H]⁻ |

| Example | Structure | ESIMS (M − H)⁻ or (M + H)⁺ |
|---|---|---|
| 343 | 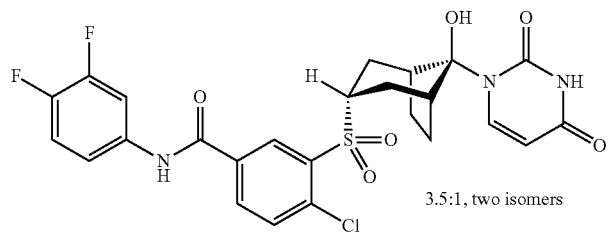 3.5:1, two isomers | 548.23, 550.23 [M − H] |
| 349 | 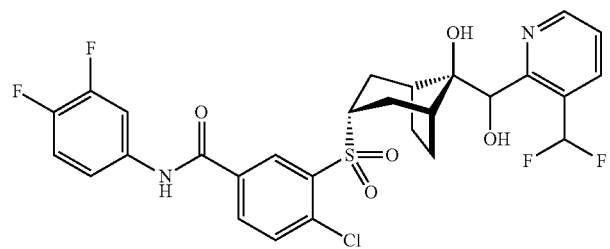 | 657.11, 659.11 [M + HCO$_2$]⁻ |
| 350 | 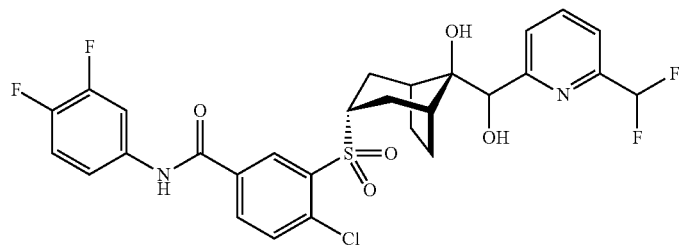 | 657.11, 659.11 [M + HCO$_2$]⁻ |
| 351 | 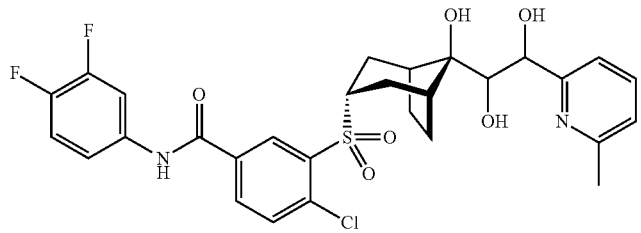 | 651.14, 653.14 [M + HCO$_2$]⁻ |
| 352 | 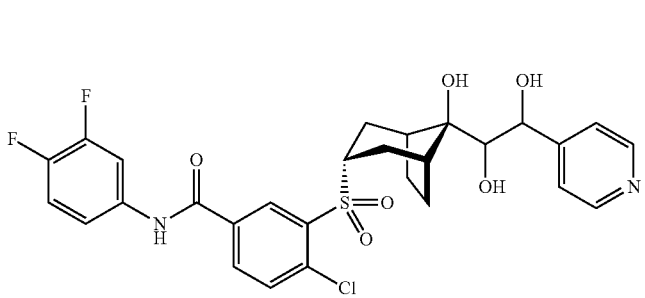 | 637.12, 639.12 [M + HCO$_2$]⁻ |

The following examples are prepared using procedures similar to those described above:
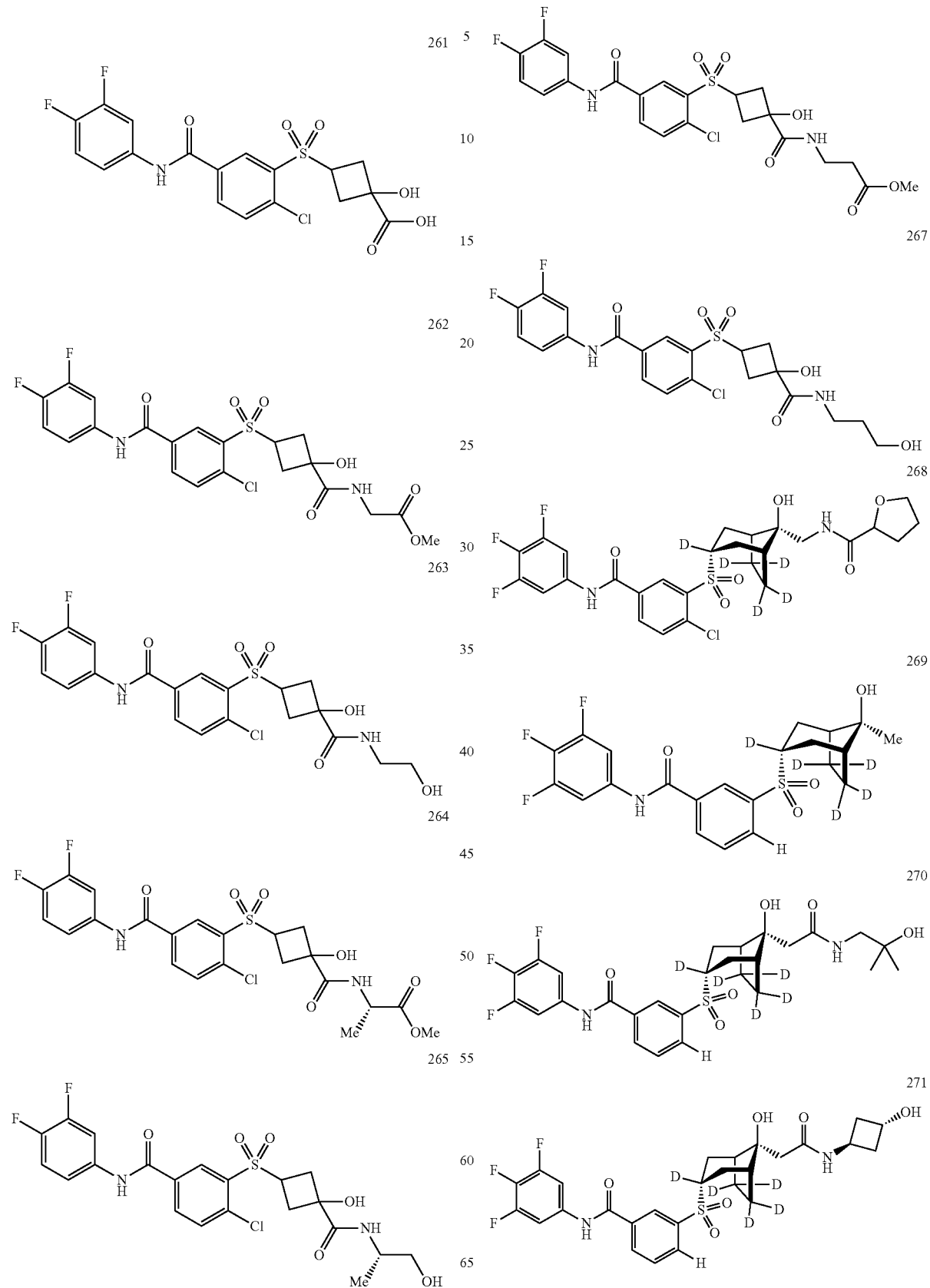

211
-continued
273
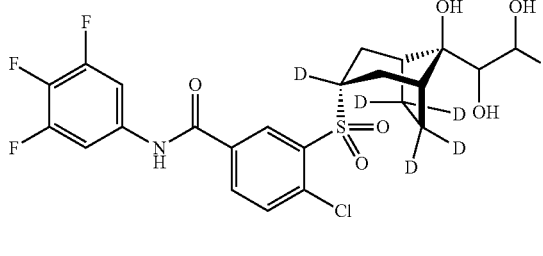
274
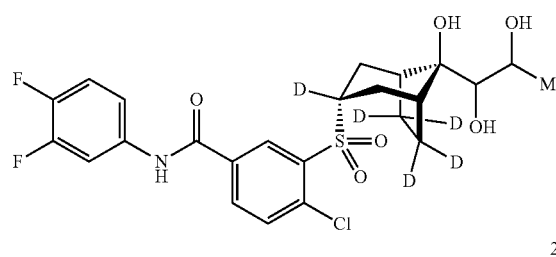
275
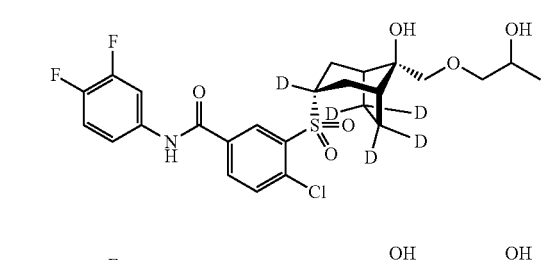
276
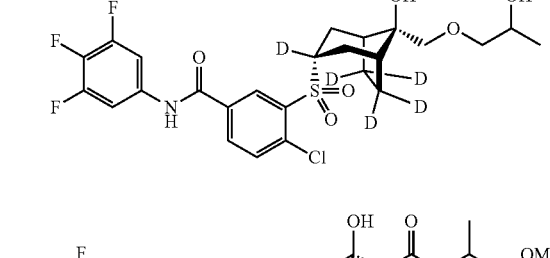
277
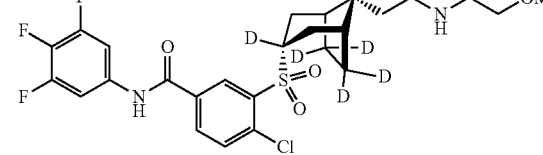
278
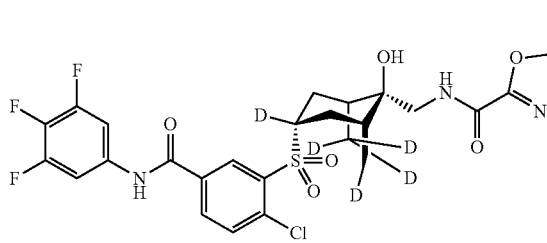
353
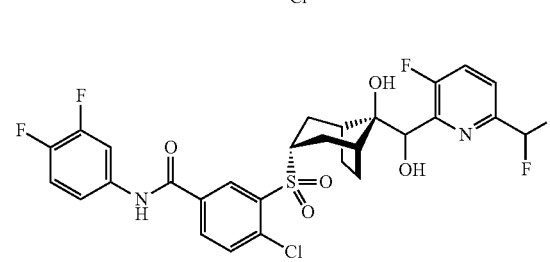
212
-continued
354
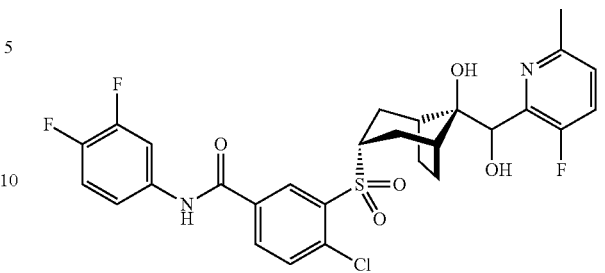
355
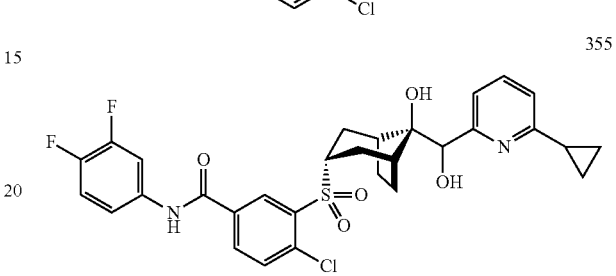
356
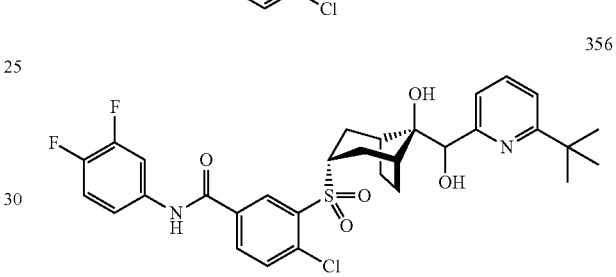
357
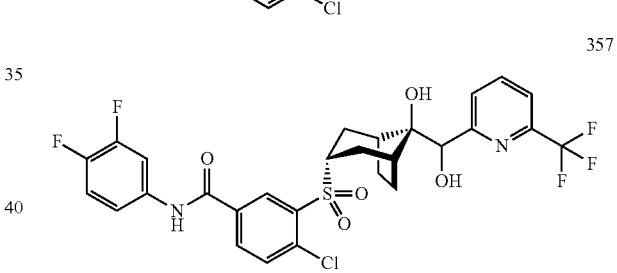
358
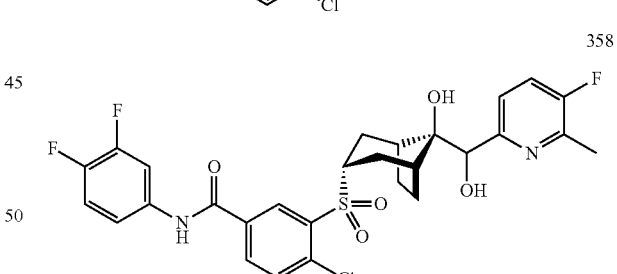
359
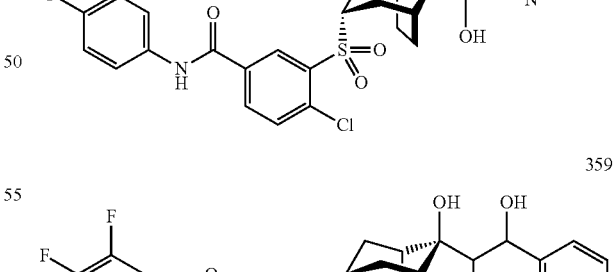

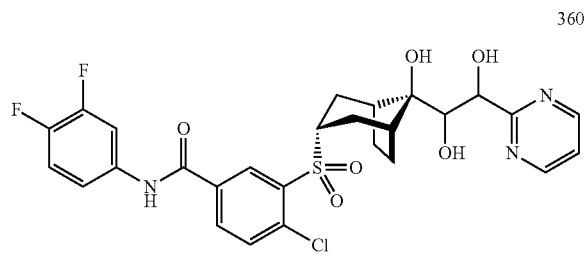
360
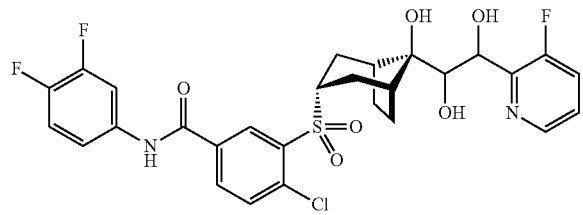
361
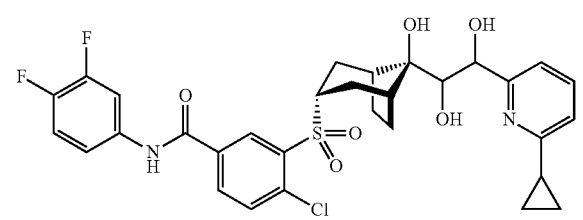
362
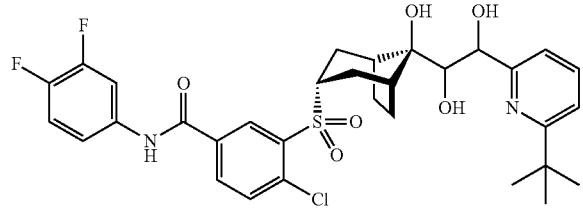
363
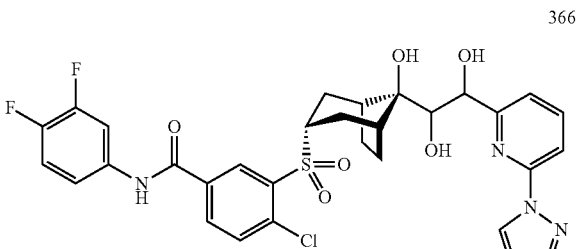
366
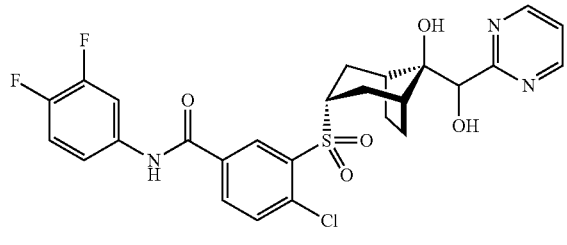
368
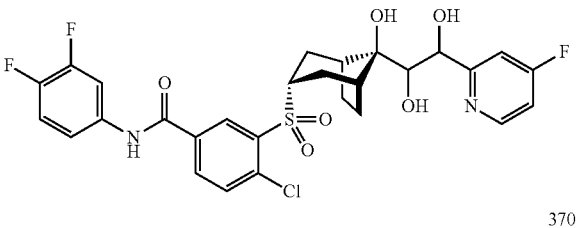
369
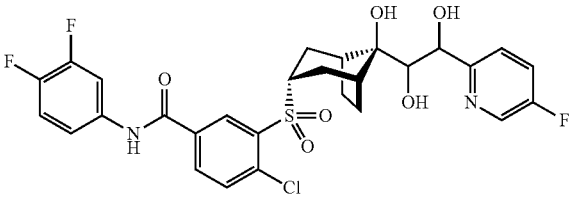
370
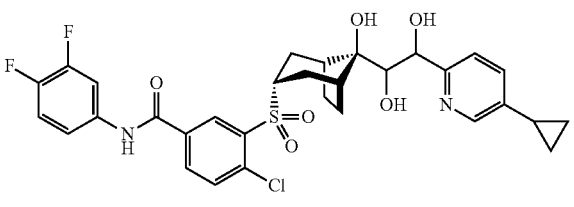
371
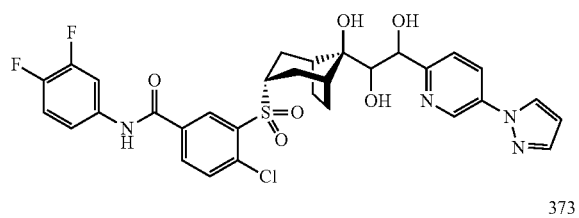
372
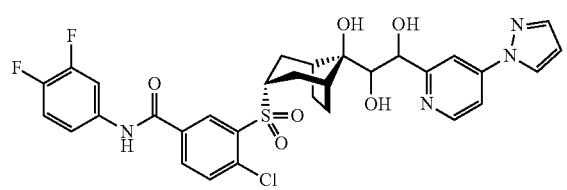
373
364
365

374

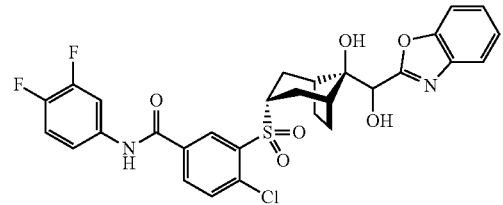

375

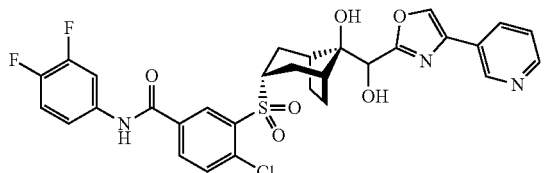

376

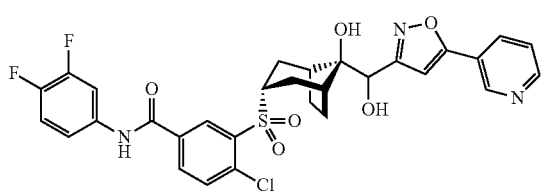

Biological Activity

Methods: HepAD38 cells are maintained as previously reported (Ladner et al, *Antimicrob. Agents Chemother.* 1997, 4, 1715). Briefly, cells are passaged upon attaining confluency in DMEM/F12 media in the presence of 10% FBS, Penn/Strep, 250 μg/mL G418, and 1 ug/ml tetracycline. Novel compounds are screened by first washing cells three times with PBS to remove tetracycline, and plating in 96 well plates at 35,000 cells/well. Compounds dissolved in DMSO are then diluted 1:200 into wells containing cells. Five days after compound addition, material is harvested for analysis. For an extended 8 days analysis, cells are plated and treated as described above, but media and compound are refreshed on d2 and d5 post initial treatment.

On harvest day, virion DNA is obtained by lysing with Sidestep Lysis and Stabilization Buffer and then quantified via quantitative real time PCR. Commercially available ELISA kits are used to quantitate the viral proteins HBsAg (Alpco) or HbeAg (US Biological) by following the manufacturer's recommended protocol after diluting samples to match the linear range of their respective assays. Irrespective of readout, compound concentrations that reduce viral product accumulation in the cell lysates or supernatants by 50% relative to no drug controls ($EC_{50}$) are reported; $EC_{50}$ ranges are as follows: A<0.1 μM; B 0.1-0.2 μM; C>0.2 μM.

Compound toxicity is evaluated by seeding cells at 15,000 cells/well and treating with compound as described above. Three days after compound addition, cells are treated with ATPLite reagent and compound concentrations that reduce total ATP levels in wells by 50% relative to no drug controls ($CC_{50}$) are reported; $CC_{50}$ ranges are as follows: A>25 μM; B 10-25 μM; C<10 μM.

TABLE 1

Summary of Activities

| Compd. Number | HepAD38 $EC_{50}$ (μM) | Compd. Number | HepAD38 $EC_{50}$ (μM) |
|---|---|---|---|
| 1 | A | 2 | B |
| 3 | A | 4 | A |
| 5 | A | 6 | A |
| 7 | A | 8 | C |
| 9 | A | 10 | A |
| 11 | A | 12 | A |
| 13 | A | 14 | A |
| 15 | A | 16 | A |
| 17 | A | 18 | A |
| 19 | C | 20 | A |
| 21 | A | 22 | A |
| 23 | A | 24 | C |
| 25 | C | 26 | A |
| 27 | C | 28 | A |
| 29 | C | 30 | A |
| 31 | B | 32 | C |
| 33 | C | 34 | A |
| 35 | A | 36 | A |
| 37 | B | 38 | C |
| 39 | A | 40 | C |
| 41 | A | 42 | A |
| 43 | C | 44 | C |
| 45 | C | 46 | C |
| 47 | B | 48 | A |
| 49 | C | 50 | A |
| 51 | A | 52 | A |
| 53 | A | 54 | A |
| 55 | A | 56 | B |
| 57 | B | 58 | A |
| 59 | B | 60 | B |
| 61 | A | 62 | A |
| 63 | A | 64 | B |
| 65 | A | 66 | A |
| 67 | C | 68 | A |
| 69 | A | 70 | A |
| 71 | A | 72 | A |
| 73 | A | 74 | B |
| 75 | A | 76 | A |
| 77 | C | 78 | C |
| 79 | C | 80 | A |
| 81 | A | 82 | A |
| 83 | C | 84 | C |
| 85 | C | 86 | A |
| 87 | A | 88 | A |
| 89 | A | 90 | A |
| 91 | A | 92 | A |
| 93 | A | 94 | A |
| 95 | C | 96 | B |
| 97 | B | 98 | A |
| 99 | A | 100 | A |
| 101 | C | 102 | C |
| 103 | A | 104 | C |
| 105 | A | 106 | A |
| 107 | C | 108 | A |
| 109 | A | 110 | A |
| 111 | A | 112 | A |
| 113 | A | 114 | A |
| 115 | A | 116 | A |
| 117 | A | 118 | A |
| 119 | C | 120 | C |
| 121 | A | 122 | A |
| 123 | A | 124 | A |
| 125 | A | 126 | A |
| 127 | C | 128 | C |
| 129 | A | 130 | A |
| 131 | A | 132 | C |
| 133 | C | 134 | C |
| 135 | A | 136 | A |
| 137 | A | 138 | A |
| 139 | C | 140 | C |
| 141 | B | 142 | B |
| 143 | C | 144 | B |
| 145 | C | 146 | C |
| 147 | A | 148 | B |
| 149 | A | 150 | A |

TABLE 1-continued

Summary of Activities

| Compd. Number | HepAD38 EC$_{50}$ (µM) | Compd. Number | HepAD38 EC$_{50}$ (µM) |
|---|---|---|---|
| 151 | A | 152 | C |
| 153 | B | 154 | C |
| 155 | A | 156 | A |
| 157 | A | 158 | A |
| 159 | A | 160 | C |
| 161 | A | 162 | A |
| 163 | A | 164 | A |
| 165 | A | 166 | A |
| 167 | A | 168 | A |
| 169 | B | 170 | A |
| 171 | C | 172 | A |
| 173 | A | 174 | A |
| 175 | A | 176 | A |
| 177 | A | 178 | A |
| 179 | A | 180 | A |
| 181 | A | 182 | A |
| 183 | A | 184 | A |
| 185 | A | 186 | A |
| 187 | A | 188 | A |
| 189 | A | 190 | A |
| 191 | A | 192 | A |
| 193 | A | 194 | B |
| 195 | C | 196 | C |
| 197 | C | 198 | B |
| 199 | C | 200 | C |
| 201 | C | 202 | A |
| 203 | A | 204 | B |
| 205 | C | 206 | B |
| 207 | C | 208 | C |
| 209 | C | 210 | A |
| 211 | C | 212 | C |
| 213 | C | 214 | C |
| 215 | A | 216 | B |
| 217 | C | 218 | A |
| 219 | C | 220 | C |
| 221 | C | 222 | B |
| 223 | B | 224 | B |
| 225 | B | 226 | C |
| 227 | C | 228 | C |
| 229 | C | 230 | C |
| 231 | C | 232 | C |
| 233 | C | 234 | C |
| 235 | C | 236 | C |
| 237 | C | 238 | C |
| 239 | C | 240 | C |
| 241 | C | 242 | C |
| 243 | C | 244 | C |
| 245 | C | 246 | C |
| 247 | C | 248 | C |
| 249 | C | 250a | C |
| 250b | C | 251 | C |
| 252a | C | 252b | C |
| 253a | C | 253b | C |
| 254 | C | 255 | C |
| 256a | C | 256b | C |
| 257a | C | 257b | C |
| 258 | C | 260 | C |
| 272 | A | 279 | A |
| 280 | A | 281 | C |
| 282 | A | 283 | B |
| 284 | A | 284a | A |
| 284b | A | 285 | A |
| 285a | A | 285b | A |
| 286 | B | 287 | C |
| 288 | A | 289 | A |
| 290 | A | 291 | A |
| 291a | A | 291b | A |
| 292 | C | 293 | A |
| 294 | A | 294a | A |
| 294b | A | 295 | A |
| 296 | A | 296a | A |
| 296b | A | 297 | A |
| 298 | A | 299 | A |
| 300 | C | 301 | A |
| 302 | A | 303 | A |
| 304 | A | 305 | A |
| 306 | A | 307 | B |
| 308 | A | 309 | B |
| 310 | C | 311 | C |
| 312 | C | 313 | A |
| 314 | A | 315 | C |
| 316 | C | 317 | A |
| 318 | C | 319 | A |
| 320 | A | 321 | A |
| 322 | A | 323 | B |
| 324 | A | 325 | A |
| 326 | A | 327 | B |
| 328 | B | 329 | A |
| 330 | C | 331 | A |
| 332 | A | 333 | A |
| 334 | A | 335 | A |
| 336 | A | 337 | C |
| 338 | A | 341 | C |
| 342 | A | 343 | A |
| 344 | A | 345 | A |
| 346 |  | 347 |  |
| 348 | A | 349 | B |
| 350 | A |  |  |

TABLE 2

Summary of Cytotoxicity

| Compd. Number | ATPlite CC$_{50}$ (µM) | Compd. Number | ATPlite CC$_{50}$ (µM) |
|---|---|---|---|
| 1 | >3 | 4 | >12.5 |
| 5 | >3 | 9 | >6.25 |
| 10 | >12.5 | 11 | >6.25 |
| 12 | >3 | 13 | >6.25 |
| 36 | A | 39 | >6.25 |
| 41 | >6.25 | 52 | A |
| 53 | >6.25 | 54 | A |
| 55 | A | 58 | >12.5 |
| 61 | >6.25 | 62 | >12.5 |
| 66 | B | 68 | A |
| 70 | A | 71 | >3 |
| 72 | >3 | 73 | >6.25 |
| 88 | >6.25 | 89 | >6.25 |
| 90 | >6.25 | 91 | B |
| 92 | >6.25 | 93 | >6.25 |
| 111 | >3 | 112 | >6.25 |
| 113 | >6.25 | 114 | >6.25 |
| 116 | >3 | 117 | >6.25 |
| 122 | A | 125 | >6.25 |
| 126 | >6.25 | 129 | A |
| 130 | >12.5 | 131 | >12.5 |
| 135 | C | 136 | >12.5 |
| 137 | >6.25 | 149 | A |
| 150 | A | 151 | A |
| 152 | A | 155 | A |
| 162 | >6.25 | 163 | A |
| 167 | >12.5 | 168 | B |
| 172 | A | 173 | >6.25 |
| 176 | >6.25 | 177 | >6.25 |
| 178 | A | 179 | A |
| 180 | A | 182 | A |
| 183 | A | 185 | >12.5 |
| 186 | >12.5 | 187 | >12.5 |
| 188 | >12.5 | 189 | >12.5 |
| 191 | A | 192 | >12.5 |
| 193 | A | 215 | A |
| 218 | B | 272 | A |
| 279 | A | 280 | A |
| 284b | A | 285a | A |
| 285b | A | 289 | A |
| 290 | A | 291 | A |

TABLE 2-continued

Summary of Cytotoxicity

| Compd. Number | ATPlite CC$_{50}$ (μM) | Compd. Number | ATPlite CC$_{50}$ (μM) |
| --- | --- | --- | --- |
| 294 | A | 296 | A |
| 302 | A | 303 | A |
| 308 | A | 317 | A |
| 319 | A | 325 | A |
| 326 | A | 329 | A |
| 331 | A | 332 | A |
| 335 | A | 338 | A |
| 343 | A | 344 | A |
| 345 | A | | |

What is claimed:

1. A pharmaceutical composition comprising a compound represented by the formula

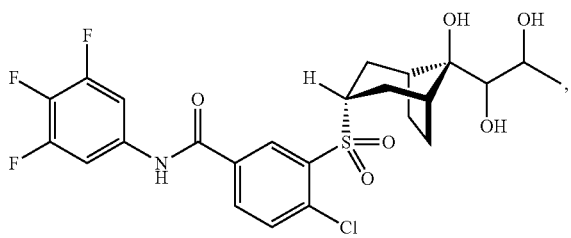

wherein R is hydrogen or fluorine;
and a pharmaceutically acceptable carrier or excipient.

2. The pharmaceutical composition of claim 1, wherein the compound is

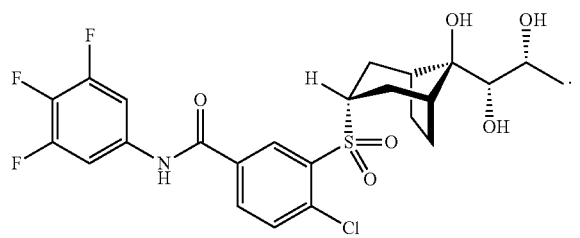

3. The pharmaceutical composition of claim 1, wherein the compound is

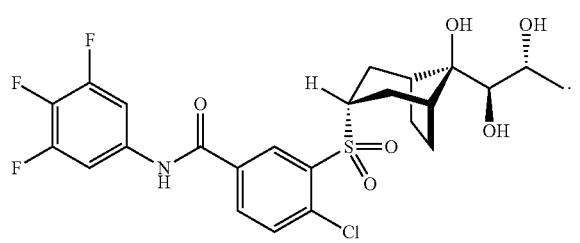

4. The pharmaceutical composition of claim 1, wherein the compound is

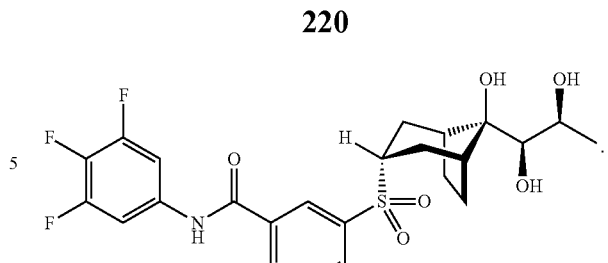

5. The pharmaceutical composition of claim 1, wherein the compound is

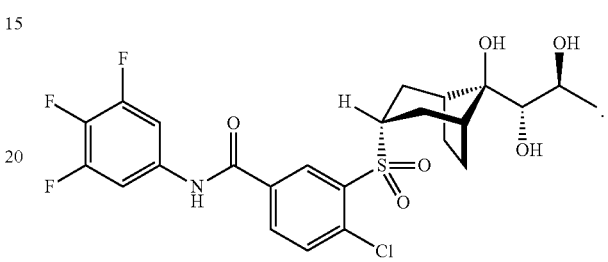

6. The pharmaceutical composition of claim 1, wherein the compound is

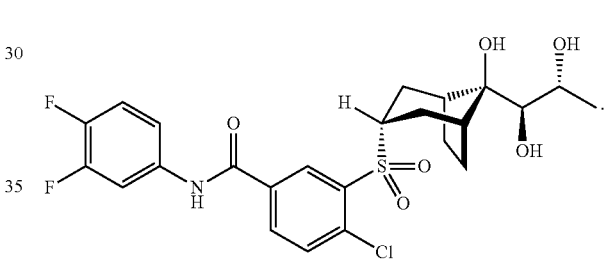

7. The pharmaceutical composition of claim 1, wherein the compound is

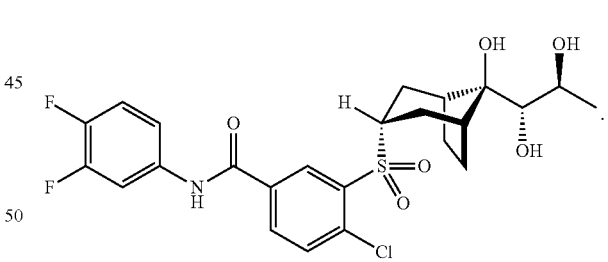

8. The pharmaceutical composition of claim 1, wherein the compound is

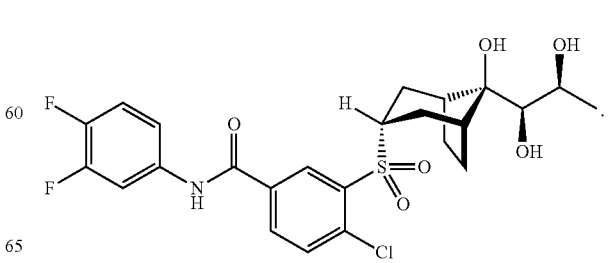

9. The pharmaceutical composition of claim 1, wherein the compound is

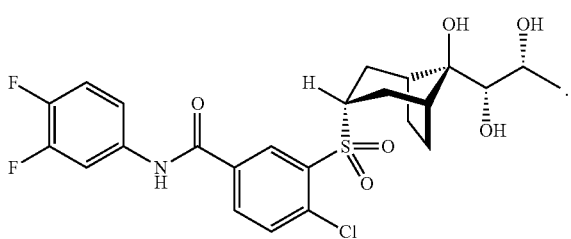

.

10. A method of treating a hepatitis B virus infection in a subject in need thereof, comprising administering to the subject a therapeutically effective amount of the pharmaceutical composition of claim 2.

11. A method of treating a hepatitis B virus infection in a subject in need thereof, comprising administering to the subject a therapeutically effective amount of the pharmaceutical composition of claim 2.

12. A method of treating a hepatitis B virus infection in a subject in need thereof, comprising administering to the subject a therapeutically effective amount of the pharmaceutical composition of claim 3.

13. A method of treating a hepatitis B virus infection in a subject in need thereof, comprising administering to the subject a therapeutically effective amount of the pharmaceutical composition of claim 4.

14. A method of treating a hepatitis B virus infection in a subject in need thereof, comprising administering to the subject a therapeutically effective amount of the pharmaceutical composition of claim 5.

15. A method of treating a hepatitis B virus infection in a subject in need thereof, comprising administering to the subject a therapeutically effective amount of the pharmaceutical composition of claim 5.

16. A method of treating a hepatitis B virus infection in a subject in need thereof, comprising administering to the subject a therapeutically effective amount of the pharmaceutical composition of claim 6.

17. A method of treating a hepatitis B virus infection in a subject in need thereof, comprising administering to the subject a therapeutically effective amount of the pharmaceutical composition of claim 7.

* * * * *

UNITED STATES PATENT AND TRADEMARK OFFICE
CERTIFICATE OF CORRECTION

PATENT NO. : 12,011,425 B2  
APPLICATION NO. : 18/101258  
DATED : June 18, 2024  
INVENTOR(S) : Yao-Ling Qiu et al.

Page 1 of 1

It is certified that error appears in the above-identified patent and that said Letters Patent is hereby corrected as shown below:

In the Claims

<u>At Column 219</u>

In Claim 1, Line 25 delete " 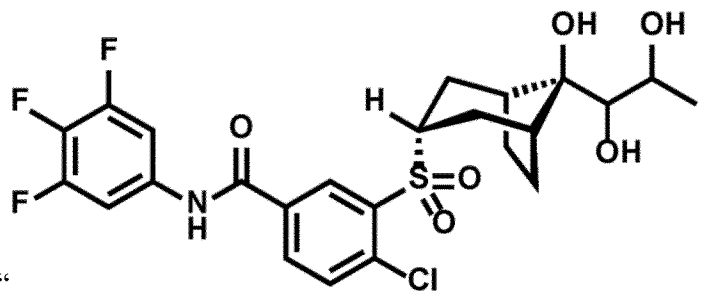 " and insert

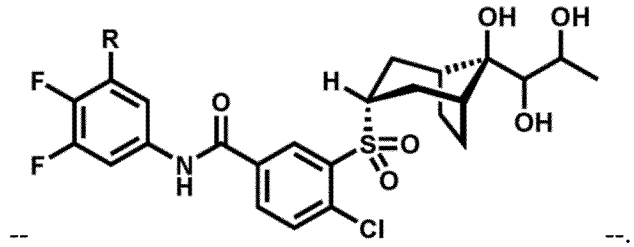

--                    --.

Signed and Sealed this  
Twenty-seventh Day of August, 2024

Katherine Kelly Vidal  
*Director of the United States Patent and Trademark Office*